(12) United States Patent
Stephan et al.

(10) Patent No.: US 10,188,749 B2
(45) Date of Patent: Jan. 29, 2019

(54) COMPOSITIONS AND METHODS TO PROGRAM THERAPEUTIC CELLS USING TARGETED NUCLEIC ACID NANOCARRIERS

(71) Applicant: FRED HUTCHINSON CANCER RESEARCH CENTER, Seattle, WA (US)

(72) Inventors: Matthias Stephan, Seattle, WA (US); Howell F. Moffett, Seattle, WA (US)

(73) Assignee: FRED HUTCHINSON CANCER RESEARCH CENTER, Seattle, WA (US)

(*) Notice: Subject to any disclaimer, the term of this patent is extended or adjusted under 35 U.S.C. 154(b) by 0 days.

(21) Appl. No.: 15/594,344

(22) Filed: May 12, 2017

(65) Prior Publication Data

US 2017/0296676 A1    Oct. 19, 2017

Related U.S. Application Data

(63) Continuation of application No. PCT/US2017/027767, filed on Apr. 14, 2017.

(60) Provisional application No. 62/322,581, filed on Apr. 14, 2016, provisional application No. 62/442,890, filed on Jan. 5, 2017.

(51) Int. Cl.
  *A61K 48/00* (2006.01)
  *C12N 9/22* (2006.01)
  *C07K 14/705* (2006.01)

(52) U.S. Cl.
  CPC .......... *A61K 48/005* (2013.01); *C07K 14/705* (2013.01); *C12N 9/22* (2013.01)

(58) Field of Classification Search
  CPC .. A61K 48/005; A61K 2300/00; A61K 31/05; A61K 31/12; A61K 31/192; A61K 31/196; A61K 31/216; A61K 31/433; A61K 31/713; A61K 47/34; A61K 9/5146; A61K 9/5192; A61K 2039/505; A61K 31/7088; A61K 31/7105; A61K 38/00; A61K 39/3955; A61K 45/06; A61K 47/26; A61K 47/36; A61K 48/0008; A61K 48/0091; A61K 9/127; A61K 9/1647; A61K 9/5123; A61K 9/5161; A61K 39/395; A61K 48/00; A61K 9/51; A61K 9/16; C07K 14/705; C07K 14/003; C12N 9/22; C12N 15/113; C12N 15/102; C12N 15/11; C12N 15/111; C12N 15/88; C12N 15/907; C12N 2310/14; C12N 2310/141; C12N 2310/15; C12N 2310/152; C12N 2310/3181; C12N 2310/334; C12N 2310/351; C12N 2310/3519; C12N 15/90; C08G 73/02; C08G 63/91; C08G 69/10;

C08G 73/028; A61B 18/04; A61B 2018/00577; A61L 2300/436; A61L 2300/606; A61L 2430/36; A61L 24/0015; A61L 24/02; A61L 24/00

See application file for complete search history.

(56) References Cited

U.S. PATENT DOCUMENTS

| 8,440,431 | B2 | 5/2013 | Voytas et al. |
| 2004/0071654 | A1* | 4/2004 | Anderson ............ A61K 9/5138 424/78.37 |
| 2012/0192298 | A1* | 7/2012 | Weinstein .......... A01K 67/0276 800/14 |
| 2014/0309177 | A1 | 10/2014 | Perez-Pinera et al. |
| 2017/0283830 | A1* | 10/2017 | Saltzman ............. C12N 15/907 |

FOREIGN PATENT DOCUMENTS

| WO | WO2014153114 | 9/2014 | |
| WO | WO-2014153114 A1 * | 9/2014 | ......... C07K 16/3069 |
| WO | WO2014191527 | 12/2014 | |

OTHER PUBLICATIONS

Bai et al., "Enhancement of the in vivo persistence and antitumor efficacy of CD19 chimeric antigen receptor T cells through the delivery of modified TERT mRNA," Cell Discov., vol. 1, 2015, 15 pages.
Boissel et al., "Assembly and Characterization of megaTALs for Hyperspecific Genome Engineering Applications," Methods Mol. Biol., vol. 1239, 2015, pp. 171-196.
Copolovici, et al., "Cell-penetrating peptides: design, synthesis, and applications," ACS Nano., vol. 8, No. 3, 2014, pp. 1972-1994.
Costa, et al., "Generation of sensory hair cells by genetic programming with a combination of transcription factors," Development, vol. 142, No. 11, 2015, pp. 1948-1959.
Cox, et al., "Therapeutic genome editing: prospects and challenges," Nat. Med., vol. 21, No. 2, 2015, pp. 121-131.
Cribbs, et al., "Simplified production and concentration of lentiviral vectors to achieve high transduction in primary human T cells," BMC Biotechnol., vol. 13, No. 98, 2013, 8 pages.
Kim, et al., "The transcription factor Foxo1 controls central-memory CD8+ T cell responses to infection," Immunity, vol. 39, No. 1, 2013, pp. 286-297.

(Continued)

*Primary Examiner* — Janet L Epps-Smith
(74) *Attorney, Agent, or Firm* — Lee & Hayes PC; C. Rachal Winger

(57) ABSTRACT

Compositions and methods that rapidly and selectively modify hematopoietic stem cells (or cells derived therefrom) to achieve therapeutic objectives by providing for transient expression of nucleic acids are described. The transient expression leads to permanent therapeutic changes in the modified cells, referred to herein as "hit and run" effects.

8 Claims, 35 Drawing Sheets

Specification includes a Sequence Listing.

(56) References Cited

OTHER PUBLICATIONS

Koh, et al., "A practical approach to immunotherapy of hepatocellular carcinoma using T cells redirected against hepatitis B virus," Mol. Ther. Nucleic Acids, vol. 2, 2013, 9 pages.
Liu, et al., "Affinity-Tuned ErbB2 or EGFR Chimeric Antigen Receptor T Cells Exhibit an Increased Therapeutic Index against Tumors in Mice," Cancer Res., vol. 75, No. 17, 2015, pp. 3596-3607.
Liu, et al., "Cell-penetrating peptide-mediated delivery of TALEN proteins via bioconjugation for genome engineering," PLoS One, vol. 9, No. 1, 2014, 7 pages.
Liu, et al., "Improved cell-penetrating zinc-finger nuclease proteins for precision genome engineering," Mol. Ther. Nucleic Acids, vol. 4, 2015, 9 pages.
Mangraviti, et al., "Polymeric nanoparticles for nonviral gene therapy extend brain tumor survival in vivo," ACS Nano., vol. 9, No. 2, 2015, pp. 1236-1249.
Search Report and Written Opinion dated Jul. 31, 2017 for International Application No. PCT/US2017/027767.
Schumann, et al., "Generation of knock-in primary human T cells using Cas9 ribonucleoproteins,"PNAS, vol. 112, No. 22, 2015, pp. 10437-10442.
Tejera, et al., "FoxO1 controls effector-to-memory transition and maintenance of functional CD8 T cell memory," J. Immunol., vol. 191, No. 1, 2013, pp. 187-199.
Themeli et al., "Generation of tumor-targeted human T lymphocytes from induced pluripotent stem cells for cancer therapy," Nat. Biotechnol., vol. 31, 2013, pp. 928-933.
Wang, et al., "Highly efficient homology-driven genome editing in human T cells by combining zinc-finger nuclease mRNA and AAV6 donor delivery," Nucleic Acids Res., vol. 44, No. 3, 2016, 9 pages.
Wurm, et al., "Ectopic expression of HOXC6 blocks myeloid differentiation and predisposes to malignant transformation," Exp. Hematol., vol. 42, No. 2, 2014, pp. 114-125.
Zhang, et al., "MicroRNA-31 negatively regulates peripherally derived regulatory T-cell generation by repressing retinoic acid-inducible protein 3," Nat. Commun., vol. 6, No. 7639 2015, 12 pages.

* cited by examiner

FIG. 1C
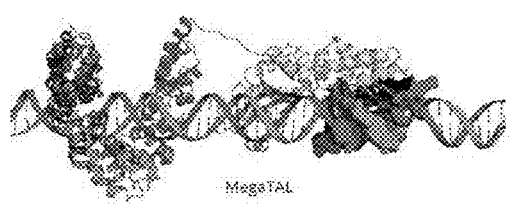
| Therapeutic area | Target gene |
|---|---|
| T cell Signaling | Shp1 phosphatase |
| Immune Checkpoint | PD1 receptor |
| Safety | endogenous TCRa |
| HIV resistance | CCR5 and or CXCR4 |
MegaTAL
| Therapeutic area | Target gene |
|---|---|
| T cell memory | FOXO1, LKB1 |
| Cellular seescence | TERT (prevents telomere shortening) |
| Cell trafficking | Chemokine receptor CCR2b or CCR4 |

FIG. 2

| Antibody Specificity | Dye | Clone | Supplier |
|---|---|---|---|
| CD34 | BV421 | 561 | Biolegend |
| CD90 | APC | 5E10 | Biolegend |
| CD105 | PE-Cy7 | 43A3 | Biolegend |
| CD49F | PE | GOH3 | Biolegend |
| CD28 | BV 510 | CD28-2 | Biolegend |
| CD62L | APC-CY7 | DERG56 | Biolegend |
| CD62L | PE-CY5 | DERG56 | Biolegend |
| CD45RA | ALEXA 700 | HI1000 | Biolegend |
| CCR7 | PE | G043H7 | Biolegend |
| CD3 | APC | HIT3A | Biolegend |
| CD3 | BV421 | HIT3A | Biolegend |
| CD45R0 | PERCP-CY5.5 | UCHL1 | Biolegend |
| CD8 | BV421 | SK1 | Biolegend |
| IL2 | BV421 | MQ1-17H12 | Biolegend |
| IFN-G | PE | B27 | Biolegend |
| CD19 | PE | H1B19 | Biolegend |
| CD133 | PE-Vio615 | AC133 | Miltenyi |
| Foxo1 | --- | C29H4 | Cell Signal |
| anti-Rabbit IG FAB2 | Alexa 647 | --- | Cell Signal |
| StrepTag II | biotin | --- | --- |
| Streptavidin | APC | --- | ebioscience |
| 7AAD | --- | --- | ebioscience |

FIG. 11

Exemplary megaTAL Specific for TCRα

MGSCRYPYDVPDYAPPKKKRKVVDLRTLGYSQQQQEKIKPKVRSTVAQHHEALVGHGFT
HAHIVALSQHPAALGTVAVTYQHIITALPEATHEDIVGVGKQWSGARALEALLTDAGELRGP
PLQLDTGQLVKIAKRGGVTAMEAVHASRNALTGAPLNLTPDQVVAIASNIGGKQALETVQR
LLPVLCQDHGLTPDQVVAIASNIGGKQALETVQRLLPVLCQDHGLTPDQVVAIASNIGGKQA
LETVQRLLPVLCQDHGLTPDQVVAIASNGGGKQALETVQRLLPVLCQDHGLTPDQVVAIAS
HDGGKQALETVQRLLPVLCQDHGLTPDQVVAIASHDGGKQALETVQRLLPVLCQDHGLTP
DQVVAIASNIGGKQALETVQRLLPVLCQDHGLTPDQVVAIASNGGKQALETVQRLLPVLC
QDHGLTPDQVVAIASNGGGKQALETVQRLLPVLCQDHGLTPDQVVAIASNNGGKQALETV
QRLLPVLCQDHGLTPDQVVAIASNIGGKQALESIVAQLSRPDPALAALTNDHLVALACLGGR
PAMDAVKKGLPHAPELIRRVNRRIGERTSHRVAISRVGGSSRRESINPWILTGFADAEGSFI
LDIRNRNNESNRYRTSLRFQITLHNKDKSILENIQSTWKVGKITNSGDRAVMLRVTRFEDLK
VIIDHFEKYPLITQKLGDYKLFKQAFSVMENKEHLKENGIKELVRIKAKMNWGLTDELKKAFP
ENISKERPLINKNIPNFKWLAGFTSGDGYFGVNLKKVKGNAKVYVGLRFSISQHIRDKNLMN
SLITYLGCGSIWEKNKSEFSWLEFVVTKFSDINDKIIPVFQENTLIGVKLEDFEDWCKVAKLIE
EKKHLTESGLDEIKKIKLNMNKGRVF*(SEQ ID NO: 1)

FIG. 11 (cont'd)

Exemplary Shp-1 phosphatase gene

ACCESSION NM_080549: Human
actctaaaacgagaagtacaagtgagttcccccaaggggtcggccgcgcctcttcctgtccccgccctgccggctgccccaggccagtgg
agtggcagcccagaactgggaccaccggggtggtgaggcggccggcactgggagctgcatctgaggcttagtccctgagctctctg
cctgcccagactagctgcacctcctcattccctgcgcccccttcctctccggaagccccaggatggtgaggtggtttcaccgagacctcagt
gggctggatgcagagaccctgctcaaggggcgaggtgtccacggtagcttcctggctcggcccagtcgcaagaaccagggtgacttctcg
ctctccgtcagggtgggggatcaggtgacccatattcggatccagaactcaggggattctatgacctgtatggaggggagaagtttgcgact
ctgacagagctggtggagtactacactcagcagcagggtgtcctgcaggaccgcgacggcaccatcatccacctcaagtacccgctgaa
ctgctccgatccactagtgagaggtggtaccatggccacatgtctggcgggcaggcagagacgctgctgcaggccaagggcgagccct
ggacgtttcttgtgcgtgagagcctcagccagcctggagacttcgtgcttctgtgctcagtgaccagcccaaggctggcccaggctcccgc
tcagggtcacccacatcaaggtcatgtgcgagggtggacgctacacagtgggtggtttggagaccttcgacagcctcacggacctggtgga
gcatttcaagaagacggggattgaggaggcctcaggcgcctttgtctacctgcgggcagccgtactatgccacgagggtgaatgcggctgac
attgagaaccgagtgttggaactgaacaagaagcaggagtccgaggatacagccaaggctggcttctgggaggagtttgagagtttgcag
aagcaggaggtgaagaacttgcaccagcgtctggaagggcagcggccagagaacaagggcaagaaccgctacaagaacattctccc
ctttgaccacagccgagtgatcctgcagggacgggacagtaacatccccgggtccgactacatcaatgccaactacatcaagaaccagct
gctaggccctgatgagaacgctaagacctacatcgccagccagggctgtctggaggccacggtcaatgacttctggcagatggcgtggca
ggagaacagccgtgtcatcgtcatgaccacccgagaggtggagaaaggccggaacaaatgcgtcccatactggcccgaggtgggcat
gcagcgtgcttatgggccctactctgtgaccaactgcggggagcatgacacaaccgaatacaaactccgtaccttacaggtctcccgctg
gacaatggagacctgattcgggagatctggcattaccagtacctgagctggcccgaccatggggtcccagtgagcctggggggtgtcctca
gcttcctggaccagatcaaccagcggcaggaaagtctgcctcacgcagggcccatcatcgtgcactgcagcgccggcatcggccgcac
aggcaccatcattgtcatcgacatgctcatggagaacatctccaccaagggcctggactgtgacattgacatccagaagaccatccagatg
gtgcgggcgcagcgctcgggcatggtgcagacggaggcgcagtacaagttcatctacgtggccatcgcccagttcattgaaaccactaag
aagaagctggaggtcctgcagtcgcagaagggccaggagtcggagtacggaacatcacctatcccccagccatgaagaatgcccatg
ccaaggcctcccgcacctcgtccaagagcttggagtctagtgcagggaccgtggctgcgtcacctgtgagacggggtggccagagggga
ctgccagtgccgggtcccctgtgctgtctcctgacctgcaccaactgcctgtacttgcccccctgcacccggctgcagacacaaggaggat
gtgtatgagaacctgcacactaagaacaagaggaggagaaagtgaagaagcagcggtcagcagacaaggagaagagcaagggtt
ccctcaagaggaagtgagcggtgctgtcctcaggtggccatgcctcagccctgaccctgtggaagcatttcgcgatggacagactcacaac
ctgaacctaggagtgccccattctttgtaatttaaatggctgcatccccccacctctccctgacctgtatatagcccagccaggccccagg
cagggccaaccttctcctctgtaaataaagccctgggatcactgtgaaaaaaaaaaaaaaaaaaaaaaaaaaaaaaaaaaaaaaaaaa
aaaaaaaaaaaaaaaaaaaaaaaaaaaaaaaaaaa (SEQ ID NO: 2)

Exemplary PD1 Receptor (PDCD1 gene)

ACCESSION AY238517: Human
atgcagatcccacaggcgccctggccagtcgtctgggcggtgctacaactgggctggcggccaggatggttcttagactcccagaca
ggccctggaaccccccaccttctcccagccctgctcgtggtgaccgaaggggacaacgccaccttcacctgcagcttctccaacac
atcggagagcttcgtgctaaactggtaccgcatgagccccagcaaccagacggacaagctggccgcctccccgaggaccgcagc
cagcccggccaggactgcgcgcttccgtgtcacacaactgcccaacgggcgtgacttccacatgagcgtggtcagggccggcgcaat
gacagcggcacctacctgtgtggggccatctcccggccccaaggcgcagatcaaagagagcctgcgggcagagctcagggtga
cagagaagggcagaagtgcccacagcccaccccagccctcacccaggccagccggccagttccaaaccctggtggttggtgt
cgtgggcggcctgctgggcagcctggtgctgctagtctgggtcctggccgtcatctgctcccggccgcacgagggacaataggagcc
aggcgcaccggccagcccctgaaggaggaccctcagccgtgcctgtgttctctgtggactatggggagctggatttccagtggcgag
agaagaccccggagcccccgtgccctgtgtcctgagcagacggagtatgccaccattgtctttcctagcggaatgggcacctcatcc
cccgccgcaggggctcagctgacggccctcggagtgccagccactgaggcctgaggatggacactgctcttggcccctctga
(SEQ ID NO: 3)

FIG. 11 (cont'd)

Exemplary TCRα gene

ACCESSION X04954: Human
atgacatccattcgagctgtatttatattcctgtggctgcagctggacttggtgaatggagagaatgtggagcagcatccttcaaccctgagtgtc
caggagggagacagcgctgttatcaagtgtacttattcagacagtgcctcaaactacttcccttggtataagcaagaacttggaaaaagacct
cagcttattatagacattcgttcaaatgtgggcgaaaagaaagaccaacgaattgctgttacattgaacaagacagccaaacattctccctgc
acatcacagagacccaacctgaagactcggctgtctacttctgtgcagcaagtaggaaggactctgggggttaccagaaagttaccttgga
actggaacaaagctccaagtcatcccaaatatccagaaccctgac (SEQ ID NO: 4)

Exemplary CCR5 gene

ACCESSION U66285: Human
ttggattatcaagtgtcaagtccaatctatgacatcaattattatacatcggagccctgccaaaaaatcaatgtgaagcaaatcgcagcccgcc
tcctgcctccgctctactcactggtgttcatctttggttttgtgggcaacatgctggtcatcctcatcctgataaactgcaaaaggctgaagagcatg
actgacatctacctgctcaacctggccatctctgacctgtttttccttcttactgtcccttctgggctcactatgctgccgcccagtgggactttgga
aatacaatgtgtcaactcttgacagggctctatttttataggcttcttctctggaatcttcttcatcatcctcctgacaatcgataggtacctggctgtcg
tccatgctgtgtttgctttaaaagccaggacggtcaccttggggtggtgacaagtgtgatcacttgggtggtggctgtgttgcgtctctcccagg
aatcatctttaccagatctcaaaaagaaggtcttcattacacctgcagctctcattttccatacattaaagatagtcatcttgggctggtcctgcc
gctgcttgtcatggtcatctgctactcgggaatcctaaaaactctgcttcggtgtcgaaatgagaagaagaggcacagggctgtgaggcttatc
ttcaccatcatgattgttatttctctcttctgggctccctacaacattgtcctctcctgaacaccttccaggaattcttggcctgaataattgcagtagc
tctaacaggttggaccaagctatgcaggtgacagagactcttgggatgacgcactgctgcatcaacccatcatctatgcctttgtcggggag
aagttcagaaactacctctctagtcttcttccaaaagcacattgccaaacgcttctgcaaatgctgttctattttccagcaagaggctcccgagcga
gcaagctcagtttacacccgatccactggggagcaggaaatatctgtgggcttgtga (SEQ ID NO: 5)

Exemplary CXCR4 gene

ACCESSION NM_001008540: Human
ttttttcttccctctagtgggcggggcagaggagttagccaagatgtgactttgaaaccctcagcgtctcagtgcccttttgttctaaacaaagaa
ttttgtaattggttctaccaaagaaggatataatgaagtcactatgggaaaagatggggaggagagttgtaggattctacattaattctcttgtgc
cctagcccactacttcagaattcctgaagaaagcaagcctgaattggttttttaaattgctttaaaaattttttttaactgggttaatgcttgctgaatt
ggaagtgaatgtccattcctttgcctctttgcagatatacacttcagataactacaccgaggaaatgggctcaggggactatgactccatgaa
ggaaccctgtttccgtgaagaaaatgctaatttcaataaaatcttcctgcccaccatctactccatcatcttcttaactggcattgtgggcaatgga
ttggtcatcctggtcatgggttaccagaagaaactgagaagcatgacggacaagtacaggctgcaccgtcagtggccgacctcctctttgtc
atcacgcttcccttctgggcagtgatgccgtggcaaactggtactttgggaacttcctatgcaaggcagtccatgtcatctacacagtcaacctc
tacagcagtgtcctcatcctggccttcatcagtctggaccgctacctggccatcgtccacgccaccaacagtcagaggccaaggaagctgttg
gctgaaaaggtggtctatgttggcgtctggatccctgccctcctgctgactattcccgacttcatctttgccaacgtcagtgaggcagatgacag
atatatctgtgaccgcttctaccccaatgacttgtgggtggttgtgttccagtttcagcacatcatggttggccttatcctgcctggtattgtcatcctgt
cctgctattgcattatcatctccaagctgtcacactccaagggccaccagaagcgcaaggcctcaagaccacagtcatcctcatcctggcttt
cttcgccttgtggctgccttactacattgggatcagcatcgactcctcatcctcctggaaatcatcaagcaagggtgtgagtttgagaacactgt
gcacaagtggatttccatcaccgaggccctagcttcttccactgttgtctgaaccccatcctctatgctttccttggagccaaatttaaaacctctg
cccagcacgcactcacctctgtgagcagagggtccagcctcaagatcctctccaaaggaaagcgaggtggacattcatctgtttccactgag
tctgagtcttcaagttttcactccagctaacacagatgtaaaagacttttttttatacgataaataacttttttttaagttacacattttcagatataaaa
gactgaccaatattgtacagttttattgcttgttggattttgtcttgtgtttctttagttttgtgaagtttaattgacttattatataaatttttttgttcatattg
atgtgtgtctaggcaggacctgtgccaagtcttagttgctgtatgtctcgtggtaggactgtagaaaagggaactgaacattccagagcgtgt
agtgaatcacgtaaagctagaaatgatcccagctgttatgcatagataatctctccattcccgtggaacgttttcctgttcttaagacgtgattt
gctgtagaagatggcacttataaccaaagcccaaagtggtatagaaatgctggttttcagttttcaggagtgggtgattcagcacctacagt
gtacagtcttgtattaagttgttaataaaagtacatgttaaacttaaaaaaaaaaaaaaaaaaaa (SEQ ID NO: 6)

FIG. 11 (cont'd)

Exemplary FOXO1 gene

ACCESSION BC021981: Human
ttccgtccttccgtccgcggccctgtcagctggagcgcggcgcaggctctgccccggcccggcggctctggccggccgtccagtccgtgcgg
cggaccccgaggagcctcgatgtggatggccccgcgaagttaagttctgggctcgcgcttccactccgccgcgccttcctcccagtttccgtcc
gctcgccgcaccggcttcgttcccccaaatctcggaccgtccttcgcgccccctcccgtccgccccagtgctgcgttctccccctcttggctc
tcctgcggctgggggagggcgggggtcaccatggccgaggcgcctcaggtggtggagatcgacccggacttcgagccgctgccccggc
cgcgctcgtgcacctggccgctgcccaggccggagtttagccagtccaactcggccacctccagcccggcgccgtcgggcagcgcggctg
ccaaccccgacgccgcggcgggcctgccctcggcctcggctgccgctgtcagcgccgacttcatgagcaacctgagcttgctggaggaga
gcgaggacttcccgcaggcgcccggctccgtggcggcggcggtggcggcggcggccgccgcggccgccaccggggggctgtgcgggg
acttccagggcccggaggcgggctgcctgcacccagcgccacgcagccccgccgccgggccgctgtcgcagcaccgccggtgcc
ccccgccgccgctgggccgctcgcggggcagccgcgcaagagcagctcgtcccgccgcaacgcgtggggcaacctgtcctacgccgac
ctcatcaccaaggccatcgagagctcggcggagaagcggctcacgctgtcgcagatctacgagtggatggtcaagagcgtgccctacttca
aggataagggtgacagcaacagctcggcgggctggaagaattcaattcgtcataatctgtccctacacagcaagttcattcgtgtgcagaat
gaaggaactggaaaaagttcttggtggatgctcaatccagagggtggcaagagcgggaaatctcctaggagaagagctgcatccatgga
caacaacagtaaatttgctaagagccgaagccgagctgccaagaagaaagcatctctccagtctggccaggagggtgctggggacagcc
ctggatcacagttttccaaatggcctgcaagccctggctctcacagcaatgatgacttgataactggagtacattcgccctcgaactagctca
aatgctagtactattagtgggagactctcacccattatgaccgaacaggatgatcttggagaagggggatgtgcattctatggtgtaccgccat
ctgccgcaaagatggcctctactttacccagtctgtctgagataagcaatcccgaaaacatggaaaatcttttggataatctcaaccttctctcat
caccaacatcattaactgtttcgacccagtcctcacctggcaccatgatgcagcagacgccgtgctactcgtttgcgccaccaaacaccagttt
gaattcacccagcccaaactaccaaaaatatacatatggccaatccagcatgagcccttttgccccagatgcctatacaaacacttcaggac
aataagtcgagttatggaggtatgagtcagtataactgtgcgcctggactcttgaaggagttgctgacttctgactctctccccataatgacatta
tgacaccagttgatcctggggtagcccagcccaacagccgggttctgggccagaacgtcatgatgggccctaattcggtcatgtcaacctatg
gcagccaggcatctcataacaaaatgatgaatcccagctcccatacccacctggacatgctcagcagacatctgcagttaacgggcgtcc
cctgccccacacggtaagcaccatgccccacacctcgggtatgaaccgcctgacccaagtgaagacacctgtacaagtgcctctgcccca
ccccatgcagatgagtgccctggggggctactcctccgtgagcagctgcaatggctatggcagaatgggccttctccaccaggagaagctc
ccaagtgacttggatggcatgttcattgagcgcttagactgtgacatggaatccatcattcggaatgacctcatggatggagatacattggatttt
aacttgacaatgtgttgcccaaccaaagcttcccacacagtgtcaagacaacgacacatagctgggtgtcaggctgagggttagtgagcag
gttacacttaaaagtacttcagattgtctgacagcaggaactgagagaagcagtccaaagatgtctttcaccaactcccttttagtttctcggtta
aaaaaaaaaaaaaaaaaaaaa (SEQ ID NO: 7)

FIG. 11 (cont'd)

Exemplary LKB1 gene

ACCESSION NM_000455: Human
gcgtgtcgggcgcggaaggggggaggcggcccgggggcgcccgcgagtgaggcgcggggcggcgaagggagcgcgggtggcg
gcacttgctgccgcggccttggatgggctgggcccccctcgccgctccgcctcctccacacgcgcggcggccgcggcgagggggga
cgcgccgccgggggcccggcaccttcgggaaccccccggcccggagcctgcggcctgcgccgcctcggccgccgggagccccg
tggagccccgccgccgcgccgccccgcggaccggacgctgagggcactcgggggcggggcgcgcgctcgggcagacgtttgcg
gggaggggggcgcctgccgggcccggcgaccaccttgggggtcgcgggccggctcgggggggcgcccagtgcgggccctcgc
gggcgccgggcagcgaccagccctgagcggagctgttggccgcggcgggaggcctccggacgccccagccccccgaacgc
tcgccgggccggcgggagtcggcgcccccgggaggtccgctcggtcgtccgcggcggagcgtttgctcctgggacaggcggtg
ggaccggggcgtcgccggagacgccccagcgaagttgggctctccaggtgtggggtcccgggggggtagcgacgtcgcggacc
cggcctgtgggatgggcggcccggagaagactgcgctcggccgtgttcatactgtccgtgggcctgaggtcccggaggatgacct
agcactgaaaagccccggccggcctccccaggggtcccgaggacgaagttgaccctgaccgggccgtctcccagttctgaggccc
gggtcccactggaactcgcgtctgagccgccgtcccggaccccggtgccgccggtcgcagacctgcaccgggcttggactcg
cagccgggactgacgtgtagaacaatcgtttctgttggaagaagggttttcccttcctttgggttttgttgcctttttttttcttttttcttgtaa
aattttggagaagggaagtcggaacacaaggaaggaccgctcaccgcgcggactcagggctggcggcgggactccaggaccctg
ggtccagcatggaggtggtggacccgcagcagctgggcatgttcacggagggcgagctgatgtcggtgggtatggacacgttcatcc
accgcatcgactccaccgaggtcatctaccagccgcgccgcaagcgggccaagctcatcggcaagtacctgatgggggacctgct
gggggaaggctcttacggcaaggtgaaggaggtgctggactcggagacgctgtgcaggagggccgtcaagatcctcaagaagaa
gaagttgcgaaggatccccaacggggaggccaacgtgaagaaggaaattcaactactgaggaggttacggcacaaaaatgtcat
ccagctggtggatgtgttatacaacgaagagaagcagaaaatgtatatggtgatggagtactgcgtgtgtggcatgcaggaaatgctg
gacagcgtgccggagaagcgtttcccagtgtgccaggcccacgggtacttctgtcagctgattgacggcctggagtacctgcatagcc
agggcattgtgcacaaggacatcaagccggggaacctgctgctcaccaccggtggcaccctcaaaatctccgacctgggcgtggc
cgaggcactgcacccgttcgcggcggacgacacctgccggaccagccagggctccccggcttccagccgcccgagattgccaac
ggcctggacaccttctccggcttcaaggtggacatctggtcggctggggtcaccctctacaacatcaccacgggtctgtaccccttcga
aggggacaacatctacaagtgtttgagaacatcgggaaggggagctacgccatcccgggcgactgtggccccccgctctctgacct
gctgaaagggatgcttgagtacgaaccggccaagaggttctccatccggcagatccggcagcacagctggttccggaagaaacat
cctccggctgaagcaccagtgcccatcccaccgagcccagacaccaaggaccggtggcgcagcatgactgtggtgccgtacttgg
aggacctgcacggcgcggacgaggacgaggacctcttcgacatcgaggatgacatcatctacactcaggacttcacggtgcccgg
acaggtcccagaagaggaggccagtcacaatggacagcgccggggcctccccaaggccgtgtgtatgaacggcacagaggcg
gcgcagctgagcaccaaatccagggcggagggccgggccccaaccctgcccgcaaggcctgctccgccagcagcaagatcc
gccggctgtcggcctgcaagcagcagtgaggctggccgcctgcagccgtgtccaggagccccgccaggtgcccgcgccaggcc
ctcagtcttcctgccggttccgcccgcctccgagaggtggccgccatgcttctgtgccgaccacgcccccaggacctccggagcg
ccctgcagggccgggcaggggggacagcagggaccgggcgcagccctccccctcggccgccggcagtgcacgcggcttgttg
actcgcagccccgggcggagccttccgggcgggcgtgggaggagggaggcggcctccatgcacttttatgtggagactactggcc
ccgcccgtgcctcgtgctccgcagggcgccagcgccgtccgcggccccgcgcagaccagctggcgggtgtgggagaccag
gctcctgaccccgccatgcatgcagcgccacctggaagccgcgcggccgctttggttttgttggttggttccattttcttttttcttttttttt
aagaaaaaataaaaggtggatttgagctgtggctgtgagggggtgtttgggagctgctggggtggcagggggggctgtggggtcgggctc
acgtcgcggccgcctttgcgctctcgggtcaccctgctttggcggcccggccggagggcaggaccctcacctctcccccaaggccac
tgcgctcttgggaccccagagaaaacccggagcaagcaggagtgtgcggtcaatatttatatcatccagaaaagaaaaacacgag
aaacgccatcgcgggatggtgcagacgcggcggggactcggaggggtgccgtgcgggcgaggccgcccaaatttggcaataaata
aagcttgggaagcttggacctgaaaaaaaaaa (SEQ ID NO: 8)

FIG. 11 (cont'd)

Exemplary EOMES gene

NCBI Reference Sequence: NC_000003.12 Human
aagtttccaagtggtcaacttgaccgatgctttggcaattgaaaaagggcagaaaggcgcgggctagtgggtggatggggacaaagat
ctaagtcaccttcttccagcgtgtgagcctgggaggagggtggggtcctgaggagcaagaggtacgaggaaggaaaaggagaggg
cttctggggttagtttccacctcctgctttccaactcacggcgctttccttccggaaaggacgctggattcagggcgcgccagtacgcgcagta
gcggcccgcgagtcggcaggtgggtagccccggcgcgggaggaaggggaagttaccttcccctcggaagagggcgctggctccccc
atcctgcctttataataaggccaccggaggagaggaagcagccagctgccgtctgcgctttgcaaagcatgcagttaggggagcagctc
ttggtgagctcagtgaacctgcctggcgcgcacttctacccgctggagagtgcgcgaggcggcagcggcgggagcgctggccacctcc
ccagcgcggccccctctcctcagaagttggacttagacaaagcgtccaagaagttttccggcagtctctcctgcgaggcggtgagcggg
gagcccgcagcgccagcgcaggggccccgcggccatgcttagtgacaccgacgcggggacgcatttgccagcgctgcggcagt
ggccaagccggggcccccggacggccgcaagggctcccctgcggggaggaggagctgcctccgccgctgcagccgccgccgc
cgccgccgcgcggctgcggccactgcgcgctactccatggacagcctgagctccgagcggtactacctccagtccccggtcctcag
gggtcggagctggctgcgccctgctcactcttcccgtaccaggcggcggctggggcgccccacggacctgtacccggctcctaacgg
ggcgcgctaccccctacggctccatgctgccccccggcggcttccccgcggctgtgtgcccacccgggagggcgcagttcggcccagga
gccggtgcgggcagtggcgcgggcggtagcagcggcgggggcggcggcccgggcacctatcagtacagccaggggggctccgctct
acgggccgtaccctggagccgcagcggcgggatcttgcggaggactggggggcctgggggttccaggttctggcttccgtgcccacgtc
tacctgtgcaaccggcctctgtggctcaaattccaccgccaccaaactgagatgatcattacgaaacagggcaggtgagcgcagcgtg
gaggggcccctgggttcggggataaagggtgacgtgtggtcctggggaaggtccgggatgagggagctgaacccagttgttccgcgcg
gtgcttagagtgtttcaccgcgcgcaataaaatctccgtagacaccgcatctccaatgcggtgtccctctgtgtcagtgcccggcggctcttg
cagggtgccaatgttacggctgtacaccgctttccctcccatcatcctcacctgaacagacctggaggaggcggaaatggaaattaggg
catgtccacaagctggattcgttagatcctcctgctcggcggtatgcttgtgcatgcctgcatgccggcaaggagccacggataggaag
gctcaagagctggccacctgagcgcagtagatgggctcccgcagttttaggcgcagggtctccacgggcgtctccggagggggc
atgaaggctagagcgccggcctcggaagctcggtcggagtaggtggttagatctgccctggagccagacctggctcgggttcggtgcgc
gagaaagttctgatatacatccaactgctaacactggctacttctggggaaaggagggtgggtgctgagagaggggcactcaaagg
ggacttttagcctaaagtttaatatatattttaacaagaataacctaatattgttctctggtacttttcaaaatgtgtgcatttaaaaattagtagttt
taacattctaggagaaaaatttaagagcgtctgaaagggccgagaatatgagccttcggaagcacgcgcgaatttggaatataccgat
gttggggcaagctttttttttttttttttttttttttttttgaaaagacggaaaggttccaagagttgccaactcaaaaatatttacatagtttc
agaccacttgatctaccagcattctgttcactgcaaactttaaatgtgttccgaccctatcccaggtgtctggggaacccgctggggcctgg
gcctgtctaggacatcccaattaaaatcgattttctgattctattcccttgcacaggcgcatgttccttcttgagcttcaacataaacggactc
aatcccactgcccactacaatgtgttcgtagaggtggtgctggcggaccccaaccactggcgcttccaggggggcaaatgggtgacctgt
ggcaaagccgacaataacatgcagggtgagcagagaagaggctcgggccggggaggaacgggcgggaagaaatcgtaaccctc
gactcacacaactcacatttaaatgtagcactttttttttcccccttccattctgaggcctagaggtgttagtatgagtgtctttgagttgctgtttgac
ggagaggagagttgctaagtcagatttcttgtctgccaatatgtagatatttagaaaccttttaactaagacatcaccccaccccccaatccct
acgtttaacaaatcagtagtcataagctctccaggtgggaaggctcctgggattctaatgttcacttgagaaagcccagccaaagtttagt
tcacccataaatatccaactgtcttccatcggatgttgccctacagctttagaaggccccaaattgaccttcaagagtcatctcttgttagctc
cgtttctaaattctgaaatgccattcaggggagtccctagtgcaaggaaggttggaagcacaggggcctggagggatatggatgtagtc
ctgctggtctccactggcctcttaagcaacttttactgggagaccaactgtaagtctagctcttatatcttgctcatagctaagagacatccctc
cgctttctccatttgtaaacagccctatatgcttgggttttgtgtttgttcatttttctcttaggcaacaaaatgtatgttcacccagagtctcctaata
ctggttcccactggatgagacaggagatttcattcgggaaattaaaactcaccaataacaaaggcgcaaataacaacaacacccaggt
agagtgacagagcaggagggggatatcttctggctttgactataaggcttttttctaataagagtccctactcttttcactgtatttataatatttgca
tttgtgacctgtttgctcgcctatttctaaccattttgttctttttgacctttctcatcttcactttcttattggattcgataacagtgagttgactattaaga
acagaaatagcgaagtattttgggaatttaggaaaccaagaggaaagcatatctatcacaaccacatacccagctatgatttaaatttcaa
aaaaaaagTgggggggcaataatgagaccttaaacttgcaataaacaaagctgttagtgaggagcatttagaagtccaataccaaa
atacataatttgtcaaaatctaattttgttgaaccactaagaggcttttagatttagcaattttttctgtactcttccagatgatagtcttacaatcc
ttacacaaataccaaccccgactgcatattgttgaagttacagaggatggcgtggaggacttgaatgagccctcaaagacccagactttta
ccttctcagaaacgcaattcattgcagtgactgcctaccaaaacaccgatgagtgtcccagacatctcaagaatctctaaagctaaggt
ccagcatgataaatcactcaatgactgttttctcccctatctagattactcaactaaagattgatcataacccctttgcaaaaggcttcagag
acaactatgattc

FIG. 11 (cont'd)

gtaagtgcagctttatccacacttgcctgatcatctctgagcaggacatacatcaacaggcactttgctgataatgtatttaggaagagctt
ttacctttgggatttttacatatttttcttttccaaaattttttcctttactaatcttgctttagattttctcagaaaggttgtgttaatttctgaagaaatgtt
aaggacttaaaaatgaagaggtttttagcatttgagtgaagatttgaaattttaagaatctgcatttatatataccttctttcatttgatccatttt
tttatcctcccaagagcagatatatattactctcccccaccccacttttttttttaacataagaaaaaactgaaactaagaggatgtaatttcac
aacacgaaatagcaaggccctgctcttttaaaatctgagttttctaccgccacagccagtgtttttccatcacattgacaaaggaggtttga
tctgagttttcgtgttctaggactagtaaaggtagattttctatagtttaaatacttgatgcctaggaggaaacttttcttgcatggtgggaaattt
ttcccaataagccaagagtccagctaaaatgggccagtgcatctcctgcctctgttcttcagcccaacagaccagcactttcggtgtagat
aaccaacacaagccttttcatttctgggaggtggtttgtttgggacaacattaggttttttttttttttaagtgtttctctttatattgtagcatgtac
accgctcagaaaatgacaggttaactccatctcccacggattctcctagatcccatcagattgtccctggaggtcggtacggcgttcaatc
cttcttcccggagcccttgtcaacactttacctcaagcccgctattataatggcgagagaaccgtgccacagaccaacggcctcctttcac
cccaacagagcgaagaggtggccaaccctccccagcggtggcttgtcacgcctgtccagcaacctgggaccaacaaactagacatc
agttcctatgaatctgaatatacttctagcacattgctcccatatggcattaaatccttgcccttcagacatcccatgccctgggtattaccc
agacccaacctttcctgcaatggcagggtggggaggtcgaggttcttaccagaggaagatggcagctggactaccatggacctccaga
acaagcccactgtgttctctgaagatcagctctccaaggagaaagtgaaagaggaaattggctcttcttggatagagacaccccctcc
atcaaatctctagattccaatgattcaggagtatacaccagtgcttgtaagcgaaggcggctgtctcctagcaactccagtaatgaaaatt
caccctccataaagtgtgaggacattaatgctgaagagtatagtaaagacacctcaaaaggcatgggagggtattatgcttttacacaa
ctccctaaagagttatttaacctcaaaaattagctaacttttgcagatggacttggtggtgttttttgttgtcttcttgcctaggttgccaaaaag
atgtttgccttccaccttgatgcatcctgttttgtgcaattctctaaaagaaggtgccaaagctttttgattgctgcaggtaactgaaacaaacct
agcatttttaaaaaataagattaatggaagactttaaggtatttaaaattcgaagggtatccaaggttctgtatttattattggggagacact
aacccttcaaagaagcaggctgtgaacattgggtgcccagtgctatcagatgagttaaaacctttgattctcatttctatttgtaaattcttaag
caaatagaagccgagtgttaaggtgtttgcttctgaaagagggctgtgccttccgtttcagaaggagacatttgctgttacattctgccagg
ggcaaaagatactaggcccaggagtcaagaaaagctttgtgaaagtgatagtttcacctgactttgattccttaaccccggctttggaa
caagccatgtttgccctagtccaggattgcctcacttgagacttgctaggcctctgctgtgtgctggggtggccagtgggactcaggagag
agcaagctaaggagtcaccaaaaaaaaaaaaaaaaaagggagaatttaaaagtgtacagttgtgtgtttagatacactatagaat
aatgtggtatatattgtacaaatagtctacataggtgtctgggataatgtaaaactggtgctttggctttgtaaagaatttgcaaatcacttaac
agctgcaggggcaaggggagagtttcatcatcccatgatatttgggaatattctgtttacttcttagatagttaagaatgtattcagctactat
gtactaacttgaaccgtgtttaaggaaaactcctattcatcctcttcttgcgccatcccctccctaacttggtaatgtgaagaaactaaaac
ctgataccacagctcctataggcattttagagatcttggattttatgtacagtcttagtcattttaataaaatgtggttcagtaagggaacgga
(SEQ ID NO: 9)

FIG. 11 (cont'd)

Exemplary ID2 gene

NCBI Reference Sequence: NC_000002.12 Human
ggggacgaagggaagctccagcgtgtggccccggcgagtgcggataaaagccgccccgccgggctcgggcttcattctgagccgag
cccggtgccaagcgcagctagctcagcaggcggcagcggcggcctgagcttcagggcagccagctccctcccggtctcgccttccctc
gcggtcagcatgaaagccttcagtcccgtgaggtccgttaggaaaaacagcctgtcggaccacagcctgggcatctcccggagcaaaa
cccctgtggacgaccgatgagcctgctatacaacatgaacgactgctactccaagctcaaggagctggtgcccagcatcccccagaa
caagaaggtgagcaagatggaaatcctgcagcacgtcatcgactacatcttggacctgcagatcgccctggactcgcatcccactattgt
cagcctgcatcaccagagacccgggcagaaccaggcgtccaggacgccgctgaccaccctcaacacggatatcagcatccgtgtcctt
gcaggtaagacctgctccggggtccccgccccgccgccgcacactcccgcggtcgtctgggctgtcactaggagatccgtagcccaga
cggtgactttcgtatgagctatttaactttattttcttcagaatctgctgtagattgagctgtgcgtgaaattgctagtaagttctgacatgttaatgc
gtctgtctttaaatctgaattgttaccataaacgtgtttaatggaacttgctggtctgtggactacaaaaaaaaaaaaaaaaaaaaaaaaaac
cctttctacttaacattgtcttaacctcgtactctttatcctctttctttccaggctctgaattcccttctgagttaatgtcaaatgacagcaaagcac
tgtgtggctgaataagcggtgagtgtttgcttgtgccaccgtgggtaaactgccctcggtgtgtgtgcgcgcgcgcgcatgtgtttttgcttgt
gtatctataaaatgtctgatttggtaaatgcatgcttacttcgcggtgttacccgtactacattgtctcactagacatgaaggagcttgtagctttg
ggtgctcgagatcacagaacatttccttttaaaaggaaatgatgccaataacttactacgaaggcggccgaggaacgtgtgtattggctttg
tagcaaatgtaatgccctggatcttcctacgagtcctctggtactatgaggtactaacctccactgtaattaatcttaccgccacaaattccata
gtgatcctccttccctaaaactatagtcctctgggattctctgggctagttgaggattgctaccctgtgccttcaaccctgtgatgtgggatccca
gacttccctatctgttaactaaagggctgttttcaatcaaataattgttacgagaagcagactggcgcctgtagcactgctgttggagatccaa
ataggagattgggttgggaagtttttcccttgagtctctgctatttaatgtttaatttgcgctgtcgaggcgagtgtgtgttgcatctggacgcc
agggtttgcccaatctttgagtgtttggttaaatgttcaaactgtggcttcctcccggcgccagtcgccgcctctgccctaggttacattctctt
aaacatgcctttctccccactctttcgcaggtgttcatgatttctttattcttttgcacaacaacaacaacaacaaattcacggaatcttttaagt
gctgaacttattttcaaccatttcacaaggaggacaagttgaatggaccttttaaaaagaaaaaaaaaaatggaaggaaaactaagaat
gatcatcttcccagggtgttctcttacttggactgtgatattcgttatttatgaaaaagacttttaaatgcccttctgcagttggaaggttttctttata
tactattcccaccatggggagcgaaaacgttaaaatcacaaggaattgcccaatctaagcagactttgccttttttcaaaggtggagcgtga
ataccagaaggatccagtattcagtcacttaaatgaagtcttttggtcagaaattaccttttgacacaagcctactgaatgctgtgtatatattt
atatataaatatatctatttgagtgaaaccttgtgaactctttaattagagttttcttgtatagtggcagagatgtctatttctgcattcaaaagtgta
atgatgtacttattcatgctaaactttttataaaagtttagttgtaaacttaacccttttatacaaaataaatcaagtgtgtttattgaatggtgattgc
ctgctttatttcagaggaccagtgctttgattttattatgctatgttataactgaacccaaataaatacaagttcaaatttatgtagactgtataag
attataataaaacatgtctgaagtcaa (SEQ ID NO: 10)

FIG. 11 (cont'd)

Exemplary TERT gene

ACCESSION NM_198253: Human
caggcagcgctgcgtcctgctgcgcacgtgggaagccctggccccggccaccccgcgatgccgcgcgctcccgctgccgagccgt
gcgctccctgctgcgcagccactaccgcgaggtgctgccgctggccacgttcgtgcggcgcctggggcccagggctggcggctggtgc
agcgcggggaccggcggctttccgcgcgctggtggcccagtgcctggtgtgcgtgccctgggacgcacggccgccccccgccgcccc
ctccttccgccaggtgtcctgcctgaaggagctggtggcccgagtgctgcagaggctgtgcgagcgcggcgcgaagaacgtgctggcctt
cggcttcgcgctgctggacgggcccgcggggccccccgaggccttcaccaccagcgtgcgcagctacctgcccaacacggtgac
cgacgcactgcggggagcggggcgtggggctgctgctgcgccgcgtgggcgacgacgtgctggttcacctgctggcacgctgcgcg
ctctttgtgctggtgctccagctgcgcctaccaggtgtgcgggcgccgctgtaccagctcggcgctgccactcaggccggcccccgc
cacacgctagtggaccccgaaggcgtctgggatgcgaacgggcctggaaccatagcgtcagggaggccggggtcccctgggcctgc
cagccccgggtgcgaggaggcgcggggcagtgccagccgaagtctgccgttgcccaagagggcccaggcgtggcgctgccctgag
ccggagcggacgcccgttgggcaggggtcctgggccacccgggcaggacgcgtggaccgagtgaccgtggtttctgtgtggtgtcacc
tgccagacccgccgaagaagccacctctttggagggtgcgctctctggcacgcgccactccaccccatccgtgggccgccagcaccac
gcgggcccccatccacatcgcggccaccacgtccctgggacacgccttgtccccggtgtacgccgagaccaagcacttcctctactcc
tcaggcgacaaggagcagctgcggccctccttcctactcagctctctgaggcccagcctgactggcgctcggaggctcgtggagaccatc
tttctgggttccaggccctggatgccaggactccccgcaggttgccccgcctgcccagcgctactggcaaatgcggcccctgttctgga
gctgcttgggaaccacgcgcagtgcccctacggggtgctcctcaagacgcactgcccgctgcgagctgcggtcacccagcagccggt
gtctgtgccgggagaagccccaggggtctgtggcggccccgaggaggaggacacagaccccgtcgcctggtgcagctgctccgc
cagcacagcagccctggcaggtgtacggcttcgtgcgggcctgcctgcgccggctggtgccccaggcctctggggctccaggcaca
acgaacgccgcttcctcaggaacaccaagaagttcatctccctggggaagcatgccaagctctcgctgcaggagctgacgtggaagatg
agcgtgcgggactgcgcttggctgcgcaggagcccaggggttggctgtgttccggccgcagagcaccgtctgcgtgaggagatcctggc
caagttcctgcactggctgatgagtgtgtacgtcgtcgagctgctcaggtctttctttatgtcacggagaccacgtttcaaaagaacaggctct
ttttctaccggaagagtgtctggagcaagttgcaaagcattggaatcagacagcacttgaagagggtgcagctgcgggagctgtcggaag
cagaggtcaggcagcatcgggaagccaggcccgccctgctgacgtccagactccgcttcatccccaagcctgacgggctgcggccgat
tgtgaacatggactacgtcgtgggagccagaacgttcgcagagaaaagagggccgagcgtctcacctcgagggtgaaggcactgttc
agcgtgctcaactacgagcgggcgcggcgcccccggcctcctgggcgcctctgtgctgggcctggacgatatccacagggcctggcgca
ccttcgtgctgcgtgtgcgggcccaggacccgccgcctgagctgtactttgtcaaggtggatgtgacgggcgcgtacgacaccatccccca
ggacaggctcacggaggtcatcgccagcatcatcaaaccccagaacacgtactgcgtgcgtcggtatgccgtggtccagaaggccgcc
catgggcacgtccgcaaggccttcaagagccacgtctctaccttgacagacctccagccgtacatgcgacagttcgtggctcacctgcag
gagaccagcccgctgagggatgccgtcgtcatcgagcagagctcctccctgaatgaggccagcagtggcctcttcgacgtcttcctacgct
tcatgtgccaccacgccgtgcgcatcaggggcaagtcctacgtccagtgccagggggatcccgcagggctccatcctctccacgctgctct
gcagcctgtgctacggcgacatggagaacaagctgtttgcggggattcggcgggacgggctgctcctgcgtttggtggatgatttcttgttgg
tgacacctcacctcacccacgcgaaaaccttcctcaggaccctggtccgaggtgtccctgagtatggctgcgtggtgaacttgcggaaga
cagtggtgaacttccctgtagaagacgaggccctgggtggcacggcttttgttcagatgccggcccacgccctattccctggtgcggcctg
ctgctggatacccggaccctggaggtgcagagcgactactccagctatgcccggacctccatcagagccagtctcaccttcaaccgcgg
cttcaaggctgggaggaacatgcgtcgcaaactctttgggggtcttgcggctgaagtgtcacagcctgtttctggatttgcaggtgaacagcct
ccagacggtgtgcaccaacatctacaagatcctcctgctgcaggcgtacaggtttcacgcatgtgtgctgcagctccccatttcatcagcaag
tttggaagaaccccacattttcctgcgcgtcatctctgacacggcctcctctgctactccatcctgaaagccaagaacgcagggatgtcgc
tgggggccaagggcgccgccggccctctgccctccgaggccgtgcagtggctgtgccaccaagcattcctgctcaagctgactcgacac
cgtgtcacctacgtgccactcctggggtcactcaggacagcccagacgcagctgagtcggaagctccggggacgacgctgactgccct
ggaggccgcagccaacccggcactgccctcagacttcaagaccatcctggactgatggccacccgcccacagccaggccgagagca
gacaccagcagccctgtcacgccgggctctacgtccaggagggagggcggcccacaccaggcccgcaccgctgggagtctga
ggcctgagtgagtgtttggccgaggcctgcatgtccggctgaaggctgagtgtccggctgaggcctgagcgagtgtccagccaagggctg
agtgtccagcacacctgccgtcttcacttccccacaggctggcgctcggctccaccccagggccagcttttcctcaccaggagcccggctt
ccactccccacataggaatagtccatcccccagattcgccattgttcaccctcgccctgccctctttgccttccaccccaccatccaggtg
gagaccctgagaaggaccctgggagctctgggaatttggagtgaccaaaggtgtgccctgtacacaggcgaggaccctgcacctggat
gggggtccctgtgggtcaaattgggggaggtgctgtgggagtaaaatactgaatatatgagttttcagttttgaaaaaaa (SEQ ID
NO: 11)

FIG. 11 (cont'd)

Exemplary CCR2b gene

ACCESSION NM_001123396: Human
gttattctctggaacatgaaacattctgttgtgctcatatcatgcaaattatcactagtaggagagcagagagtggaaatgttccaggtataa
agacccacaagataaagaagctcagagtcgttagaaacaggagcagatgtacagggtttgcctgactcacactcaaggttgcataag
caagatttcaaaatiaatcctattctggagacctcaacccaatgtacaatgttcctgactggaaaagaagaactatattttctgattttttttc
aaatctttaccattagttgcccigtatctccgccttcactttctgcaggaaacttiatttcctacttctgcatgccaagtttctacctctagatctgttt
ggtcagttgctgagaagcctgacataccaggactgcctgagacaagccacaagctgaacagagaaagtggattgaacaaggacgc
atttccccagtacatccacaacatgctgtccacatctcgttctcggtttatcagaaataccaacgagagcggtgaagaagtcaccacctttt
tgattatgattacggtgctccctgtcataaaatttgacgtgaagcaaattgggcccaactcctgcctccgctctactcgctggtgtcatctttg
gtttgtgggcaacatgctggtcgtcctcatcttaataaaactgcaaaaagctgaagtgcttgactgacatttacctgctcaacctggccatctc
tgatctgcttttcttattactctcccattgtgggctcactctgctgcaaatgagtgggtctttgggaatgcaatgtgcaaattattcacagggctgt
atcacatcggttatttggcggaatcttcttcatcatcctcctgacaatcgatagatacctggctattgtccatgctgtgtttgctttaaaagccag
gacggtcacctttggggtggtgacaagtgtgatcacctggttggtggctgtgttgcttctgtcccaggaatcatctttactaaatgccagaaa
gaagattctgtttatgtctgtggcccttattttccacgaggatggaataatttccacacaataatgaggaacattttggggctggtcctgccgct
gctcatcatggtcatctgctactcgggaatcctgaaaaccctgcttcggtgtcgaaacgagaagaagaggcatagggcagtgagagtc
atcttcaccatcatgattgtttactttctcttctggactccctataatattgtcattctcctgaacaccttccaggaattcttcggcctgagtaactgt
gaaagcaccagtcaactggaccaagccacgcaggtgacagagactcttgggatgactcactgctgcatcaatcccatcatctatgcctt
cgttggggagaagttcagaaggtatctctcggtgttcttccgaaagcacatcaccaagcgcttctgcaaacaatgtccagttttctacaggg
agacagtggatggagtgacttcaacaaacacgccttccactggggagcaggaagtctcggctggtttataaaacgaggagcagtttgat
tgttgtttataaagggagataacaatctgtatataacaacaaacttcaagggtttgttgaacaatagaaacctgtaaagcaggtgcccagg
aacctcagggctgtgtgtactaatacagactatgtcacccaatgcatatccaacatgtgctcagggaataatccagaaaaactgtgggta
gagactttgactctccagaaagctcatctcagctcctgaaaaatgcctcattaccttgtgctaatcctcttttctagtcttcataatttcttcactc
aatctctgattctgtcaatgtcttgaaatcaagggccagctggaggtgaagaagagaatgtgacaggcacagatgaatggagtgagg
gatagtggggtcagggctgagaggagaaggagggagacatgagcatggctgagcctggacaaagacaaaggtgagcaaagggc
tcacgcattcagccaggagatgatactggtccttagccccatctgccacgtgtatttaaccttgaagggttcaccaggtcagggagagtttg
ggaactgcaataacctgggagttttggtggagtccatgattctcttttgcataagtgcatgacatatttttgctttattacagtttatctatggcac
ccatgcacctiacatttgaaatctatgaaatatcatgctccattgttcagatgcttcttaggccacatcccctgtctaaaaaatlcagaaaatttt
tgtttataaaaga (SEQ ID NO: 12)

FIG. 11 (cont'd)

Exemplary CCR4 gene

ACCESSION NM_005508: Human
tctcacaggaagccacgcacccttgaaaggcaccgggtccttcttagcatcgtgcttcctgagcaagcctggcattgcctcacagaccttcctc
agagccgctttcagaaaagcaagctgcttctggttgggcccagacctgccttgaggagcctgtagagttaaaaaatgaacccacggatata
gcagacaccaccctcgatgaaagcatatacagcaattactatctgtatgaaagtatccccaagccttgcaccaaagaaggcatcaaggcatt
tggggagctcttcctgcccccactgtattccttggttttgtatttggtctgcttggaaattctgtggtggttctggtcctgttcaaatacaagcggctcag
gtccatgactgatgtgtacctgctcaaccttgccatctcggatctgctcttcgtgttttccctcccttttgggggctactatgcagcagaccagtgggttt
tgggctaggtctgtgcaagatgatttcctggatgtacttggtgggcttttacagtggcatattcttgtcatgctcatgagcattgatagatacctggca
attgtgcacgcggtgttttccttgagggcaaggaccttgacttatggggtcatcaccagtttggctacatggtcagtggctgttcgcctccttcct
ggctttctgttcagcacttgttatactgagcgcaaccatacctactgcaaaaccaagtactctctcaactccacgacgtggaaggttctcagctcc
ctggaaatcaacattctcggattggtgatcccctagggatcatgctgtttgctactccatgatcatcaggaccttgcagcattgtaaaaatgaga
agaagaacaaggcggtgaagatgatctttgccgtggtggtcctcttccttgggtctggacaccttacaacatagtgctcttcctagagaccctgg
tggagctagaagtccttcaggactgcacccttgaaagatacttggactatgccatccaggccacagaaactctggcttttgttcactgctgccttaa
tcccatcatctacttttctgggggagaaatttcgcaagtacatcctacagctcttcaaaacctgcaggggcctttgtgtctgccaatactgtgg
gctcctccaaatttactctgctgacaccccagctcatcttacacgcagtccaccatggatcatgatctccatgatgctctgtagaaaaatgaaat
ggtgaaatgcagagtcaatgaactttccacattcagagcttacttaaaattgtattttagtaagagattcctgagccagtgtcaggaggaaggctt
acacccacagtggaaagacagcttctcatcctgcaggcagcttttctctcccactagacaagtccagcctggcaagggttcacctgggctga
ggcatccttcctcacaccaggcttgcctgcaggcatgagtcagtctgatgagaactctgagcagtgcttgaatgaagttgtaggtaatattgcaa
ggcaaagactattcccttctaacctgaactgatgggtttctccagagggaattgcagagtactggctgatggagtaaatcgctaccttttgctgtgg
caaatgggccctct (SEQ ID NO: 13)

FIG. 11 (cont'd)

anti-CD19 scFv (VH-VL) FMC63

Cacatccagatgacccagaccacctccagcctgagcgccagcctgggcgaccgggtgaccatcagctgccgggccagccaggacat
cagcaagtacctgaactggtatcagcagaagcccgacggcaccgtcaagctgctgatctaccacaccagccggctgcacagcggcgt
gcccagccggtttagcggcagcggctccggcaccgactacagcctgaccatctccaacctggaacaggaagatatcgccacctactttt
gccagcagggcaacacactgccctacacctttggcggcggaacaaagctggaaatcaccggcagcacctccggcagcggcaagcct
ggcagcggcgagggcagcaccaagggcgaggtgaagctgcaggaaagcggccctggcctggtggcccccagccagagcctgagc
gtgacctgcaccgtgagcggcgtgagcctgcccgactacggcgtgagctggatccggcagccccccaggaagggcctggaatggctg
ggcgtgatctgggcagcgagaccacctactacaacagcgccctgaagagccggctgaccatcatcaaggacaacagcaagagcc
aggtgttcctgaagatgaacagcctgcagaccgacgacaccgccatctactactgcgccaagcactactactacggcggcagctacgc
catggactactggggccagggcaccagcgtgaccgtgagcag (SEQ ID NO: 28)

anti-CD19 scFv (VH-VL) FMC63

DIQMTQTTSSLSASLGDRVTISCRASQDISKYLNWYQQKPDGTVKLLIYHTSRLHSGVPSRFSGS
GSGTDYSLTISNLEQEDIATYFCQQGNTLPYTFGGGTKLEITGSTSGSGKPGSGEGSTKGEVKLQ
ESGPGLVAPSQSLSVTCTVSGVSLPDYGVSWIRQPPRKGLEWLGVIWGSETTYYNSALKSRLTIIK
DNSKSQVFLKMNSLQTDDTAIYYCAKHYYYGGSYAMDYWGQGTSVTVSS (SEQ ID NO: 29)

CD28 effector domain cggagcaagcggagcagaggcggccacagcgactacatgaacatgacccccagacggcctggccccacccggaagcactacc
agccctacgccccacccagggactttgccgcctacagaagc (SEQ ID NO: 36)

FIG. 11 (cont'd)

P28z CAR

Gtggcctcaccgttgacccgctttctgtcgctgaacctgctgctgctgggtgagtcgattatcctggggagtggagaagctgaggtgcag
ctgcagcagtcaggacctgaactggtgaagcctgggacttcagtgaggatatcctgcaagacttctggatacacattcactgaatatacc
atacactgggtgaagcagagccatggaaagagccttgagtggattggaaacatcaatcctaacaatggtggtaccacctacaatcag
aagttcgaggacaaggccacattgactgtagacaagtcctccagtacagcctacatggagctccgcagcctaacatctgaggattctg
cagtctattattgtgcagctggttggaactttgactactggggccaagggaccacggtcaccgtctcctcaggtggaggtggatcaggtg
gaggtggatctggtggaggtggatctgacattgtgatgacccagtctcacaaattcatgtccacatcagtaggagacagggtcagcatc
atctgtaaggccagtcaagatgtgggtactgctgtagactggtatcaacagaaaccaggacaatctcctaaactactgatttattgggcat
ccactcggcacactggagtccctgatcgcttcacaggcagtggatctgggacagacttcactctcaccattactaatgttcagtctgaaga
cttggcagattatttctgtcagcaatataacagctatcccctcacgttcggtgctgggaccatgctggacctgaaacgggcggccgcatct
actactaccaagccagtgctgcgaactccctcacctgtgcacctaccgggacatctcagccccagagaccagaagattgtcggccc
cgtggctcagtgaaggggaccggattggacttcgcctgtgatatttacatctgggcaccctggccggaatctgcgtggcccttctgctgtc
cttgatcatcactctcatctgctacaatagtagaaggaacagactccttcaaagtgactacatgaacatgactccccggaggcctgggct
cactcgaaagccttaccagccctacgccctgccagagactttgcagcgtaccgccccagagcaaaattcagcaggagtgcagaga
ctgctgccaacctgcaggaccccaaccagctctacaatgagctcaatctagggcgaagagaggaatatgacgtcttggagaagaag
cgggctcgggatccagagatgggaggcaaacagcagaggaggaggaaccccaggaaggcgtatacaatgcactgcagaaag
acaagatggcagaagcctacagtgagatcggcacaaaaggcgagaggcggagaggcaaggggcacgatggcctttaccagggt
ctcagcactgccaccaaggacacctatgatgccctgcatatgcagaccctggcccctcgctaa (SEQ ID NO: 37)

FIG. 11 (cont'd)

IgG4-Fc
ASTKGPSVFPLAPCSRSTSESTAALGCLVKDYFPEPVTVSWNSGALTSGVHTFPAVLQSSGLYSL
SSVVTVPSSSLGTKTYTCNVDHKPSNTKVDKRVESKYGPPCPSCPAPEFLGGPSVFLFPPKPKD
TLMISRTPEVTCVVVDVSQEDPEVQFNWYVDGVEVHNAKTKPREEQFNSTYRVVSVLTVLHQD
WLNGKEYKCKVSNKGLPSSIEKTISKAKGQPREPQVYTLPPSQEEMTKNQVSLTCLVKGFYPSDI
AVEWESNGQPENNYKTTPPVLDSDGSFFLYSRLTVDKSRWQEG
NVFSCSVMHEALHNHYTQKSLSLSLGK (SEQ ID NO: 39)

Hinge-CH2-CH3
ESKYGPPCPPCPAPEFLGGPSVFLFPPKPKDTLMISRTPEVTCVVVDVSQEDPEVQFNWYVD
GVEVHNAKTKPREEQFNSTYRVVSVLTVLHQDWLNGKEYKCKVSNKGLPSSIEKTISKAKGQP
REPQVYTLPPSQEEMTKNQVSLTCLVKGFYPSDIAVEWESNGQPENNYKTTPPVLDSDGSFFL
YSRLTVDKSRWQEGNVFSCSVMHEALHNHYTQKSLSLSLGK (SEQ ID NO: 40)

Hinge-CH3
ESKYGPPCPPCPGQPREPQVYTLPPSQEEMTKNQVSLTCLVKGFYPSDIAVEWESNGQPE
NNYKTTPPVLDSDGSFFLYSRLTVDKSRWQEGNVFSCSVMHEALHNHYTQKSLSLSLGK
(SEQ ID NO: 41)

Hinge only
ESKYGPPCPPCP (SEQ ID NO: 42)

CD28 Transmembrane domain
MFWVLVVVGGVLACYSLLVTVAFIIFWV (SEQ ID NO: 43)

CD28 Cytoplasmic domain (LL to GG)
 RSKRSRGGHSDYMNMTPRRPGPTRKHYQPYAPPRDFAAYRS (SEQ ID NO: 44)

4-1BB Cytoplasmic domain
KRGRKKLLYIFKQPFMRPVQTTQEEDGCSCRFPEEEEGGCEL (SEQ ID NO: 45)

CD3-ζ Cytoplasmic domain
RVKFSRSADAPAYQQGQNQLYNELNLGRREEYDVLDKRRGRDPEMGGKPRRKNPQEGLYNE
LQKDKMAEAYSEIGMKGERRRGKGHDGLYQGLSTATKDTYDALHMQALPPR (SEQ ID NO: 46)

FIG. 11 (cont'd)

T2A
LEGGGEGRGSLLTCGDVEENPGPR (SEQ ID NO: 47)

tEGFR
MLLLVTSLLLCELPHPAFLLIPRKVCNGIGIGEFKDSLSINATNIKHFKNCTSISGDLHILPVAFRGD
SFTHTPPLDPQELDILKTVKEITGFLLIQAWPENRTDLHAFENLEIIRGRTQHGQFSLAVVSLNITS
LGLRSLKEISDGDVIISGNKNLCYANTINWKKLFGTSGQKTKIISNRGENSCKATGQVCHALCSP
EGCWGPEPRDCVSCRNVSRGRECVDKCNLLEGEPREFVENSECIQCHPECLPQAMNITCTGR
GPDNCIQCAHYIDGPHCVKTCPAGVMGENNTLVWKYADAGHVCHLCHPNCTYGCTGPGLEGC
PTNGPKIPSIATGMVGALLLLLVVALGIGLFM (SEQ ID NO: 48)

Strep tag II
WSHPQFEK (SEQ ID NO: 49)

Myc tag
EQKLISEEDL (SEQ ID NO: 50)

V5 tag
GKPIPNPLLGLDST (SEQ ID NO: 51)

FLAG tag
DYKDDDDK (SEQ ID NO: 52)

COMPOSITIONS AND METHODS TO PROGRAM THERAPEUTIC CELLS USING TARGETED NUCLEIC ACID NANOCARRIERS

CROSS REFERENCES TO RELATED APPLICATIONS

This application is a continuation of International Patent Application No. PCT/US2017/027767, filed Apr. 14, 2017, which claims priority to U.S. Provisional Patent Application No. 62/442,890 filed Jan. 5, 2017 and U.S. Provisional Patent Application No. 62/322,581 filed Apr. 14, 2016, the entire contents of each of which are incorporated by reference herein.

FIELD OF THE DISCLOSURE

The present disclosure provides compositions and methods that rapidly and selectively modify hematopoietic stem cells (or cells derived therefrom) to achieve therapeutic objectives by providing for transient expression of nucleic acids. The transient expression leads to permanent therapeutic changes in the modified cells, referred to herein as "hit and run" effects. The methods can be practiced in cultured cells or in situ.

REFERENCE TO SEQUENCE LISTING

A computer readable text file, entitled "DN1039358.txt (Sequence Listing.txt)" created on or about Apr. 27, 2017, with a file size of 100 KB, contains the sequence listing for this application and is hereby incorporated by reference in its entirety.

BACKGROUND OF THE DISCLOSURE

Successful genetic therapies depend on successful gene delivery mechanisms into selected cells of interest. Currently, viral systems, such as those utilizing lentiviral vectors, are the most common way to achieve long-lasting genetic therapies. These genetic therapies rely on the ongoing cellular expression of proteins with therapeutic value. While such viral systems can effectively deliver genes for genetic therapies, they are non-selective, expensive and not widely available. Moreover, continued therapeutic protein expression can decrease over time due to cellular events that occur over time.

Electroporation has also been developed as a mechanism to deliver genes into cells for genetic therapies. Electroporation, however, relies on the mechanical disruption and permeabilization of cellular membranes, thus compromising the viability of cells, rendering them less than ideal for therapeutic use. Further, like virus-based methods, electroporation does not selectively deliver genes to specific cell types out of a heterogeneous pool, so it must be preceded by a cell selection and purification process.

SUMMARY OF THE DISCLOSURE

The current disclosure provides compositions and methods that rapidly and selectively modify hematopoietic stem cells (or cells derived therefrom) to achieve therapeutic objectives by providing for transient expression of nucleic acids. The transient expression leads to permanent therapeutic changes in the modified cells, referred to herein as "hit and run" effects. Because only transient expression is required to achieve a lasting therapeutic effect, concerns regarding decreased therapeutic protein expression over time are overcome. Moreover, because the compositions and methods selectively modify selected cell types, no cell selection or purification processes are required before the modification. This expedites the manufacturing of therapeutic cells ex vivo and also allows the targeted genetic modification of cells in vivo.

The hit and run effects described herein are allowed by utilizing transient expression of nucleic acids that result in gene editing or transient expression of proteins that permanently alter the phenotype of the cell. Examples of nucleic acids that result in gene editing include TALENs, megaTALS, zinc finger nucleases and CRISPR-Cas systems. Examples of phenotype changing proteins include transcription factors, kinases, and cell surface receptors.

There are numerous applications for the compositions and methods disclosed herein. Examples in cultured cells include editing the genome of hematopoietic cells (including hematopoietic stem cells) with targeted nucleases; imprinting a therapeutically desirable phenotype in adoptively transferred cells by transiently expressing a defined transcription factor, reducing cellular senescence in adoptively transferred cells by expressing telomerase reverse transcriptase or anti-apoptotic genes, or altering their intrinsic cell tropism via expression of chemokine receptors. In situ examples include augmenting the potency of vaccines by co-injecting nucleic acid-loaded carriers that selectively transfect dendritic cells to boost their ability to present antigens; or transfecting vaccine-primed T cells to induce a long-lived memory phenotype.

BRIEF DESCRIPTION OF THE FIGURES

Many of the drawings submitted herein are better understood in color, which is not available in patent application publications at the time of filing. Applicants consider the color versions of the drawings as part of the original submission and reserve the right to present color images of the drawings in later proceedings.

FIGS. 1A-1C. Creating mRNA nanocarriers to genetically program therapeutic T cells. (FIG. 1A) Schematic explaining how cultured T cells can be programmed to express therapeutically relevant transgenes carried by polymeric nanoparticles. These particles are coated with ligands that target them to specific cell types, enabling them to introduce their mRNA cargoes and cause the targeted cells to express selected proteins (like transcription factors or genome-editing agents). (FIG. 1B) Design of targeted mRNA-carrying nanoparticles. The inset shows a transmission electron micrograph of a representative nanoparticle; scale bar, 50 nm. Also depicted is the synthetic mRNA encapsulated in the nanoparticle. FIG. 1C. Examples of gene editing agents, phenotype-altering proteins, targeted genes, and uses thereof that can be used in embodiments disclosed herein.

FIG. 2. Flow cytometry antibodies.

(FIG. 3A) Finite track length adjustment size distribution of individual particles. (FIG. 3B) Transmission electron microscopy of a single nanoparticle (left, scale bar=100 nm) and a population of nanoparticles (right, scale bar=2 μm). (FIG. 3C) Zeta potential of control nanoparticles (−PGA-Ab) compared with those coated with PGA coupled with antibodies (+PGA-Ab), measured after diluting them 1:40 in PBS pH 7.4 (n=5).

(FIG. 4A) Primary T cells were mixed with CD3-targeted polymeric nanoparticles carrying Cy5-labeled mRNA. Confocal microscopy establishes that these particles are rapidly internalized from the cell surface. The images are representative of 15 randomly chosen fields. (FIG. 4B) Flow cytometry of T cells 24 h after incubation with CD3-targeted nanoparticles bearing eGFP-encoding mRNA. (FIG. 4C, FIG. 4D) Comparison of the effects electroporation and nanoparticle gene delivery have on cell expansion. Left panels show the workflow for transfection with nanoparticles (top) and electroporation (bottom). Right panels show the -fold expansion of PBMC cultures from three independent donors treated with stimulatory beads on days 0 and 12. Matched cultures from each donor were not treated, or transfected with CD3/CD28-targeted nanoparticles (FIG. 4C, right) or via electroporation (FIG. 4D, right) on days 5 and 12. Every line represents one donor and each dot reflects the -fold T cell expansion. Pairwise differences between groups were analyzed with the Student's t Test; ns, non-significant; *, significant, n=3).

(FIG. 5A) eGFP expression in $10^6$ activated T cells that were either untreated, or measured 5 h after addition of eGFP-encoding NPs targeted with anti-CD3. (FIG. 5B) Transfection efficiency of NPs is maintained after lyophilization and resuspension. $10^6$ activated T cells per condition were transfected with NPs (targeted via anti-CD3 or anti-CD8 antibodies) which were either prepared freshly, or lyophilized, stored at $-80°$ C., and then suspended to their original volume.

(FIG. 7A) Integration of nanoparticle transfection into normal manufacturing of CAR-T cells. After stimulation with anti-CD3/CD28- coated beads (day 0), CD8- targeted mRNA NPs were introduced on days 1 and 2, then lentiviral transduction with a vector encoding the leukemia-specific 19-41BBζ CAR was performed on day 3. Either NPs carrying mRNAs encoding megaTAL nuclease plus eGFP, or control particles loaded with eGFP mRNA alone were added. (FIG. 7B) Flow cytometry of NP transfection efficiencies (based on eGFP signals) correlated with surface expression levels of TCRs (based on CD3 signals) by T cells following NP treatments. (FIG. 7C) Summary plot showing editing efficiency as measured by loss of CD3 surface expression at day 14 (n=5). (FIG. 7D) Surveyor assay confirming TCRα chain gene locus disruption. (FIG. 7E) Flow cytometry of lentiviral transduction in genome-edited versus control T cells. (FIG. 7F) Proliferation of TCR+(controls) and TCR- (mTAL NP-treated) CAR-T cells co-cultured on irradiated TM-LCL leukemia cells. (FIG. 7G) Cytotoxicity assays for lysis of CD19-K562 target cells by CAR-T cells. (FIG. 7H) intracellular cytokine expression of IL-2 and IFN-γ following stimulation with PMA and ionomycin (P/I).

(FIG. 8A) Expression of total Foxo1 protein measured by intracellular labeling in Jurkat and primary T cells treated with CD3-targeted control (GFP+) or Foxo13A-GFP NPs. (FIG. 8B) qPCR measurements of relative Foxo13A mRNA expression over time after cells were exposed to Foxo13A-eGFP NPs. Effect of CD8-targeted Foxo13A-GFP NPs on CD62L expression after 24 h of particle treatment. (FIG. 8D) Percentage of CD62L+ cells in sorted CD8+ eGFP+ cells treated with CD8- targeting control or Foxo13A/eGFP-encoding NPs at 1, 8, and 20 days of culture after the particles were introduced. These results are from 3 independent donors. * P<0.05; ** P<0.01 between the indicated conditions as calculated from a ratio-paired t-test. (FIG. 8E) Heat map of TCM signature gene expression in TCM, naïve, and control cells 8 days after treatment. (FIG. 8F) Volcano plot of differential gene expression in Foxo13A NP-treated cells after 8 days. TCM signature genes and selected memory phenotype genes are indicated. P value of overlap between Foxo13A and the TCM signature gene set was determined by GSEA (via analysis shown in FIG. 9B).

(FIG. 9A) Heat map of TCM Down signature gene expression in TCM, naïve, and control cells after 8 days of the treatment. (FIG. 9B) Gene set enrichment analysis of genes differentially expressed in Foxo13A NP-treated versus control NP-treated cells tested against the TCM-Up and TCM-Down signature gene sets.

(FIG. 10A) Targeting of CD105 enables specific transfection of HSC CD34+ cells obtained from mobilized PBSC. These cells were left untreated, or transfected with eGFP-encoding mRNA in NPs coated with PGA coupled to a non-specific control antibody (control Ab-eGFP NPs) or anti-CD105 (α-CD105 NPs). Transfection efficiency was assayed by flow cytometry 24 h after NP exposure. (FIG. 10B) NP transfection efficiency in CD34+ samples from 3 independent donors. (FIG. 10C) Expansion of CD34+ HSC in vitro after addition of control or CD105-targeted NPs. Cells were transfected as in FIG. 10A, then total cell numbers were assessed at days 0, 4 and 8 days after particle exposure. (FIG. 10D) Flow cytometric analysis of the HSC markers CD34, CD133 and CD49f in untransfected cells (dashed line) or cells treated with anti-CD105 mRNA (solid line) after 8 days in culture. The results indicate that addition of NPs does not alter surface expression of key stem cell markers.

FIG. 11. Exemplary supporting sequences.

DETAILED DESCRIPTION

Figure 1A:
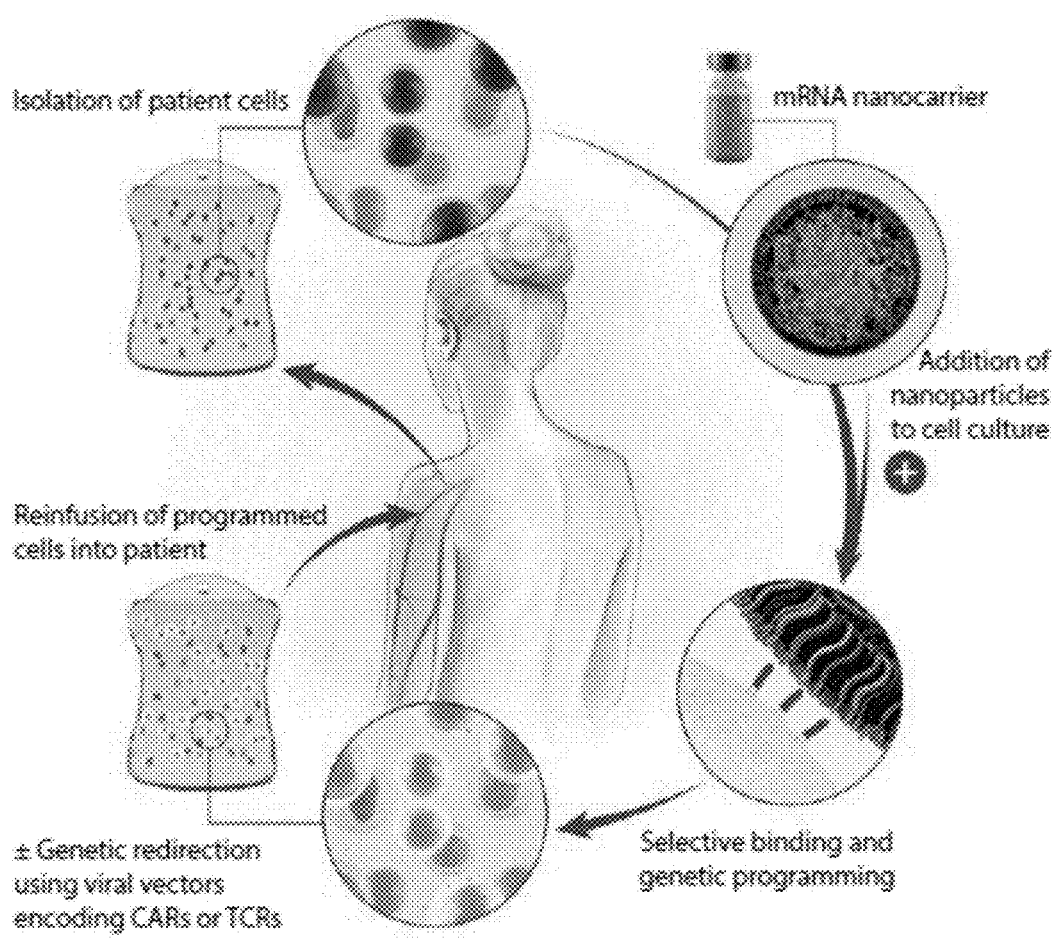

Successful genetic therapies depend on successful gene delivery mechanisms into selected cells of interest. Currently, viral systems, such as those utilizing lentiviral vectors, are the most common way to achieve long-lasting genetic therapies. These genetic therapies rely on the ongoing cellular expression of proteins with therapeutic value. While such viral systems can effectively deliver genes for genetic therapies, they are non-selective, expensive and not widely available. Moreover, continued therapeutic protein expression can decrease over time due to cellular events that occur over time.

Electroporation has also been developed as a mechanism to deliver genes into cells for genetic therapies. Electroporation, however, relies on the mechanical disruption and permeabilization of cellular membranes, thus compromising the viability of cells, rendering them less than ideal for therapeutic use. Further, like virus-based methods, electroporation does not selectively deliver genes to specific cell types out of a heterogeneous pool, so it must be preceded by a cell selection and purification process.

The current disclosure provides compositions and methods that rapidly and selectively modify cells to achieve therapeutic objectives by providing for transient expression of nucleic acids. The transient expression leads to permanent therapeutic changes in the modified cells, referred to herein as "hit and run" effects. Because only transient expression is required to achieve a lasting therapeutic effect, concerns regarding decreased therapeutic protein expression over time are overcome. Moreover, because the compositions and methods selectively modify selected cell types, no cell selection or purification processes are required before the modification. This expedites the manufacturing of therapeutic cells ex vivo and also allows the targeted genetic modification of cells in vivo.

The hit and run effects described herein are allowed by utilizing transient expression of nucleic acids that result in gene editing or transient expression of proteins that permanently alter the phenotype of the cell. Examples of nucleic acids that result in gene editing include TALENs, megaTALS, zinc finger nucleases and CRISPR-Cas systems. Examples of proteins that permanently alter the phenotype of a cell include transcription factors, kinases, and cell surface receptors. Transient expression refers to the production of a recombinant gene product over a short time period following nucleic acid transfer into cells. In particular embodiments, transient expression lasts from 12 hours to 20 days; from 18 hours to 18 days; from 24 hours to 14 days; or from 36 hours to 10 days. The phenotype of a cell refers to its physical characteristics and/or its location within the body.

There are numerous applications for the compositions and methods disclosed herein. Examples include editing the genome of lymphocytes (e.g., hematopoietic stem cells (HSCs)) with targeted nucleases; augmenting the potency of vaccines by co-injecting nucleic acid-loaded carriers that transfect dendritic cells to boost their ability to present antigens; and transfecting vaccine-primed T cells to induce a long-lived memory phenotype.

Particular embodiments include nanocarriers that can be targeted to specific selected cells and accomplish dose-controlled delivery of nucleic acids simply by mixing the nanocarriers with cells in culture ex vivo or cells within a subject, in vivo. In particular embodiments, the nanocarriers include: (1) a selected cell targeting ligand; (2) a carrier; and (3) nucleic acids within the carrier. Particular embodiments include nanocarriers including (1) a selected cell targeting ligand; (2) a carrier; (3) nucleic acids within the carrier; and (4) a coating.

In particular embodiments, selected cell targeting ligands can include surface-anchored targeting ligands that selectively bind the nanocarriers to selected cells and initiate rapid receptor-induced endocytosis to internalize them. As disclosed in more detail elsewhere herein, selected cell targeting ligands can include antibodies, scFv proteins, DART molecules, peptides, and/or aptamers. Particular embodiments utilize anti-CD8 antibodies to transfect human T cells, and antibodies recognizing CD34, CD133, or CD46 to target HSCs.

In particular embodiments, carriers include a carrier molecule that condenses and protects nucleic acids from enzymatic degradation. As disclosed in more detail elsewhere herein, carriers can include positively charged lipids and/or polymers. Particular embodiments utilize poly($\beta$-amino ester).

In particular embodiments, nucleic acids are encapsulated within the carrier and, following cellular uptake by a selected cell, express a gene-editing agent and/or a protein that permanently alters the phenotype of a cell. As disclosed in more detail elsewhere herein, nucleic acids can include synthetic mRNA that expresses a megaTAL or a transcription factor. Particular embodiments utilize in vitro-transcribed mRNA (see, e.g., Grudzien-Nogalska et al., Methods Mol. Biol. 969, 55-72 (2013)) expressing (i) the transcription factor FOXO1, which induces memory CD8 T cells; or (ii) a rare-cleaving megaTAL nuclease (see, e.g., Boissel & Scharenberg, Methods Mol. Biol. 1239, 171-196 (2015)) to disrupt T cell receptor expression by lymphocytes.

In particular embodiments, the nanocarriers disclosed herein include a coating that shields the encapsulated nucleic acids and reduces or prevents off-target binding. Off-target binding is reduced or prevented by reducing the surface charge of the nanocarriers to neutral or negative. As disclosed in more detail elsewhere herein, coatings can include neutral or negative polymer- and/or liposome-based coatings. Particular embodiments utilize polyglutamic acid (PGA) as a nanocarrier coating. When used, the coating need not necessarily coat the entire nanocarrier, but must be sufficient to reduce off-target binding by the nanocarrier.

When the disclosed nanocarriers are added to a heterogeneous mixture of cells (e.g., an ex vivo cell culture or an in vivo environment), the engineered nanocarriers bind to selected cell populations and stimulate receptor-mediated endocytosis; this process provides entry for the nucleic acid (e.g., synthetic mRNA) they carry, and consequently the selected cells begin to express the encoded molecule (FIG. 1A). Because nuclear transport and transcription of the transgene is not required, this process is rapid and efficient. If required, additional applications of the nanocarriers can be performed until the desired results are achieved. In particular embodiments, the nanocarriers are biodegradable and biocompatible, and, in ex vivo cell manufacturing, modified cells can easily be separated from unbound nanoparticles by centrifugation before they are infused into a subject for treatment.

In particular embodiments, rapid means that expression of an encoded nucleic acid begins within a selected cell type within 24 hours or within 12 hours of exposure of a heterogeneous sample of cells to nanocarriers disclosed herein. This timeline is possible utilizing nucleic acids such as mRNA which start being transcribed almost immediately (e.g., within minutes) of release into targeted cell cytoplasm.

In particular embodiments, efficient means that gene transfer into targeted cells (e.g., primary human T cells) is >80% and phenotype modification occurs in at least 80% of these cells, at least 90% of these cells or 100% of these cells. In particular embodiments, efficient means that gene transfer into targeted cells is >80% and phenotype modification occurs in at least 25% of these cells, at least 33% of these cells or at least 50% of these cells. In particular embodiments, phenotype modification can occur in ⅓ of selected cells that uptake nanocarriers wherein the delivered nucleic acid encodes a nuclease.

Additional options and embodiments of the disclosure are now described in more detail.

Selected Cell Targeting Ligands. The selected cell targeting ligands of the disclosed nanocarriers selectively bind immune cells of interest within a heterogeneous cell population. In particular embodiments, the immune cells of interest are lymphocytes. Lymphocytes include T-cells, B cells, natural killer (NK) cells, monocytes/macrophages and HSCs.

Several different subsets of T-cells have been discovered, each with a distinct function. In particular embodiments, selected cell targeting ligands achieve selective direction to particular lymphocyte populations through receptor-mediated endocytosis. For example, a majority of T-cells have a T-cell receptor (TCR) existing as a complex of several proteins. The actual T-cell receptor is composed of two separate peptide chains, which are produced from the independent T-cell receptor alpha and beta (TCRα and TCRβ) genes and are called α- and β-TCR chains. Selected cell targeting ligands disclosed herein can bind α- and/or β-TCR chains to achieve selective delivery of nucleic acids to these T cells.

γδ T-cells represent a small subset of T-cells that possess a distinct T-cell receptor (TCR) on their surface. In γδ T-cells, the TCR is made up of one γ-chain and one δ-chain. This group of T-cells is much less common (2% of total T-cells) than the αβ T-cells. Nonetheless, selected cell targeting ligands disclosed herein can bind γ- and/or δ TCR chains to achieve selective delivery of nucleic acids to these T cells.

CD3 is expressed on all mature T cells. Accordingly, selected cell targeting ligands disclosed herein can bind CD3 to achieve selective delivery of nucleic acids to all mature T-cells. Activated T-cells express 4-1BB (CD137), CD69, and CD25. Accordingly, selected cell targeting ligands disclosed herein can bind 4-1BB, CD69 or CD25 to achieve selective delivery of nucleic acids to activated T-cells. CD5 and transferrin receptor are also expressed on T-cells and can be used to achieve selective delivery of nucleic acids to T-cells.

T-cells can further be classified into helper cells (CD4+ T-cells) and cytotoxic T-cells (CTLs, CD8+ T-cells), which include cytolytic T-cells. T helper cells assist other white blood cells in immunologic processes, including maturation of B cells into plasma cells and activation of cytotoxic T-cells and macrophages, among other functions. These cells are also known as CD4+ T-cells because they express the CD4 protein on their surface. Helper T-cells become activated when they are presented with peptide antigens by MHC class II molecules that are expressed on the surface of antigen presenting cells (APCs). Once activated, they divide rapidly and secrete small proteins called cytokines that regulate or assist in the active immune response. Selected cell targeting ligands disclosed herein can bind CD4 to achieve selective delivery of nucleic acids to T helper cells.

Cytotoxic T-cells destroy virally infected cells and tumor cells, and are also implicated in transplant rejection. These cells are also known as CD8+ T-cells because they express the CD8 glycoprotein on their surface. These cells recognize their targets by binding to antigen associated with MHC class I, which is present on the surface of nearly every cell of the body. Selected cell targeting ligands disclosed herein can bind CD8 to achieve selective delivery of nucleic acids to CTL.

"Central memory" T-cells (or "TCM") as used herein refers to an antigen experienced CTL that expresses CD62L or CCR7 and CD45RO on the surface thereof, and does not express or has decreased expression of CD45RA as compared to naive cells. In particular embodiments, central memory cells are positive for expression of CD62L, CCR7, CD25, CD127, CD45RO, and CD95, and have decreased expression of CD45RA as compared to naive cells. Selected cell targeting ligands disclosed herein can bind CD62L, CCR7, CD25, CD127, CD45RO and/or CD95 to achieve selective delivery of nucleic acids to TCM.

"Effector memory" T-cell (or "TEM") as used herein refers to an antigen experienced T-cell that does not express or has decreased expression of CD62L on the surface thereof as compared to central memory cells, and does not express or has decreased expression of CD45RA as compared to a naive cell. In particular embodiments, effector memory cells are negative for expression of CD62L and CCR7, compared to naive cells or central memory cells, and have variable expression of CD28 and CD45RA. Effector T-cells are positive for granzyme B and perform as compared to memory or naive T-cells. Selected cell targeting ligands disclosed herein can bind granzyme B and/or perform to achieve selective delivery of nucleic acids to TEM.

Regulatory T cells ("TREG") are a subpopulation of T cells, which modulate the immune system, maintain tolerance to self-antigens, and abrogate autoimmune disease. TREG express CD25, CTLA-4, GITR, GARP and LAP. Selected cell targeting ligands disclosed herein can bind CD25, CTLA-4, GITR, GARP and/or LAP to achieve selective delivery of nucleic acids to naïve TREG.

"Naïve" T-cells as used herein refers to a non-antigen experienced T cell that expresses CD62L and CD45RA, and does not express CD45RO as compared to central or effector memory cells. In particular embodiments, naive CD8+ T lymphocytes are characterized by the expression of phenotypic markers of naive T-cells including CD62L, CCR7, CD28, CD127, and CD45RA. Selected cell targeting ligands disclosed herein can bind CD62L, CCR7, CD28, CD127 and/or CD45RA to achieve selective delivery of nucleic acids to naïve T-cells.

Natural killer cells (also known as NK cells, K cells, and killer cells) are activated in response to interferons or macrophage-derived cytokines. They serve to contain viral infections while the adaptive immune response is generating antigen-specific cytotoxic T cells that can clear the infection. NK cells express CD8, CD16 and CD56 but do not express CD3. Selected cell targeting ligands disclosed herein can bind CD8, CD16 and/or CD56 to achieve selective delivery of nucleic acids to NK cells.

Macrophages (and their precursors, monocytes) reside in every tissue of the body (in certain instances as microglia, Kupffer cells and osteoclasts) where they engulf apoptotic cells, pathogens and other non-self-components. Because monocytes/macrophages engulf non-self-components, a particular macrophage- or monocyte-directing agent is not required on the nanocarriers described herein for selective uptake by these cells. Alternatively, selected cell targeting ligands disclosed herein can bind CD11b, F4/80; CD68; CD11c; IL-4Rα; and/or CD163 to achieve selective delivery of nucleic acid to monocytes/macrophages.

Immature dendritic cells (i.e., pre-activation) engulf antigens and other non-self-components in the periphery and subsequently, in activated form, migrate to T-cell areas of lymphoid tissues where they provide antigen presentation to T cells. Thus, like macrophages, the targeting of dendritic cells need not rely on a selected cell targeting ligand. When a selected cell targeting ligand is used to selectively target dendritic cells, it can bind the following CD antigens: CD1a, CD1b, CD1c, CD1d, CD21, CD35, CD39, CD40, CD86, CD101, CD148, CD209, and DEC-205.

B cells can be distinguished from other lymphocytes by the presence of the B cell receptor (BCR). The principal function of B cells is to make antibodies. B cells express CD5, CD19, CD20, CD21, CD22, CD35, CD40, CD52, and CD80. Selected cell targeting ligands disclosed herein can bind CD5, CD19, CD20, CD21, CD22, CD35, CD40, CD52, and/or CD80 to achieve selective delivery of nucleic acids to B-cells. Also antibodies targeting the B-cell receptor isotype constant regions (IgM, IgG, IgA, IgE) can be used to target B-cell subtypes.

Lymphocyte function-associated antigen 1 (LFA-1) is expressed by all T-cells, B-cells and monocytes/macrophages. Accordingly, selected cell targeting ligands disclosed herein can bind LFA-1 to achieve selective delivery of nucleic acids to T-cells, B-cells and monocytes/macrophages.

HSCs can also be targeted for selective delivery of nanocarriers disclosed herein. HSCs express CD34, CD46, CD133, Sca-1 and CD117. Selected cell targeting ligands disclosed herein can bind CD34, CD46, CD133, Sca-1 and/or CD117 to achieve selective delivery of nucleic acids to hematopoietic stem cells.

"Selective delivery" means that nucleic acids are delivered and expressed by one or more selected lymphocyte populations. In particular embodiments, selective delivery is exclusive to a selected lymphocyte population. In particular embodiments, at least 65%, 70%, 75%, 80%, 85%, 90%, 95% or 99% of administered nucleic acids are delivered and/or expressed by a selected lymphocyte population. In particular embodiments, selective delivery ensures that non-lymphocyte cells do not express delivered nucleic acids. For example, when the targeting agent is a T-cell receptor (TCR) gene, selectivity is ensured because only T cells have the zeta chains required for TCR expression. Selective delivery can also be based on lack of nucleic acid uptake into unselected cells or based on the presence of a specific promoter within the nucleic acid sequence. For example, transiently-expressed nucleic acids can include a T-cell-specific CD3-delta promoter. Additional promoters that can achieve selective delivery include: the murine stem cell virus promoter or the distal lck promoter for T cells or HSCs; the CD45 promoter, WASP promoter or IFN-beta promoter for HSCs; the B29 promoter for B cells; or the CD14 promoter or the CD11b promoter for monocytes/macrophages.

As indicated, selected cell targeting ligands can include binding domains for motifs found on lymphocyte cells. Selected cell targeting ligands can also include any selective binding mechanism allowing selective uptake into lymphocytes. In particular embodiments, selected cell targeting ligands include binding domains for T-cell receptor motifs; T-cell α chains; T-cell β chains; T-cell γ chains; T-cell δ chains; CCR7; CD1a; CD1b; CD1c; CD1d; CD3; CD4; CD5; CD7; CD8; CD11b; CD11c; CD16; CD19; CD20; CD21; CD22; CD25; CD28; CD34; CD35; CD39; CD40; CD45RA; CD45RO; CD46, CD52; CD56; CD62L; CD68; CD80; CD86; CD95; CD101; CD117; CD127; CD133; CD137 (4-1BB); CD148; CD163; F4/80; IL-4Rα; Sca-1; CTLA-4; GITR; GARP; LAP; granzyme B; LFA-1; transferrin receptor; and combinations thereof.

In particular embodiments, binding domains include cell marker ligands, receptor ligands, antibodies, peptides, peptide aptamers, nucleic acids, nucleic acid aptamers, spiegelmers or combinations thereof. Within the context of selected cell targeting ligands, binding domains include any substance that binds to another substance to form a complex capable of mediating endocytosis.

"Antibodies" are one example of binding domains and include whole antibodies or binding fragments of an antibody, e.g., Fv, Fab, Fab', F(ab')2, Fc, and single chain Fv fragments (scFvs) or any biologically effective fragments of an immunoglobulin that bind specifically to a motif expressed by a lymphocyte. Antibodies or antigen binding fragments include all or a portion of polyclonal antibodies, monoclonal antibodies, human antibodies, humanized antibodies, synthetic antibodies, chimeric antibodies, bispecific antibodies, mini bodies, and linear antibodies.

Antibodies from human origin or humanized antibodies have lowered or no immunogenicity in humans and have a lower number of non-immunogenic epitopes compared to non-human antibodies. Antibodies and their fragments will generally be selected to have a reduced level or no antigenicity in human subjects.

Antibodies that specifically bind a motif expressed by a lymphocyte can be prepared using methods of obtaining monoclonal antibodies, methods of phage display, methods to generate human or humanized antibodies, or methods using a transgenic animal or plant engineered to produce antibodies as is known to those of ordinary skill in the art (see, for example, U.S. Pat. Nos. 6,291,161 and 6,291,158). Phage display libraries of partially or fully synthetic antibodies are available and can be screened for an antibody or fragment thereof that can bind to a lymphocyte motif. For example, binding domains may be identified by screening a Fab phage library for Fab fragments that specifically bind to a target of interest (see Hoet et al., *Nat. Biotechnol.* 23:344, 2005). Phage display libraries of human antibodies are also available. Additionally, traditional strategies for hybridoma development using a target of interest as an immunogen in convenient systems (e.g., mice, HuMAb Mouse®, TCmouse™, KM-Mouse®, llamas, chicken, rats, hamsters, rabbits, etc.) can be used to develop binding domains. In particular embodiments, antibodies specifically bind to motifs expressed by a selected lymphocyte and do not cross react with nonspecific components or unrelated targets. Once identified, the amino acid sequence or nucleic acid sequence coding for the antibody can be isolated and/or determined.

In particular embodiments, binding domains of selected cell targeting ligands include T-cell receptor motif antibodies; T-cell α chain antibodies; T-cell β chain antibodies; T-cell γ chain antibodies; T-cell δ chain antibodies; CCR7 antibodies; CD1a antibodies; CD1b antibodies; CD1c antibodies; CD1d antibodies; CD3 antibodies; CD4 antibodies; CD5 antibodies; CD7 antibodies; CD8 antibodies; CD11 b antibodies; CD11c antibodies; CD16 antibodies; CD19 antibodies; CD20 antibodies; CD21 antibodies; CD22 antibodies; CD25 antibodies; CD28 antibodies; CD34 antibodies; CD35 antibodies; CD39 antibodies; CD40 antibodies; CD45RA antibodies; CD45RO antibodies; CD46 antibodies; CD52 antibodies; CD56 antibodies; CD62L antibodies; CD68 antibodies; CD80 antibodies; CD86 antibodies CD95 antibodies; CD101 antibodies; CD117 antibodies; CD127 antibodies; CD133 antibodies; CD137 (4-1BB) antibodies; CD148 antibodies; CD163 antibodies; F4/80 antibodies; IL-4Rα antibodies; Sca-1 antibodies; CTLA-4 antibodies; GITR antibodies; GARP antibodies; LAP antibodies; granzyme B antibodies; LFA-1 antibodies; or transferrin receptor antibodies. These binding domains also can consist of scFv fragments of the foregoing antibodies.

Peptide aptamers include a peptide loop (which is specific for a target protein) attached at both ends to a protein scaffold. This double structural constraint greatly increases the binding affinity of the peptide aptamer to levels comparable to an antibody. The variable loop length is typically 8 to 20 amino acids (e.g., 8 to 12 amino acids), and the scaffold may be any protein which is stable, soluble, small, and non-toxic (e.g., thioredoxin-A, stefin A triple mutant, green fluorescent protein, eglin C, and cellular transcription factor Sp1). Peptide aptamer selection can be made using different systems, such as the yeast two-hybrid system (e.g., Gal4 yeast-two-hybrid system) or the LexA interaction trap system.

Nucleic acid aptamers are single-stranded nucleic acid (DNA or RNA) ligands that function by folding into a specific globular structure that dictates binding to target proteins or other molecules with high affinity and specificity, as described by Osborne et al., Curr. Opin. Chem. Biol. 1:5-9, 1997; and Cerchia et al., FEBS Letters 528:12-16, 2002. In particular embodiments, aptamers are small (15 KD; or between 15-80 nucleotides or between 20-50 nucleotides). Aptamers are generally isolated from libraries consisting of $10^{14}$-$10^{15}$ random oligonucleotide sequences by a procedure termed SELEX (systematic evolution of ligands by exponential enrichment; see, for example, Tuerk et al., Science, 249:505-510, 1990; Green et al., Methods Enzymology. 75-86, 1991; and Gold et al., Annu. Rev. Biochem., 64: 763-797, 1995). Further methods of generating aptamers are described in, for example, U.S. Pat. Nos. 6,344,318; 6,331,398; 6,110,900; 5,817,785; 5,756,291; 5,696,249; 5,670,637; 5,637,461; 5,595,877; 5,527,894; 5,496,938; 5,475,096; and 5,270,16. Spiegelmers are similar to nucleic acid aptamers except that at least one β-ribose unit is replaced by β-D-deoxyribose or a modified sugar unit selected from, for example, β-D-ribose, α-D-ribose, β-L-ribose.

Other agents that can facilitate internalization by and/or transfection of lymphocytes, such as poly(ethyleneimine)/DNA (PEI/DNA) complexes can also be used.

Carriers. As indicated, carriers of the disclosed nanocarriers function to condense and protect nucleic acids from enzymatic degradation. Particularly useful materials to use as carriers include positively charged lipids and/or polymers, including poly(β-amino ester).

Additional examples of positively charged lipids include esters of phosphatidic acid with an aminoalcohol, such as an ester of dipalmitoyl phosphatidic acid or distearoyl phosphatidic acid with hydroxyethylenediamine. More particular examples of positively charged lipids include 3β-[N—(N', N'-dimethylaminoethyl)carbamoyl) cholesterol (DC-chol); N,N'-dimethyl-N,N'-dioctacyl ammonium bromide (DDAB); N,N'-dimethyl-N,N'-dioctacyl ammonium chloride (DDAC); 1,2-dioleoyloxypropyl-3-dimethyl-hydroxyethyl ammonium chloride (DORI); 1,2-dioleoyloxy-3-[trimethylammonio]-propane (DOTAP); N-(1-(2,3-dioleyloxy)propyl)-N,N,N-trimethylammonium chloride (DOTMA); dipalmitoylphosphatidylcholine (DPPC); 1,2-dioctadecyloxy-3-[trimethylammonio]-propane (DSTAP); and the cationic lipids described in e.g. Martin et al., Current Pharmaceutical Design 2005, 11, 375-394.

Examples of positively charged polymers that can be used as carriers within the current disclosure include polyamines; polyorganic amines (e.g., polyethyleneimine (PEI), polyethyleneimine celluloses); poly(amidoamines) (PAMAM); polyamino acids (e.g., polylysine (PLL), polyarginine); polysaccharides (e.g, cellulose, dextran, DEAE dextran, starch); spermine, spermidine, poly(vinylbenzyl trialkyl ammonium), poly(4-vinyl-N-alkyl-pyridiumiun), poly(acryloyl-trialkyl ammonium), and Tat proteins.

Blends of lipids and polymers in any concentration and in any ratio can also be used. Blending different polymer types in different ratios using various grades can result in characteristics that borrow from each of the contributing polymers. Various terminal group chemistries can also be adopted.

Without limiting the foregoing, particular embodiments disclosed herein can also utilize porous nanoparticles constructed from any material capable of forming a porous network. Exemplary materials include metals, transition metals and metalloids. Exemplary metals, transition metals and metalloids include lithium, magnesium, zinc, aluminum and silica. In particular embodiments, the porous nanocarriers include silica. The exceptionally high surface area of mesoporous silica (exceeding 1,000 m2/g) enables nucleic acid loading at levels exceeding conventional DNA carriers such as liposomes.

Carriers can be formed in a variety of different shapes, including spheroidal, cuboidal, pyramidal, oblong, cylindrical, toroidal, and the like. The nucleic acids can be included in the pores of the carriers in a variety of ways. For example, the nucleic acids can be encapsulated in the porous nanocarriers. In other aspects, the nucleic acids can be associated (e.g., covalently and/or non-covalently) with the surface or close underlying vicinity of the surface of the porous nanocarriers. In particular embodiments, the nucleic acids can be incorporated in the porous nanocarriers e.g., integrated in the material of the porous nanocarriers. For example, the nucleic acids can be incorporated into a polymer matrix of polymer nanocarriers.

Coatings. In particular embodiments, the nanocarriers disclosed herein include a coating that shields the encapsulated nucleic acids and reduces or prevents off-target binding. Off-target binding is reduced or prevented by reducing the surface charge of the nanocarriers to neutral or negative. As disclosed in more detail elsewhere herein, coatings can include neutral or negatively charged polymer- and/or liposome-based coatings. In particular embodiments, the coating is a dense surface coating of hydrophilic and/or neutrally charged hydrophilic polymer sufficient to prevent the encapsulated nucleic acids from being exposed to the environment before release into a selected cell. In particular embodiments, the coating covers at least 80% or at least 90% of the surface of the nanocarrier. In particular embodiments, the coating includes polyglutamic acid (PGA).

Examples of neutrally charged polymers that can be used as coating within embodiments of the disclosure include polyethylene glycol (PEG); poly(propylene glycol); and polyalkylene oxide copolymers, (PLURONIC®, BASF Corp., Mount Olive, N.J.).

Neutrally charged polymers also include zwitterionic polymers. Zwitterionic refers to the property of overall charge neutrality while having both a positive and a negative electrical charge. Zwitterionic polymers can behave like regions of cell membranes that resist cell and protein adhesion.

Zwitterionic polymers include zwitterionic constitutional units including pendant groups (i.e., groups pendant from the polymer backbone) with zwitterionic groups. Exemplary zwitterionic pendant groups include carboxybetaine groups (e.g., —Ra-N+(Rb)(Rc)-Rd-CO2-, where Ra is a linker group that covalently couples the polymer backbone to the cationic nitrogen center of the carboxybetaine groups, Rb and Rc are nitrogen substituents, and Rd is a linker group that covalently couples the cationic nitrogen center to the carboxy group of the carboxybetaine group).

Examples of negatively charged polymers include alginic acids; carboxylic acid polysaccharides; carboxymethyl cellulose; carboxymethyl cellulose-cysteine; carrageenan (e.g., Gelcarin® 209, Gelcarin® 379); chondroitin sulfate; glycosaminoglycans; mucopolysaccharides; negatively charged polysaccharides (e.g., dextran sulfate); poly(acrylic acid); poly(D-aspartic acid); poly(L-aspartic acid); poly(L-aspartic acid) sodium salt; poly(D-glutamic acid); poly(L-glutamic acid); poly(L-glutamic acid) sodium salt; poly(methacrylic acid); sodium alginate (e.g., Protanal® LF 120M, Protanal® LF 200M, Protanal® LF 200D); sodium carboxymethyl cellulose (CMC); sulfated polysaccharides (heparins, agaropectins); pectin, gelatin and hyalouronic acid.

In particular embodiments, polymers disclosed herein can include "star shaped polymers," which refer to branched polymers in which two or more polymer branches extend from a core. The core is a group of atoms having two or more functional groups from which the branches can be extended by polymerization.

In particular embodiments, the branches are zwitterionic or negatively-charged polymeric branches. For star polymers, the branch precursors can be converted to zwitterionic or negatively-charged polymers via hydrolysis, ultraviolet irradiation, or heat. The polymers also may be obtained by any polymerization method effective for polymerization of unsaturated monomers, including atom transfer radical polymerization (ATRP), reversible addition-fragmentation chain transfer polymerization (RAFT), photo-polymerization, ring-opening polymerization (ROP), condensation, Michael addition, branch generation/propagation reaction, or other reactions.

Liposomes are microscopic vesicles including at least one concentric lipid bilayer. Vesicle-forming lipids are selected to achieve a specified degree of fluidity or rigidity of the final complex. In particular embodiments, liposomes provide a lipid composition that is an outer layer surrounding a porous nanoparticle.

Liposomes can be neutral (cholesterol) or bipolar and include phospholipids, such as phosphatidylcholine (PC), phosphatidylethanolamine (PE), phosphatidylinositol (PI), and sphingomyelin (SM) and other type of bipolar lipids including dioleoylphosphatidylethanolamine (DOPE), with a hydrocarbon chain length in the range of 14-22, and saturated or with one or more double C=C bonds. Examples of lipids capable of producing a stable liposome, alone, or in combination with other lipid components are phospholipids, such as hydrogenated soy phosphatidylcholine (HSPC), lecithin, phosphatidylethanolamine, lysolecithin, lysophosphatidylethanolamine, phosphatidylserine, phosphatidylinositol, sphingomyelin, cephalin, cardiolipin, phosphatidic acid, cerebro sides, distearoylphosphatidylethanolamine (DSPE), dioleoylphosphatidylcholine (DOPC), dipalmitoylphosphatidylcholine (DPPC), palmitoyloleoylphosphatidylcholine (POPC), palmitoyloleoylphosphatidylethanolamine (POPE) and dioleoylphosphatidylethanolamine 4-(N-maleimido-methyl)cyclohexane-1-carboxylate (DOPE-mal). Additional non-phosphorous containing lipids that can become incorporated into liposomes include stearylamine, dodecylamine, hexadecylamine, isopropyl myristate, triethanolamine-lauryl sulfate, alkyl-aryl sulfate, acetyl palmitate, glycerol ricinoleate, hexadecyl stereate, amphoteric acrylic polymers, polyethyloxylated fatty acid amides, DDAB, dioctadecyl dimethyl ammonium chloride (DODAC), 1,2-dimyristoyl-3-trimethylammonium propane (DMTAP), DOTAP, DOTMA, DC-Chol, phosphatidic acid (PA), dipalmitoylphosphatidylglycerol (DPPG), dioleoylphosphatidylglycerol, DOPG, and dicetylphosphate. In particular embodiments, lipids used to create liposomes disclosed herein include cholesterol, hydrogenated soy phosphatidylcholine (HSPC) and, the derivatized vesicle-forming lipid PEG-DSPE.

Methods of forming liposomes are described in, for example, U.S. Pat. Nos. 4,229,360; 4,224,179; 4,241,046; 4,737,323; 4,078,052; 4,235,871; 4,501,728; and 4,837,028, as well as in Szoka et al., Ann. Rev. Biophys. Bioeng. 9:467 (1980) and Hope et al., Chem. Phys. Lip. 40:89 (1986).

Figure 1B:
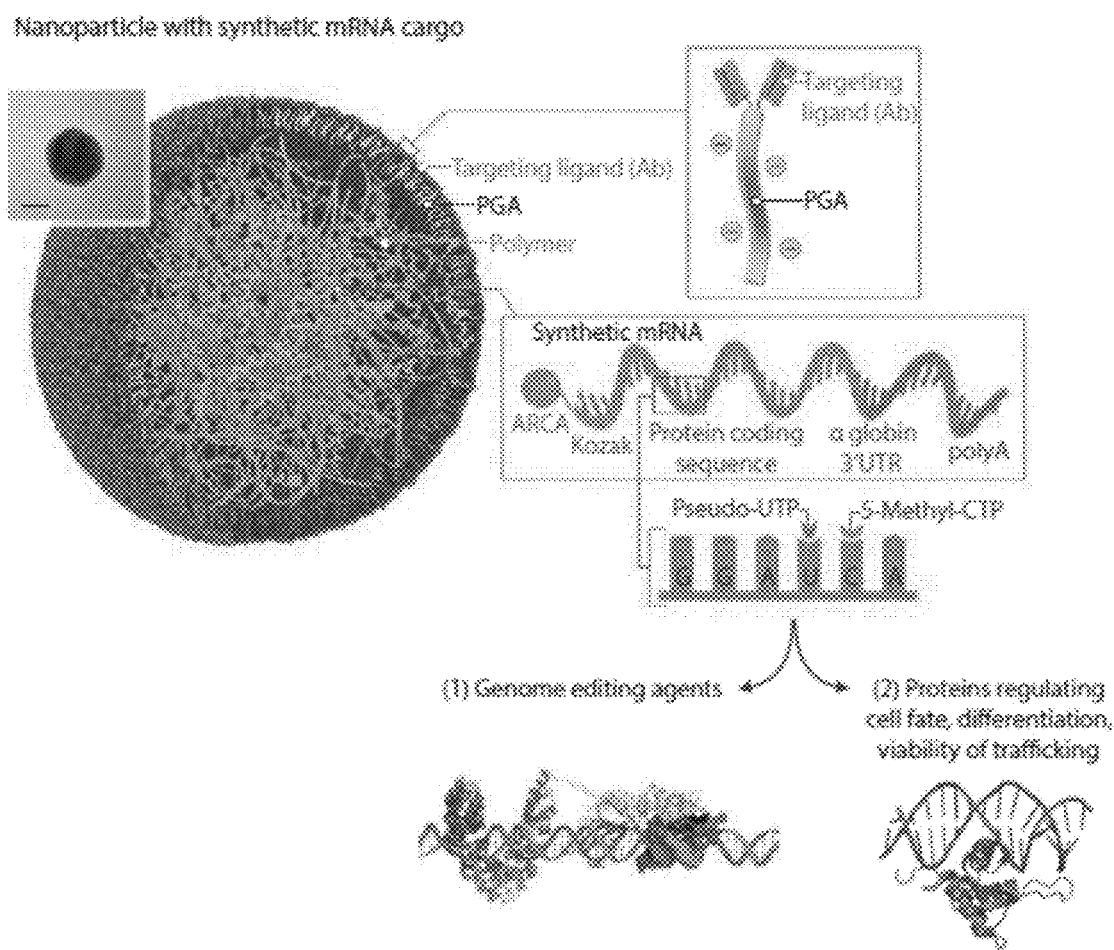

Nucleic acids. Nucleic acids used within nanocarriers disclosed herein can transiently express gene editing agents and/or phenotype-altering proteins that regulate cell fate, differentiation, viability and/or trafficking (see, e.g., FIGS. 1B, 1C).

In particular embodiments, nucleic acids include synthetic mRNA. In particular embodiments, synthetic mRNA is engineered for increased intracellular stability using 5'-capping. Multiple distinct 5'-cap structures can be used to generate the 5'-cap of a synthetic mRNA molecule. For example, the Anti-Reverse Cap Analog (ARCA) cap contains a 5'-5'-triphosphate guanine-guanine linkage where one guanine contains an N7 methyl group as well as a 3'-O-methyl group. Synthetic mRNA molecules may also be capped post-transcriptionally using enzymes responsible for generating 5'-cap structures. For example, recombinant Vaccinia Virus Capping Enzyme and recombinant 2'-O-methyltransferase enzyme can create a canonical 5'-5'-triphosphate linkage between the 5'-most nucleotide of an mRNA and a guanine nucleotide where the guanine contains an N7 methylation and the ultimate 5'-nucleotide contains a 2'-O-methyl generating the Cap1 structure. This results in a cap with higher translational-competency and cellular stability and reduced activation of cellular pro-inflammatory cytokines.

Synthetic mRNA or other nucleic acids may also be made cyclic. Synthetic mRNA may be cyclized, or concatemerized, to generate a translation competent molecule to assist interactions between poly-A binding proteins and 5'-end binding proteins. The mechanism of cyclization or concatemerization may occur through at least 3 different routes: 1) chemical, 2) enzymatic, and 3) ribozyme catalyzed. The newly formed 5'-/3'-linkage may be intramolecular or intermolecular.

In the first route, the 5'-end and the 3'-end of the nucleic acid may contain chemically reactive groups that, when close together, form a new covalent linkage between the 5'-end and the 3'-end of the molecule. The 5'-end may contain an NHS-ester reactive group and the 3'-end may contain a 3'-amino-terminated nucleotide such that in an organic solvent the 3'-amino-terminated nucleotide on the 3'-end of a synthetic mRNA molecule will undergo a nucleophilic attack on the 5'-NHS-ester moiety forming a new 5'-/3'-amide bond.

In the second route, T4 RNA ligase may be used to enzymatically link a 5'-phosphorylated nucleic acid molecule to the 3'-hydroxyl group of a nucleic acid forming a new phosphorodiester linkage. In an example reaction, 1 µg of a nucleic acid molecule can be incubated at 37° C. for 1 hour with 1-10 units of T4 RNA ligase (New England Biolabs, Ipswich, Mass.) according to the manufacturer's protocol. The ligation reaction may occur in the presence of a split oligonucleotide capable of base-pairing with both the 5'- and 3'-region in juxtaposition to assist the enzymatic ligation reaction.

In the third route, either the 5'- or 3'-end of a cDNA template encodes a ligase ribozyme sequence such that during in vitro transcription, the resultant nucleic acid molecule can contain an active ribozyme sequence capable of ligating the 5'-end of a nucleic acid molecule to the 3'-end of a nucleic acid molecule. The ligase ribozyme may be derived from the Group I Intron, Group I Intron, Hepatitis Delta Virus, Hairpin ribozyme or may be selected by SELEX (systematic evolution of ligands by exponential enrichment). The ribozyme ligase reaction may take 1 to 24 hours at temperatures between 0 and 37° C.

In particular embodiments, the nucleic acid includes a plasmid, a cDNA, or an mRNA that can include, e.g., a sequence (e.g., a gene) for expressing a gene editing agent or phenotype-altering protein. Suitable plasmids include standard plasmid vectors and minicircle plasmids that can be used to transfer a gene to a lymphocyte. The nucleic acids (e.g., minicircle plasmids) can further include any additional sequence information to facilitate transient expression in a selectively modified cell. For example, the nucleic acids can include promoters, such as general promoters, tissue-specific promoters, cell-specific promoters, and/or promoters specific for the cytoplasm. As indicated, promoters and plasmids (e.g., minicircle plasmids) are generally well known in the art and can be prepared using conventional techniques.

As used herein, the term "gene" refers to a nucleic acid sequence that encodes a gene editing agent or phenotype-altering protein. This definition includes various sequence polymorphisms, mutations, and/or sequence variants wherein such alterations do not affect the function of the gene editing agent or phenotype-altering protein. The term "gene" may include not only coding sequences but also regulatory regions such as promoters, enhancers, and termination regions. The term further can include all introns and other DNA sequences spliced from the mRNA transcript, along with variants resulting from alternative splice sites. Nucleic acid sequences encoding the gene editing agent or phenotype-altering protein can be RNA that directs the expression of the gene editing agent or phenotype-altering protein. These nucleic acid sequences include RNA sequences that are translated, in particular embodiments, into protein. The nucleic acid sequences include both the full-length nucleic acid sequences as well as non-full-length sequences derived from the full-length protein. The sequences can also include degenerate codons of the native sequence or sequences that may be introduced to provide codon preference in a specific lymphocyte. Gene sequences to encode gene editing agents or phenotype-altering proteins disclosed herein are available in publicly available databases and publications. As used herein, the term "encoding" refers to a property of sequences of nucleic acids, such as a plasmid, a gene, cDNA, mRNA, to serve as templates for synthesis of gene editing agents or phenotype-altering proteins.

Gene editing agents. As used herein, gene editing agents include expression products of transient nucleic acid expression as described herein that modify or affect particular sequences of a selected cell's endogenous genome. In particular embodiments, the modification includes removal or disruption of an endogenous gene such that the endogenous gene's encoded protein is no longer expressed, expressed to a reduced degree, expressed as an incomplete protein, an unstable protein, an incorrectly folded protein and/or a nonfunctional protein. In particular embodiments, the effect is reduced expression of a protein through an interfering RNA-type mechanism. Thus, gene editing agents are useful for genome editing, for example gene disruption, gene editing by homologous recombination, and gene therapy to insert therapeutic genes at the appropriate chromosomal target sites with a human genome.

Particular embodiments utilize transcription activator-like effector nucleases (TALENs) as gene editing agents. TALENs refer to fusion proteins including a transcription activator-like effector (TALE) DNA binding protein and a DNA cleavage domain. TALENs are used to edit genes and genomes by inducing double strand breaks (DSBs) in the DNA, which induce repair mechanisms in cells. Generally, two TALENs must bind and flank each side of the target DNA site for the DNA cleavage domain to dimerize and induce a DSB. The DSB is repaired in the cell by non-homologous end-joining (NHEJ) or by homologous recombination (HR) with an exogenous double-stranded donor DNA fragment.

As indicated, TALENs have been engineered to bind a target sequence of, for example, an endogenous genome, and cut DNA at the location of the target sequence. The TALEs of TALENs are DNA binding proteins secreted by *Xanthomonas* bacteria. The DNA binding domain of TALEs include a highly conserved 33 or 34 amino acid repeat, with divergent residues at the 12th and 13th positions of each repeat. These two positions, referred to as the Repeat Variable Diresidue (RVD), show a strong correlation with specific nucleotide recognition. Accordingly, targeting specificity can be improved by changing the amino acids in the RVD and incorporating nonconventional RVD amino acids.

Examples of DNA cleavage domains that can be used in TALEN fusions are wild-type and variant FokI endonucleases. The FokI domain functions as a dimer requiring two constructs with unique DNA binding domains for sites on the target sequence. The FokI cleavage domain cleaves within a five or six base pair spacer sequence separating the two inverted half-sites.

Particular embodiments utilize MegaTALs as gene editing agents. MegaTALs have a single chain rare-cleaving nuclease structure in which a TALE is fused with the DNA cleavage domain of a meganuclease. Meganucleases, also known as homing endonucleases, are single peptide chains that have both DNA recognition and nuclease function in the same domain. In contrast to the TALEN, the megaTAL only requires the delivery of a single peptide chain for functional activity. An exemplary megaTAL protein specific for TCRα is provided as SEQ ID NO: 1 in FIG. 11.

Particular embodiments utilize zinc finger nucleases (ZFNs) as gene editing agents. ZFNs are a class of site-specific nucleases engineered to bind and cleave DNA at specific positions. ZFNs are used to introduce DSBs at a specific site in a DNA sequence which enables the ZFNs to target unique sequences within a genome in a variety of different cells. Moreover, subsequent to double-stranded breakage, homologous recombination or non-homologous end joining takes place to repair the DSB, thus enabling genome editing.

ZFNs are synthesized by fusing a zinc finger DNA-binding domain to a DNA cleavage domain. The DNA-binding domain includes three to six zinc finger proteins which are transcription factors. The DNA cleavage domain includes the catalytic domain of, for example, FokI endonuclease.

Guide RNA can be used, for example, with gene-editing agents such as CRISPR-Cas systems. CRISPR-Cas systems include CRISPR repeats and a set of CRISPR-associated genes (Cas).

The CRISPR repeats (clustered regularly interspaced short palindromic repeats) include a cluster of short direct repeats separated by spacers of short variable sequences of similar size as the repeats. The repeats range in size from 24 to 48 base pairs and have some dyad symmetry which implies the formation of a secondary structure, such as a hairpin, although the repeats are not truly palindromic. The spacers, separating the repeats, match exactly the sequences from prokaryotic viruses, plasmids, and transposons. The Cas genes encode nucleases, helicases, RNA-binding proteins, and a polymerase that unwind and cut DNA. Cas1, Cas2, and Cas9 are examples of Cas genes.

The source of CRISPR spacers indicate that CRISPR-Cas systems play a role in adaptive immunity in bacteria. There are at least three types of CRISPR-Cas immune system reactions, and Cas1 and Cas2 genes are involved in spacer acquisition in all three. Spacer acquisition, involving the capture and insertion of invading viral DNA into a CRISPR locus occurs in the first stage of adaptive immunity. More particularly, spacer acquisition begins with Cas1 and Cas2 recognizing invading DNA and cleaving a protospacer, which is ligated to the direct repeat adjacent to a leader sequence. Subsequently, single strand extension repairs take place and the direct repeat is duplicated.

The next stage of CRISPR-related adaptive immunity involves CRISPR RNA (crRNA) biogenesis, which occurs differently in each type of CRISPR-Cas system. In general, during this stage, the CRISPR transcript is cleaved by Cas genes to produce crRNAs. In the type I system, Cas6e/Cas6f cleaves the transcript. The type II system employs a trans-activating (tracr) RNA to form a dsRNA, which is cleaved by Cas9 and RNase III. The type III system uses a Cas6 homolog for cleavage.

In the final stage of CRISPR-related adaptive immunity, processed crRNAs associate with Cas proteins to form interference complexes. In type I and type II systems, the Cas proteins interact with protospacer adjacent motifs (PAMs), which are short 3-5 bp DNA sequences, for degradation of invading DNA, while the type III systems do not require interaction with a PAM for degradation. In the type III-B system, the crRNA basepairs with the mRNA, instead of the targeted DNA, for degradation.

CRISPR-Cas systems thus function as an RNAi-like immune system in prokaryotes. The CRISPR-Cas technology has been exploited to inactivate genes in human cell lines and cells. As an example, the CRISPR-Cas9 system, which is based on the type II system, has been used as an agent for genome editing.

The type II system requires three components: Cas9, crRNA, and tracrRNA. The system can be simplified by combining tracrRNA and crRNA into a single synthetic single guide RNA (sgRNA).

At least three different Cas9 nucleases have been developed for genome editing. The first is the wild type Cas9 which introduces DSBs at a specific DNA site, resulting in the activation of DSB repair machinery. DSBs can be repaired by the NHEJ pathway or by homology-directed repair (HDR) pathway. The second is a mutant Cas9, known as the Cas9D10A, with only nickase activity, which means that it only cleaves one DNA strand and does not activate NHEJ. Thus, the DNA repairs proceed via the HDR pathway only. The third is a nuclease-deficient Cas9 (dCas9) which does not have cleavage activity but is able to bind DNA. Therefore, dCas9 is able to target specific sequences of a genome without cleavage. By fusing dCas9 with various effector domains, dCas9 can be used either as a gene silencing or activation tool.

Numerous genes can be targeted for gene editing agents selectively delivered by the nanocarriers disclosed herein. Particular examples include targeting Shp1 phosphatase genes (e.g., SEQ ID NO: 2), PD1 receptor genes (e.g., SEQ ID NO: 3), TCRα genes (e.g., SEQ ID NO: 4); CCR5 genes (e.g., SEQ ID NO: 5) and/or CXCR4 genes (e.g., SEQ ID NO: 6).

Shp-1 (src homology region 2 domain-containing phosphatase-1; also known as tyrosine-protein phosphatase non-receptor type 6 (PTPN6)), is encoded by the PTPN6 gene in humans. The N-terminal portion of Shp-1 contains two Src homolog (SH2) domains, which act as protein phosphotyrosine binding domains interacting with other cellular components to modulate its interaction with substrates. Shp-1 plays a key role as a regulator of multiple signaling pathways involved in hematopoiesis, and interacts with various phospho-proteins involved in hematopoietic cell signaling. Shp-1 links growth factor receptors, such as the receptors for EPO, IL-3, GM-CSF, and M-CSF, and other signaling proteins through protein-tyrosine phosphorylation. Shp-1 also mediates inhibitory signals triggered by immunoglobulin γFc domains (Fc VRIIB1), NK cell inhibitory receptor, T cell receptor (TCR), B cell receptor (BCR), CD22, and CD72. There exist alternatively spliced variants of the PTPN6 gene, encoding distinct isoforms. Exemplary nucleic acid sequences encoding mammalian Shp-1s can be found at GenBank Accession Numbers: NM_080549, NM_053908.1, and NM_013545.

Particular embodiments disclosed herein include targeting Shp1 phosphatase genes to alter T cell signaling. Shp1 phosphatase activity limits the functional activity of high affinity T cell receptors, impairing therapeutic use of these receptors to target rare or low affinity tumor antigens. (Hebeisen M, et al. SHP-1 phosphatase activity counteracts increased T cell receptor affinity. *JCI.* 2013). In addition, Shp1 activity is linked to impaired anti-tumor activity of T cell therapeutic products in solid tumors. (Moon E K, et al. Multifactorial T-cell Hypofunction That Is Reversible Can Limit the Efficacy of Chimeric Antigen Receptor-Transduced Human T cells in Solid Tumors, *Clinical Cancer Research,* 2014) For these reasons, down-regulation of Shp1 can enhance specific recognition and functional activity of T cells and therapeutic T cell products.

PD1 (programmed cell death protein 1; also known as cluster of differentiation 279 (CD279)), is a cell surface receptor belonging to the immunoglobulin superfamily. It is expressed on the surface of activated T cells, B cells, and macrophages and is encoded by the PDCD gene in human. Structurally, PD-1 includes an extracellular IgV domain, a transmembrane region, and an intracellular tail. The intracellular tail includes two phosphorylation sites located in an immunoreceptor-tyrosine-based inhibitory motif and an immunoreceptor tyrosine based switch motif, suggesting that PD-1 is involved in negatively regulating TCR signals. PD-1 is an immune checkpoint. It negatively regulates the immune system by preventing the activation of T cells, which reduces autoimmunity and promotes self-tolerance. PD-1 achieves its function through promoting apoptosis in antigen specific T cells in lymph nodes while simultaneously reducing apoptosis in regulatory T cells (suppressor T cells). PD-1 binds the ligands PD-L1 and PD-L2. Exemplary nucleic acid sequences encoding mammalian PD-1s can be found at Genbank Accession Numbers: AY238517, NM_001106927, and KJ865858.

Particular embodiments disclosed herein include targeting PD1 receptor genes. PD1 antibody blockade has strong demonstrated therapeutic efficiency, but can also potentially lead to immune related adverse events affecting the gastrointestinal, hepatic, and endocrine systems as well as other organs. (Postow M A, Managing Immune Checkpoint-Blocking Antibody Side Effects, ASCO, 2015). By selectively removing or reducing PD1 receptor expression on infused therapeutic T cell products through gene editing, off target inflammatory side effects can be minimized while maintaining the enhanced in vivo activity of the infused T cells.

As previously indicated, T cell receptors (TCRs) are expressed on the surface of T lymphocytes that play a role in recognizing fragments of antigen as peptides bound to major histocompatibility complex (MHC) molecules. TCRα chain genes can be found at GenBank Accession Numbers: X04954, X72904.1, and L21699.1.

Particular embodiments disclosed herein include targeting TCRα chain genes. Expression of endogenous TCR can interfere with the expression of engineered T cell receptors, and mediate autoimmune or alloreactive responses. Targeting TCRα chain genes can improve expression of engineered T cell receptors, and allow for partial donor independence in T cell product manufacture.

CCR5 (chemokine receptor type 5; also known as CD195), is expressed on the surface of T cells, macrophages, dendritic cells, eosinophils, and microglia. It is encoded by the CCR5 gene in human. CCR5 is a G protein-coupled receptor belonging to the beta chemokine receptor family of integral protein.

Many forms of viruses, including HIV, use CCR5 as a co-receptor to enter host cells. CCR5 is designated as co-receptors because HIV entry requires the binding of its glycoprotein (gp120) to both CD4 and a co-receptor (CCR5) for entry into the host cell.

Accordingly one way to interfere with viral infection is to block or reduce expression of CCR5. Several CCR5 receptor antagonists have been developed to interfere with the interaction between CCR5 and HIV's envelope glycoprotein gp120. Examples of such antagonists include PRO140 (Progenics), Vicriviroc (Schering Plough), Aplaviroc (GlaxoSmithKline), and Maraviroc (Pfizer). Examples of ligands for CCR5 include RANTES, MIP-1β, and MIP-1α. These ligands are able to suppress HIV-1 infection in vitro. Exemplary nucleic acid sequences encoding mammalian CCR5 can be found at Genbank Accession Numbers: U66285, FJ573195, and AF022990.

Particular embodiments disclosed herein include targeting CCR5 genes to reduce viral entry, such as HIV entry into cells.

CXCR4 (CXC chemokine receptor type 4; also known as fusin or CD184) is encoded by the CXCR4 gene in humans. Like CCR5, CXCR4 is a co-receptor for viral entry into cells, including HIV entry into cells. CXCR4 is also expressed in many types of cancer cells. CXCR4 is also an alpha-chemokine receptor specific for stromal-derived-factor-1 (SDF-1, or CXCL12), a molecule with chemotactic activity for lymphocytes. SDF-1 suppresses replication of T-tropic HIV-1 isolates. Exemplary nucleic acid sequences encoding mammalian CCR4 can be found at Genbank Accession Numbers: NM_001008540, NM_022205, and NM_009911.

Particular embodiments disclosed herein include targeting CXCR4 genes to reduce viral entry, such as HIV entry into cells.

As indicated, particular embodiments disclosed herein rely on expression of phenotype-altering proteins. Phenotype-altering proteins can regulate, for example, cell differentiation, viability or trafficking. Examples of phenotype-altering proteins include, for example, FOXO1, LKB1, TERT, CCR2b and CCR4.

FOXO1 (Forkhead box protein 01 or forkhead in rhabdomyosarcoma) is a transcription factor that is encoded by the FOXO1 gene in humans (e.g., SEQ ID NO: 7). FOXO1 is selectively incorporated into the genetic program that regulates memory CD8+ T cell responses to infection (Kim et al., Immunity, 2013, 39(2): 286-97). Kim et al. showed that mice lacking FOXO1 in activated CD8+ T cell have defective secondary, but not primary, responses to *Listeria monocytogenes* infection. Id. Memory-precursor T cells expressed higher amounts of FOXO1, as compared to short-lived effector T cells, which promoted the generation and maintenance of memory-precursor T cells. Id. It was also shown that transcription factor Tcf7 and chemokine receptor CCR7 interacts with FOXO1. Id.

FOXO1 also plays a role in facilitating effector-to-memory transition and functional maturation of memory CD4 and CD8 T cells (Tejara et al. J. of Immunology, 2013, 191(1):187-199). Although FOXO1 is not required for differentiation of effector cells, memory CD8 T cells displayed features of senescence in the absence of FOXO1, which led to impaired recall responses and poor protective immunity. Id. Exemplary nucleic acid sequences encoding mammalian FOXO1s can be found at GenBank Accession Numbers: BC021981, NM_001191846, and NM_019739. Particular embodiments disclosed herein include expression of FOXO1.

LKB1 (Liver kinase B1, also known as renal carcinoma antigen NY-REN-19 or serine/threonine kinase 11 (STK11)), is a serine/threonine protein kinase encoded by the STK11 gene in humans. LKB1 is a critical regulator of T cell development, viability, activation, and metabolism (MacIver, J. Immunol. 2011, 187(8): 4187-4198). LKB1-deficient T cells exhibit defects in cell proliferation and viability, and altered glycolytic and lipid metabolism. Id. LKB1 also activates a group of kinases including AMPK and AMPK related kinases that suppress growth and proliferation when energy nutrients are scarce. AMPK, AMPK-related kinases, and LKB1 play an important role in maintaining cell polarity thereby inhibiting growth of tumor cells. Exemplary nucleic acid sequences encoding mammalian LKB1s can be found at GenBank Accession Numbers: NM_000455, NM_001108069, and AB015801. Particular embodiments disclosed herein include expression of LKB1. An exemplary LKB1 sequence is SEQ ID NO: 8.

Transcription factor 7, T cell specific (TCF7) is a transcriptional activator that plays an important role in lymphocyte differentiation. This gene is expressed predominantly in T-cells. The encoded protein can bind an enhancer element and activate the CD3E gene, and it also may repress the CTNNB1 and TCF7L2 genes through a feedback mechanism. An exemplary nucleic acid sequence encoding human TCF7 can be found at NCBI Reference Sequence: NC_000005.10. Particular embodiments disclosed herein include expression of TCF7.

Eomesodermin (EOMES) is a transcription factor that is crucial for embryonic development of mesoderm and the central nervous system in vertebrates. It is also involved in the differentiation of effector CD8+ T cells. An exemplary nucleic acid sequence encoding human EOMES can be found at NCBI Reference Sequence: NC_000003.12 and SEQ ID NO: 9. Particular embodiments disclosed herein include expression of EOMES.

Inhibitor of DNA binding 2, HLH protein (ID2) is a transcriptional regulator that contains a helix-loop-helix (HLH) domain but not a basic domain. Members of the inhibitor of DNA binding family inhibit the functions of basic helix-loop-helix transcription factors in a dominant-negative manner by suppressing their heterodimerization partners through the HLH domains. ID2 plays a role in negatively regulating cell differentiation. An exemplary nucleic acid sequence encoding human ID2 can be found at NCBI Reference Sequence: NC_000002.12 and SEQ ID NO: 10. Particular embodiments disclosed herein include expression of ID2.

Particular embodiments disclosed herein include altering differentiation of T cells through expression of transcription factors and signaling molecules such as FOXO1, LKB1, TCF7, EOMES, and/or ID2 in order produce specified cellular phenotypes such as TEM, TCM, or TREG cells as required for therapeutic efficiency. TCM, and TEM cells have demonstrated enhanced therapeutic efficiency in anti-tumor models.

Telomerases are RNA-dependent polymerases that lengthen telomeres in DNA strands, thereby allowing senescent cells to become potentially immortal instead of post-mitotic and apoptotic. The human telomerase complex includes two molecules of human telomerase reverse transcriptase (TERT), telomerase RNA (TR or TERC), and dyskerin (DKC1). TERT, together with TERC, catalyzes the addition of nucleotides in a TTAGGG sequence to the ends of a telomere. The addition of the repetitive DNA sequences prevents degradation of the chromosomal ends following cell division via mitosis. Thus, telomerase repairs and elongates the telomeres enabling senescent cells to divide and exceed the Hayflick limit of between 50-70 cell divisions. Exemplary nucleic acid sequences encoding mammalian TERTs can be found at GenBank Accession Numbers: NM_198253, NM_053423, NM_009354; and SEQ ID NO: 11.

Normal somatic cells do not have detectable telomerase activity. Particular embodiments disclosed herein include expression of TERT. Studies have shown that the in vivo persistence and antitumor efficacy of adoptively transferred T cells can be enhanced through the delivery of TERT mRNA (using electroporation, Cell Discovery (2015) 1, 15040).

Malignant tumor cells, however, have been found to have increased telomerase activity. Accordingly, gene-editing tools as described above could be used to target TERT in malignant cancers.

CCR2b (C—C chemokine receptor type 2 or CD192 (cluster of differentiation 192)) is a G-protein coupled receptor. In humans, CCR2 is encoded by the CCR2 gene. This gene encodes two isoforms of the receptor, CCR2a and CCR2b, by alternative splicing of a single gene.

CCR2b is related to MIP-1 (RANTES receptor) and is a receptor for monocyte chemoattractant protein-1 (MCP-1), a chemokine which mediates monocyte chemotaxis. CCR2 also binds MCP-2, MCP-3, and MCP-4 but with a lower affinity. CCR2a and CCR2b differ by their C-terminal tail. MCP-1 is a small chemokine belonging to the C—C chemokine family. MCP-1 is involved in recruiting monocytes, memory T cells, and dendritic cells to the sites of inflammation produced by either tissue injury or infection. MCP-1 is involved in monocyte infiltration in inflammatory diseases such as psoriasis, rheumatoid arthritis, atherosclerosis, as well as inflammatory response against tumors. Exemplary nucleic acid sequences encoding mammalian CCR2bs can be found at GenBank Accession Numbers: NM_001123396 and NM_009915, and SEQ ID NO: 12.

Particular embodiments disclosed herein include expression of CCR2b to enhance tumor trafficking of therapeutic T cells (J. Immunother. 2010 October; 33(8):780-8).

CCR4 (C—C chemokine receptor 4 or CD194 (cluster of differentiation 194)) belongs to the G-protein coupled receptor family. In human it is encoded by the CCR4 gene. CCR4 is a receptor for MCP-1, MIP-1, RANTES, TARC, and Macrophage-derived chemokine, which are CC chemokines. CC chemokines induce the migration of monocytes as well as other cells such as NK cells and dendritic cells. As an example, MCP-1 induces monocytes to leave the bloodstream and enter the surrounding tissue to become tissue macrophages. RANTES attracts T cells, eosinophils, and basophils. Accordingly, CCR4 and its ligands, the CC chemokines, regulate cell trafficking of various types of leukocytes. Exemplary nucleic acid sequences encoding mammalian CCR4s can be found at GenBank Accession Numbers: NM_005508, NM_133532, and NM_009916.2, and SEQ ID NO: 13.

Particular embodiments disclosed herein include expression of CCR4 to improve tumor homing and anti-tumor activity of therapeutic T cells (Blood. 2009 Jun. 18; 113 (25):6392-402).

Particular embodiments utilize nanocarriers disclosed herein to deliver the nucleic acid for expression by the selected cell wherein a use is independent of or in addition to a hit and run effect. In particular embodiments, such embodiments can enhance growth, survival, immune function and/or tumor cell targeting of a selected cell. Examples of genetic modifications include those allowing expression of a chimeric antigen receptor (CAR), a αβ T-cell receptor (or modification thereof), and/or pro-inflammatory cytokines. CAR modification and/or αβ T-cell receptor modifications allow modified lymphocytes to specifically target cell types.

In one aspect, genetically-modified lymphocytes can have improved tumor recognition, trigger increased native T-cell proliferation and/or cytokine production.

"Chimeric antigen receptors" or "CARs" refer to synthetically designed receptors including at least a binding domain and an effector domain and optionally a spacer domain and/or a transmembrane domain.

Binding domains can particularly include any peptide that specifically binds a marker on a targeted cell. Sources of binding domains include antibody variable regions from various species (which can be in the form of antibodies, sFvs, scFvs, Fabs, scFv-based grababody, or soluble VH domain or domain antibodies). These antibodies can form antigen-binding regions using only a heavy chain variable region, i.e., these functional antibodies are homodimers of heavy chains only (referred to as "heavy chain antibodies") (Jespers et al., *Nat. Biotechnol.* 22:1161, 2004; Cortez-Retamozo et al., *Cancer Res.* 64:2853, 2004; Baral et al., *Nature Med.* 12:580, 2006; and Barthelemy et al., *J. Biol. Chem.* 283:3639, 2008).

An alternative source of binding domains includes sequences that encode random peptide libraries or sequences that encode an engineered diversity of amino acids in loop regions of alternative non-antibody scaffolds, such as scTCR (see, e.g., Lake et al., *Int. Immunol.* 11:745, 1999; Maynard et al., *J. Immunol. Methods* 306:51, 2005; U.S. Pat. No. 8,361,794), fibrinogen domains (see, e.g., Weisel et al., *Science* 230:1388, 1985), Kunitz domains (see, e.g., U.S. Pat. No. 6,423,498), designed ankyrin repeat proteins (DARPins) (Binz et al., *J. Mol. Biol.* 332:489, 2003 and Binz et al., *Nat. Biotechnol.* 22:575, 2004), fibronectin binding domains (adnectins or monobodies) (Richards et al., *J. Mol. Biol.* 326:1475, 2003; Parker et al., *Protein Eng. Des. Selec.* 18:435, 2005 and Hackel et al. (2008) *J. Mol. Biol.* 381: 1238-1252), cysteine-knot miniproteins (Vita et al. (1995) *Proc. Nat'l. Acad. Sci.* (*USA*) 92:6404-6408; Martin et al. (2002) *Nat. Biotechnol.* 21:71, 2002 and Huang et al. (2005) *Structure* 13:755, 2005), tetratricopeptide repeat domains (Main et al., *Structure* 11:497, 2003 and Cortajarena et al., *ACS Chem. Biol.* 3:161, 2008), leucine-rich repeat domains (Stumpp et al., *J. Mol. Biol.* 332:471, 2003), lipocalin domains (see, e.g., WO 2006/095164, Beste et al., *Proc. Nat'l. Acad. Sci.* (*USA*) 96:1898, 1999 and Schönfeld et al., *Proc. Nat'l. Acad. Sci.* (*USA*) 106:8198, 2009), V-like domains (see, e.g., US Patent Application Publication No. 2007/0065431), C-type lectin domains (Zelensky and Gready, *FEBS J.* 272:6179, 2005; Beavil et al., *Proc. Nat'l.*

Acad. Sci. (USA) 89:753, 1992 and Sato et al., Proc. Nat'l. Acad. Sci. (USA) 100:7779, 2003), mAb² or Fcab™ (see, e.g., PCT Patent Application Publication Nos. WO 2007/098934; WO 2006/072620), armadillo repeat proteins (see, e.g., Madhurantakam et al., Protein Sci. 21: 1015, 2012; PCT Patent Application Publication No. WO 2009/040338), affilin (Ebersbach et al., J. Mol. Biol. 372: 172, 2007), affibody, avimers, knottins, fynomers, atrimers, cytotoxic T-lymphocyte associated protein-4 (Weidle et al., Cancer Gen. Proteo. 10:155, 2013) or the like (Nord et al., Protein Eng. 8:601, 1995; Nord et al., Nat. Biotechnol. 15:772, 1997; Nord et al., Euro. J. Biochem. 268:4269, 2001; Binz et al., Nat. Biotechnol. 23:1257, 2005; Boersma and Plückthun, Curr. Opin. Biotechnol. 22:849, 2011).

In particular embodiments, a binding domain is a single chain T cell receptor (scTCR) including $V_{\alpha/\beta}$ and $C_{\alpha/\beta}$ chains (e.g., $V_\alpha$-$C_\alpha$, $V_\beta$-$C_\beta$, $V_\alpha$-$V_\beta$) or including $V_\alpha$-$C_\alpha$, $V_\beta$-$C_\beta$, $V_\alpha$-$V_\beta$ pair specific for a target of interest (e.g., peptide-MHC complex).

Exemplary CARs express ligand binding domains targeting, for example, mesothelin, Her2, WT-1 and/or EGRF. An exemplary T-cell receptor modification targets melanoma-associated antigen (MAGE) A3 TCR.

The particular following cancers can be targeted by including within an extracellular component of a TCR or CAR a binding domain that binds the associated cellular marker(s):

| Targeted Cancer | Cellular Marker(s) |
|---|---|
| Prostate Cancer | PSMA, WT1, Prostate Stem Cell antigen (PSCA), SV40 T |
| Breast Cancer | HER2, ERBB2, ROR1 |
| Stem Cell Cancer | CD133 |
| Ovarian Cancer | L1-CAM, extracellular domain of MUC16 (MUC-CD), folate binding protein (folate receptor), Lewis Y, ROR1, mesothelin, WT-1 |
| Mesothelioma | mesothelin |
| Renal Cell Carcinoma | carboxy-anhydrase-IX (CAIX); |
| Melanoma | GD2 |
| Pancreatic Cancer | mesothelin, CEA, CD24, ROR1 |
| Lung Cancer | ROR1 |

Without limiting the foregoing, cellular markers also include A33; BAGE; Bcl-2; β-catenin; B7H4; BTLA; CA125; CA19-9; CD3, CD5; CD19; CD20; CD21; CD22; CD25; CD28; CD30; CD33; CD37; CD40; CD52; CD44v6; CD45; CD56; CD79b; CD80; CD81; CD86; CD123; CD134; CD137; CD151; CD171; CD276; CEA; CEACAM6; c-Met; CS-1; CTLA-4; cyclin B1; DAGE; EBNA; EGFR; EGFRvIII, ephrinB2; ErbB2; ErbB3; ErbB4; EphA2; estrogen receptor; FAP; ferritin; α-fetoprotein (AFP); FLT1; FLT4; folate-binding protein; Frizzled; GAGE; G250; GD-2; GHRHR; GHR; GITR; GM2; gp75; gp100 (Pmel 17); gp130; HLA; HER-2/neu; HPV E6; HPV E7; hTERT; HVEM; IGF1R; IL6R; KDR; Ki-67; Lewis A; Lewis Y; LIFRβ; LRP; LRPS; LTβR; MAGE; MART; mesothelin; MUC; MUC1; MUM-1-B; myc; NYESO-1; O-acetyl GD-2; O-acetyl GD3; OSMRβ; p53; PD1; PD-L1; PD-L2; PRAME; progesterone receptor; PSA; PSMA; PTCH1; RANK; ras; Robo1; RORI; survivin; TCRα; TCRβ; tenascin; TGFBR1; TGFBR2; TLR7; TLR9; TNFR1; TNFR2; TNFRSF4; TWEAK-R; TSTA tyrosinase; VEGF; and WT1.

Particular cancer cell cellular markers include:

| Cancer Antigen | Sequence |
|---|---|
| PSMA | MWNLLHETDSAVATARRPRWLCAGALVLAGGFFLLGFLFGWFIKSSNEATNITPKH NMKAFLDELKAENIKKFLYNFTQIPHLAGTEQNFQLAKQIQSQWKEFGLDSVELAH YDVLLSYPNKTHPNYISIINEDGNEIFNTSLFEPPPPGYENVSDIVPPFSAFSPQG MPEGDLVYVNYARTEDFPKLERDMKINCSGKIVIARYGKVFRGNKVKNAQLAGAKG VILYSDPADYFAPGVKSYPDGWNLPGGGVQRGNILNLNGAGDPLTPGYPANEYAYR RGIAEAVGLPSIPVHPIGYYDAQKLLEKMGGSAPPDSSWRGSLKVPYNVGPGFTGN FSTQKVKMHIHSTNEVTRIYNVIGTLRGAVEPDRYVILGGHRDSWVFGGIDPQSGA AVVHEIVRSFGTLKKEGWRPRRTILFASWDAEEFGLLGSTEWAEENSRLLQERGVA YINADSSIEGNYTLRVDCTPLMYSLVHNLTKELKSPDEGFEGKSLYESWTKKSPSP EFSGMPRISKLGSGNDFEVFFQRLGIASGRARYTKNWETNKFSGYPLYHSVYETYE LVEKFYDPMFKYHLTVAQVRGGMVFELANSIVLPFDCRDYAVVLRKYADKIYSISM KHPQEMKTYSVSFDSLFSAVKNFTEIASKFSERLQDFDKSNPIVLRMMNDQLMFLE RAFIDPLGLPDRPFYRHVIYAPSSHNKYAGESFPGIYDALFDIESKVDPSKAWGEV KRQIYVAAFTVQAAAETLSEVA (SEQ ID NO: 14) |
| PSCA | MKAVLLALLMAGLALQPGTALLCYSCKAQVSNEDCLQVENCTQLGEQCWTARIRAV GLLTVISKGCSLNCVDDSQDYYVGKKNITCCDTDLCNASGAHALQPAAAILALLPA LGLLLWGPGQL (SEQ ID NO: 15) |
| Mesothelin | MALPTARPLLGSCGTPALGSLLFLLFSLGWVQPSRTLAGETGQEAAPLDGVLANPP NISSLSPRQLLGFPCAEVSGLSTERVRELAVALAQKNVKLSTEQLRCLAHRLSEPP EDLDALPLDLLLFLNPDAFSGPQACTHFFSRITKANVDLLPRGAPERQRLLPAALA CWGVRGSLLSEADVRALGGLACDLPGRFVAESAEVLLPRLVSCPGPLDQDQQEAAR AALQGGGPPYGPPSTWSVSTMDALRGLLPVLGQPIIRSIPGIVAAWRQRSSRDPS WRQPERTILRPRFRREVEKTACPSGKKAREIDESLIFYKKWELEACVDAALLATQM DRVNAIPFTYEQLDVLKHKLDELYPQGYPESVIQHLGYLFLKMSPEDIRKWNVTSL ETLKALLEVNKGHEMSPQVATLIDRFVKGRGQLDKDTLDTLTAFYPGYLCSLSPEE LSSVPPSSIWAVRPQDLDTCDPRQLDVLYPKARLAFQNMNGSEYFVKIQSFLGGAP TEDLKALSQQNVSMDLATFMKLRTDAVLPLTVAEVQKLLGPHVEGLKAEERHRPVR DWILRQRQDDLDTLGLGLQGGIPNGYLVLDLSVQEALSGTPCLLGPGPVLTVLALL LASTLA (SEQ ID NO: 16) |
| CD19 | MPPPRLLFFLLFLTPMEVRPEEPLVVKVEEGDNAVLQCLKGTSDGPTQQLTWSRES PLKPFLKLSLGLPGLGIHMRPLASWLFIFNVSQQMGGFYLCQPGPPSEKAWQPGWT |

| Cancer Antigen | Sequence |
|---|---|
| | VNVEGSGELFRWNVSDLGGLGCGLKNRSSEGPSSPSGKLMSPKLYVWAKDRPEIWE<br>GEPPCVPPRDSLNQSLSQDLTMAPGSTLWLSCGVPPDSVSRGPLSWTHVHPKGPKS<br>LLSLELKDDRPARDMWVMETGLLLPRATAQDAGKYYCHRGNLTMSFHLEITARPVL<br>WHWLLRTGGWKVSAVTLAYLIFCLCSLVGILHLQRALVLRRKRKRMTDPTRRFFKV<br>TPPPGSGPQNQYGNVLSLPTPTSGLGRAQRWAAGLGGTAPSYGNPSSDVQADGALG<br>SRSPPGVGPEEEEGEGYEEPDSEEDSEFYENDSNLGQDQLSQDGSGYENPEDEPLG<br>PEDEDSFSNAESYENEDEELTQPVARTMDFLSPHGSAWDPSREATSLGSQSYEDMR<br>GILYAAPQLRSIRGQPGPNHEEDADSYENMDNPDGPDPAWGGGGRMGTWSTR<br>(SEQ ID NO: 17) |
| CD20 | MTTPRNSVNGTFPAEPMKGPIAMQSGPKPLFRRMSSLVGPTQSFFMRESKTLGAVQ<br>IMNGLFHIALGGLLMIPAGIYAPICVTVWYPLWGGIMYIISGSLLAATEKNSRKCL<br>VKGKMIMNSLSLFAAISGMILSIMDILNIKISHFLKMESLNFIRAHTPYINIYNCE<br>PANPSEKNSPSTQYCYSIQSLFLGILSVMLIFAFFQELVIAGIVENEWKRTCSRPK<br>SNIVLLSAEEKKEQTIEIKEEVVGLTETSSQPKNEEDIEIIPIQEEEEEETETNFP<br>EPPQDQESSPIENDSSP (SEQ ID NO: 18) |
| ROR1 | MHRPRRGTRPPLLALLAALLLAARGAAAQETELSVSAELVPTSSWNISSELNKDS<br>YLTLDEPMNNITTSLGQTAELHCKVSGNPPPTIRWFKNDAPVVQEPRRLSFRSTIY<br>GSRLRIRNLDTTDTGYFQCVATNGKEVVSSTGVLFVKFGPPPTASPGYSDEYEEDG<br>FCQPYRGIACARFIGNRTVYMESLHMQGEIENQITAAFTMIGTSSHLSDKCSQFAI<br>PSLCHYAFPYCDETSSVPKPRDLCRDECEILENVLCQTEYIFARSNPMILMRLKLP<br>NCEDLPQPESPEAANCIRIGIPMADPINKNHKCYNSTGVDYRGTVSVTKSGRQCQP<br>WNSQYPHTHTFTALRFPELNGGHSYCRNPGNQKEAPWCFTLDENFKSDLCDIPACD<br>SKDSKEKNKMEILYILVPSVAIPLAIALLFFFICVCRNNQKSSSAPVQRQPKHVRG<br>QNVEMSMLNAYKPKSKAKELPLSAVRFMEELGECAFGKIYKGHLYLPGMDHAQLVA<br>IKTLKDYNNPQQWTEFQQEASLMAELHHPNIVCLLGAVTQEQPVCMLFEYINQGDL<br>HEFLIMRSPHSDVGCSSDEDGTVKSSLDHGDFLHIAIQIAAGMEYLSSHFFVHKDL<br>AARNILIGEQLHVKISDLGLSREIYSADYYRVQSKSLLPIRWMPPEAIMYGKFSSD<br>SDIWSFGVVLWEIFSFGLQPYYGFSNQEVIEMVRKRQLLPCSEDCPPRMYSLMTEC<br>WNEIPSRRPRFKDIHVRLRSWEGLSSHTSSTTPSGGNATTQTTSLSASPVSNLSNP<br>RYPNYMFPSQGITPQGQIAGFIGPPIPQNQRFIPINGYPIPPGYAAFPAAHYQPTG<br>PPRVIQHCPPPKSRSPSSASGSTSTGHVTSLPSSGSNQEANIPLLPHMSIPNHPGG<br>MGITVFGNKSQKPYKIDSKQASLLGDANIHGHTESMISAEL<br>(SEQ ID NO: 19) |
| WT1 | MGHHHHHHHHHSSGHIEGRHMRRVPGVAPTLVRSASETSEKRPFMCAYPGCNKRY<br>FKLSHLQMHSRKHTGEKPYQCDFKDCERRFFRSDQLKRHQRRHTGVKPFQCKTCQR<br>KFSRSDHLKTHTRTHTGEKPFSCRWPSCQKKFARSDELVRHHNMHQRNMTKLQLAL<br>(SEQ ID NO: 20) |
| CD33 | DPNFWLQVQESVTVQEGLCVLVPCTFFHPIPYYDKNSPVHGYWFREGAIISRDSPV<br>ATNKLDQEVQEETQGRFRLLGDPSRNNCSLSIVDARRRDNGSYFFRMERGSTKYSY<br>KSPQLSVHVTDLTHRPKILIPGTLEPGHSKNLTCSVSWACEQGTPPIFSWLSAAPT<br>SLGPRTTHSSVLIITPRPQDHGTNLTCQVKFAGAGVTTERTIQLNVTYVPQNPTTG<br>IFPGDGSGKQETRAGVVHGAIGGAGVTALLALCLCLIFFIVKTHRRKAARTAVGRN<br>DTHPTTGSASPKHQKKSKLHGPTETSSCSGAAPTVEMDEELHYASLNFHGMNPSKD<br>TSTEYSEVRTQ (SEQ ID NO: 21) |

In particular embodiments, the binding domain can bind PSMA. A number of antibodies specific for PSMA are known to those of skill in the art and can be readily characterized for sequence, epitope binding, and affinity. In particular embodiments, the binding domain can include anti-Mesothelin ligands (associated with treating ovarian cancer, pancreatic cancer, and mesothelioma); anti-WT-1 (associated with treating leukemia and ovarian cancer); anti-HIV-gag (associated with treating HIV infections); or anti-cytomegalovirus (associated with treating CMV diseases such as herpes virus).

In particular embodiments, the binding domain can bind CD19. In particular embodiments, a binding domain is a single chain Fv fragment (scFv) that includes VH and VL regions specific for CD19. In particular embodiments, the $V_H$ and $V_L$ regions are human. Exemplary $V_H$ and $V_L$ regions include the segments of anti-CD19 specific monoclonal antibody FMC63. In particular embodiments, the scFV is a human or humanized scFV including a variable light chain including a CDRL1 sequence of RASQDISKYLN (SEQ ID NO: 22), CDRL2 sequence of SRLHSGV (SEQ ID NO: 23), and a CDRL3 sequence of GNTLPYTFG (SEQ ID NO: 24). In particular embodiments, the scFV is a human or humanized ScFv including a variable heavy chain including CDRHI sequence of DYGVS (SEQ ID NO: 25), CDRH2 sequence of VTWGSETTYYNSALKS (SEQ ID NO: 26), and a CDRH3 sequence of YAMDYWG (SEQ ID NO: 27). Other CD19-targeting antibodies such as SJ25C1 and HD37 are known. (SJ25C1: Bejcek et al. Cancer Res 2005, PMID 7538901; HD37: Pezutto et al. JI 1987, PMID 2437199). SEQ ID NO: 28 provides the anti-CD19 scFv (VH-VL) FMC63 DNA sequence and SEQ ID NO: 29 provides the anti-CD19 scFv (VH-VL) FMC63 amino acid sequence.

In particular embodiments, the binding domain can bind RORI. In particular embodiments, the scFV is a human or humanized scFv including a variable light chain including a CDRL1 sequence of ASGFDFSAYYM (SEQ ID NO: 30), CDRL2 sequence of TIYPSSG (SEQ ID NO: 31), and a CDRL3 sequence of ADRATYFCA (SEQ ID NO: 32). In particular embodiments, the scFV is a human or humanized scFv including a variable heavy chain including CDRH1 sequence of DTIDWY (SEQ ID NO: 33), CDRH2 sequence of VQSDGSYTKRPGVPDR (SEQ ID NO: 34), and a CDRH3 sequence of YIGGYVFG (SEQ ID NO: 35). A number of antibodies specific for RORI are known to those of skill in the art and can be readily characterized for sequence, epitope binding, and affinity.

In particular embodiments, the binding domain includes a sequence that is at least 90%, at least 91%, at least 92%, at least 93%, at least 94%, at least 95%, at least 96%, at least 97%, at least 98%, at least 99%, at least 99.5%, or 100% identical to an amino acid sequence of a TCR Vα, Vβ, Cα, or Cβ, wherein each CDR includes zero changes or at most one, two, or three changes, from a TCR or fragment or derivative thereof that specifically binds to target of interest.

In particular embodiments, the binding domain Vα, Vβ, Cα, or Cβ region can be derived from or based on a Vα, Vβ, Cα, or Cβ of a known TCR (e.g., a high-affinity TCR) and contains one or more (e.g., 2, 3, 4, 5, 6, 7, 8, 9, 10) insertions, one or more (e.g., 2, 3, 4, 5, 6, 7, 8, 9, 10) deletions, one or more (e.g., 2, 3, 4, 5, 6, 7, 8, 9, 10) amino acid substitutions (e.g., conservative amino acid substitutions or non-conservative amino acid substitutions), or a combination of the above-noted changes, when compared with the Vα, Vβ, Cα, or Cβ of a known TCR. An insertion, deletion or substitution may be anywhere in a Vα, Vβ, Cα, or Cβ region, including at the amino- or carboxy-terminus or both ends of these regions, provided that each CDR includes zero changes or at most one, two, or three changes and provided a binding domain containing a modified Vα, Vβ, Cα, or Cβ region can still specifically bind its target with an affinity similar to wild type.

In particular embodiments, a binding domain VH region of the present disclosure can be derived from or based on a VH of a known monoclonal antibody and can contain one or more (e.g., 2, 3, 4, 5, 6, 7, 8, 9, 10) insertions, one or more (e.g., 2, 3, 4, 5, 6, 7, 8, 9, 10) deletions, one or more (e.g., 2, 3, 4, 5, 6, 7, 8, 9, 10) amino acid substitutions (e.g., conservative amino acid substitutions or non-conservative amino acid substitutions), or a combination of the above-noted changes, when compared with the $V_H$ of a known monoclonal antibody. An insertion, deletion or substitution may be anywhere in the $V_H$ region, including at the amino- or carboxy-terminus or both ends of this region, provided that each CDR includes zero changes or at most one, two, or three changes and provided a binding domain containing the modified $V_H$ region can still specifically bind its target with an affinity similar to the wild type binding domain.

In particular embodiments, a VL region in a binding domain of the present disclosure is derived from or based on a VL of a known monoclonal antibody and contains one or more (e.g., 2, 3, 4, 5, 6, 7, 8, 9, 10) insertions, one or more (e.g., 2, 3, 4, 5, 6, 7, 8, 9, 10) deletions, one or more (e.g., 2, 3, 4, 5, 6, 7, 8, 9, 10) amino acid substitutions (e.g., conservative amino acid substitutions), or a combination of the above-noted changes, when compared with the VL of the known monoclonal antibody. An insertion, deletion or substitution may be anywhere in the VL region, including at the amino- or carboxy-terminus or both ends of this region, provided that each CDR includes zero changes or at most one, two, or three changes and provided a binding domain containing the modified VL region can still specifically bind its target with an affinity similar to the wild type binding domain.

In particular embodiments, a binding domain includes or is a sequence that is at least 90%, at least 91%, at least 92%, at least 93%, at least 94%, at least 95%, at least 96%, at least 97%, at least 98%, at least 99%, at least 99.5%, or 100% identical to an amino acid sequence of a light chain variable region (VL) or to a heavy chain variable region (VH), or both, wherein each CDR includes zero changes or at most one, two, or three changes, from a monoclonal antibody or fragment or derivative thereof that specifically binds to target of interest.

Effector domains are capable of transmitting functional signals to a cell. In particular embodiments, an effector domain will directly or indirectly promote a cellular response by associating with one or more other proteins that directly promote a cellular response. Effector domains can provide for activation of at least one function of a transduced lymphocyte expressing the CAR upon binding to the marker expressed on a targeted cell. Activation of the lymphocyte can include one or more of proliferation, differentiation, activation or other effector functions. In particular embodiments, the delivered polynucleotide encodes for the effector domain.

An effector domain may include one, two, three or more receptor signaling domains, intracellular signaling domains, costimulatory domains, or combinations thereof. Any intracellular effector domain, costimulatory domain or both from any of a variety of signaling molecules (e.g., signal transduction receptors) may be used in the CARs of this disclosure.

Exemplary effector domains include those from 4-1BB, CD3ε, CD3δ, CD3ζ, CD27, CD28 (e.g., SEQ ID NO: 36), CD79A, CD79B, CARD11, DAP10, FcRα, FcRβ, FcRγ, Fyn, HVEM, ICOS, Lck, LAG3, LAT, LRP, NOTCH1, Wnt, NKG2D, OX40, ROR2, Ryk, SLAMF1, SIp76, pTα, TCRα, TCRβ, TRIM, Zap70, PTCH2, or any combination thereof.

T cell activation can be said to be mediated by two distinct classes of cytoplasmic signaling sequence: those that initiate antigen-dependent primary activation and provide a T cell receptor like signal (primary cytoplasmic signaling sequences) and those that act in an antigen-independent manner to provide a secondary or co-stimulatory signal (secondary cytoplasmic signaling sequences). Primary cytoplasmic signaling sequences that act in a stimulatory manner may contain signaling motifs which are known as receptor tyrosine-based activation motifs or iTAMs. Examples of iTAM containing primary cytoplasmic signaling sequences include those derived from CD3 zeta, FeR gamma, CD3 gamma, CD3 delta, CD3 epsilon, CD5, CD22, CD79a, CD79b, and CD66d.

In particular embodiments, an effector domain includes a cytoplasmic portion that associates with a cytoplasmic signaling protein, wherein the cytoplasmic signaling protein is a lymphocyte receptor or signaling domain thereof, a protein including a plurality of ITAMs, a costimulatory factor, or any combination thereof.

Examples of intracellular signaling domains include the cytoplasmic sequences of the CD3 zeta chain, and/or co-receptors that act in concert to initiate signal transduction following CAR engagement, as well as any derivative or variant of these sequences and any synthetic sequence that has the same functional capability. In particular embodiments, an intracellular signaling domain of a CAR can be designed to include an intracellular signaling domain combined with any other desired cytoplasmic domain(s). For example, the intracellular signaling domain of a CAR can include an intracellular signaling domain and a costimulatory signaling region. The costimulatory signaling region refers to a portion of the CAR including the intracellular domain of a costimulatory molecule. A costimulatory molecule is a cell surface molecule other than the expressed marker ligand that is required for a response of lymphocytes to a marker. Examples of such molecules include CD27, CD28, 4-1BB (CD 137), OX40, CD30, CD40, lymphocyte function-associated antigen-1 (LFA-1), CD2, CD7, LIGHT, NKG2C, B7-H3, and a ligand that specifically binds with CD83.

Spacer regions can be customized for individual markers on targets to optimize target recognition. In particular embodiments, a spacer length can be selected based upon the location of a marker epitope, affinity of an antibody for the epitope, and/or the ability of the lymphocytes expressing the CAR to proliferate in vitro and/or in vivo in response to marker recognition.

Typically a spacer region is found between the binding domain and a transmembrane domain of the CAR. Spacer regions can provide for flexibility of the binding domain and allows for high expression levels in the modified cells. In particular embodiments, a spacer region can have at least 10 to 250 amino acids, at least 10 to 200 amino acids, at least 10 to 150 amino acids, at least 10 to 100 amino acids, at least 10 to 50 amino acids or at least 10 to 25 amino acids and including any integer between the endpoints of any of the listed ranges. particular embodiments, a spacer region has 250 amino acids or less; 200 amino acids or less, 150 amino acids or less; 100 amino acids or less; 50 amino acids or less; 40 amino acids or less; 30 amino acids or less; 20 amino acids or less; or 10 amino acids or less.

In particular embodiments, spacer regions can be derived from a hinge region of an immunoglobulin like molecule, for example all or a portion of the hinge region from a human IgG1, human IgG2, a human IgG3, or a human IgG4. Hinge regions can be modified to avoid undesirable structural interactions such as dimerization. In particular embodiments, all or a portion of a hinge region can be combined with one or more domains of a constant region of an immunoglobulin. For example, a portion of a hinge region can be combined with all or a portion of a CH2 or CH3 domain or variant thereof.

CARs disclosed herein can also include transmembrane domains. In particular embodiments, the CAR polynucleotide encodes the transmembrane domain. The transmembrane domain provides for anchoring of the CAR in the lymphocyte membrane. The transmembrane domain may be derived either from a natural or a synthetic source. When the source is natural, the domain may be derived from any membrane-bound or transmembrane protein.

Transmembrane regions include at least the transmembrane region(s) of) the alpha, beta or zeta chain of the T-cell receptor, CD28, CD3, CD45, CD4, CD5, CD9, CDl6, CD22; CD33, CD37, CD64, CD80, CD86, CDl34, CDl37 and CD154. In particular embodiments, synthetic or variant transmembrane domains include predominantly hydrophobic residues such as leucine and valine.

In particular embodiments, the CAR includes a P28z fusion receptor composed of a single-chain antibody (scFv) specific for the extracellular domain of PSMA (J591) combined with CD28 and CD3 cytoplasmic signaling domains. In particular embodiments, the CAR includes a P28z CAR of SEQ ID NO: 37. SEQ ID NO: 37 includes murine components. Amino acid positions 1-797 include the anti-PSMA scFv (J592) whereas positions 797-1477 include the murine CD8 transmembrane domain, murine CD28 signaling domain and the murine CD3zeta signaling domain. Any P28z domain can be individually replaced with optimized domains. In particular embodiments, the transmembrane domain and signaling domains within positions 797-1477 of SEQ ID NO: 37 can be particularly replaced with domains optimized for use in humans or other animals. In particular embodiments, any whole or portion of a binding domain, any whole or portion of an effector domain, any whole or portion of a spacer domain and/or any whole or portion of a transmembrane domain can be optimized for use in humans or other animals. In particular embodiments, the P28z CAR is optimized for use in humans. When optimized for humans, the P28z CAR can have lowered immunogenicity in humans and have a lower number of non-immunogenic epitopes compared to non-human antibodies.

In particular embodiments, ROR1-specific and CD19-specific CARs can be constructed using VL and VH chain segments of the 2A2, R12, and R11 mAhs (ROR1) and FMC63 mAb (CD19). Variable region sequences for R11 and R12 are provided in Yang et al, Plos One 6(6):e21018, Jun. 15, 2011. Each scFV can be linked by a $(Gly_4Ser)_3$ (SEQ ID NO: 38) protein to a spacer domain derived from IgG4-Fc (UniProt Database: P01861, SEQ ID NO: 39) including either 'Hinge-CH2-CH3' (229 AA, SEQ ID NO: 40), 'Hinge-CH3' (119 AA, SEQ ID NO: 41) or 'Hinge' only (12 AA, SEQ ID NO: 42) sequences. All spacers can contain a S→P substitution within the 'Hinge' domain located at position 108 of the native IgG4-Fc protein, and can be linked to the 27 AA transmembrane domain of human CD28 (SEQ ID NO: 43, for an exemplary full-length CD28 see UniProt: P10747) and to an effector domain signaling module including either (i) the 41 AA cytoplasmic domain of human CD28 with an LL→GG substitution located at positions 186-187 of the native CD28 protein (SEQ ID NO: 44) or (ii) the 42 AA cytoplasmic domain of human 4-1BB (UniProt: Q07011, SEQ ID NO: 45), each of which can be linked to the 112 AA cytoplasmic domain of isoform 3 of human CD3ζ (UniProt: P20963, SEQ ID NO: 46). The construct encodes a T2A ribosomal skip element (SEQ ID NO: 47) and a tEGFR sequence (SEQ ID NO: 48) downstream of the chimeric receptor. tEGFR can be replaced or supplemented with a tag cassette binding a sequence, such as STREP TAG® II (SEQ ID NO: 49), Myc tag (SEQ ID NO: 50), V5 tag (SEQ ID NO: 51), FLAG® tag (SEQ ID NO: 52), His tag, or other peptides or molecules as disclosed herein. Codon-optimized gene sequences encoding each transgene can be synthesized (Life Technologies) and cloned into the epHIV7 lentiviral vector using NheI and Not1 restriction sites. The epHIV7 lentiviral vector can be derived from the pHIV7 vector by replacing the cytomegalovirus promoter of pHIV7 with an EF-1 promoter. ROR1-chimeric receptor, CD19-chimeric receptor, tEGFR, or tag cassette-encoding lentiviruses can be produced in 293T cells using the packaging vectors pCHGP-2, pCMV-Rev2 and pCMV-G, and CALPHOS® transfection reagent (Clontech).

HER2-specific chimeric receptors can be constructed using VL and VH chain segments of a HER2-specific mAb that recognizes a membrane proximal epitope on HER2, and the scFVs can be linked to IgG4 hinge/CH2/CH3, IgG4 hinge/CH3, and IgG4 hinge only extracellular spacer domains and to the CD28 transmembrane domain, 4-1BB and CD3 signaling domains.

A CD19 chimeric receptor can include a single chain variable fragment corresponding to the sequence of the CD19-specific mAb FMC63 (scFv: VL-VH), a spacer derived from IgG4-Fc including either the 'Hinge-CH2-CH3' domain (229 AA, long spacer) or the 'Hinge' domain only (12 AA, short spacer), and a signaling module of CD3ζ with membrane proximal CD28 or 4-1BB costimulatory domains, either alone or in tandem. The transgene cassette can include a truncated EGFR (tEGFR) downstream from the chimeric receptor gene and be separated by a cleavable T2A element, to serve as a tag sequence for transduction, selection and in vivo tracking for chimeric receptor-modified cells. tEGFR can be replaced or supplemented with a tag cassette binding a ExoCBM, such as STREP TAG® II (SEQ ID NO: 49), Myc tag (SEQ ID NO: 50), V5 tag (SEQ ID NO: 51), FLAG® tag (SEQ ID NO: 52), His tag, or other peptides or molecules as disclosed herein.

Different potential CAR nucleic acid constructs that encode different ligand binding domains, different spacer region lengths, different intracellular binding domains and/or different transmembrane domains, can be tested in vivo (in an animal model) and/or in vitro to identify CARs with improved function over non-genetically modified lymphocytes and/or other CARs. In particular embodiments CAR are expressed independently of or in addition to a hit and run effect described herein.

The size of the nanocarriers disclosed herein can vary over a wide range and can be measured in different ways. For example, the nanocarriers of the present disclosure can have a minimum dimension of 100 nm. The nanocarriers of the present disclosure can also have a minimum dimension of equal to or less than 500 nm, less than 150 nm, less than 100 nm, less than 90 nm, less than 80 nm, less than 70 nm, less than 60 nm, less than 50 nm, less than 40 nm, less than 30 nm, less than 20 nm, or less than 10 nm. In particular embodiments, the nanocarriers can have a minimum dimension ranging between 5 nm and 500 nm, between 10 nm and 100 nm, between 20 nm and 90 nm, between 30 nm and 80 nm, between 40 nm and 70 nm, and between 40 nm and 60 nm. In particular embodiments, the dimension is the diameter of nanoparticles or coated nanoparticles. In particular embodiments, a population of nanocarriers of the present disclosure can have a mean minimum dimension of equal to or less than 500 nm, less than 100 nm, less than 90 nm, less than 80 nm, less than 70 nm, less than 60 nm, less than 50 nm, less than 40 nm, less than 30 nm, less than 20 nm, or less than 10 nm. In particular embodiments, a population of nanocarriers in a composition of the present disclosure can have a mean diameter ranging between 5 nm and 500 nm, between 10 nm and 100 nm, between 20 nm and 90 nm, between 30 nm and 80 nm, between 40 nm and 70 nm, and between 40 nm and 60 nm. Dimensions of the nanocarriers can be determined using, e.g., conventional techniques, such as dynamic lightscattering and/or electron microscopy.

Ex Vivo Methods of Use. The nanocarriers disclosed herein can be used in ex vivo cell manufacturing (see, e.g., FIGS. 1A and 4C). For example, the methods can include obtaining lymphocytes from a subject. Lymphocytes can, e.g., be obtained from a subject using any procedure generally known in the art.

Sources of lymphocytes include umbilical cord blood, placental blood, and peripheral blood. Methods regarding collection, anti-coagulation and processing, etc. of blood samples are known. See, for example, Alsever et al., 1941, N.Y. St. J. Med. 41:126; De Gowin, et al., 1940, J. Am. Med. Ass. 114:850; Smith, et al., 1959, J. Thorac. Cardiovasc. Surg. 38:573; Rous and Turner, 1916, J. Exp. Med. 23:219; and Hum, 1968, Storage of Blood, Academic Press, New York, pp. 26-160. Sources of lymphocytes also include bone marrow (see Kodo et al., 1984, J. Clin Invest. 73:1377-1384), embryonic cells, aortal-gonadal-mesonephros derived cells, lymph, liver, thymus, and spleen from age-appropriate donors. All collected samples of lymphocytes can be screened for undesirable components and discarded, treated, or used according to accepted current standards at the time.

In particular embodiments, no further collection or isolation of lymphocytes is needed before exposing the lymphocytes to nanocarriers disclosed herein because the nanocarriers selectively target selected cell types within a heterogeneous cell population.

In particular embodiments, it may be beneficial to engage in some further cell collection and isolation before exposure to nanocarriers disclosed herein. Lymphocytes can be collected and isolated from a sample using any appropriate technique. Appropriate collection and isolation procedures include magnetic separation; fluorescence activated cell sorting (FACS; Williams et al., 1985, J. Immunol. 135:1004; Lu et al., 1986, Blood 68(1):126-133); affinity chromatography; agents joined to a monoclonal antibody or used in conjunction with a monoclonal antibody; "panning" with antibody attached to a solid matrix (Broxmeyer et al., 1984, J. Clin. Invest. 73:939-953); selective agglutination using a lectin such as soybean (Reisner et al., 1980, Proc. Natl. Acad. Sci. U.S.A. 77:1164); etc. Particular embodiments can utilize limited isolation. Limited isolation refers to crude cell enrichment, for example, by removal of red blood cells and/or adherent phagocytes.

In particular embodiments, a subject sample (e.g., a blood sample) can be processed to select/enrich for CD8+ T cells or CD34+ HSPC using anti-CD8 or anti-CD34 antibodies directly or indirectly conjugated to magnetic particles in connection with a magnetic cell separator, for example, the CliniMACS® Cell Separation System (Miltenyi Biotec, Bergisch Gladbach, Germany). Similarly, lymphocytes expressing any of the markers described above (e.g., T-cell α chains; T-cell β chains; T-cell γ chains; T-cell δ chains; CCR7; CD1a; CD1b; CD1c; CD1d; CD3; CD4; CD5; CD7; CD8; CD11b; CD11c; CD16; CD19; CD20; CD21; CD22; CD25; CD28; CD34; CD35; CD40; CD39; CD45RA; CD45RO; CD46; CD52; CD56; CD62L; CD68; CD69; CD80; CD86; CD95; CD101; CD117; CD127; CD133; CD137 (4-1BB); CD148; CD163; CD209; DEC-205; F4/80; IL-4Rα; Sca-1; CTLA-4; GITR; GARP; LAP; granzyme B; LFA-1; transferrin receptor) can be isolated and enriched for using antibodies or other binding domains for these markers.

In particular embodiments, nanocarriers will be combined with lymphocytes before or at the early stages of an expansion procedure. This approach will allow modification of a smaller number of cells, with the modification being propagated throughout the cell population as it expands. In particular embodiments, following exposure to nanocarriers disclosed herein that provide a hit-and-run effect based on transient expression, expansion of the modified lymphocytes can occur.

Expansion can occur in the presence of one more growth factors, such as: angiopoietin-like proteins (Angptls, e.g., Angptl2, Angptl3, Angptl7, Angpt15, and Mfap4); erythropoietin; fibroblast growth factor-1 (FGF-1); Flt-3 ligand (Flt-3L); granulocyte colony stimulating factor (G-CSF); granulocyte-macrophage colony stimulating factor (GM-CSF); insulin growth factor-2 (IFG-2); interleukin-3 (IL-3); interleukin-6 (IL-6); interleukin-7 (IL-7); interleukin-11 (IL-11); stem cell factor (SCF; also known as the c-kit ligand or mast cell growth factor); thrombopoietin (TPO); and analogs thereof (wherein the analogs include any structural variants of the growth factors having the biological activity of the naturally occurring growth factor; see, e.g., WO 2007/1145227 and U.S. Patent Publication No. 2010/0183564).

In particular embodiments, the amount or concentration of growth factors suitable for expanding lymphocytes is the amount or concentration effective to promote proliferation. Lymphocyte populations are preferably expanded until a sufficient number of cells are obtained to provide for at least one infusion into a human subject, typically around $10^4$ cells/kg to $10^9$ cells/kg.

The amount or concentration of growth factors suitable for expanding lymphocytes depends on the activity of the growth factor preparation, and the species correspondence between the growth factors and lymphocytes, etc. Generally, when the growth factor(s) and lymphocytes are of the same species, the total amount of growth factor in the culture medium ranges from 1 ng/ml to 5 µg/ml, from 5 ng/ml to 1 µg/ml, or from 5 ng/ml to 250 ng/ml. In particular embodiments, the amount of growth factors can be in the range of 5-1000 or 50-100 ng/ml.

In particular embodiments, growth factors are present in an expansion culture condition at the following concentrations: 25-300 ng/ml SCF, 25-300 ng/ml Flt-3L, 25-100 ng/ml TPO, 25-100 ng/ml IL-6 and 10 ng/ml IL-3. In particular embodiments, 50, 100, or 200 ng/ml SCF; 50, 100, or 200 ng/ml of Flt-3L; 50 or 100 ng/ml TPO; 50 or 100 ng/ml IL-6; and 10 ng/ml IL-3 can be used.

Lymphocytes can be expanded in a tissue culture dish onto which an extracellular matrix protein such as fibronectin (FN), or a fragment thereof (e.g., CH-296 (Dao et. al., 1998, Blood 92(12):4612-21)) or RetroNectin® (a recombinant human fibronectin fragment; (Clontech Laboratories, Inc., Madison, Wis.) is bound.

Notch agonists can be particularly useful for expanding HSC. In particular embodiments, HSC can be expanded by exposing the HSC to an immobilized Notch agonist, and 50 ng/ml or 100 ng/ml SCF; to an immobilized Notch agonist, and 50 ng/ml or 100 ng/ml of each of Flt-3L, IL-6, TPO, and SCF; or an immobilized Notch agonist, and 50 ng/ml or 100 ng/ml of each of Flt-3L, IL-6, TPO, and SCF, and 10 ng/ml of IL-11 or IL-3.

As indicated, lymphocytes are obtained from a subject. In particular embodiments, the hit-and-run modified and expanded lymphocytes are re-introduced into the same subject from whom the original sample was derived in a therapeutically effective amount. In particular embodiments, the hit-and-run modified and expanded lymphocytes are administered to a different subject in a therapeutically effective amount. Therapeutically effective amounts are described in more detail elsewhere herein.

In these embodiments, hit-and-run modified and expanded lymphocytes can be formulated into cell-based compositions for administration to the subject. A cell-based composition refers to expanded cells prepared with a pharmaceutically acceptable carrier for administration to a subject. In particular embodiments, cell-based compositions are administered to a subject in need thereof as soon as is reasonably possible following the completion of expansion and formulation for administration.

In particular embodiments, it can be necessary or beneficial to cryopreserve a cell. The terms "frozen/freezing" and "cryopreserved/cryopreserving" can be used interchangeably. Freezing includes freeze drying.

As is understood by one of ordinary skill in the art, the freezing of cells can be destructive (see Mazur, P., 1977, Cryobiology 14:251-272) but there are numerous procedures available to prevent such damage. For example, damage can be avoided by (a) use of a cryoprotective agent, (b) control of the freezing rate, and/or (c) storage at a temperature sufficiently low to minimize degradative reactions. Exemplary cryoprotective agents include dimethyl sulfoxide (DMSO) (Lovelock and Bishop, 1959, Nature 183:1394-1395; Ashwood-Smith, 1961, Nature 190:1204-1205), glycerol, polyvinylpyrrolidine (Rinfret, 1960, Ann. N.Y. Acad. Sci. 85:576), polyethylene glycol (Sloviter and Ravdin, 1962, Nature 196:548), albumin, dextran, sucrose, ethylene glycol, i-erythritol, D-ribitol, D-mannitol (Rowe et al., 1962, Fed. Proc. 21:157), D-sorbitol, i-inositol, D-lactose, choline chloride (Bender et al., 1960, J. Appl. Physiol. 15:520), amino acids (Phan The Tran and Bender, 1960, Exp. Cell Res. 20:651), methanol, acetamide, glycerol monoacetate (Lovelock, 1954, Biochem. J. 56:265), and inorganic salts (Phan The Tran and Bender, 1960, Proc. Soc. Exp. Biol. Med. 104:388; Phan The Tran and Bender, 1961, in Radiobiology, Proceedings of the Third Australian Conference on Radiobiology, Ilbery ed., Butterworth, London, p. 59). In particular embodiments, DMSO can be used. Addition of plasma (e.g., to a concentration of 20-25%) can augment the protective effects of DMSO. After addition of DMSO, cells can be kept at 0° C. until freezing, because DMSO concentrations of 1% can be toxic at temperatures above 4° C.

In the cryopreservation of cells, slow controlled cooling rates can be critical and different cryoprotective agents (Rapatz et al., 1968, Cryobiology 5(1): 18-25) and different cell types have different optimal cooling rates (see e.g., Rowe and Rinfret, 1962, Blood 20:636; Rowe, 1966, Cryobiology 3(1):12-18; Lewis, et al., 1967, Transfusion 7(1): 17-32; and Mazur, 1970, Science 168:939-949 for effects of cooling velocity on survival of stem cells and on their transplantation potential). The heat of fusion phase where water turns to ice should be minimal. The cooling procedure can be carried out by use of, e.g., a programmable freezing device or a methanol bath procedure. Programmable freezing apparatuses allow determination of optimal cooling rates and facilitate standard reproducible cooling.

In particular embodiments, DMSO-treated cells can be pre-cooled on ice and transferred to a tray containing chilled methanol which is placed, in turn, in a mechanical refrigerator (e.g., Harris or Revco) at −80° C. Thermocouple measurements of the methanol bath and the samples indicate a cooling rate of 1° to 3° C./minute can be preferred. After at least two hours, the specimens can have reached a temperature of −80° C. and can be placed directly into liquid nitrogen (−196° C.).

After thorough freezing, the cells can be rapidly transferred to a long term cryogenic storage vessel. In particular embodiments, samples can be cryogenically stored in liquid nitrogen (−196° C.) or vapor (−1° C.). Such storage is facilitated by the availability of highly efficient liquid nitrogen refrigerators.

Further considerations and procedures for the manipulation, cryopreservation, and long term storage of cells, can be found in the following exemplary references: U.S. Pat. Nos. 4,199,022; 3,753,357; and 4,559,298; Gorin, 1986, Clinics In Haematology 15(1):19-48; Bone-Marrow Conservation, Culture and Transplantation, Proceedings of a Panel, Moscow, Jul. 22-26, 1968, International Atomic Energy Agency, Vienna, pp. 107-186; Livesey and Linner, 1987, Nature 327:255; Linner et al., 1986, J. Histochem. Cytochem. 34(9):1123-1135; Simione, 1992, J. Parenter. Sci. Technol. 46(6):226-32).

Following cryopreservation, frozen cells can be thawed for use in accordance with methods known to those of ordinary skill in the art. Frozen cells are preferably thawed quickly and chilled immediately upon thawing. In particular embodiments, the vial containing the frozen cells can be immersed up to its neck in a warm water bath; gentle rotation will ensure mixing of the cell suspension as it thaws and increase heat transfer from the warm water to the internal ice mass. As soon as the ice has completely melted, the vial can be immediately placed on ice.

In particular embodiments, methods can be used to prevent cellular clumping during thawing. Exemplary methods include: the addition before and/or after freezing of DNase (Spitzer et al., 1980, Cancer 45:3075-3085), low molecular weight dextran and citrate, hydroxyethyl starch (Stiff et al., 1983, Cryobiology 20:17-24), etc.

As is understood by one of ordinary skill in the art, if a cryoprotective agent that is toxic to humans is used, it should be removed prior to therapeutic use. DMSO has no serious toxicity.

Exemplary carriers and modes of administration of cells are described at pages 14-15 of U.S. Patent Publication No. 2010/0183564. Additional pharmaceutical carriers are described in Remington: The Science and Practice of Pharmacy, 21st Edition, David B. Troy, ed., Lippicott Williams & Wilkins (2005).

In particular embodiments, cells can be harvested from a culture medium, and washed and concentrated into a carrier in a therapeutically-effective amount. Exemplary carriers include saline, buffered saline, physiological saline, water, Hanks' solution, Ringer's solution, Nonnosol-R (Abbott Labs), Plasma-Lyte A® (Baxter Laboratories, Inc., Morton Grove, Ill.), glycerol, ethanol, and combinations thereof.

In particular embodiments, carriers can be supplemented with human serum albumin (HSA) or other human serum components or fetal bovine serum. In particular embodiments, a carrier for infusion includes buffered saline with 5% HAS or dextrose. Additional isotonic agents include polyhydric sugar alcohols including trihydric or higher sugar alcohols, such as glycerin, erythritol, arabitol, xylitol, sorbitol, or mannitol.

Carriers can include buffering agents, such as citrate buffers, succinate buffers, tartrate buffers, fumarate buffers, gluconate buffers, oxalate buffers, lactate buffers, acetate buffers, phosphate buffers, histidine buffers, and/or trimethylamine salts.

Stabilizers refer to a broad category of excipients which can range in function from a bulking agent to an additive which helps to prevent cell adherence to container walls. Typical stabilizers can include polyhydric sugar alcohols; amino acids, such as arginine, lysine, glycine, glutamine, asparagine, histidine, alanine, ornithine, L-leucine, 2-phenylalanine, glutamic acid, and threonine; organic sugars or sugar alcohols, such as lactose, trehalose, stachyose, mannitol, sorbitol, xylitol, ribitol, myoinisitol, galactitol, glycerol, and cyclitols, such as inositol; PEG; amino acid polymers; sulfur-containing reducing agents, such as urea, glutathione, thioctic acid, sodium thioglycolate, thioglycerol, alpha-monothioglycerol, and sodium thiosulfate; low molecular weight polypeptides (i.e., <10 residues); proteins such as HSA, bovine serum albumin, gelatin or immunoglobulins; hydrophilic polymers such as polyvinylpyrrolidone; monosaccharides such as xylose, mannose, fructose and glucose; disaccharides such as lactose, maltose and sucrose; trisaccharides such as raffinose, and polysaccharides such as dextran.

Where necessary or beneficial, cell-based compositions can include a local anesthetic such as lidocaine to ease pain at a site of injection.

Exemplary preservatives include phenol, benzyl alcohol, meta-cresol, methyl paraben, propyl paraben, octadecyldimethylbenzyl ammonium chloride, benzalkonium halides, hexamethonium chloride, alkyl parabens such as methyl or propyl paraben, catechol, resorcinol, cyclohexanol, and 3-pentanol.

Therapeutically effective amounts of cells within cell-based compositions can be greater than $10^2$ cells, greater than $10^3$ cells, greater than $10^4$ cells, greater than $10^5$ cells, greater than $10^6$ cells, greater than $10^7$ cells, greater than $10^8$ cells, greater than $10^9$ cells, greater than $10^{10}$ cells, or greater than $10^{11}$.

In cell-based compositions disclosed herein, cells are generally in a volume of a liter or less, 500 mL or less, 250 mL or less, or 100 mL or less. Hence the density of administered cells is typically greater than $10^4$ cells/mL, $10^7$ cells/mL, or $10^8$ cells/mL.

The cell-based compositions disclosed herein can be prepared for administration by, for example, injection, infusion, perfusion, or lavage. The cell-based compositions can further be formulated for bone marrow, intravenous, intradermal, intraarterial, intranodal, intralymphatic, intraperitoneal, intralesional, intraprostatic, intravaginal, intrarectal, topical, intrathecal, intratumoral, intramuscular, intravesicular, and/or subcutaneous injection.

Compositions for In Vivo Methods of Use. The nanocarriers disclosed herein can also be formulated into compositions for direct administration to a subject wherein the selective targeting and hit-and-run modification occurs in vivo (as is understood by one of ordinary skill in the art, the ex vivo and in vivo approaches described herein are not mutually exclusive and can be practiced in combination). These compositions are referred to herein as nanocarrier-based compositions.

In particular embodiments, the nanocarriers are provided as part of a nanocarrier-based composition that can include at least 0.1% w/v or w/w of nanocarriers; at least 1% w/v or w/w/ of nanocarriers; at least 10% w/v or w/w/ of nanocarriers; at least 20% w/v or w/w/ of nanocarriers; at least 30% w/v or w/w/ of nanocarriers; at least 40% w/v or w/w/ of nanocarriers; at least 50% w/v or w/w/ of nanocarriers; at least 60% w/v or w/w/ of nanocarriers; at least 70% w/v or w/w/ of nanocarriers; at least 80% w/v or w/w/ of nanocarriers; at least 90% w/v or w/w/ of nanocarriers; at least 95% w/v or w/w/ of nanocarriers; or at least 99% w/v or w/w/ of nanocarriers.

The nanocarrier-based compositions disclosed herein can be formulated for administration by, injection, inhalation, infusion, perfusion, lavage or ingestion. The nanocarrier-based compositions disclosed herein can further be formulated for intravenous, intradermal, intraarterial, intranodal, intralymphatic, intraperitoneal, intralesional, intraprostatic, intravaginal, intrarectal, topical, intrathecal, intratumoral, intramuscular, intravesicular, oral and/or subcutaneous administration and more particularly by intravenous, intradermal, intraarterial, intranodal, intralymphatic, intraperitoneal, intralesional, intraprostatic, intravaginal, intrarectal, topical, intrathecal, intratumoral, intramuscular, intravesicular, oral and/or subcutaneous injection.

For injection, nanocarrier-based compositions can be formulated as aqueous solutions, such as in buffers including Hanks' solution, Ringer's solution, or physiological saline. The aqueous solutions can contain formulatory agents such as suspending, stabilizing and/or dispersing agents. Alternatively, the formulation can be in lyophilized and/or powder form for constitution with a suitable vehicle, e.g., sterile pyrogen-free water, before use.

For oral administration, the nanocarrier-based compositions can be formulated as tablets, pills, dragees, capsules, liquids, gels, syrups, slurries, suspensions and the like. For oral solid formulations such as, for example, powders, capsules and tablets, suitable excipients include binders (gum tragacanth, acacia, cornstarch, gelatin), fillers such as sugars, e.g. lactose, sucrose, mannitol and sorbitol; dicalcium phosphate, starch, magnesium stearate, sodium saccharine, cellulose, magnesium carbonate; cellulose preparations such as maize starch, wheat starch, rice starch, potato starch, gelatin, gum tragacanth, methyl cellulose, hydroxypropylmethyl-cellulose, sodium carboxy-methylcellulose, and/or polyvinylpyrrolidone (PVP); granulating agents; and binding agents. If desired, disintegrating agents can be added, such as corn starch, potato starch, alginic acid, cross-linked polyvinylpyrrolidone, agar, or alginic acid or a salt thereof such as sodium alginate. If desired, solid dosage forms can be sugar-coated or enteric-coated using standard techniques. Flavoring agents, such as peppermint, oil of wintergreen, cherry flavoring, orange flavoring, etc. can also be used.

For administration by inhalation, nanocarrier-based compositions can be formulated as aerosol sprays from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator may be formulated containing a powder mix of the therapeutic and a suitable powder base such as lactose or starch.

Any nanocarrier-based composition formulation disclosed herein can advantageously include any other pharmaceutically acceptable carriers which include those that do not produce significantly adverse, allergic or other untoward reactions that outweigh the benefit of administration, whether for research, prophylactic and/or therapeutic treatments. Exemplary pharmaceutically acceptable carriers and formulations are disclosed in Remington's Pharmaceutical Sciences, 18th Ed. Mack Printing Company, 1990. Moreover, formulations can be prepared to meet sterility, pyrogenicity, general safety and purity standards as required by United States FDA Office of Biological Standards and/or other relevant foreign regulatory agencies.

Exemplary generally used pharmaceutically acceptable carriers include any and all bulking agents or fillers, solvents or co-solvents, dispersion media, coatings, surfactants, antioxidants (e.g., ascorbic acid, methionine, vitamin E), preservatives, isotonic agents, absorption delaying agents, salts, stabilizers, buffering agents, chelating agents (e.g., EDTA), gels, binders, disintegration agents, and/or lubricants.

Exemplary buffering agents include citrate buffers, succinate buffers, tartrate buffers, fumarate buffers, gluconate buffers, oxalate buffers, lactate buffers, acetate buffers, phosphate buffers, histidine buffers and/or trimethylamine salts.

Exemplary preservatives include phenol, benzyl alcohol, meta-cresol, methyl paraben, propyl paraben, octadecyldimethylbenzyl ammonium chloride, benzalkonium halides, hexamethonium chloride, alkyl parabens such as methyl or propyl paraben, catechol, resorcinol, cyclohexanol and 3-pentanol.

Exemplary isotonic agents include polyhydric sugar alcohols including trihydric or higher sugar alcohols, such as glycerin, erythritol, arabitol, xylitol, sorbitol or mannitol.

Exemplary stabilizers include organic sugars, polyhydric sugar alcohols, polyethylene glycol; sulfur-containing reducing agents, amino acids, low molecular weight polypeptides, proteins, immunoglobulins, hydrophilic polymers or polysaccharides.

Nanocarrier-based compositions can also be formulated as depot preparations. Depot preparations can be formulated with suitable polymeric or hydrophobic materials (for example as an emulsion in an acceptable oil) or ion exchange resins, or as sparingly soluble derivatives, for example, as a sparingly soluble salts.

Additionally, nanocarrier-based compositions can be formulated as sustained-release systems utilizing semipermeable matrices of solid polymers containing at least one active ingredient. Various sustained-release materials have been established and are well known by those of ordinary skill in the art. Sustained-release systems may, depending on their chemical nature, release active ingredients following administration for a few weeks up to over 100 days.

Methods of Use. Methods disclosed herein include treating subjects (humans, veterinary animals, livestock and research animals) with cell-based compositions and nanocarrier-based compositions disclosed herein. As indicated the compositions can treat a variety of different conditions, ranging from cancer to infectious disease. The compositions can also be used as vaccine adjuvants.

Treating subjects includes delivering therapeutically effective amounts. Therapeutically effective amounts can provide effective amounts, prophylactic treatments and/or therapeutic treatments.

An "effective amount" is the amount of a compound necessary to result in a desired physiological change in the subject. Effective amounts are often administered for research purposes. Effective amounts disclosed herein alter the phenotype of a cell, as an effect of gene-editing or expression of a phenotype-altering protein.

A "prophylactic treatment" includes a treatment administered to a subject who does not display signs or symptoms of a disease or condition or displays only early signs or symptoms of the disease or condition such that treatment is administered for the purpose of diminishing, preventing, or decreasing the risk of developing the disease or condition further. Thus, a prophylactic treatment functions as a preventative treatment against a disease or disorder. Vaccines are one example of prophylactic treatments.

In particular embodiments, prophylactic treatments are administered to treat viral infections, such as HIV. For example, the compositions can be administered prophylactically in subjects who are at risk of developing a viral infection, or who have been exposed to a virus, to prevent, reduce, or delay the development of viral infection or disease. For example, the compositions can be administered to a subject likely to have been exposed to a virus (e.g., HIV) or to a subject who is at high risk for exposure to a virus.

A "therapeutic treatment" includes a treatment administered to a subject who displays symptoms or signs of a disease or condition and is administered to the subject for the purpose of diminishing or eliminating those signs or symptoms of the disease or condition.

Prophylactic and therapeutic treatments need not fully prevent or cure a disease or condition but can also provide a partial benefit.

In the context of cancers, therapeutically effective amounts can decrease the number of tumor cells, decrease the number of metastases, decrease tumor volume, increase life expectancy, induce apoptosis of cancer cells, induce cancer cell death, induce chemo- or radiosensitivity in cancer cells, inhibit angiogenesis near cancer cells, inhibit cancer cell proliferation, inhibit tumor growth, prevent metastasis, prolong a subject's life, reduce cancer-associated pain, reduce the number of metastases, and/or reduce relapse or re-occurrence of the cancer following treatment.

In the context of viruses, therapeutically effective amounts can decrease the number of virally-infected cells, and reduce one or more symptoms associated with the viral infection, such as fever, chills, vomiting, joint pain, etc.

In the context of HIV, therapeutically effective amounts can decrease the number of HIV-infected cells, increase a subject's number of T cells, reduce incidence, frequency, or severity of infections, increase life expectancy, prolong a subject's life, and/or reduce HIV-associated pain or cognitive impairments.

In the context of vaccine adjuvants, vaccines increase the immunity of a subject against a particular disease, and a vaccine adjuvant potentiates and/or prolongs this increase. The skilled artisan will appreciate that the immune system generally is capable of producing an innate immune response and an adaptive immune response. An innate immune response generally can be characterized as not being substantially antigen specific and/or not generating immune memory. An adaptive immune response can be characterized as being substantially antigen specific, maturing over time (e.g., increasing affinity and/or avidity for antigen), and in general can produce immunologic memory. Even though these and other functional distinctions between innate and adaptive immunity can be discerned, the skilled artisan will appreciate that the innate and adaptive immune systems can be integrated and therefore can act in concert.

For administration, therapeutically effective amounts (also referred to herein as doses) can be initially estimated based on results from in vitro assays and/or animal model studies. Such information can be used to more accurately determine useful doses in subjects of interest.

The actual dose amount administered to a particular subject can be determined by a physician, veterinarian or researcher taking into account parameters such as physical and physiological factors including target, body weight, severity of condition, type of disease, previous or concurrent therapeutic interventions, idiopathy of the subject and route of administration.

Useful doses of cell-based compositions are provided elsewhere herein. Useful doses of nanocarrier-based compositions can include from 0.1 to 5 µg/kg or from 0.5 to 1 µg/kg. In other examples, a nanocarrier-based composition dose can include, for example, 1 µg/kg, 10 µg/kg, 20 µg/kg, 30 µg/kg, 40 µg/kg, 50 µg/kg, 60 µg/kg, 70 µg/kg, 80 µg/kg, 90 µg/kg, 100 µg/kg, 150 µg/kg, 200 µg/kg, 250 µg/kg, 350 µg/kg, 400 µg/kg, 450 µg/kg, 500 µg/kg, 550 µg/kg, 600 µg/kg, 650 µg/kg, 700 µg/kg, 750 µg/kg, 800 µg/kg, 850 µg/kg, 900 µg/kg, 950 µg/kg, 1000 µg/kg, 0.1 to 5 mg/kg or from 0.5 to 1 mg/kg. In other non-limiting examples, a dose can include 1 mg/kg, 10 mg/kg, 20 mg/kg, 30 mg/kg, 40 mg/kg, 50 mg/kg, 60 mg/kg, 70 mg/kg, 80 mg/kg, 90 mg/kg, 100 mg/kg, 150 mg/kg, 200 mg/kg, 250 mg/kg, 350 mg/kg, 400 mg/kg, 450 mg/kg, 500 mg/kg, 550 mg/kg, 600 mg/kg, 650 mg/kg, 700 mg/kg, 750 mg/kg, 800 mg/kg, 850 mg/kg, 900 mg/kg, 950 mg/kg, 1000 mg/kg or more.

Therapeutically effective amounts can be achieved by administering single or multiple doses during the course of a treatment regimen (e.g., daily, every other day, every 3 days, every 4 days, every 5 days, every 6 days, weekly, every 2 weeks, every 3 weeks, monthly, every 2 months, every 3 months, every 4 months, every 5 months, every 6 months, every 7 months, every 8 months, every 9 months, every 10 months, every 11 months or yearly.

Unless otherwise indicated, the practice of the present disclosure can employ conventional techniques of immunology, molecular biology, microbiology, cell biology and recombinant DNA. These methods are described in the following publications. See, e.g., Sambrook, et al. Molecular Cloning: A Laboratory Manual, 2nd Edition (1989); F. M. Ausubel, et al. eds., Current Protocols in Molecular Biology, (1987); the series Methods IN Enzymology (Academic Press, Inc.); M. MacPherson, et al., PCR: A Practical Approach, IRL Press at Oxford University Press (1991); MacPherson et al., eds. PCR 2: Practical Approach, (1995); Harlow and Lane, eds. Antibodies, A Laboratory Manual, (1988); and R. I. Freshney, ed. Animal Cell Culture (1987).

Sequence information provided by public database can be used to identify gene sequences to target and nucleic acid sequences encoding phenotype-altering proteins as disclosed herein. Exemplary sequences are provided in FIG. 11.

Variants of the sequences disclosed and referenced herein are also included. Variants of proteins can include those having one or more conservative amino acid substitutions. As used herein, a "conservative substitution" involves a substitution found in one of the following conservative substitutions groups: Group 1: Alanine (Ala), Glycine (Gly), Serine (Ser), Threonine (Thr); Group 2: Aspartic acid (Asp), Glutamic acid (Glu); Group 3: Asparagine (Asn), Glutamine (Gln); Group 4: Arginine (Arg), Lysine (Lys), Histidine (His); Group 5: Isoleucine (Ile), Leucine (Leu), Methionine (Met), Valine (Val); and Group 6: Phenylalanine (Phe), Tyrosine (Tyr), Tryptophan (Trp).

Additionally, amino acids can be grouped into conservative substitution groups by similar function or chemical structure or composition (e.g., acidic, basic, aliphatic, aromatic, sulfur-containing). For example, an aliphatic grouping may include, for purposes of substitution, Gly, Ala, Val, Leu, and Ile. Other groups containing amino acids that are considered conservative substitutions for one another include: sulfur-containing: Met and Cysteine (Cys); acidic: Asp, Glu, Asn, and Gln; small aliphatic, nonpolar or slightly polar residues: Ala, Ser, Thr, Pro, and Gly; polar, negatively charged residues and their amides: Asp, Asn, Glu, and Gln; polar, positively charged residues: His, Arg, and Lys; large aliphatic, nonpolar residues: Met, Leu, Ile, Val, and Cys; and large aromatic residues: Phe, Tyr, and Trp. Additional information is found in Creighton (1984) Proteins, W.H. Freeman and Company.

As indicated elsewhere, variants of gene sequences can include codon optimized variants, sequence polymorphisms, splice variants, and/or mutations that do not affect the function of an encoded product to a statistically-significant degree.

Variants of the protein, nucleic acid, and gene sequences disclosed herein also include sequences with at least 70% sequence identity, 80% sequence identity, 85% sequence, 90% sequence identity, 95% sequence identity, 96% sequence identity, 97% sequence identity, 98% sequence identity, or 99% sequence identity to the protein, nucleic acid, or gene sequences disclosed herein.

"% sequence identity" refers to a relationship between two or more sequences, as determined by comparing the sequences. In the art, "identity" also means the degree of sequence relatedness between protein, nucleic acid, or gene sequences as determined by the match between strings of such sequences. "Identity" (often referred to as "similarity") can be readily calculated by known methods, including (but not limited to) those described in: Computational Molecular Biology (Lesk, A. M., ed.) Oxford University Press, N Y (1988); Biocomputing: Informatics and Genome Projects (Smith, D. W., ed.) Academic Press, N Y (1994); Computer Analysis of Sequence Data, Part I (Griffin, A. M., and Griffin, H. G., eds.) Humana Press, N J (1994); Sequence Analysis in Molecular Biology (Von Heijne, G., ed.) Academic Press (1987); and Sequence Analysis Primer (Gribskov, M. and Devereux, J., eds.) Oxford University Press, NY (1992). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR, Inc., Madison, Wis.). Multiple alignment of the sequences can also be performed using the Clustal method of alignment (Higgins and Sharp CABIOS, 5, 151-153 (1989) with default parameters (GAP PENALTY=10, GAP LENGTH PENALTY=10). Relevant programs also include the GCG suite of programs (Wisconsin Package Version 9.0, Genetics Computer Group (GCG), Madison, Wis.); BLASTP, BLASTN, BLASTX (Altschul, et al., J. Mol. Biol. 215:403-410 (1990); DNASTAR (DNASTAR, Inc., Madison, Wis.); and the FASTA program incorporating the Smith-Waterman algorithm (Pearson, Comput. Methods Genome Res., [Proc. Int. Symp.] (1994), Meeting Date 1992, 111-20. Editor(s): Suhai, Sandor. Publisher: Plenum, New York, N.Y. Within the context of this disclosure it will be understood that where sequence analysis software is used for analysis, the results of the analysis are based on the "default values" of the program referenced. As used herein "default values" will mean any set of values or parameters, which originally load with the software when first initialized.

Exemplary Embodiments

1. A method of preparing a selected cell population of hematopoietic origin for administration to a subject including:
    obtaining a sample from the subject wherein the sample includes a heterogeneous mixture of cells including a selected cell population of hematopoietic origin;
    exposing the sample to a synthetic nanocarrier including
        (i) a synthetic nucleic acid encapsulated within a positively-charged carrier wherein the synthetic nucleic acid encodes a gene editing agent or a phenotype-altering protein;
        (ii) a neutrally or negatively-charged coating on the outer surface of the carrier; and
        (iii) a selected cell targeting ligand extending from the surface of the coating;
    wherein the exposing results in selective delivery of the nanocarrier to the selected cell population resulting in a modification of cells within the selected cell population; and expanding cells within the sample;
    thereby preparing the selected cell population for administration to the subject.
2. A method of embodiment 1 wherein the expanded cells within the sample include modified cells of the selected cell population.
3. A method of embodiment 1 or 2 further including formulating the prepared selected cell population into a cell-based composition.
4. A method of embodiment 3 further including administering the cell-based composition to the subject.
5. A method of any of embodiments 1-4 wherein no isolation steps or only limited isolation steps are taken to increase the percentage of the selected cell population in the heterogeneous mixture of cells before the exposing.
6. A method of any of embodiments 1-5 wherein the synthetic nucleic acid encodes a gene editing agent selected from transcription activator-like effector nucleases (TALENs); megaTALs; and/or zinc finger nucleases.
7. A method of embodiment 6 wherein the synthetic nucleic acid encodes a megaTAL of SEQ ID NO: 1.
8. A method of any of embodiments 1-7 wherein the gene editing agent disrupts endogenous genes encoding Shp-1 phosphatase, PD1 receptor, T cell receptors (TCRs), CCR5 and/or CXCR4.
9. A method of any of embodiments 1-8 wherein the gene editing agent disrupts endogenous genes encoding TCRα chains.
10. A method of any of embodiments 1-9 wherein the synthetic nucleic acid encodes a phenotype-altering protein selected from a transcription factor, a kinase, and/or a cell surface receptor.
11. A method of embodiment 10 wherein the phenotype-altering protein is selected from FOXO1, LKB1, TCF7, EOMES, ID2, TERT, CCR2b, and/or CCR4.
12. A method of any of embodiments 1-11 wherein the selected cell targeting ligand selectively binds lymphocytes within a heterogeneous cell population.
13. A method of embodiment 12 wherein the heterogeneous cell population is an ex vivo cell culture.
14. A method of embodiment 12 wherein the heterogeneous cell population is in vivo.
15. A method of any of embodiments 1-14 wherein the selected cell targeting ligand selectively binds T cells, NK cells, monocytes, macrophages, dendritic cells, B cells, hematopoietic stem cells, or a combination thereof.
16. A method of any of embodiments 1-15 wherein the selected cell targeting ligand includes a binding domain selected from a lymphocyte receptor ligand, lymphocyte receptor antibody, lymphocyte receptor peptide aptamer, lymphocyte receptor nucleic acid aptamer, lymphocyte receptor spiegelmer, or a combination thereof.
17. A method of any of embodiments 1-16 wherein the selected cell targeting ligand selectively binds T-cell receptor motifs; T-cell α chains; T-cell β chains; T-cell γ chains; T-cell δ chains; CCR7; CD1a; CD1b; CD1c; CD1d; CD3; CD4; CD5; CD7; CD8; CD11b; CD11c; CD16; CD19; CD20; CD21; CD22; CD25; CD28; CD34; CD35; CD39; CD40; CD45RA; CD45RO; CD46, CD52; CD56; CD62L; CD68; CD69; CD80; CD86; CD95; CD101; CD117; CD127; CD133; CD137 (4-1BB); CD148; CD163; CD209; DEC-205; F4/80; IL-4Rα; Sca-1; CTLA-4; GITR; GARP; LAP; granzyme B; LFA-1; or transferrin receptor.
18. A method of any of embodiments 1-17 wherein the selected cell targeting ligand selectively binds CD1a; CD1b; CD1c; CD1d; CCR7; CD3; CD4; CD5; CD8; CD16; CD19; CD20; CD21; CD22; CD25; CD28; CD35; CD40; CD45RA; CD45RO; CD46; CD52; CD69; CD62L; CD80; CD95; CD127; CD137; CD209; or DEC-205.
19. A method of any of embodiments 1-18 wherein the selected cell targeting ligand includes a binding domain selected from a T-cell α chain antibody; a T-cell β chain antibody; a T-cell γ chain antibody; a T-cell δ chain antibody; a CCR7 antibody; a CD1a antibody; a CD1b antibody; a CD1c antibody; a CD1d antibody; a CD3 antibody; a CD4 antibody; a CD5 antibody; a CD7 antibody; a CD8 antibody; a CD11b antibody; a CD11c antibody; a CD16 antibody; a CD19 antibody; a CD20 antibody; a CD21 antibody; a CD22 antibody; a CD25 antibody; a CD28 antibody; a CD34 antibody; a CD35 antibody; a CD39 antibody; a CD40 antibody; a CD45RA antibody; a CD45RO antibody; a CD46 antibody; a CD52 antibody; a CD56 antibody; a CD62L antibody; a CD68 antibody; a CD69 antibody; a CD80 antibody; a CD86 antibody a CD95 antibody; a CD101 antibody; a CD117 antibody; a CD127 antibody; a CD133 antibody; a CD137

(4-1BB) antibody; a CD148 antibody; a CD163 antibody; a CD209 antibody; a DEC-205 antibody; a F4/80 antibody; an IL-4Rα antibody; a Sca-1 antibody; a CTLA-4 antibody; a GITR antibody; a GARP antibody; a LAP antibody; a granzyme B antibody; a LFA-1 antibody; or a transferrin receptor antibody.
20. A method of any of embodiments 1-19 wherein the binding domain consists of or consists essentially of an scFv fragment of a T-cell α chain antibody; a T-cell β chain antibody; a T-cell γ chain antibody; a T-cell δ chain antibody; a CCR7 antibody; a CD1a antibody; a CD1b antibody; a CD1c antibody; a CD1d antibody; a CD3 antibody; a CD4 antibody; a CD5 antibody; a CD7 antibody; a CD8 antibody; a CD11b antibody; a CD11c antibody; a CD16 antibody; a CD19 antibody; a CD20 antibody; a CD21 antibody; a CD22 antibody; a CD25 antibody; a CD28 antibody; a CD34 antibody; a CD35 antibody; a CD39 antibody; a CD40 antibody; a CD45RA antibody; a CD45RO antibody; a CD46 antibody; a CD52 antibody; a CD56 antibody; a CD62L antibody; a CD68 antibody; a CD69 antibody; a CD80 antibody; a CD86 antibody a CD95 antibody; a CD101 antibody; a CD117 antibody; a CD127 antibody; a CD133 antibody; a CD137 (4-1BB) antibody; a CD148 antibody; a CD163 antibody; a CD209 antibody; a DEC-205 antibody; a F4/80 antibody; an IL-4Rα antibody; a Sca-1 antibody; a CTLA-4 antibody; a GITR antibody; a GARP antibody; a LAP antibody; a granzyme B antibody; a LFA-1 antibody; or a transferrin receptor antibody.
21. A method of any of embodiments 1-20 wherein the synthetic nucleic acid is synthetic mRNA.
22. A method of any of embodiments 1-21 wherein the carrier includes a positively charged lipid or polymer.
23. A method of embodiment 22 wherein the positively charged polymer includes poly(β-amino ester, poly(L-lysine), poly(ethylene imine) (PEI), poly-(amidoamine) dendrimers (PAMAMs), poly(amine-co-esters), poly(dimethylaminoethyl methacrylate) (PDMAEMA), chitosan, poly-(L-lactide-co-L-lysine), poly[α-(4-aminobutyl)-L-glycolic acid] (PAGA), or poly(4-hydroxy-L-proline ester) (PHP).
24. A method of any of embodiments 1-23 wherein the coating includes a neutrally or negatively-charged lipid or polymer.
25. A method of embodiment 24 wherein the neutrally or negatively-charged coating includes polyglutamic acid (PGA), poly(acrylic acid), alginic acid, or cholesteryl hemisuccinate/1,2-dioleoyl-sn-glycero-3-phosphoethanolamine.
26. A method of embodiment 24 or 25 wherein the neutrally or negatively-charged coating includes a zwitterionic polymer.
27. A method of any of embodiments 24-26 wherein the neutrally or negatively-charged coating includes a liposome.
28. A method of embodiment 27 wherein the liposome includes 1,2-dioleoyl-3-trimethylammonium-propane (DOTAP), 1,2-di-O-octadecenyl-3-trimethylammonium propane (DOTMA), 3β[N—(N',N'-dimethylaminoethane)-carbamoyl]cholesterol (DC-Chol), dioctadecyl-amidoglycylspermine (DOGS), cholesterol, 1,2-dioleoyl-sn-glycero-3-phosphoethanolamine (DOPE), or 1,2-dioleoyl-sn-glycero-3-phosphocholine (DOPC).
29. A method of any of embodiments 1-28 wherein the selected cell targeting ligand selectively binds CD4 and/or CD8.
30. A method of any of embodiments 1-29 wherein the selected cell targeting ligand includes a binding domain selected from a CD4 antibody and/or a CD8 antibody.
31. A method of any of embodiments 1-30 wherein the selected cell targeting ligand includes a binding domain selected from an scFv fragment of a CD4 antibody and/or a CD8 antibody.
32. A method of any of embodiments 1-31 wherein the carrier includes poly(β-amino ester).
33. A method of any of embodiments 1-32 wherein the coating includes polyglutamic acid (PGA).
34. A method of any of embodiments 1-33 wherein the selected cell targeting ligand includes a binding domain selected from a CD4 antibody and/or a CD8 antibody; the carrier includes poly(β-amino ester); and the coating includes polyglutamic acid (PGA).
35. A method for preparing cells to treat a subject including:
obtaining lymphocytes from a subject;
combining the lymphocytes with a synthetic nanocarrier including
(i) a synthetic nucleic acid encapsulated within a positively-charged carrier wherein the synthetic nucleic acid encodes a gene editing agent or a phenotype-altering protein;
(ii) a neutrally or negatively-charged coating on the outer surface of the carrier; and
(iii) a selected cell targeting ligand extending from the surface of the coating;
wherein following the combining the nanocarriers are selectively incorporated into the lymphocytes such that the lymphocytes transiently express the nucleic acid.
36. A method of embodiment 35 further including expanding the lymphocytes.
37. A method of embodiment 35 or 36 further including formulating the lymphocytes into a cell-based composition.
38. A method of any of embodiments 35-37 wherein no isolation steps or only limited isolation steps are taken to increase the percentage of the selected cell population in the heterogeneous mixture of cells before the exposing.
39. A method of any of embodiments 35-38 wherein the synthetic nucleic acid encodes a gene editing agent selected from transcription activator-like effector nucleases (TALENs); megaTALs; and/or zinc finger nucleases.
40. A method of any of embodiments 35-39 wherein the synthetic nucleic acid encodes a megaTAL of SEQ ID NO: 1.
41. A method of any of embodiments 35-40 wherein the gene editing agents disrupt endogenous genes encoding Shp-1 phosphatase, PD1 receptor, T cell receptors (TCRs), CCR5 and/or CXCR4.
42. A method of any of embodiments 35-41 wherein the gene editing agents disrupt endogenous genes encoding TCRα chains.
43. A method of any of embodiments 35-42 wherein the synthetic nucleic acid encodes a phenotype-altering protein selected from a transcription factor, a kinase, and/or a cell surface receptor.
44. A method of embodiment 43 wherein the phenotype-altering protein is selected from FOXO1, LKB1, TCF7, EOMES, ID2, TERT, CCR2b, and/or CCR4.
45. A method of any of embodiments 35-44 wherein the selected cell targeting ligand selectively binds lymphocytes within a heterogeneous cell population.
46. A method of embodiment 45 wherein the heterogeneous cell population is an ex vivo cell culture.

47. A method of embodiment 45 wherein the heterogeneous cell population is in vivo.
48. A method of any of embodiments 35-47 wherein the selected cell targeting ligand selectively binds T cells, NK cells, monocytes, macrophages, dendritic cells, B cells, hematopoietic stem cells, or a combination thereof.
49. A method of any of embodiments 35-48 wherein the selected cell targeting ligand includes a binding domain selected from a lymphocyte receptor ligand, lymphocyte receptor antibody, lymphocyte receptor peptide aptamer, lymphocyte receptor nucleic acid aptamer, lymphocyte receptor spiegelmer, or a combination thereof.
50. A method of any of embodiments 35-49 wherein the selected cell targeting ligand selectively binds T-cell receptor motifs; T-cell α chains; T-cell β chains; T-cell γ chains; T-cell δ chains; CCR7; CD1a; CD1b; CD1c; CD1d; CD3; CD4; CD5; CD7; CD8; CD11b; CD11c; CD16; CD19; CD20; CD21; CD22; CD25; CD28; CD34; CD35; CD39; CD40; CD45RA; CD45RO; CD46, CD52; CD56; CD62L; CD68; CD69; CD80; CD86; CD95; CD101; CD117; CD127; CD133; CD137 (4-1BB); CD148; CD163; CD209; DEC-205; F4/80; IL-4Rα; Sca-1; CTLA-4; GITR; GARP; LAP; granzyme B; LFA-1; or transferrin receptor.
51. A method of any of embodiments 35-50 wherein the selected cell targeting ligand selectively binds CD1a; CD1b; CD1c; CD1d; CCR7; CD3; CD4; CD5; CD8; CD16; CD19; CD20; CD21; CD22; CD25; CD28; CD35; CD40; CD45RA; CD45RO; CD46; CD52; CD62L; CD69; CD80; CD95; CD127; CD137; CD209; or DEC-205.
52. A method of any of embodiments 35-51 wherein the selected cell targeting ligand includes a binding domain selected from a T-cell α chain antibody; a T-cell β chain antibody; a T-cell γ chain antibody; a T-cell δ chain antibody; a CCR7 antibody; a CD1a antibody; a CD1b antibody; a CD1c antibody; a CD1d antibody; a CD3 antibody; a CD4 antibody; a CD5 antibody; a CD7 antibody; a CD8 antibody; a CD11b antibody; a CD11c antibody; a CD16 antibody; a CD19 antibody; a CD20 antibody; a CD21 antibody; a CD22 antibody; a CD25 antibody; a CD28 antibody; a CD34 antibody; a CD35 antibody; a CD39 antibody; a CD40 antibody; a CD45RA antibody; a CD45RO antibody; a CD46 antibody; a CD52 antibody; a CD56 antibody; a CD62L antibody; a CD68 antibody; a CD69 antibody; a CD80 antibody; a CD86 antibody a CD95 antibody; a CD101 antibody; a CD117 antibody; a CD127 antibody; a CD133 antibody; a CD137 (4-1BB) antibody; a CD148 antibody; a CD163 antibody; a CD209 antibody; a DEC-205 antibody; a F4/80 antibody; an IL-4Rα antibody; a Sca-1 antibody; a CTLA-4 antibody; a GITR antibody; a GARP antibody; a LAP antibody; a granzyme B antibody; a LFA-1 antibody; or a transferrin receptor antibody.
53. A method of any of embodiments 35-52 wherein the binding domain consists of or consists essentially of an scFv fragment of a T-cell α chain antibody; a T-cell β chain antibody; a T-cell γ chain antibody; a T-cell δ chain antibody; a CCR7 antibody; a CD1a antibody; a CD1b antibody; a CD1c antibody; a CD1d antibody; a CD3 antibody; a CD4 antibody; a CD5 antibody; a CD7 antibody; a CD8 antibody; a CD11b antibody; a CD11c antibody; a CD16 antibody; a CD19 antibody; a CD20 antibody; a CD21 antibody; a CD22 antibody; a CD25 antibody; a CD28 antibody; a CD34 antibody; a CD35 antibody; a CD39 antibody; a CD40 antibody; a CD45RA antibody; a CD45RO antibody; a CD46 antibody; a CD52 antibody; a CD56 antibody; a CD62L antibody; a CD68 antibody; a CD69 antibody; a CD80 antibody; a CD86 antibody a CD95 antibody; a CD101 antibody; a CD117 antibody; a CD127 antibody; a CD133 antibody; a CD137 (4-1BB) antibody; a CD148 antibody; a CD163 antibody; a CD209 antibody; a DEC-205 antibody; a F4/80 antibody; an IL-4Rα antibody; a Sca-1 antibody; a CTLA-4 antibody; a GITR antibody; a GARP antibody; a LAP antibody; a granzyme B antibody; a LFA-1 antibody; or a transferrin receptor antibody.
54. A method of any of embodiments 35-53 wherein the synthetic nucleic acid is synthetic mRNA.
55. A method of any of embodiments 35-54 wherein the carrier includes a positively charged lipid or polymer.
56. A method of embodiment 55 wherein the positively charged lipid or polymer includes poly(β-amino ester, poly(L-lysine), poly(ethylene imine) (PEI), poly-(amido-amine) dendrimers (PAMAMs), poly(amine-co-esters), poly(dimethylaminoethyl methacrylate) (PDMAEMA), chitosan, poly-(L-lactide-co-L-lysine), poly[α-(4-aminobutyl)-L-glycolic acid] (PAGA), or poly(4-hydroxy-L-proline ester) (PHP).
57. A method of any of embodiments 35-56 wherein the coating includes a neutrally or negatively-charged lipid or polymer.
58. A method of embodiment 57 wherein the neutrally or negatively-charged coating includes polyglutamic acid (PGA), poly(acrylic acid), alginic acid, or cholesteryl hemisuccinate/1,2-dioleoyl-sn-glycero-3-phosphoethanolamine.
59. A method of embodiment 57 or 58 wherein the neutrally or negatively-charged coating includes a zwitterionic polymer.
60. A method of any of embodiments 57-59 wherein the neutrally or negatively-charged coating includes a liposome.
61. A method of embodiment 60 wherein the liposome includes 1,2-dioleoyl-3-trimethylammonium-propane (DOTAP), 1,2-di-O-octadecenyl-3-trimethylammonium propane (DOTMA), 3β[N—(N',N'-dimethylaminoethane)-carbamoyl]cholesterol (DC-Chol), dioctadecyl-amidoglycylspermine (DOGS), cholesterol, 1,2-dioleoyl-sn-glycero-3-phosphoethanolamine (DOPE), or 1,2-dioleoyl-sn-glycero-3-phosphocholine (DOPC).
62. A method of any of embodiments 35-61 wherein the selected cell targeting ligand selectively binds CD4 and/or CD8.
63. A method of any of embodiments 35-62 wherein the selected cell targeting ligand includes a binding domain selected from a CD4 antibody and/or a CD8 antibody.
64. A method of any of embodiments 35-63 wherein the selected cell targeting ligand includes a binding domain selected from an scFv fragment of a CD4 antibody and/or a CD8 antibody.
65. A method of any of embodiments 35-64 wherein the carrier includes poly(β-amino ester).
66. A method of any of embodiments 35-65 wherein the coating includes polyglutamic acid (PGA).
67. A method of any of embodiments 35-66 wherein the selected cell targeting ligand includes a binding domain selected from a CD4 antibody and/or a CD8 antibody; the carrier includes poly(β-amino ester); and the coating includes polyglutamic acid (PGA).
68. A method for treating a subject in need thereof including administering a therapeutically effective amount of cells modified by transient expression of a nucleic acid selectively delivered to the cells by a nanocarrier including:

(i) the nucleic acid encapsulated within a positively-charged carrier wherein the synthetic nucleic acid encodes a gene editing agent or a phenotype-altering protein;
(ii) a neutrally or negatively-charged coating on the outer surface of the carrier; and
(iii) a selected cell targeting ligand extending from the surface of the coating;
wherein following the combining the nanocarriers are selectively incorporated into the lymphocytes such that the lymphocytes transiently express the nucleic acid thereby treating the subject in need thereof.

69. A method of preparing a selected cell population for administration to a subject including:
obtaining a sample from the subject wherein the sample includes a heterogeneous mixture of cells including a selected cell population;
exposing the sample to a synthetic nanocarrier including
(i) a synthetic nucleic acid encapsulated within a positively-charged carrier wherein the synthetic nucleic acid encodes a gene editing agent or a phenotype-altering protein;
(ii) a neutrally or negatively-charged coating on the outer surface of the carrier; and
(iii) a selected cell targeting ligand extending from the surface of the coating;
wherein the exposing results in selective delivery of the nanocarrier to the selected cell population resulting in a modification of cells within the selected cell population; and
expanding cells within the sample;
thereby preparing the selected cell population for administration to the subject.

70. A synthetic nanocarrier including
(i) a synthetic nucleic acid encapsulated within a positively-charged carrier wherein the nucleic acid encodes a gene editing agent or a phenotype-altering protein;
(ii) a neutrally or negatively-charged coating on the outer surface of the carrier; and
(iii) a selected cell targeting ligand extending from the surface of the coating;

71. A synthetic nanocarrier of embodiment 70 wherein the synthetic nucleic acid encodes a gene editing agent selected from transcription activator-like effector nucleases (TALENs); megaTALs; and/or zinc finger nucleases.

72. A synthetic nanocarrier of embodiment 70 or 71 wherein the synthetic nucleic acid encodes a megaTAL of SEQ ID NO: 1.

73. A synthetic nanocarrier of any of embodiments 70-72 wherein the gene editing agents disrupt endogenous genes encoding Shp-1 phosphatase, PD1 receptor, T cell receptors (TCRs), CCR5 and/or CXCR4.

74. A synthetic nanocarrier of any of embodiments 70-73 wherein the gene editing agents disrupt endogenous genes encoding TCRα chains.

75. A synthetic nanocarrier of any of embodiments 70-74 wherein the synthetic nucleic acid encodes a phenotype-altering protein selected from a transcription factor, a kinase, and/or a cell surface receptor.

76. A synthetic nanocarrier of embodiment 75 wherein the phenotype-altering protein is selected from FOXO1, LKB1, TCF7, EOMES, ID2, TERT, CCR2b, and/or CCR4.

77. A synthetic nanocarrier of any of embodiments 70-76 wherein the selected cell targeting ligand selectively binds lymphocytes within a heterogeneous cell population.

78. A synthetic nanocarrier of embodiment 77 wherein the heterogeneous cell population is an ex vivo cell culture.

79. A synthetic nanocarrier of embodiment 77 wherein the heterogeneous cell population is in vivo.

80. A synthetic nanocarrier of any of embodiments 70-79 wherein the selected cell targeting ligand selectively binds T cells, NK cells, monocytes, macrophages, dendritic cells, B cells, hematopoietic stem cells, or a combination thereof.

81. A synthetic nanocarrier of any of embodiments 70-80 wherein the selected cell targeting ligand includes a binding domain selected from a lymphocyte receptor ligand, lymphocyte receptor antibody, lymphocyte receptor peptide aptamer, lymphocyte receptor nucleic acid aptamer, lymphocyte receptor spiegelmer, or a combination thereof.

82. A synthetic nanocarrier of any of embodiments 70-81 wherein the selected cell targeting ligand selectively binds T-cell receptor motifs; T-cell α chains; T-cell β chains; T-cell γ chains; T-cell δ chains; CCR7; CD1a; CD1b; CD1c; CD1d; CD3; CD4; CD5; CD7; CD8; CD11b; CD11c; CD16; CD19; CD20; CD21; CD22; CD25; CD28; CD34; CD35; CD39; CD40; CD45RA; CD45RO; CD46; CD52; CD56; CD62L; CD68; CD69; CD80; CD86; CD95; CD101; CD117; CD127; CD133; CD137 (4-1BB); CD148; CD163; CD209; DEC-205; F4/80; IL-4Rα; Sca-1; CTLA-4; GITR; GARP; LAP; granzyme B; LFA-1; or transferrin receptor.

83. A synthetic nanocarrier of any of embodiments 70-82 wherein the selected cell targeting ligand selectively binds CD1a; CD1b; CD1c; CD1d; CCR7; CD3; CD4; CD5; CD8; CD16; CD19; CD20; CD21; CD22; CD25; CD28; CD35; CD40; CD45RA; CD45RO; CD46; CD52; CD62L; CD69; CD80; CD95; CD127; CD137, CD209 or DEC-205.

84. A synthetic nanocarrier of any of embodiments 70-83 wherein the selected cell targeting ligand includes a binding domain selected from a T-cell α chain antibody; a T-cell β chain antibody; a T-cell γ chain antibody; a T-cell δ chain antibody; a CCR7 antibody; a CD1a antibody; a CD1b antibody; a CD1c antibody; a CD1d antibody; a CD3 antibody; a CD4 antibody; a CD5 antibody; a CD7 antibody; a CD8 antibody; a CD11b antibody; a CD11c antibody; a CD16 antibody; a CD19 antibody; a CD20 antibody; a CD21 antibody; a CD22 antibody; a CD25 antibody; a CD28 antibody; a CD34 antibody; a CD35 antibody; a CD39 antibody; a CD40 antibody; a CD45RA antibody; a CD45RO antibody; a CD46 antibody; a CD52 antibody; a CD56 antibody; a CD62L antibody; a CD68 antibody; a CD69 antibody; a CD80 antibody; a CD86 antibody a CD95 antibody; a CD101 antibody; a CD117 antibody; a CD127 antibody; a CD133 antibody; a CD137 (4-1BB) antibody; a CD148 antibody; a CD163 antibody; a CD209 antibody; a DEC-205 antibody; a F4/80 antibody; an IL-4Rα antibody; a Sca-1 antibody; a CTLA-4 antibody; a GITR antibody; a GARP antibody; a LAP antibody; a granzyme B antibody; a LFA-1 antibody; or a transferrin receptor antibody.

85. A synthetic nanocarrier of any of embodiments 70-84 wherein the binding domain consists of or consists essentially of an scFv fragment of a T-cell α chain antibody; a T-cell β chain antibody; a T-cell γ chain antibody; a T-cell δ chain antibody; a CCR7 antibody; a CD1a antibody; a CD1b antibody; a CD1c antibody; a CD1d antibody; a CD3 antibody; a CD4 antibody; a CD5 antibody; a CD7 antibody; a CD8 antibody; a CD11b antibody; a CD11c antibody; a CD16 antibody; a CD19 antibody; a CD20 antibody; a CD21 antibody; a CD22 antibody; a CD25 antibody; a CD28 antibody; a CD34 antibody; a CD35 antibody; a CD39 antibody; a CD40 antibody; a CD45RA antibody; a CD45RO antibody; a CD46 antibody; a CD52 antibody; a CD56 antibody; a CD62L antibody; a CD68 antibody; a CD69 antibody; a CD80 antibody; a CD86 antibody a CD95 antibody; a CD101 antibody; a CD117 antibody; a CD127 antibody; a CD133 antibody; a CD137 (4-1BB) antibody; a CD148 antibody; a CD163 antibody; a CD209 antibody; a DEC-205 antibody; a F4/80 antibody; an IL-4Rα antibody; a Sca-1 antibody; a CTLA-4 antibody; a GITR antibody; a GARP antibody; a LAP antibody; a granzyme B antibody; a LFA-1 antibody; or a transferrin receptor antibody.

86. A synthetic nanocarrier of any of embodiments 70-85 wherein the synthetic nucleic acid is synthetic mRNA.
87. A synthetic nanocarrier of any of embodiments 70-86 wherein the carrier includes a positively charged lipid or polymer.
88. A synthetic nanocarrier of embodiment 87 wherein the positively charged lipid or polymer includes poly(β-amino ester, poly(L-lysine), poly(ethylene imine) (PEI), poly-(amidoamine) dendrimers (PAMAMs), poly(amine-co-esters), poly(dimethylaminoethyl methacrylate) (PD-MAEMA), chitosan, poly-(L-lactide-co-L-lysine), poly[α-(4-aminobutyl)-L-glycolic acid] (PAGA), or poly(4-hydroxy-L-proline ester) (PHP).
89. A synthetic nanocarrier of any of embodiments 70-88 wherein the coating includes a neutrally or negatively-charged lipid or polymer.
90. A synthetic nanocarrier of embodiment 89 wherein the neutrally or negatively-charged coating includes polyglutamic acid (PGA), poly(acrylic acid), alginic acid, or cholesteryl hemisuccinate/1,2-dioleoyl-sn-glycero-3-phosphoethanolamine.
91. A synthetic nanocarrier of embodiment 89 or 90 wherein the neutrally or negatively-charged coating includes a zwitterionic polymer.
92. A synthetic nanocarrier of any of embodiments 89-91 wherein the neutrally or negatively-charged coating includes a liposome.
93. A synthetic nanocarrier of embodiment 92 wherein the liposome includes 1,2-dioleoyl-3-trimethylammonium-propane (DOTAP), 1,2-di-O-octadecenyl-3-trimethylammonium propane (DOTMA), 3β-[N—(N',N'-dimethylaminoethane)-carbamoyl]cholesterol (DC-Chol), dioctadecyl-amidoglycylspermine (DOGS), cholesterol, 1,2-dioleoyl-sn-glycero-3-phosphoethanolamine (DOPE), or 1,2-dioleoyl-sn-glycero-3-phosphocholine (DOPC).
94. A synthetic nanocarrier of any of embodiments 70-93 wherein the selected cell targeting ligand selectively binds CD4 and/or CD8.
95. A synthetic nanocarrier of any of embodiments 70-94 wherein the selected cell targeting ligand includes a binding domain selected from a CD4 antibody and/or a CD8 antibody.
96. A synthetic nanocarrier of any of embodiments 70-95 wherein the selected cell targeting ligand includes a binding domain selected from an scFv fragment of a CD4 antibody and/or a CD8 antibody.
97. A synthetic nanocarrier of any of embodiments 70-96 wherein the carrier includes poly(β-amino ester).
98. A synthetic nanocarrier of any of embodiments 70-97 wherein the coating includes polyglutamic acid (PGA).
99. A synthetic nanocarrier of any of embodiments 70-98 wherein the selected cell targeting ligand includes a binding domain selected from a CD4 antibody and/or a CD8 antibody; the carrier includes poly(β-amino ester); and the coating includes polyglutamic acid (PGA).
100. A composition including a synthetic nanocarrier of any of embodiments 70-99.
101. A method of treating a subject in need thereof including administering a therapeutically effective amount of a nanocarrier of any of embodiments 70-99 or a composition of embodiment 100 thereby treating the subject in need thereof.
102. Use of a nanocarrier disclosed herein to selectively deliver a nucleic acid encoding a CAR or TCR to a selected cell type.

Example 1

Introduction. Directing immune responses toward cancer by genetically engineering T cells to express chimeric antigen receptors (CARs) or T cell receptors (TCRs) is a therapy that is beginning to yield significant results, and important clinical trials are on the horizon. The process of bioengineering T cells into 'living drugs' that can increase in number, serially destroy tumor cells, and ultimately differentiate into long-lived memory T cells requires stable integration of receptor transgenes into the lymphocyte's genome. Despite the time and cost required for their production, as well as restrictions on the size and number of genes that they can package, viral vectors are currently the most effective means to program these cells with tumor-recognizing capabilities for applications (Zhang et al., *Nat Commun* 6, 7639 (2015); Cribbs et al., *BMC Biotechnol* 13, 98 (2013)).

Aside from these chronic gene expression systems, it is also possible to induce phenotypic changes in cells via transient expression of macromolecules that target 'hit-and-run' mechanisms. In most of these transient applications, permanent expression of the therapeutic transgene is undesirable and potentially dangerous (Wurm et al., *Exp Hematol* 42, 114-125 e114 (2014)); examples include the use of transcription factors to control cell differentiation (Themeli et al., *Nat Biotechnol* 31, 928-933 (2013); Costa et al., *Development* 142, 1948-1959 (2015)), and the expression of sequence-specific nucleases to engineer genomes (Cox et al., *Nat Med* 21, 121-131 (2015)).

Although there is a growing number of applications where transient gene therapy could substantially improve the curative potential of engineered T cells, currently available methods (which, like the chronic expression methods described above, are mostly based on viral vectors) are complicated by the expense of the elaborate protocols required to perform the transduction (Nightingale et al., *Mol Ther* 13, 1121-1132 (2006)). Electroporation was developed as an alternative transfection method, but mechanical permeabilization of plasma membranes compromises the viability of T cells, which means these approaches are not suited for scale-up applications. Besides, like virus-based methods, electroporation cannot selectively transfect specific cell types from a heterogeneous pool, so it must be preceded by a cell purification process.

This example describes a nanoreagent that produces transient gene expression in cultured T cells, and does so without involved protocols or complex ancillary equipment. An appropriately designed mRNA nanocarrier can accomplish dose-controlled delivery of functional macromolecules to lymphocytes simply by mixing the reagent with the cells in vitro (FIG. 1A).

These nanoparticles (NPs) can bind to targeted cell subtypes and stimulate receptor-mediated endocytosis, which provides entry for the synthetic mRNA they carry and enables the lymphocytes to express the encoded molecule. Because nuclear transport and transcription of the transgene is not required, this process is fast and efficient. How this new platform can be implemented to manufacture superior CAR-T cell products for clinical use is illustrated in at least two examples. In the first application, targeted mRNA nanocarriers were used as a genome-editing tool for T cells. The delivery of mRNA encoding a rare-cleaving megaTAL nuclease (Boissel et al., Methods Mol Biol 1239, 171-196 (2015)) can efficiently disrupt T cell receptor expression by lymphocytes. In the second application, Foxo1, a key regulator that reprograms the differentiation of effector cells into functionally competent memory cells (Tejera, et al., J Immunol 191, 187-199 (2013); Kim et al., Immunity 39, 286-297 (2013)) was transiently expressed. The results demonstrate that exposure to the engineered nanoparticles biases T cells toward a central memory phenotype.

The most significant benefit of the system is its simplicity in achieving genetic modifications of therapeutic cells at a clinical scale: all that is required is mixing the appropriate nanoparticle reagent with the lymphocytes. The approach patently contrasts with those currently used to transiently deliver genetic materials, which are less effective and involve many specialized, expensive, and proprietary procedures that limit their availability. Beyond T cell therapy, the transient gene delivery platform could easily be integrated into existing manufacturing processes for other therapeutic cell types (e.g. natural killer cells, dendritic cells, hematopoietic stem cells, or mesenchymal stem cells) to substantially improve their curative potentials without increasing handling time, risk, or complexity.

Materials and Methods. Study Design. The objective of this project was to develop a nanomaterial for targeted mRNA delivery to primary T cells in vitro. Pilot experiments were performed to optimize nanocarrier-mediated delivery for specific applications using cells obtained from individual donors, followed by replication of the optimized protocols using samples from multiple donors.

PBAE 447 Synthesis. This polymer was synthesized using a method similar to that described by Mangraviti et al (Mangraviti et al., ACS Nano 9, 1236-1249 (2015)). 1,4-butanediol diacrylate was combined with 4-amino-1-butanol in a 1.1:1 molar ratio of diacrylate to amine monomer. The mixture was heated to 90° C. with stirring for 24 h to produce acrylate-terminated poly(4-amino-1-butanol-co-1, 4-butanediol diacrylate). 2.3 g of this polymer was dissolved in 2 ml tetrahydrofuran (THF). To form the piperazine-capped 447 polymer, 786 mg of 1-(3-aminopropyl)-4-methylpiperazine dissolved in 13 ml THF was added to the polymer/THF solution. The resulting mixture was stirred at RT for 2 h, then the capped polymer was precipitated with 5 volumes of diethyl ether. After the solvent was decanted, the polymer was washed with 2 volumes of fresh ether, then the residue was dried under vacuum for 2 days before use to form a stock of 100 mg/ml in DMSO, which was stored at −20° C.

PGA-antibody Conjugation. 15 kD poly-glutamic acid (from Alamanda Polymers) was dissolved in water to form 20 mg/ml and sonicated for 10 min. An equal volume of 4 mg/ml 1-ethyl-3-(3-dimethylaminopropyl) carbodiimide hydrochloride (Thermo Fisher) in water was added, and the solution was mixed for 5 min at RT. The resulting activated PGA was then combined with antibodies at a 4:1 molar ratio in phosphate buffered saline (PBS) and mixed for 6 h at RT. To remove unlinked PGA, the solution was exchanged 3 times against PBS across a 50,000 NMWCO membrane (Millipore). Antibody concentrations were determined using a NanoDrop 2000 spectrophotometer (Thermo Scientific). The antibodies used for T cell experiments were anti-CD3 (clone OKT3), anti-CD4 (clone OKT4), anti-CD8 (clone OKT8), and anti-CD28 (clone 9.3, all from BioXCell). Clone C1.18.4 was used as a control antibody. For HSC transduction, polyclonal goat anti-mouse IgG and polyclonal goat anti-mouse CD105 antibodies (Fisher) were used.

mRNA Synthesis. Codon-optimized mRNA for eGFP, Foxo1, Trex2, and TRAC-megaTAL fully substituted with the modified ribonucleotides pseudouridine ($\psi$) and 5-methylcytidine (m5C) and capped with ARCA was produced by TriLink Biotechnologies. We conjugated $\psi$ and m5C-modified eGFP mRNA with cy5 (also from TriLink) were conjugated for tracking delivery of these transcripts.

Nanoparticle Preparation. mRNA stocks were diluted to 100 µg/ml in sterile, nuclease-free 25 mM sodium acetate buffer, pH 5.2 (NaOAc). PBAE-447 polymer in DMSO was diluted to 6 mg/ml in NaOAc, and added to mRNA at a 60:1 (w:w) ratio. After the resulting mixture was vortexed for 15 sec at medium speed, it was incubated for 5 min at room temperature so NPs could form. To add targeting elements to the nanoparticles, PGA-linked antibodies were diluted to 250 µg/ml in NaOAc and added at a 2.5:1 (w:w) ratio to the mRNA. The resulting mixture was vortexed for 15 sec at medium speed, and then incubated for 5 min at room temperature to permit binding of PGA-Ab to the NPs.

The nanoparticles were lyophilized by mixing them with 60 mg/ml D-sucrose as a cryoprotectant, and flash-freezing them in liquid nitrogen, before processing them in a FreeZone 2.5 L Freeze Dry System (Labconco). The lyophilized NPs were stored at −80° C. until use. For application, lyophilized NPs were re-suspended in a volume of sterile water to restore their original concentration.

Nanoparticle Characterization. The hydrodynamic radius of the created particles was measured with a Nanosite (Malvern), and their zeta potential was determined using dynamic light scattering detected with a Zetapals instrument (Brookhaven Instrument Corporation). The particles were diluted 1:400 (v/v) in PBS (pH 7.4) for size measurements, and 1:40 for zeta potential quantitation. For transmission electron microscopy, a 25-µl sample of nanoparticles was applied each to glow discharge-activated 200 mesh carbon/formvar-coated copper grids. After 30 sec, grids were touched sequentially to a drop of ½ Karnovsky's fixative, a drop of 0.1 M cacodylate buffer, 8 drops of dH2O, and then a drop of 1% (w/v) filtered uranyl acetate. These samples were examined using a JEOL JEM-1400 transmission electron microscope (JEOL USA).

Cell Lines and Culture Media. K562-CD19 and control K562 cells were provided by Dr. Stanley Riddell (Fred Hutchinson Cancer Research Center). TM-LCL is a CD19+ EBV-transformed lymphoblastoid cell line that has been optimized to use as a feeder for T cell expansion (36). The Jurkat-E6 T cell line was obtained from the American Type Culture Collection. These lines were cultured in T cell medium (TCM): RPMI-1640 containing 10% fetal bovine serum, 0.8 mM I-glutamine, 25 mM HEPES buffer, and 1% penicillin-streptomycin.

Primary human peripheral blood mononuclear cells (PBMC) and T cells were cultured in TCM supplemented with 50 IU IL-2/ml (Preprotech), or in ImmunoCult-XF T Cell Expansion Medium (XFSFM) (Stemcell) as indicated.

mRNA Transfection of T cells. Cryopreserved PBMC from normal donors were thawed by drop-wise addition of warm TCM, followed by centrifugation. Where indicated, CD8 T cells were isolated by negative selection (Stemcell). Cells were cultured in TCM+IL-2 at $10^6$ cells/ml and stimulated with CD3/CD28 beads (Dynabeads, Life Technologies) at a 1:1 bead:cell ratio. For experiments involving αCD3-targeted nanoparticle transduction, these beads were removed 24 h before NP addition.

For NP-mediated transfections, the T cells were resuspended in XFSFM to a concentration of $2 \times 10^6$/ml. Antibody-targeted NPs containing 2.5 μg of mRNA/$10^6$ cells were added to this suspension for an exposure of 2 h at 37° C., then the cells were washed with 3 volumes of TCM+IL-2. Control NPs contained eGFP mRNA. TCRα gene editing NPs contained TRAC-megaTAL, Trex2, and eGFP mRNAs at a 42:42:16 w:w:w ratio. Foxo1$_{3A}$ NPs contained Foxo1$_{3A}$ and eGFP mRNAs at an 84:16 w:w ratio.

For electroporation, $2 \times 10^6$ T cells were washed twice with PBS containing 0.5% bovine serum albumin (BSA), resuspended in 100 μl of T cell electroporation medium (Lonza) containing 3 μg of eGFP mRNA, transferred to an electroporation cuvette, and treated in a Nucleofector (Lonza) instrument using program T-20. The porated cells were transferred into a plate containing 2 ml TCM+IL-2 without antibiotics.

NP transduction of CD34+ cells. CD34+ cells purified from PBSC previously mobilized from normal donors were obtained from the Hematopoietic Cell Processing and Repository Core at the Fred Hutchinson Cancer Research Center. After thawing, the cells were counted then cultured overnight at a concentration of $10^6$/ml in HSC medium: StemSpan SFEMII serum-free medium supplemented with 50 ng/ml human Stem Cell Factor (Scf), 50 ng/ml murine Flt3/Flk-2 ligand, and 25 ng/ml human thrombopoietin (Stemcell Technologies)]. The next day the cells were harvested, counted, and resuspended in 100 μl HSC without cytokines at $2.5 \times 10^4$ cells/well in a 96-well tissue culture plate (Costar). The cells were left untreated, or treated with CD105-targeted or control anti-mouse-targeted NPs containing 1 μg eGFP mRNA per well. The cells were treated with the NPs for 1 h, then washed twice with 1 ml HSC medium without cytokines. Washed cells were then transferred into 500 μl complete HSC media in 24-well tissue culture plates; 48 h later, the cells were labeled for CD34 and CD105 (BioLegend) for analysis by flow cytometry.

PCR Amplification and Detection of Indels for TCRα. Indel detection was performed with a Geneart Genomic Cleavage Detection Kit (Invitrogen) according to the manufacturer's instructions. Briefly, T cells were lysed, and genomic DNA flanking the TCRα MegaTAL target site was amplified by PCR using these primers: TRAC-Forward CCCGTGTCATTCTCTGGACT (SEQ ID NO: 53), and TRAC-Reverse ATCACGAGCAGCTGGTTTCT (SEQ ID NO: 54). The PCR product was denatured, re-annealed, and treated with the detection enzyme so indel formation could be assessed by comparing gel band density for germline vs specifically cleaved bands.

Lentiviral Transduction and Expansion of T cells using 19-41BBζ CAR. Human anti-CD19 CAR construct containing 41BB and CD3ζ signaling domains (19-41BB□) was modified with a single StrepTag as described (Liu et al., Nat Biotechnol 34, 430-434 (2016)) and transferred into the epHIV7 lentiviral vector. VSVG pseudotyped lentivirus was produced via calcium phosphate transfection (Invitrogen) of Lenti-X 293T cells (Clontech) with epHIV7 lentiviral vector and the viral packaging plasmids pCMVdR8.91 and pMD2.G. For lentiviral transduction, T cells were transferred to retronectin-coated plates (Takara) with 8 μg/ml polybrene and 19-41BBζ-CAR encoding lentivirus at a MOI of 5:1, then spin infected for 1 h at 800×g at 34° C. For selective expansion of 19-41BBζ-transduced cells, the lymphocytes were stimulated with irradiated (7000 rads) CD19+ TM-LCL cells at a 1:7 ratio in TCM+IL-2.

Cell sorting and Flow Cytometry. Data were acquired using BD LSRFortessa or FacsCanto II cell analyzers running FACSDIVA software, sorted on the BD FACS ARIA-II, and analyzed with FlowJo v10.1. Antibodies used in flow cytometry are listed in FIG. 2.

Intracellular Cytokine Staining. Cells were cultured for 6 h in TCM with 3 μg/ml brefeldin A+/−20 ng/ml PMA and 1 μg/ml ionomycin (Sigma-Aldrich). Before fixation, anti-CD8 and anti-CD3 staining was used to identify TCR+ CD8+ and TCR− CD8+ cell subsets. Cells were then subjected to a Fix and Perm kit (BD Biosciences) before labeling with anti-IFN-γ− and IL-2 mAbs (BioLegend).

Intracellular Staining for Foxo1. $10^6$ Jurkat T cells were transfected with anti-CD3 targeted NPs containing 3 μg eGFP mRNA, or 2.5 μg Foxo13A and 0.5 μg eGFP mRNA. 24 h later, cells were fixed with 4% paraformaldehyde in PBS, washed once, and permeabilized with 90% ice-cold methanol for 30 min. These samples were blocked with 0.5% BSA in PBS at room temperature, then stained with rabbit anti-Foxo1 (clone C29H4) or isotype (clone DAE1), followed by anti-rabbit IgG F(aB')2 Alexa-647 (Cell Signaling).

CAR T Cell Killing Assay. Specific cytolysis of CAR target cells was assayed by flow cytometry. Target K562–CD19 cells were labeled with low (0.4 μM), and control K562 with high (4.0 μM) carboxyfluorescein succinimidyl ester (CFSE) for 15 min at 37° C. Both samples were washed in complete medium containing serum, mixed at a ratio of 1:1, then co-cultured with 19-41BBζ at the indicated effector:target ratios. To assess specific cytolysis, each condition was stained with anti-CD8 mAbs (BioLegend) to identify T cells and with 7AAD to exclude dead cells, and analyzed by flow cytometry. Specific cell killing was assessed by measuring the ratio of viable CD19+ target cells (low CFSE) to control CD19− K562 cells (high CFSE).

Microscopy. $10^6$ T cells in 400 μl of XFSFM were treated with anti-CD3 targeted NPs containing 3 μg cy5-labeled eGFP mRNA for 1 h at 4° C. for surface binding, followed by a 2-h incubation at 37° C. for internalization. Following these treatments, the cells were washed 3 times with cold PBS, and loaded onto poly-1-lysine (Sigma)-coated slides for 30 min at 4° C. The samples were fixed in 2% paraformaldehyde, mounted in ProLong Gold Antifade reagent (Invitrogen), and imaged with a Zeiss LSM 780 NLO laser scanning confocal microscope.

RNA Purification, RT-PCR, Sequencing, and Bioinformatic Analysis. After T cells were lysed in Trizol reagent (Ambion), total RNA was isolated using a DirectZol kit (Zymo) with on-column DNA digestion following the manufacturer's instructions. For real-time quantitative PCR (qPCR), cDNA was prepared with a high capacity cDNA kit (Applied Biosystems). Expression levels of endogenous FOXO1 and codon-optimized FOXO13A relative to the housekeeping gene B2M were measured using PrimeTime qPCR assays (Integrated DNA technology) and a QuantStudio5 machine (Applied Biosystems). The primers used to detect codon-optimized Foxo13A were selected to avoid cross-detection of endogenous Foxo1 mRNA:

```
Foxo13A Forward:    GGACAGCCTAGAAAGAGCAG        (SEQ ID NO: 55)

Foxo13A Probe:      AGGTCGGCGTAGCTCAGATTGC      (SEQ ID NO: 56)

Foxo13A Reverse:    CTCTTGACCATCCACTCGTAG       (SEQ ID NO: 57)
```

For RNAseq analysis, RNA samples were isolated from in vitro cultured control NP- and Foxo13A NP-treated CD8+ cells after 3 and 8 days, and compared with sorted reference naïve (CD8+ CD45RA+ CD62L+ CCR7+) and TCM (CD8+ CD45RA− CD62L+ CCR7+) cells from two independent donor-matched cryopreserved PBMC samples. RNASeq libraries were prepared using the TruSeq sample preparation kit (Illumina) according to the manufacturer's instructions. Libraries were sequenced for 50 cycles (paired end) with a HiSeq platform (Illumina). Results that passed Illumina's base call and quality filters to the human hg38 genome using TopHat v2.1.0 were aligned. Counts were generated for each gene with htseq-count (v0.6.1p1), implemented in the "intersection-strict" overlap mode. The GLM method in edgeR was used for data normalization and differential expression analysis. TCM signature gene sets were defined as the top 500 genes ranked by statistical significance with higher (TCM Up) or lower (TCM Down) expression in CD8+ TCM versus donor-matched control NP-treated CD8+ T cells at day 8. Gene set enrichment was analyzed with GSEAPreranked software using gene lists ranked by the sign of the fold change×1/(p value) (37). Raw and processed data from RNAseq analysis have been deposited in NCBI's Gene Expression Omnibus, GEO series accession number GSE89134. (38)

Statistical Analysis. Unless otherwise stated, graphs show mean±standard error of the mean. Statistical analysis was done with Prism software (Graphpad).

Results. Designing mRNA nanocarriers to choreograph robust transgene expression in T cells. To create a reagent that can genetically modify primary T lymphocytes (which are notoriously refractory to non-viral transfection methods), polymeric nanoparticles including four functional components (FIG. 1B) were bioengineered: (i) surface-anchored targeting ligands that selectively bind the nanoparticles to T cells and initiate rapid receptor-induced endocytosis to internalize them. In the experiments anti-CD3 and anti-CD8 antibodies were used; (ii) a negatively-charged coating that shields the nanoparticles to minimize off-target binding by reducing the surface charge of the nanoparticles. Because it is already widely used in drug delivery platforms, polyglutamic acid (PGA) was selected to accomplish this; (iii) a carrier matrix that condenses and protects the nucleic acids from enzymatic degradation while they are in the endosome, but releases them once the particles are transported into the cytoplasm, thereby enabling transcription of the encoded protein. For this, a biodegradable poly(β-amino ester) (PBAE) polymer formulation that has a half-life between 1 and 7 hours in aqueous conditions was used; and (iv) nucleic acids that are encapsulated within the carrier and result in gene editing or transient expression of proteins that can permanently alter the phenotype of the T cell. mRNA is an ideal platform for transient therapeutic protein expression, because it has no potential for genomic integration and does not require nuclear localization for expression. However, unmodified mRNA can activate intracellular toll-like receptors, limiting protein expression and leading to toxicity (Kariko et al., *Immunity* 23, 165-175 (2005)). To improve the stability and reduce the immunogenic potential of the delivered mRNA, synthetic versions that incorporate modified nucleotides were used. For example, substitution of uridine and cytidine with the engineered bases pseudouridine and 5-methyl-cytidine synergistically blocks recognition by innate pattern recognition receptors and increases mRNA translation.

Figure 3A:
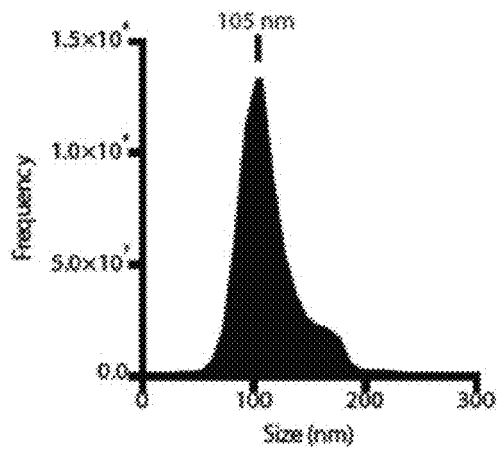
FIGS. 3A-3C. Physical properties of mRNA-loaded nanoparticles.
Figure 3B:
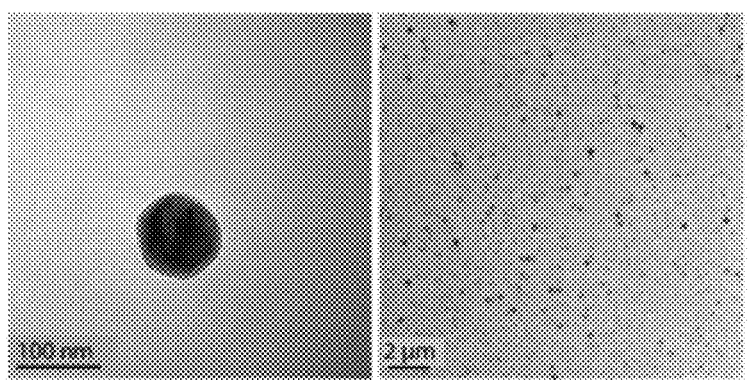
Figure 3C:
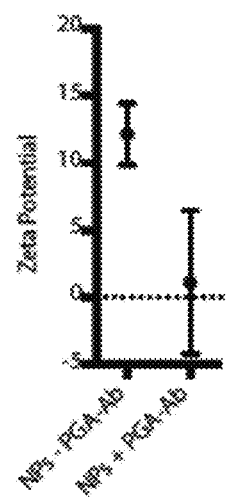
Figure 4A:
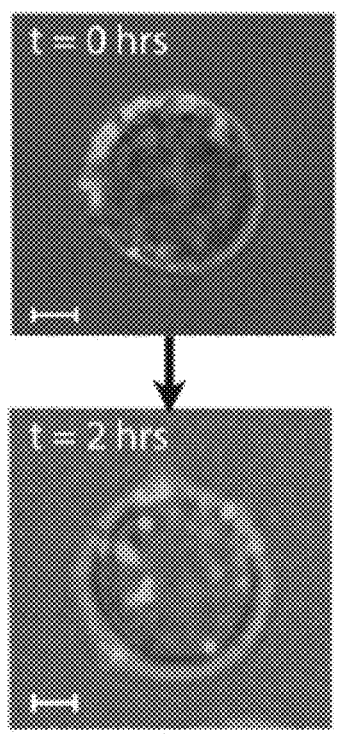
FIGS. 4A-4D. mRNA nanoparticle transfection requires minimal cell handling and choreographs robust transgene expression by lymphocytes without affecting their viability.
Figure 4B:
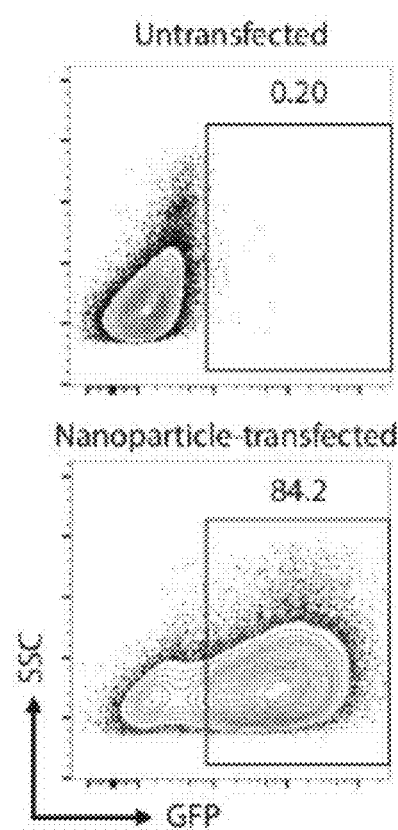
Figure 5A:
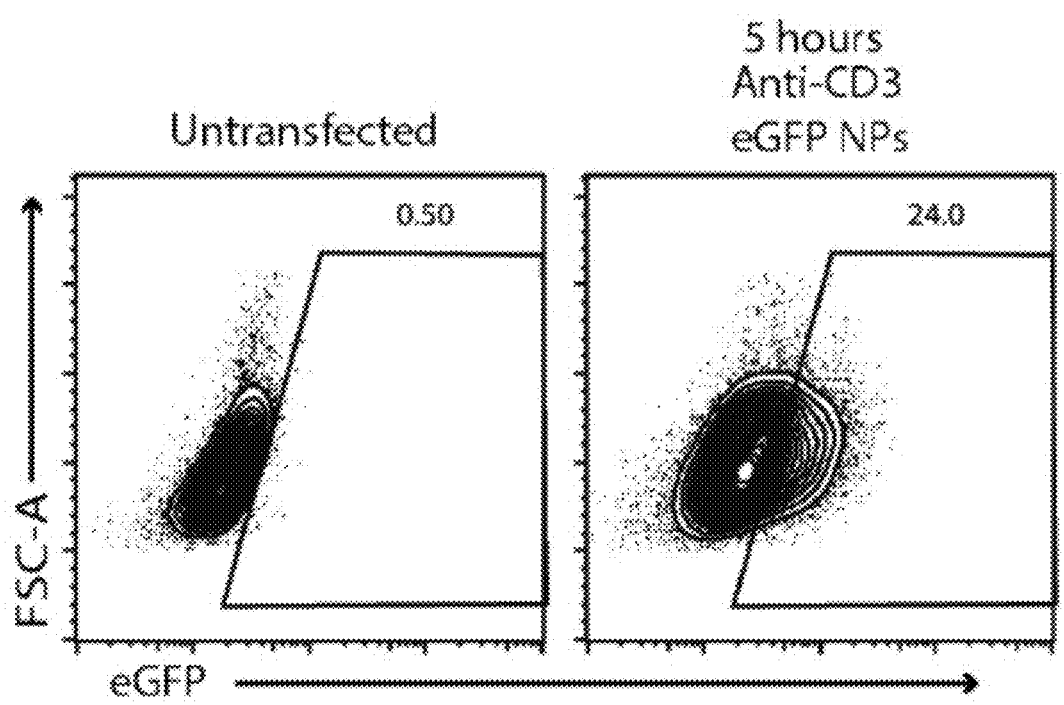
FIG. 5A, 5B. Nanoparticle transfection is rapid and not deteriorated by lyophilization.
Figure 5B:
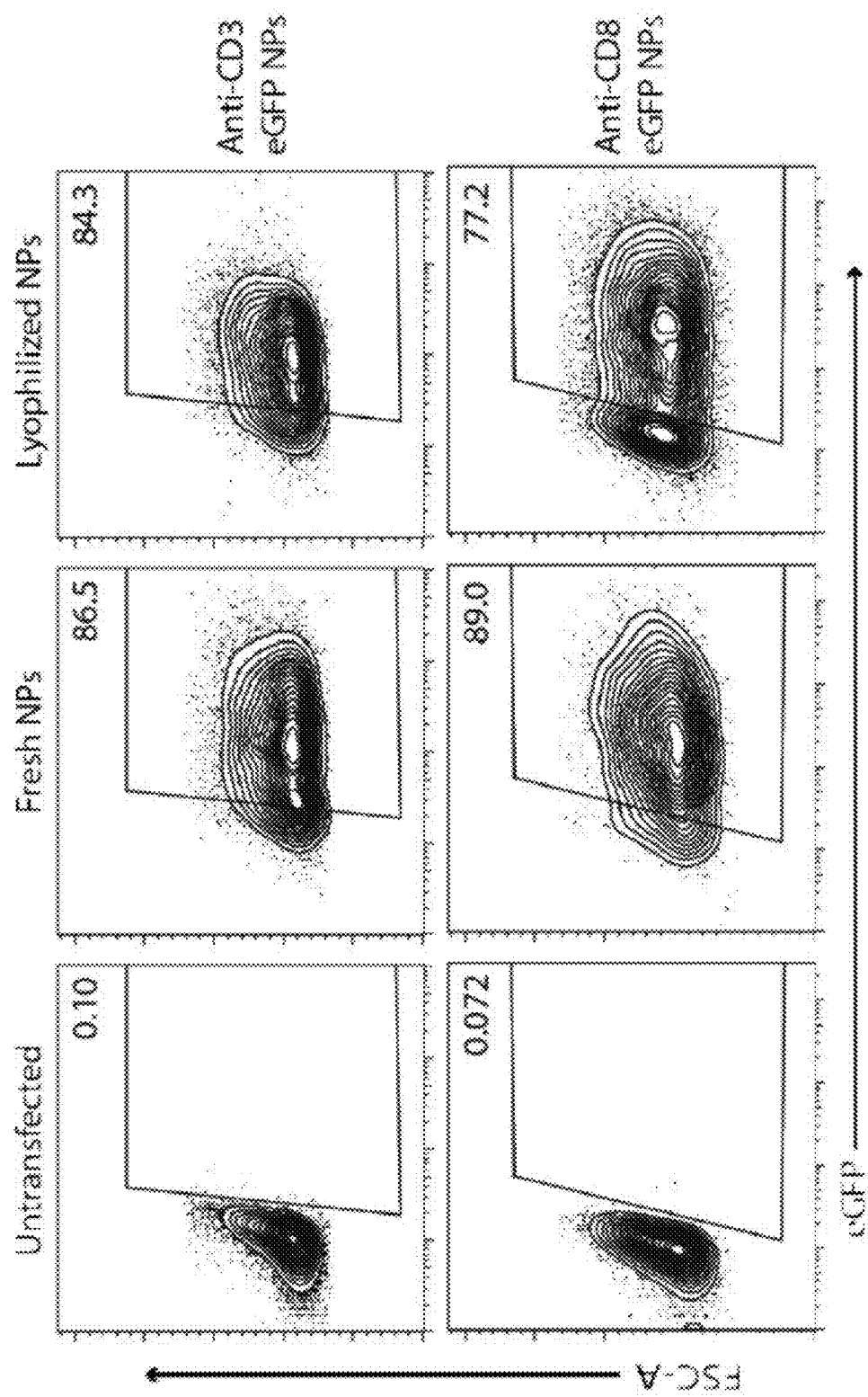

The NPs were manufactured utilizing a two-step, charge-driven self-assembly process. First, the synthetic mRNA was complexed with a positively-charged PBAE polymer, which condenses the mRNA into nano-sized complexes (FIG. 3A, 3B). This step was followed by the addition of antibody-functionalized PGA, which shields the positive charge of the PBAE-mRNA particles and confers lymphocyte-targeting. The resulting mRNA nanocarriers had a size of 109.6±26.6 nm and an almost neutral surface charge (1.1±5.3 mV zeta potential, FIG. 3C).

mRNA nanocarriers achieve T cell transfection efficiencies similar to electroporation, but do not reduce viability. The goal is to streamline the manufacture of cell-based therapies, so it was first tested whether simply adding targeted mRNA nanocarriers to an established culture of human lymphocytes is sufficient to choreograph robust transfection of them. When CD3− targeted NPs carrying mRNA encoding a reporter (enhanced green fluorescent protein, eGFP) are incubated with these cells, they not only bind to them but also stimulate receptor-mediated endocytosis, providing entry for the genes the particles carry (FIG. 4A). Following a single NP application (NP:T cell ratio=2× $10^4$:1) 85% of these primary T cells (FIG. 4B) were routinely transfected with transgene expression observed as early as 5 hours post-transfection (FIG. 5A). Thus, this process is fast and efficient. Importantly, it was not necessary to prepare mRNA NPs freshly for each application, but rather it was possible to lyophilize them before their use with no change in properties or efficacy (FIG. 5B).

Figure 4C:
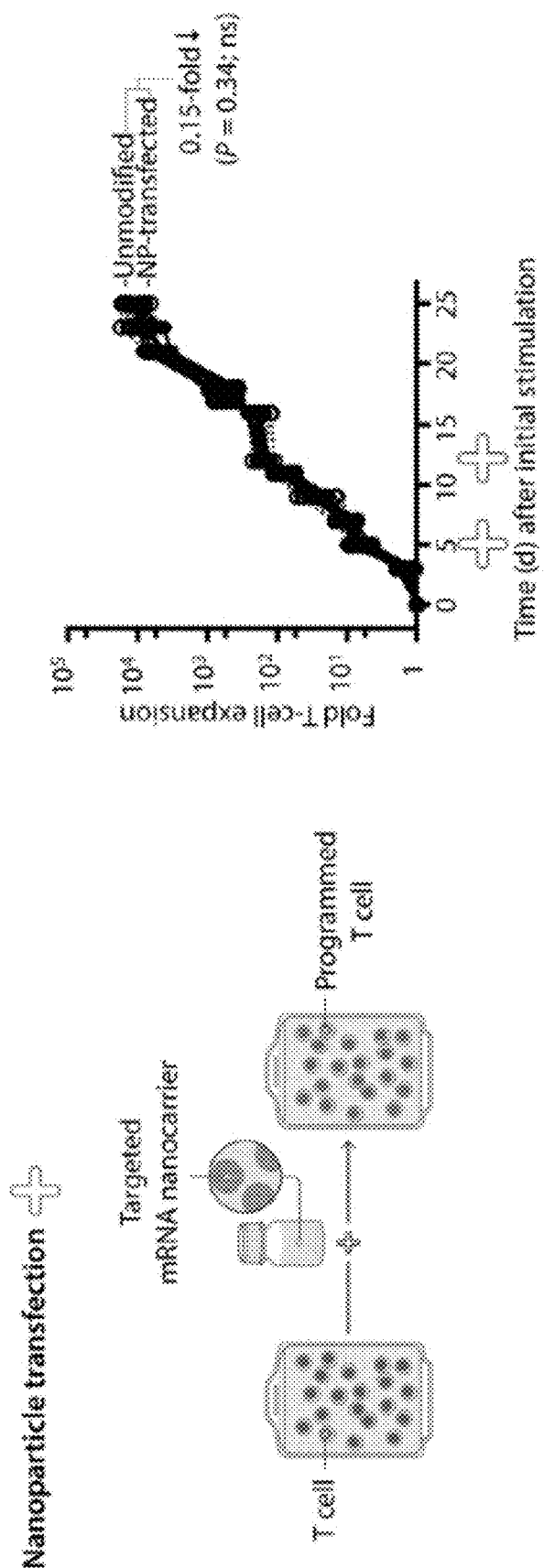
Figure 4D:
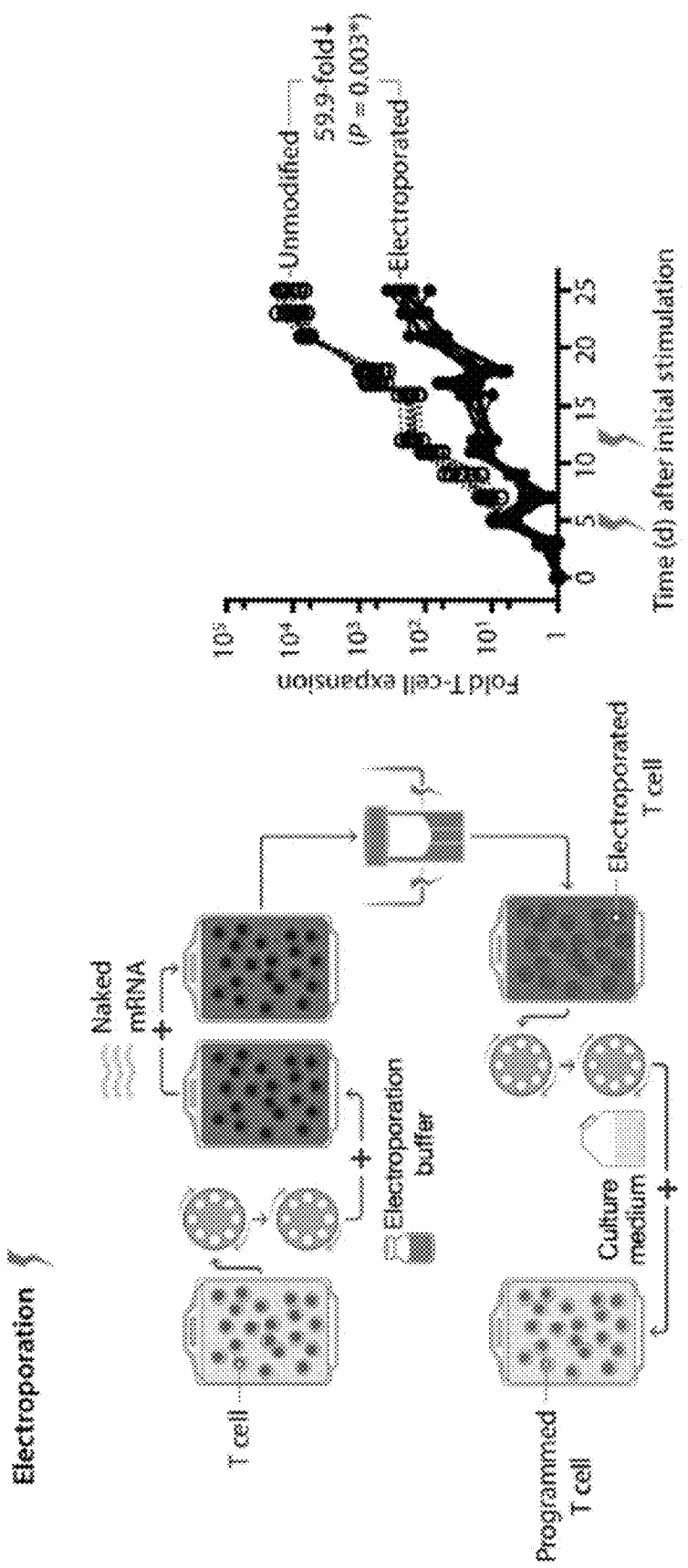
Figure 6:
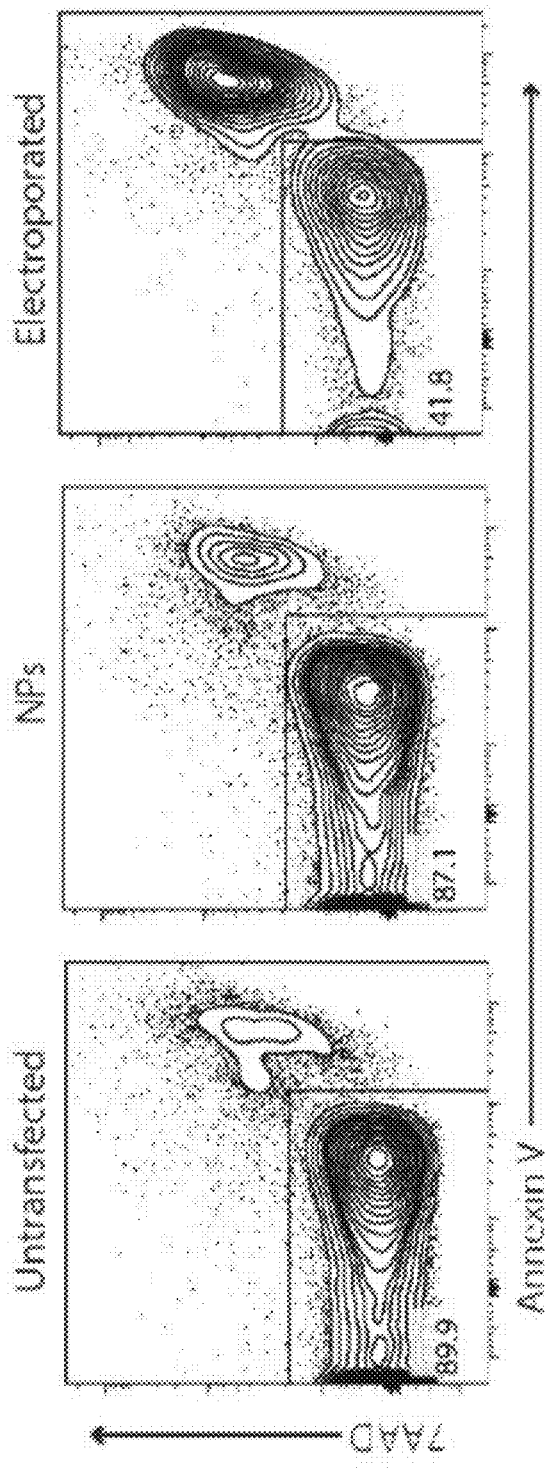
FIG. 6. Relative viability of nanoparticle-transfected and electroporated T cells. Samples of $2\times10^6$ activated T cells per condition were untreated, transfected with NPs, or electroporated as described in FIG. 2C. 18 h after treatment, cells were labeled with fluorescent dyes to assess viability. The results shown here are representative of three separate experiments.

It was next assessed the impact of targeted mRNA-carrying NPs on T cell expansion. Because malignancies often progress quickly, it is important that engineered T cells can be expanded to clinically relevant scales rapidly. One widely used approach to multiply polyclonal lymphocytes in clinical laboratories is to incubate them with beads that are coated with antibodies against TCR/CD3 and co-stimulatory CD28 receptors. Even repeated transfections with CD3-targeted NPs (NP:T-cell ratio: 2×$10^4$:1) did not interfere with the expansion of T cells stimulated by these coated beads (FIG. 4C). This result is in sharp contrast to T cell electroporation, which was tested side-by-side. Not only did electroporation add complex cell handling steps (such as medium exchanges and centrifugation cycles, FIG. 4D), this method compromised the viability of the lymphocytes (FIG. 6), which reduced the yield of T cells by 60-fold (FIG. 4D, right panel).

Figure 7A:
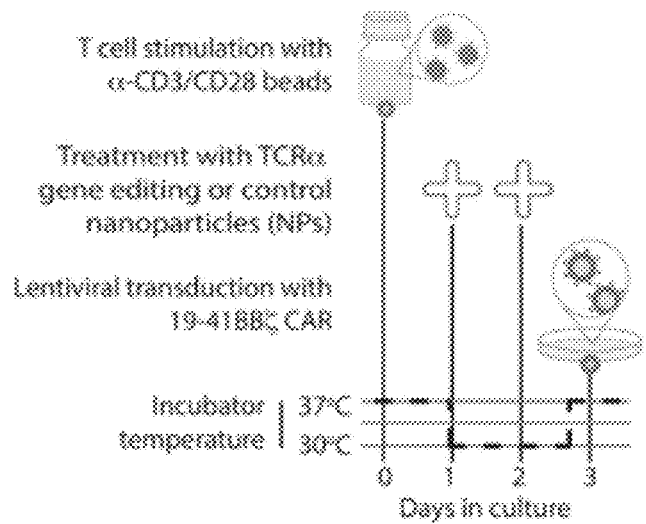
FIGS. 7A-7H Nanocarriers carrying mRNA encoding a TCRα-targeting megaTAL nuclease can knock out T cell receptors in CAR-programmed lymphocytes.
Figure 7B:
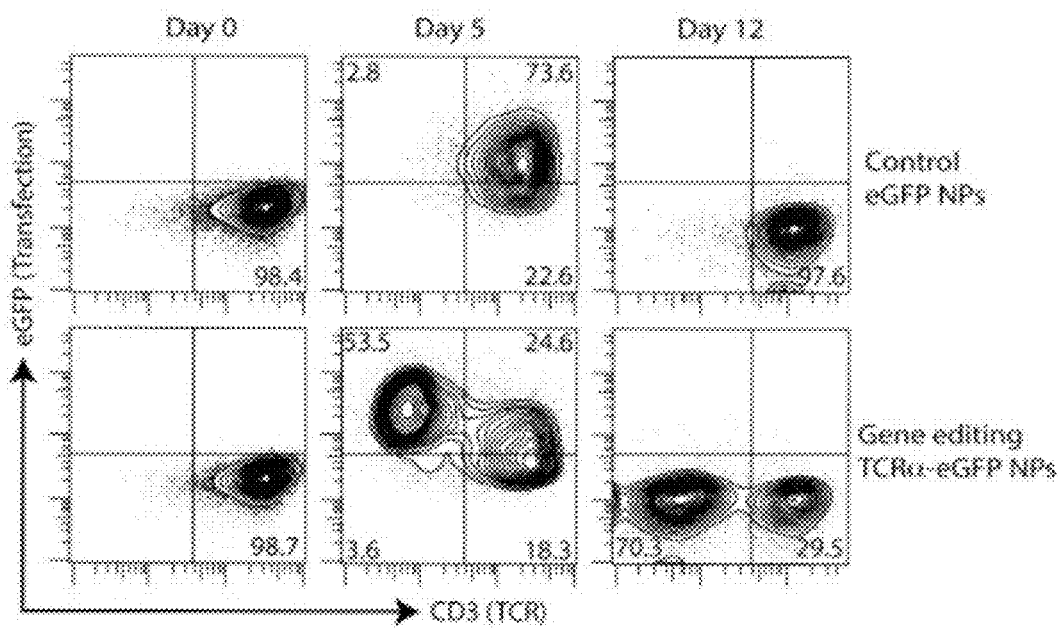
Figure 7C:
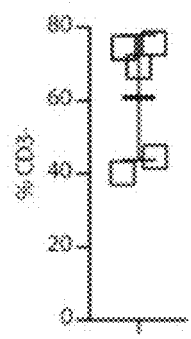
Figure 7D:
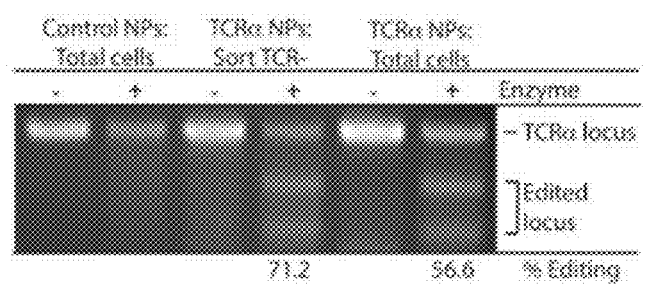
Figure 7E:
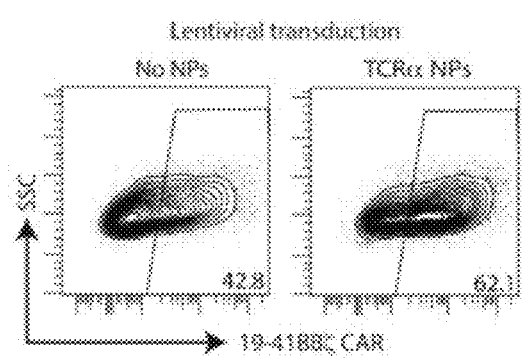
Figure 7F:
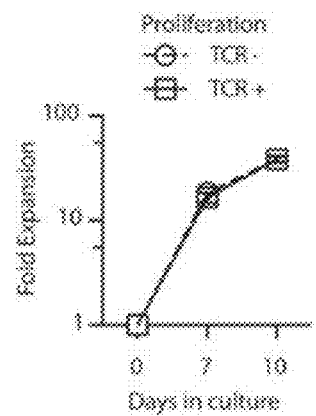
Figure 7G:
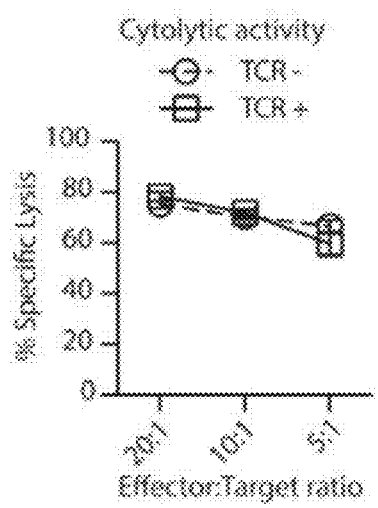
Figure 7H:
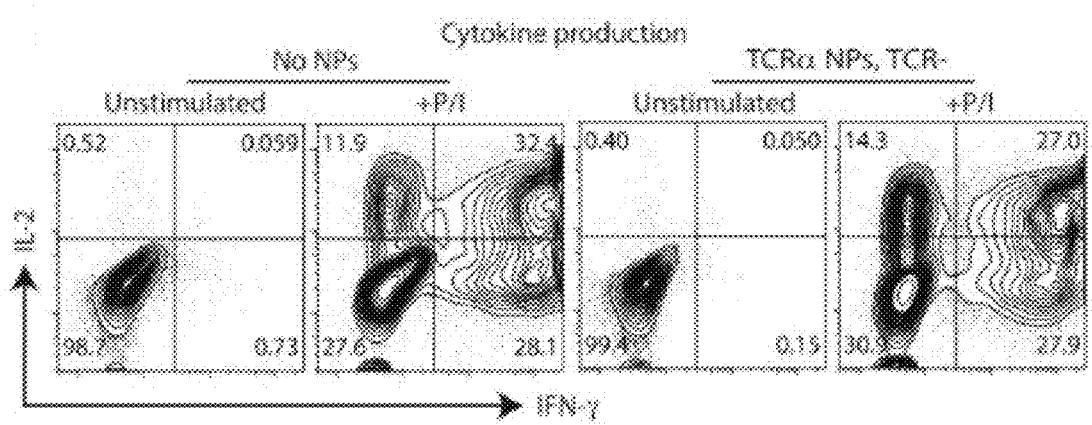

Nanoparticle transfection seamlessly integrates into the CAR-T cell manufacturing workflow to achieve efficient genome editing. The approach was tested in a clinically-relevant application by incorporating NP-mediated mRNA transfection into the manufacture of leukemia-specific 19-41BBζ CAR T cells (FIG. 7A). CD19-targeted receptors are the most investigated CAR-T cell product today, with nearly 30 ongoing clinical trials internationally (Sadelain et al., *J Clin Invest* 125, 3392-3400 (2015)). The ability to now perform genome engineering offers the potential to improve the safety and efficacy of CAR-T cells. For example, expression of endogenous TCRs can be eliminated to avoid graft-versus-host disease. Further, immune checkpoint genes can be selectively deleted to strengthen their activity in the suppressive tumor milieu (Menger et al., *Cancer Res* 76, 2087-2093 (2016); Torikai et al., *Blood* 119, 5697-5705 (2012)). However, using electroporation to deliver genome-editing agents into cells poses a substantial barrier for scaling-up T cell manufacture. Accordingly, the ability of NPs to deliver gene-editing agents was measured by preparing particles carrying mRNA encoding megaTAL nuclease, which targets the constant region (TRAC) of the TCR alpha gene. Taking advantage of the flexibility offered by the NP formulation methods, mRNA encoding the DNA repair endonuclease TREX2 were included to improve knockout efficiency, along with eGFP mRNA to track transfection. Control particles were loaded with eGFP mRNA only. In contrast to eGFP-transfection (which did not impact TCR expression; FIG. 7B, top row), the addition of TCRα-megaTAL particles to the T cell culture efficiently disrupted TCR expression by day 5, an effect that was maintained after loss of the mRNA by day 12 (FIG. 7B, bottom row). Average TCR levels were 60.8% compared to controls (±17.7%; FIG. 73C), which corresponds with the percentage of indel frequencies (a measure of targeting efficiency) determined using the Surveyor assay (FIG. 7D). Importantly, the presence of mRNA-carrying nanoparticles did not affect virus-mediated gene transfer of the tumor-specific CAR, as equal transduction efficiencies with a lentiviral vector encoding 19-41BBζ CAR was achieved in NP-transfected and non-transfected T cells (FIG. 7E). Following NP-mediated genome editing and lentiviral transduction, CAR-programmed T cells fully maintained their capacities to proliferate, secrete cytokines, and kill leukemia target cells (FIG. 7F-7H). In summary, these findings establish that lymphocyte-targeted mRNA nanocarriers can mediate efficient genome editing of CAR-T cells without compromising their function.

Figure 8A:
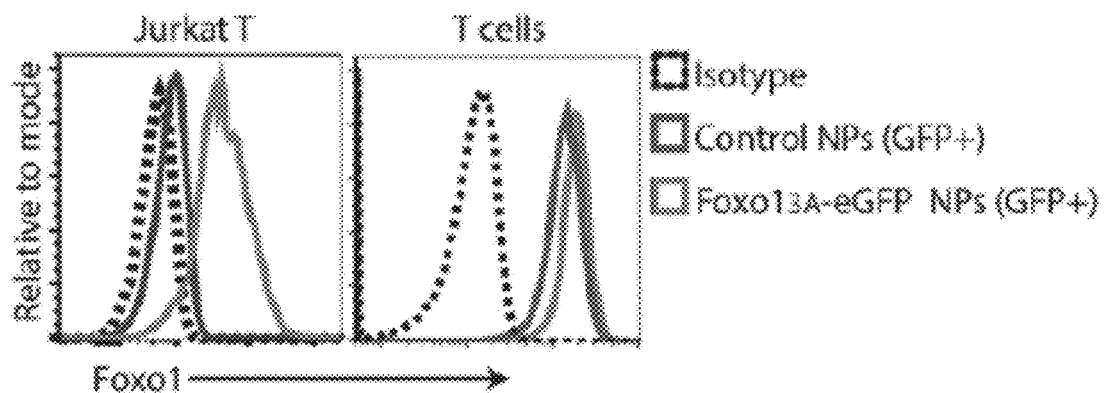
FIGS. 8A-8F. Nanocarriers with mRNA encoding the Foxo13A transcription factor induce surface markers and transcriptional patterns characteristic of CD8+ central memory T cells.
Figure 8B:
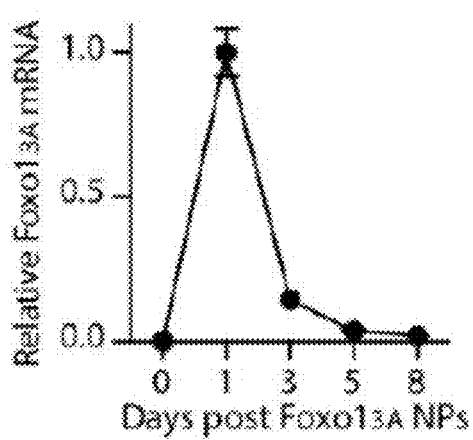
Figure 8C:
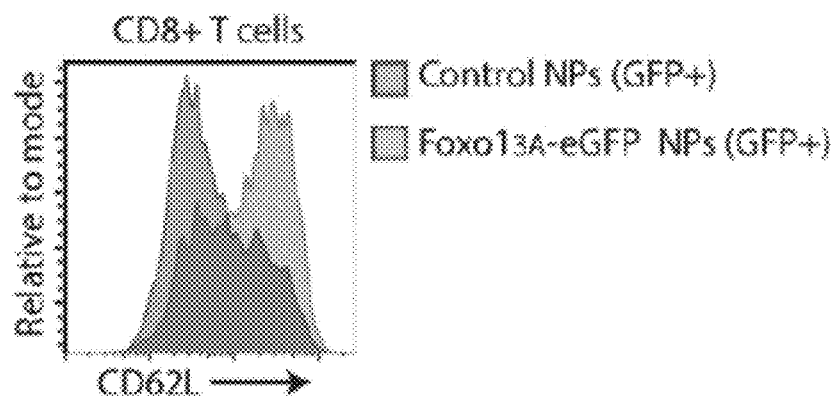
Figure 8D:
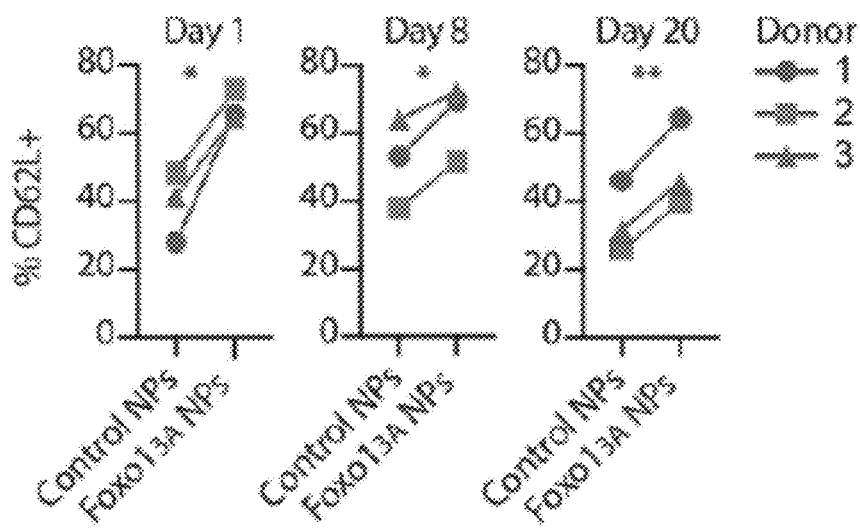

NP-delivered mRNA encoding the transcription factor Foxo1 imprints memory CAR– T cells. It was next examined whether lymphocyte-targeted mRNA NPs can improve the therapeutic activity of CAR-T cells by delivering mRNAs that program them toward a favorable phenotype. Clinical findings have already established that T cell products derived from CD62L+ central memory T cells (TCM) display improved engraftment and function in animal models, and the fraction of CD62L+ TCM phenotype cells in infused products is linked to successful CAR therapy (Louis et al., *Blood* 118, 6050-6056 (2011); Sommermeyer et al., *Leukemia* 30, 492-500 (2016)). However, to achieve therapeutically relevant lymphocyte numbers, these cells must undergo rounds of in vitro stimulation/expansion—a process that drives cells away from the TCM lineage and toward terminal differentiation and senescence (Wang et al., *Journal of immunotherapy* 35, 689-701 (2012)). To address this problem, T cell-targeted NPs loaded with mRNA encoding the forkhead family transcription factor Foxo1, which controls the effector-to-memory transition in CD8 T cells (Tejera, et al., *J Immunol* 191, 187-199 (2013); Kim et al., *Immunity* 39, 286-297 (2013) were manufactured. During in vitro stimulation/expansion, TCR and cytokine signaling activate AKT kinase. This enzyme phosphorylates Foxo1, which leads to its cytoplasmic segregation and blockade of transcriptional activity. To maintain Foxo1 in cultured T cells, an AKT-insensitive variant of the factor was used in which three key phosphorylated residues are mutated to alanine (Foxo13A). It was hypothesized that addition of Foxo13A-containing NPs to T cell culture medium during ex vivo expansion would promote the development of CD62L+ TCM cells that have improved therapeutic potential. The effect transcription factors have on reprogramming is sensitive to the magnitude and duration of their expression. To determine these values after Foxo13A-NP addition, Foxo1 protein and mRNA expression in nanoparticle-treated cells was measured. In the Jurkat T cell line, endogenous expression of Foxo1 is low and Foxo13A NP treatment led to large increases in total expression of the factor, measured by intracellular labeling (FIG. 8A, left panel). In primary T cells, expression levels of Foxo1 protein is already high, and Foxo13A-NPs only led to modest increases. This indicates that NP treatment can induce near-physiological levels of the active Foxo13A transcription factor (FIG. 8A, right panel). To determine mRNA dynamics after NP transfection of activated, proliferating T cells, the expression of Foxo13A was measured using real-time quantitative PCR specific for the engineered mRNA. mRNA expression was maximal at day 1, and was close to baseline by 8 days post-transfection (FIG. 8B). Treatment with Foxo13A NPs after T cell priming in vitro rapidly increased expression of CD62L (FIG. 8C), which is the primary surface marker that distinguishes TCM from effector and effector memory populations (Sallusto et al., *Nature* 401, 708-712 (1999)). To determine if transient expression of Foxo13A can lead to persistent alterations in CD8+ T cell differentiation, cells from 3 independent donors were treated with CD8-targeted Foxo13A-eGFP NPs, sorted based on eGFP expression, and maintained in vitro. An increased frequency of CD62L+ cells was observed by 24 hours after transfection, and this was maintained even 8 and 20 days after NP addition (FIG. 8D).

Figure 8E:
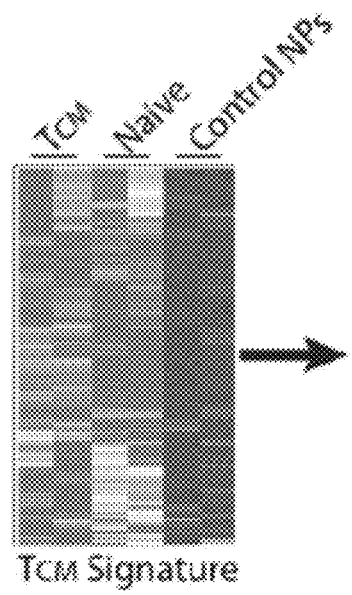
Figure 8F:
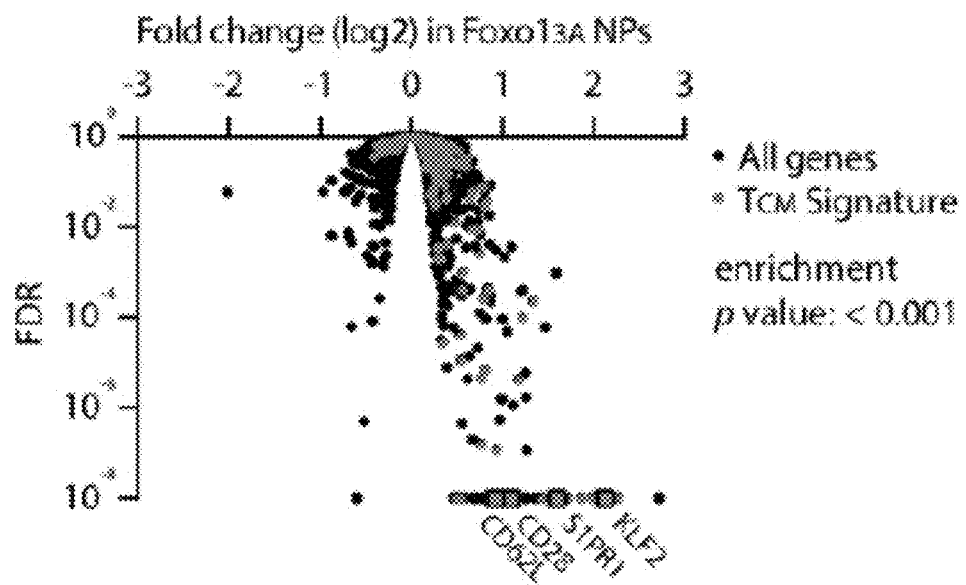
Figure 9A:
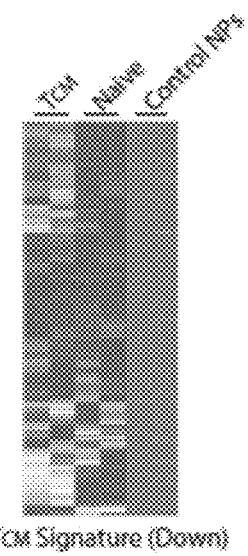
FIG. 9A, 9B. Gene set enrichment reveals strong correlations between TCM and Foxo13A nanoparticle-treated cells.
Figure 9B:
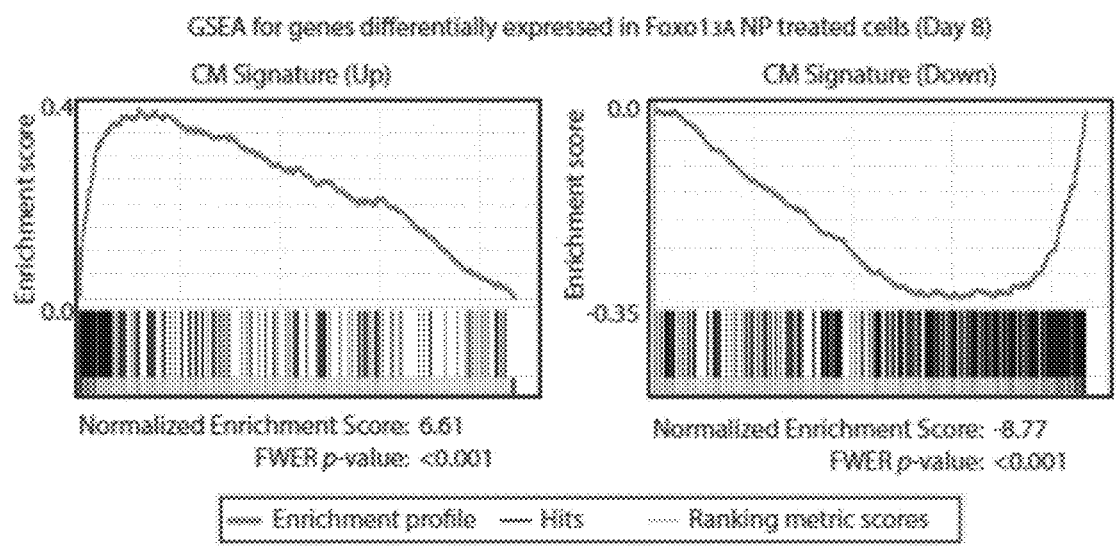
Figure 10A:
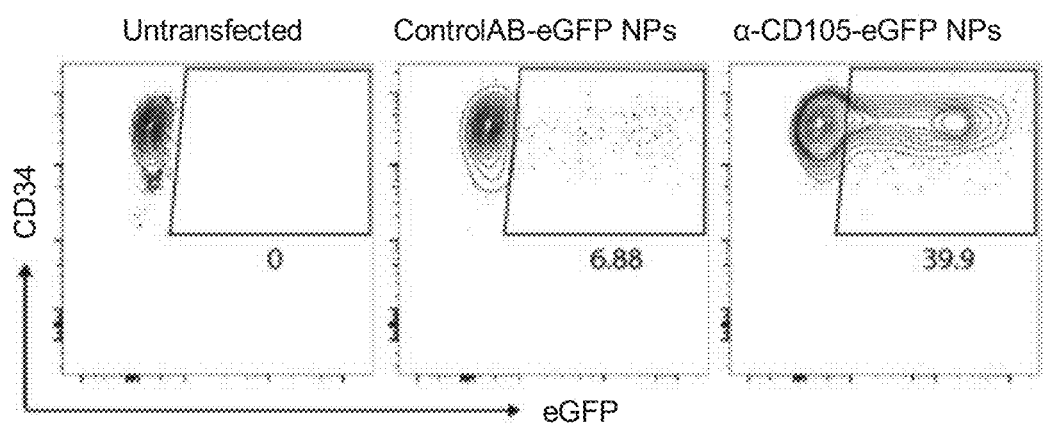
FIGS. 10A-10D. mRNA nanocarriers enable specific transfection of CD34+ human hematopoietic stem cells with minimal effects on expansion or phenotype.
Figure 10B:
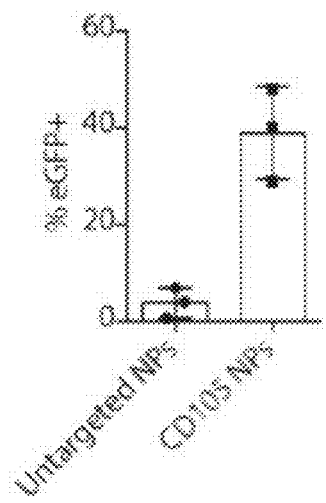
Figure 10C:
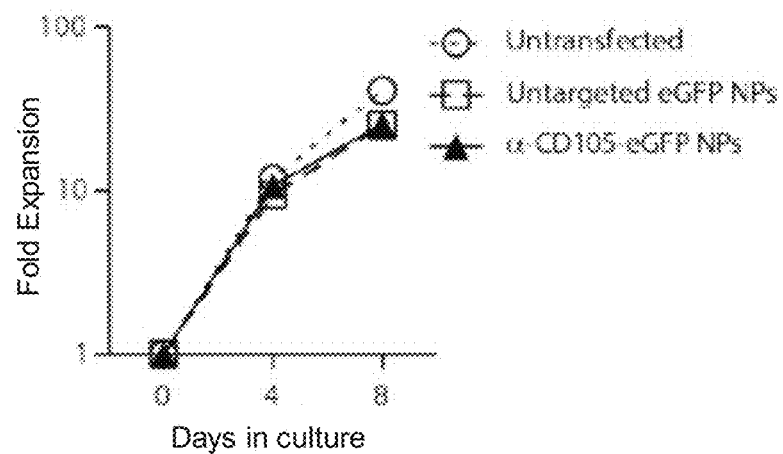
Figure 10D:
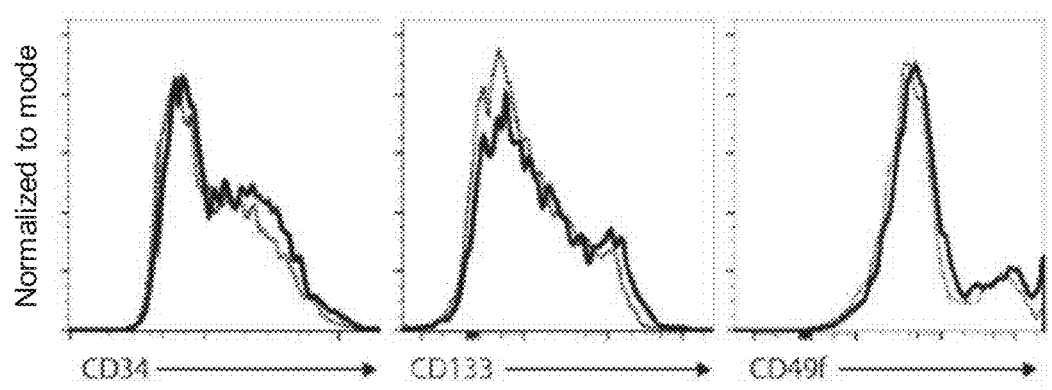

To understand the genetic regulatory network induced by Foxo13A and its connections to the TCM lineage, RNASeq was performed on ex vivo isolated naïve CD8, TCM CD8, and in vitro-cultured CD8 T cells that were treated with Foxo13A-encoding NPs or control particles. A TCM signature consisting of the top 500 genes that have higher or lower expression in TCM vs. average CD8 T cells (FIG. 8E and FIG. 9A) was identified. The majority of these genes are coordinately regulated in naïve CD8 T cells, which is consistent with the close transcriptional relationship between naïve and TCM (Kaech & Cui, Immunol 12, 749-761 (2012)). Foxo13A-encoding NP treatments led to differential expression of a large number of genes. As expected, these included those encoding the key memory transcriptional effector KLF2, and the surface molecules SELL (CD62L), CD28, and S1PR1, all crucial mediators of CD8 TCM trafficking and function (FIG. 8F) (Skon et al., *Nature immunology* 14, 1285-1293 (2013); Boesteanu et al., *Seminars in immunology* 21, 69-77 (2009)). Overlaying the TCM gene signature onto the Foxo13A volcano plot reveals a strong concordance of transcripts: TCM signature genes were up-regulated in Foxo13A-programmed CD8 cells. Gene set enrichment analysis confirmed the strong connection between Foxo13A-regulated transcripts and TCM-associated gene expression (FIG. 9B). In summary, these results indicate that Foxo13A-encoding NPs induce persistent alterations in surface markers, and transcriptional programming toward a TCM-like phenotype.

Discussion. This example demonstrates that appropriately designed mRNA nanocarriers can transiently program gene expression in primary lymphocytes. As examples, memory phenotype induction and therapeutic genome editing are shown, demonstrating how cell function and/or differentiation can be permanently reprogrammed via the simple addition of bioengineered nanoparticles to cultures of T cells. This nanotechnology platform does not require special cell handling, so it can be easily integrated into established protocols for the manufacture of therapeutic T cells without changing the workflow, or the equipment used in the process. This could be a significant advantage in manufacturing compared to RNA electroporation, which is currently the method of choice for hit-and-run gene therapy in T cells (Schumann et al., Proc Natl Acad Sci USA 112, 10437-10442 (2015); Wang et al., Nucleic Acids Res 44, e30 (2016); Bai et al., Cell Discovery, (2015)). As depicted in FIG. 2, in addition to the expensive equipment involved, electroporation requires many culture medium exchanges, centrifugation steps, and washing cycles. Each of these steps is prone to error, increasing the risk of contamination and compromising the output of disease-battling lymphocytes. Even state-of-the-art flow electroporation devices reduce T cell viability, and hence product yield and quality (Koh et al., Mol Ther Nucleic Acids 2, e114 (2013); Liu et al., Cancer Res 75, 3596-3607 (2015)). The approach does not rely on mechanical permeabilization of cell membranes to deliver transgenes. Instead, engineered nanoparticles bind to T cells and stimulate receptor-mediated endocytosis—a physiological process that provides entry for the RNA they carry without compromising cell viability (FIG. 4C).

Cell-penetrating peptides (CPPs), which are small proteins that facilitate cellular uptake of various molecular cargos, have also been used to transport therapeutics into primary T cells (Copolovici, *ACS Nano* 8, 1972-1994 (2014)). Even large proteins that harbor CPP domains can be introduced into the cytoplasm using this approach. However, specific targeting of selected cell types is not possible with CPPs, and protein transfer is relatively inefficient (Liu et al., *PLoS One* 9, e85755 (2014); Liu et al., *Mol Ther Nucleic Acids* 4, e232 (2015)). The duration of therapeutic impact also strongly depends on the half-life of the transferred protein. By contrast, nanocarriers loaded with synthetic mRNA are targeted to particular cells, and every delivered RNA molecule serves as a template for the translation of multiple protein copies.

The CD3 and CD8 molecules targeted in these experiments are just two of many antigens that could be used to selectively shuttle mRNA into lymphocytes. To selectively modify only defined T cell subsets, such as antigen-experienced lymphocytes, activation markers (e.g., CD25, 4-1BB, OX40, or CD40L) could be targeted. Also, the choices for the core polymer and the charge-negating coating material are flexible, and will likely be optimized before production in a clinical setting comes about. In terms of the former, panel of cationic polymers, including hyperbranched STAR polymer, polyethylene glycol-grafted polyethylenimine, and mesoporous silica nanoparticles, were tested and PBAE 447 was selected based on its superior transfection efficacy and low biomaterial-mediated cytotoxicity in primary T cells. The latter is the result of the high biodegradability of this formulation, which has a half-life between 1 and 7 hours in aqueous conditions (Mangraviti et al., *ACS Nano* 9, 1236-1249 (2015)). This time frame is ideal for gene therapy, as the polymer condenses and effectively protects mRNA against degradation while it is encapsulated in the endosome, but releases it soon after transfer into the cytoplasm, thus enabling transcription of the encoded protein. Importantly, in all nanoparticle designs tested, a negatively charged nanoparticle coating was required to shield the positive charge of RNA/PBAE polyplexes and prevent off-target binding.

Beyond T cell therapy, the use of the described approach has been explored for the manufacture of more effective hematopoietic stem cell (HSC) products, using mRNA nanocarriers targeting CD105 (FIG. 10). In particular, strategies to improve the self-renewal properties of HSCs or to modulate their fate decisions have substantial clinical appeal ((Galeev et al., *Cell Rep* 14, 2988-3000 (2016); Rentas et al., *Nature* 532, 508-511 (2016)). Like the field of adoptive T cell therapy, where pharmacological compounds are being tested as supplements to manufacture lymphocytes with greater longevity and/or in vivo efficacy, high-throughput screening of libraries has identified small molecules that can modify stem cell expansion (Nikiforow & Ritz, *Cell Stem Cell* 18, 10-12 (2016). However, many chemical compounds can only inhibit protein function, and their specificity for the desired target is often debatable (Schenone et al., Nat Chem Biol 9, 232-240 (2013). In addition, various types of proteins cannot be controlled using small molecules. By contrast, targeted mRNA nanocarriers can selectively induce expression of virtually any known protein (or combinations of proteins). Furthermore, the nucleotides they carry can easily be fabricated based on published sequences.

In summary, Example 1 demonstrates that a single nanoparticle reagent added to a leukocyte culture can efficiently reprogram T cells for therapeutic purposes using 'hit-and-run' gene modification. This platform does not add complexity to manufacturing because it does not require special equipment or training. Thus, it can substantially streamline the manufacture of genetic cell-based therapies at clinical scales, which means that treating patients with genetically engineered T cells could become lower in cost and more broadly applicable.

As will be understood by one of ordinary skill in the art, each embodiment disclosed herein can comprise, consist essentially of or consist of its particular stated element, step, ingredient or component. As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. As used herein, a material effect would cause a statistically-significant reduction in the ability of a nanocarrier disclosed herein to change the phenotype of a selected cell type following exposure of the selected cell type to the nanocarrier for 48 hours.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference for their particular cited teachings.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

What is claimed is:

1. A method of selectively modifying a selected cell population of hematopoietic origin comprising:
   (a) forming selected cell-targeted synthetic nanocarriers by
      (i) adding polyglutamic acid (PGA) conjugated to selected cell targeting ligands that bind the selected cell population of hematopoietic origin to a solution comprising nucleic acid encapsulated within a positively-charged carrier comprising poly(β-amino ester); and
      (ii) incubating the solution wherein selected cell-targeted synthetic nanocarriers form within 5 minutes of the adding and comprise
         (A) nucleic acid encapsulated within the positively-charged carrier comprising poly(β-amino ester);
         (B) a neutrally or negatively-charged coating comprising about a 15 kDa PGA on the outer surface of the positively-charged carrier; and
         (C) the selected cell targeting ligands extending from the outer surface of the neutrally or negatively-charged coating and conjugated to PGA within the neutrally or negatively-charged coating; and
   (b) administering the formed selected cell-targeted synthetic nanocarriers to a heterogenous mixture of ex vivo cells comprising the selected cell population of hematopoietic origin within a serum-free media thereby selectively modifying the selected cell population of hematopoietic origin.

2. A method of claim 1 wherein the nucleic acid encodes a megaTAL of SEQ ID NO: 1 or a humanized chimeric antigen receptor of SEQ ID NO: 37.

3. A method of claim 1 wherein the nucleic acid is synthetic mRNA.

4. A method of claim 3 wherein the synthetic mRNA encodes a gene editing agent selected from transcription activator-like effector nucleases (TALENs); megaTALs; and/or zinc finger nucleases.

5. A method of claim 3 wherein the synthetic mRNA encodes a phenotype-altering protein selected from FOXO1, LKB1, TCF7, EOMES, ID2, TERT, CCR2b, and/or CCR4.

6. A method of claim 1 wherein the selected cell population of hematopoietic origin is selected from T cells, natural killer cells, monocytes, macrophages, dendritic cells, B cells, or hematopoietic stem cells.

7. A method of claim 1 wherein the selected cell targeting ligand comprises a CD4 binding domain or a CD8 binding domain.

8. A method of claim 1 wherein no cell selection or purification processes that increase the percentage of the selected cell population relative to other cells within the heterogenous mixture are performed prior to the administering.

* * * * *

SEQUENCE LISTING

```
<160> NUMBER OF SEQ ID NOS: 57

<210> SEQ ID NO 1
<211> LENGTH: 887
<212> TYPE: PRT
<213> ORGANISM: Artificial Sequence
<220> FEATURE:
<223> OTHER INFORMATION: megaTAL protein specific for TCRalpha

<400> SEQUENCE: 1

Met Gly Ser Cys Arg Tyr Pro Tyr Asp Val Pro Asp Tyr Ala Pro Pro
1               5                   10                  15

Lys Lys Lys Arg Lys Val Val Asp Leu Arg Thr Leu Gly Tyr Ser Gln
            20                  25                  30

Gln Gln Gln Glu Lys Ile Lys Pro Lys Val Arg Ser Thr Val Ala Gln
```

-continued

```
                35                  40                  45
His His Glu Ala Leu Val Gly His Gly Phe Thr His Ala His Ile Val
 50                  55                  60
Ala Leu Ser Gln His Pro Ala Leu Gly Thr Val Ala Val Thr Tyr
 65                  70                  75                  80
Gln His Ile Ile Thr Ala Leu Pro Glu Ala Thr His Glu Asp Ile Val
                 85                  90                  95
Gly Val Gly Lys Gln Trp Ser Gly Ala Arg Ala Leu Glu Ala Leu Leu
                100                 105                 110
Thr Asp Ala Gly Glu Leu Arg Gly Pro Pro Leu Gln Leu Asp Thr Gly
                115                 120                 125
Gln Leu Val Lys Ile Ala Lys Arg Gly Gly Val Thr Ala Met Glu Ala
 130                 135                 140
Val His Ala Ser Arg Asn Ala Leu Thr Gly Ala Pro Leu Asn Leu Thr
 145                 150                 155                 160
Pro Asp Gln Val Val Ala Ile Ala Ser Asn Ile Gly Gly Lys Gln Ala
                165                 170                 175
Leu Glu Thr Val Gln Arg Leu Leu Pro Val Leu Cys Gln Asp His Gly
                180                 185                 190
Leu Thr Pro Asp Gln Val Val Ala Ile Ala Ser Asn Ile Gly Gly Lys
                195                 200                 205
Gln Ala Leu Glu Thr Val Gln Arg Leu Leu Pro Val Leu Cys Gln Asp
 210                 215                 220
His Gly Leu Thr Pro Asp Gln Val Val Ala Ile Ala Ser Asn Ile Gly
 225                 230                 235                 240
Gly Lys Gln Ala Leu Glu Thr Val Gln Arg Leu Leu Pro Val Leu Cys
                245                 250                 255
Gln Asp His Gly Leu Thr Pro Asp Gln Val Val Ala Ile Ala Ser Asn
                260                 265                 270
Gly Gly Gly Lys Gln Ala Leu Glu Thr Val Gln Arg Leu Leu Pro Val
                275                 280                 285
Leu Cys Gln Asp His Gly Leu Thr Pro Asp Gln Val Val Ala Ile Ala
 290                 295                 300
Ser His Asp Gly Gly Lys Gln Ala Leu Glu Thr Val Gln Arg Leu Leu
 305                 310                 315                 320
Pro Val Leu Cys Gln Asp His Gly Leu Thr Pro Asp Gln Val Val Ala
                325                 330                 335
Ile Ala Ser His Asp Gly Gly Lys Gln Ala Leu Glu Thr Val Gln Arg
                340                 345                 350
Leu Leu Pro Val Leu Cys Gln Asp His Gly Leu Thr Pro Asp Gln Val
                355                 360                 365
Val Ala Ile Ala Ser Asn Ile Gly Gly Lys Gln Ala Leu Glu Thr Val
 370                 375                 380
Gln Arg Leu Leu Pro Val Leu Cys Gln Asp His Gly Leu Thr Pro Asp
 385                 390                 395                 400
Gln Val Val Ala Ile Ala Ser Asn Gly Gly Lys Gln Ala Leu Glu
                405                 410                 415
Thr Val Gln Arg Leu Leu Pro Val Leu Cys Gln Asp His Gly Leu Thr
                420                 425                 430
Pro Asp Gln Val Val Ala Ile Ala Ser Asn Gly Gly Gly Lys Gln Ala
                435                 440                 445
Leu Glu Thr Val Gln Arg Leu Leu Pro Val Leu Cys Gln Asp His Gly
 450                 455                 460
```

```
Leu Thr Pro Asp Gln Val Val Ala Ile Ala Ser Asn Asn Gly Gly Lys
465                 470                 475                 480

Gln Ala Leu Glu Thr Val Gln Arg Leu Leu Pro Val Leu Cys Gln Asp
            485                 490                 495

His Gly Leu Thr Pro Asp Gln Val Val Ala Ile Ala Ser Asn Ile Gly
            500                 505                 510

Gly Lys Gln Ala Leu Glu Ser Ile Val Ala Gln Leu Ser Arg Pro Asp
        515                 520                 525

Pro Ala Leu Ala Ala Leu Thr Asn Asp His Leu Val Ala Leu Ala Cys
        530                 535                 540

Leu Gly Gly Arg Pro Ala Met Asp Ala Val Lys Lys Gly Leu Pro His
545                 550                 555                 560

Ala Pro Glu Leu Ile Arg Arg Val Asn Arg Arg Ile Gly Glu Arg Thr
                565                 570                 575

Ser His Arg Val Ala Ile Ser Arg Val Gly Ser Ser Arg Arg Glu
            580                 585                 590

Ser Ile Asn Pro Trp Ile Leu Thr Gly Phe Ala Asp Ala Glu Gly Ser
        595                 600                 605

Phe Ile Leu Asp Ile Arg Asn Arg Asn Asn Glu Ser Asn Arg Tyr Arg
        610                 615                 620

Thr Ser Leu Arg Phe Gln Ile Thr Leu His Asn Lys Asp Lys Ser Ile
625                 630                 635                 640

Leu Glu Asn Ile Gln Ser Thr Trp Lys Val Gly Lys Ile Thr Asn Ser
                645                 650                 655

Gly Asp Arg Ala Val Met Leu Arg Val Thr Arg Phe Glu Asp Leu Lys
            660                 665                 670

Val Ile Ile Asp His Phe Glu Lys Tyr Pro Leu Ile Thr Gln Lys Leu
        675                 680                 685

Gly Asp Tyr Lys Leu Phe Lys Gln Ala Phe Ser Val Met Glu Asn Lys
690                 695                 700

Glu His Leu Lys Glu Asn Gly Ile Lys Glu Leu Val Arg Ile Lys Ala
705                 710                 715                 720

Lys Met Asn Trp Gly Leu Thr Asp Glu Leu Lys Lys Ala Phe Pro Glu
                725                 730                 735

Asn Ile Ser Lys Glu Arg Pro Leu Ile Asn Lys Asn Ile Pro Asn Phe
            740                 745                 750

Lys Trp Leu Ala Gly Phe Thr Ser Gly Asp Gly Tyr Phe Gly Val Asn
        755                 760                 765

Leu Lys Lys Val Lys Gly Asn Ala Lys Val Tyr Val Gly Leu Arg Phe
770                 775                 780

Ser Ile Ser Gln His Ile Arg Asp Lys Asn Leu Met Asn Ser Leu Ile
785                 790                 795                 800

Thr Tyr Leu Gly Cys Gly Ser Ile Trp Glu Lys Asn Lys Ser Glu Phe
                805                 810                 815

Ser Trp Leu Glu Phe Val Val Thr Lys Phe Ser Asp Ile Asn Asp Lys
            820                 825                 830

Ile Ile Pro Val Phe Gln Glu Asn Thr Leu Ile Gly Val Lys Leu Glu
        835                 840                 845

Asp Phe Glu Asp Trp Cys Lys Val Ala Lys Leu Ile Glu Glu Lys Lys
        850                 855                 860

His Leu Thr Glu Ser Gly Leu Asp Glu Ile Lys Lys Ile Lys Leu Asn
865                 870                 875                 880
```

Met Asn Lys Gly Arg Val Phe
            885

<210> SEQ ID NO 2
<211> LENGTH: 2464
<212> TYPE: DNA
<213> ORGANISM: Homo sapiens

<400> SEQUENCE: 2

| | | | | | |
|---|---|---|---|---|---|
| actctaaaac | gagaagtaca | agtgagttcc | cccaagggt | cggccgcgcc | tcttcctgtc | 60 |
| cccgccctgc | cggctgcccc | aggccagtgg | agtggcagcc | ccagaactgg | gaccaccggg | 120 |
| ggtggtgagg | cggcccggca | ctgggagctg | catctgaggc | ttagtccctg | agctctctgc | 180 |
| ctgcccagac | tagctgcacc | tcctcattcc | ctgcgccccc | ttcctctccg | gaagccccca | 240 |
| ggatggtgag | gtggtttcac | cgagacctca | gtgggctgga | tgcagagacc | ctgctcaagg | 300 |
| gccgaggtgt | ccacggtagc | ttcctggctc | ggcccagtcg | caagaaccag | ggtgacttct | 360 |
| cgctctccgt | cagggtgggg | gatcaggtga | cccatattcg | gatccagaac | tcaggggatt | 420 |
| tctatgacct | gtatggaggg | gagaagtttg | cgactctgac | agagctggtg | gagtactaca | 480 |
| ctcagcagca | gggtgtcctg | caggaccgcg | acggcaccat | catccacctc | aagtacccgc | 540 |
| tgaactgctc | cgatcccact | agtgagaggt | ggtaccatgg | ccacatgtct | ggcgggcagg | 600 |
| cagagacgct | gctgcaggcc | aagggcgagc | cctggacgtt | tcttgtgcgt | gagagcctca | 660 |
| gccagcctgg | agacttcgtg | ctttctgtgc | tcagtgacca | gcccaaggct | ggcccaggct | 720 |
| ccccgctcag | ggtcacccac | atcaaggtca | tgtgcgaggg | tggacgctac | acagtgggtg | 780 |
| gtttggagac | cttcgacagc | ctcacggacc | tggtggagca | tttcaagaag | acggggattg | 840 |
| aggaggcctc | aggcgccttt | gtctacctgc | ggcagccgta | ctatgccacg | agggtgaatg | 900 |
| cggctgacat | tgagaaccga | gtgttggaac | tgaacaagaa | gcaggagtcc | gaggatacag | 960 |
| ccaaggctgg | cttctgggag | gagtttgaga | gtttgcagaa | gcaggaggtg | aagaacttgc | 1020 |
| accagcgtct | ggaagggcag | cggccagaga | acaagggcaa | gaaccgctac | aagaacattc | 1080 |
| tccccttga | ccacagccga | gtgatcctgc | agggacggga | cagtaacatc | cccgggtccg | 1140 |
| actacatcaa | tgccaactac | atcaagaacc | agctgctagg | ccctgatgag | aacgctaaga | 1200 |
| cctacatcgc | cagccagggc | tgtctggagg | ccacggtcaa | tgacttctgg | cagatggcgt | 1260 |
| ggcaggagaa | cagccgtgtc | atcgtcatga | ccacccgaga | ggtggagaaa | ggccggaaca | 1320 |
| aatgcgtccc | atactggccc | gaggtgggca | tgcagcgtgc | ttatgggccc | tactctgtga | 1380 |
| ccaactgcgg | ggagcatgac | acaaccgaat | acaaactccg | taccttacag | gtctccccgc | 1440 |
| tggacaatgg | agacctgatt | cgggagatct | ggcattacca | gtacctgagc | tggcccgacc | 1500 |
| atgggtccc | cagtgagcct | gggggtgtcc | tcagcttcct | ggaccagatc | aaccagcggc | 1560 |
| aggaaagtct | gcctcacgca | gggcccatca | tcgtgcactg | cagcgccggc | atcggccgca | 1620 |
| caggcaccat | cattgtcatc | gacatgctca | tggagaacat | ctccaccaag | ggcctggact | 1680 |
| gtgacattga | catccagaag | accatccaga | tggtgcgggc | gcagcgctcg | ggcatggtgc | 1740 |
| agacggaggc | gcagtacaag | ttcatctacg | tggccatcgc | ccagttcatt | gaaaccacta | 1800 |
| agaagaagct | ggaggtcctg | cagtcgcaga | agggccagga | gtcggagtac | gggaacatca | 1860 |
| cctatccccc | agccatgaag | aatgcccatg | ccaaggcctc | ccgcacctcg | tccaagagct | 1920 |
| tggagtctag | tgcagggacc | gtggctgcgt | cacctgtgag | acggggtggc | cagaggggac | 1980 |
| tgccagtgcc | gggtccccct | gtgctgtctc | ctgacctgca | ccaactgcct | gtacttgccc | 2040 |

| | |
|---|---|
| ccctgcaccc ggctgcagac acaaggagga tgtgtatgag aacctgcaca ctaagaacaa | 2100 |
| gagggaggag aaagtgaaga agcagcggtc agcagacaag gagaagagca agggttccct | 2160 |
| caagaggaag tgagcggtgc tgtcctcagg tggccatgcc tcagccctga ccctgtggaa | 2220 |
| gcatttcgcg atggacagac tcacaacctg aacctaggag tgccccattc ttttgtaatt | 2280 |
| taaatggctg catccccccc acctctccct gaccctgtat atagcccagc caggccccag | 2340 |
| gcagggccaa cccttctcct cttgtaaata aagccctggg atcactgtga aaaaaaaaa | 2400 |
| aaaaaaaaa aaaaaaaaa aaaaaaaaa aaaaaaaaa aaaaaaaaa aaaaaaaaa | 2460 |
| aaaa | 2464 |

<210> SEQ ID NO 3
<211> LENGTH: 867
<212> TYPE: DNA
<213> ORGANISM: Homo sapiens

<400> SEQUENCE: 3

| | |
|---|---|
| atgcagatcc cacaggcgcc ctggccagtc gtctgggcgg tgctacaact gggctggcgg | 60 |
| ccaggatggt tcttagactc cccagacagg ccctggaacc cccccacctt ctccccagcc | 120 |
| ctgctcgtgg tgaccgaagg ggacaacgcc accttcacct gcagcttctc caacacatcg | 180 |
| gagagcttcg tgctaaactg gtaccgcatg agccccagca accagacgga caagctggcc | 240 |
| gccttccccg aggaccgcag ccagcccggc caggactgcc gcttccgtgt cacacaactg | 300 |
| cccaacgggc gtgacttcca catgagcgtg gtcagggccc ggcgcaatga cagcggcacc | 360 |
| tacctctgtg gggccatctc cctggccccc aaggcgcaga tcaaagagag cctgcgggca | 420 |
| gagctcaggg tgacagagag aagggcagaa gtgcccacag cccacccag cccctcaccc | 480 |
| aggccagccg ccagttccaa accctggtg gttggtgtcg tgggcggcct gctgggcagc | 540 |
| ctggtgctgc tagtctgggt cctggccgtc atctgctccc gggccgcacg agggacaata | 600 |
| ggagccaggc gcaccggcca gcccctgaag gaggacccct cagccgtgcc tgtgttctct | 660 |
| gtggactatg gggagctgga tttccagtgg cgagagaaga cccggagcc ccccgtgccc | 720 |
| tgtgtccctg agcagacgga gtatgccacc attgtctttc ctagcggaat gggcacctca | 780 |
| tcccccgccc gcaggggctc agctgacggc cctcggagtg cccagccact gaggcctgag | 840 |
| gatggacact gctcttggcc cctctga | 867 |

<210> SEQ ID NO 4
<211> LENGTH: 420
<212> TYPE: DNA
<213> ORGANISM: Homo sapiens

<400> SEQUENCE: 4

| | |
|---|---|
| atgacatcca ttcgagctgt atttatattc ctgtggctgc agctggactt ggtgaatgga | 60 |
| gagaatgtgg agcagcatcc ttcaaccctg agtgtccagg agggagacag cgctgttatc | 120 |
| aagtgtactt attcagacag tgcctcaaac tacttccctt ggtataagca agaacttgga | 180 |
| aaaagacctc agcttattat agacattcgt tcaaatgtgg gcgaaaagaa agaccaacga | 240 |
| attgctgtta cattgaacaa gacagccaaa catttctccc tgcacatcac agagacccaa | 300 |
| cctgaagact cggctgtcta cttctgtgca gcaagtagga aggactctgg gggttaccag | 360 |
| aaagttacct ttggaactgg aacaaagctc caagtcatcc caaatatcca gaaccctgac | 420 |

<210> SEQ ID NO 5
<211> LENGTH: 1027

<212> TYPE: DNA
<213> ORGANISM: Homo sapiens

<400> SEQUENCE: 5

```
ttggattatc aagtgtcaag tccaatctat gacatcaatt attatacatc ggagccctgc      60
caaaaaatca atgtgaagca aatcgcagcc cgcctcctgc ctccgctcta ctcactggtg     120
ttcatctttg gttttgtggg caacatgctg gtcatcctca tcctgataaa ctgcaaaagg     180
ctgaagagca tgactgacat ctacctgctc aacctggcca tctctgacct gttttttcctt   240
cttactgtcc ccttctgggc tcactatgct gccgcccagt gggactttgg aaatacaatg     300
tgtcaactct tgacagggct ctattttata ggcttcttct ctggaatctt cttcatcatc     360
ctcctgacaa tcgataggta cctggctgtc gtccatgctg tgtttgcttt aaaagccagg     420
acggtcaccc ttggggtggt gacaagtgtg atcacttggg tggtggctgt gtttgcgtct     480
ctcccaggaa tcatctttac cagatctcaa aaagaaggtc ttcattacac ctgcagctct     540
cattttccat acattaaaga tagtcatctt ggggctggtc ctgccgctgc ttgtcatggt     600
catctgctac tcgggaatcc taaaaactct gcttcggtgt cgaaatgaga agaagaggca     660
cagggctgtg aggcttatct tcaccatcat gattgtttat tttctcttct gggctcccta     720
caacattgtc cttctcctga acaccttcca ggaattcttt ggcctgaata attgcagtag     780
ctctaacagg ttggaccaag ctatgcaggt gacagagact cttgggatga cgcactgctg     840
catcaacccc atcatctatg cctttgtcgg ggagaagttc agaaactacc tcttagtctt     900
cttccaaaag cacattgcca aacgcttctg caaatgctgt tctatttttcc agcaagaggc    960
tcccgagcga gcaagctcag tttacacccg atccactggg gagcaggaaa tatctgtggg   1020
cttgtga                                                             1027
```

<210> SEQ ID NO 6
<211> LENGTH: 1912
<212> TYPE: DNA
<213> ORGANISM: Homo sapiens

<400> SEQUENCE: 6

```
ttttttttct tccctctagt gggcggggca gaggagttag ccaagatgtg actttgaaac      60
cctcagcgtc tcagtgccct tttgttctaa acaaagaatt ttgtaattgg ttctaccaaa     120
gaaggatata atgaagtcac tatgggaaaa gatggggagg agagttgtag gattctacat     180
taattctctt gtgcccttag cccactactt cagaatttcc tgaagaaagc aagcctgaat     240
tggttttttta aattgcttta aaatttttt ttaactgggt taatgcttgc tgaattggaa    300
gtgaatgtcc attcctttgc ctcttttgca gatatacact tcagataact acaccgagga     360
aatgggctca ggggactatg actccatgaa ggaaccctgt ttccgtgaag aaaatgctaa     420
tttcaataaa atcttcctgc ccaccatcta ctccatcatc ttcttaactg gcattgtggg     480
caatggattg gtcatcctgg tcatgggtta ccagaagaaa ctgagaagca tgacggacaa     540
gtacaggctg cacctgtcag tggccgacct cctctttgtc atcacgcttc ccttctgggc     600
agttgatgcc gtggcaaact ggtactttgg aaacttccta tgcaaggcag tccatgtcat     660
ctacacagtc aacctctaca gcagtgtcct catcctggcc ttcatcagtc tggaccgcta     720
cctggccatc gtccacgcca ccaacagtca gaggccaagg aagctgttgg ctgaaaaggt     780
ggtctatgtt ggcgtctgga tccctgccct cctgctgact attccgactt catctttgc     840
caacgtcagt gaggcagatg acagatatat ctgtgaccgc ttctaccccca atgacttgtg     900
```

```
ggtggttgtg ttccagtttc agcacatcat ggttggcctt atcctgcctg gtattgtcat      960
cctgtcctgc tattgcatta tcatctccaa gctgtcacac tccaagggcc accagaagcg     1020
caaggccctc aagaccacag tcatcctcat cctggctttc ttcgcctgtt ggctgcctta     1080
ctacattggg atcagcatcg actccttcat cctcctggaa atcatcaagc aagggtgtga     1140
gtttgagaac actgtgcaca agtggatttc catcaccgag gccctagctt tcttccactg     1200
ttgtctgaac cccatcctct atgctttcct tggagccaaa tttaaaacct ctgcccagca     1260
cgcactcacc tctgtgagca gagggtccag cctcaagatc ctctccaaag gaaagcgagg     1320
tggacattca tctgtttcca ctgagtctga gtcttcaagt tttcactcca gctaacacag     1380
atgtaaaaga ctttttttta tacgataaat aactttttt taagttacac attttttcaga     1440
tataaaagac tgaccaatat tgtacagttt ttattgcttg ttggatttt gtcttgtgtt       1500
tctttagttt ttgtgaagtt taattgactt atttatataa attttttttg tttcatattg     1560
atgtgtgtct aggcaggacc tgtggccaag ttcttagttg ctgtatgtct cgtggtagga     1620
ctgtagaaaa gggaactgaa cattccagag cgtgtagtga atcacgtaaa gctagaaatg     1680
atccccagct gtttatgcat agataatctc tccattcccg tggaacgttt ttcctgttct     1740
taagacgtga ttttgctgta gaagatggca cttataacca aagcccaaag tggtatagaa     1800
atgctggttt ttcagttttc aggagtgggt tgatttcagc acctacagtg tacagtcttg     1860
tattaagttg ttaataaaag tacatgttaa acttaaaaaa aaaaaaaaaa aa             1912

<210> SEQ ID NO 7
<211> LENGTH: 2413
<212> TYPE: DNA
<213> ORGANISM: Homo sapiens

<400> SEQUENCE: 7
ttccgtcctt ccgtccgcgg ccctgtcagc tggagcgcgg cgcaggctct gccccggccc      60
ggcggctctg gccggccgtc cagtccgtgc ggcggacccc gaggagcctc gatgtggatg     120
gccccgcgaa gttaagttct gggctcgcgc ttccactccg ccgcgccttc ctcccagttt     180
ccgtccgctc gccgcaccgg cttcgttccc ccaaatctcg gaccgtccct tcgcgccccc     240
tccccgtccg cccccagtgc tgcgttctcc ccctcttggc tctcctgcgg ctgggggagg     300
ggcggggtc accatggccg aggcgcctca gtggtggag atcgacccgg acttcgagcc      360
gctgccccgg ccgcgctcgt gcacctggcc gctgcccagg ccggagttta gccagtccaa     420
ctcggccacc tccagcccgg cgccgtcggg cagcgcggct gccaacccg acgccgcggc     480
gggcctgccc tcggcctcgg ctgccgctgt cagcgccgac ttcatgagca acctgagctt     540
gctggaggag agcgaggact ccccgcaggc gcccggctcc gtggcggcgg cggtggcggc     600
ggcggccgcc gcggccgcca ccgggggggct gtgcgggggac ttccagggcc cggaggcggg     660
ctgcctgcac ccagcgccac cgcagccccc gccgccgggg ccgctgtcgc agcaccgcc      720
ggtgcccccc gccgccgctg gccgctcgc ggggcagccg cgcaagagca gctcgtcccg     780
ccgcaacgcg tggggcaacc tgtcctacgc cgacctcatc accaaggcca tcgagagctc     840
ggcggagaag cggctcacgc tgtcgcagat ctacgagtgg atggtcaaga gcgtgccta      900
cttcaaggat aagggtgaca gcaacagctc ggcgggctgg aagaattcaa ttcgtcataa     960
tctgtcccta cacagcaagt tcattcgtgt gcagaatgaa ggaactggaa aaagttcttg    1020
gtggatgctc aatccagagg gtggcaagag cgggaaatct cctaggagaa gagctgcatc    1080
catggacaac aacagtaaat ttgctaagag ccgaagccga gctgccaaga gaaaagcatc    1140
```

| | |
|---|---|
| tctccagtct ggccaggagg gtgctgggga cagccctgga tcacagtttt ccaaatggcc | 1200 |
| tgcaagccct ggctctcaca gcaatgatga ctttgataac tggagtacat ttcgccctcg | 1260 |
| aactagctca aatgctagta ctattagtgg gagactctca cccattatga ccgaacagga | 1320 |
| tgatcttgga gaaggggatg tgcattctat ggtgtacccg ccatctgccg caaagatggc | 1380 |
| ctctacttta cccagtctgt ctgagataag caatcccgaa acatggaaa atcttttgga | 1440 |
| taatctcaac cttctctcat caccaacatc attaactgtt tcgacccagt cctcacctgg | 1500 |
| caccatgatg cagcagacgc cgtgctactc gtttgcgcca ccaaacacca gtttgaattc | 1560 |
| acccagccca aactaccaaa aatatacata tggccaatcc agcatgagcc ctttgcccca | 1620 |
| gatgcctata caaacacttc aggacaataa gtcgagttat ggaggtatga gtcagtataa | 1680 |
| ctgtgcgcct ggactcttga aggagttgct gacttctgac tctcctcccc ataatgacat | 1740 |
| tatgacacca gttgatcctg ggtagcccca gcccaacagc cgggttctgg gccagaacgt | 1800 |
| catgatgggc cctaattcgg tcatgtcaac ctatggcagc caggcatctc ataacaaaat | 1860 |
| gatgaatccc agctcccata cccaccctgg acatgctcag cagacatctg cagttaacgg | 1920 |
| gcgtcccctg ccccacacgg taagcaccat gccccacacc tcgggtatga accgcctgac | 1980 |
| ccaagtgaag acacctgtac aagtgcctct gccccacccc atgcagatga gtgccctggg | 2040 |
| gggctactcc tccgtgagca gctgcaatgg ctatggcaga atgggccttc tccaccagga | 2100 |
| gaagctccca agtgacttgg atggcatgtt cattgagcgc ttagactgtg acatggaatc | 2160 |
| catcattcgg aatgacctca tggatggaga tacattggat tttaactttg acaatgtgtt | 2220 |
| gcccaaccaa agcttcccac acagtgtcaa gacaacgaca catagctggg tgtcaggctg | 2280 |
| agggttagtg agcaggttac acttaaaagt acttcagatt gtctgacagc aggaactgag | 2340 |
| agaagcagtc caaagatgtc tttcaccaac tcccttttag ttttctcggt taaaaaaaaa | 2400 |
| aaaaaaaaa aaa | 2413 |

<210> SEQ ID NO 8
<211> LENGTH: 3286
<212> TYPE: DNA
<213> ORGANISM: Homo sapiens

<400> SEQUENCE: 8

| | |
|---|---|
| gcgtgtcggg cgcggaaggg ggaggcggcc cggggcgccc gcgagtgagg cgcggggcgg | 60 |
| cgaagggagc gcgggtggcg gcacttgctg ccgcggcctt ggatgggctg gccccccctc | 120 |
| gccgctccgc ctcctccaca cgcgcggcgg ccgcggcgag ggggacgcgc cgcccggggc | 180 |
| ccggcacctt cgggaacccc ccggcccgga gcctgcggcc tgcgccgcct cggccgccgg | 240 |
| gagcccgtg gagcccccgc cgccgcgccg ccccgcggac cggacgctga gggcactcgg | 300 |
| ggcggggcgc gcgctcgggc agacgttttgc ggggaggggg gcgcctgccg gccccggcg | 360 |
| accaccttgg gggtcgcggg ccggctcggg gggcgcccag tgcgggccct cgcgggcgcc | 420 |
| gggcagcgac cagccctgag cggagctgtt ggccgcggcg ggaggcctcc cggacgcccc | 480 |
| cagccccccg aacgctcgcc cgggccggcc ggagtcggcg ccccccggga ggtccgctcg | 540 |
| gtcgtccgcg gcggagcgtt tgctcctggg acaggcggtg ggaccggggc gtcgccggag | 600 |
| acgcccccag cgaagttggg ctctccaggt gtgggggtcc cggggggtag cgacgtcgcg | 660 |
| gacccggcct gtgggatggg cggcccggag aagactgcgc tcggccgtgt tcatacttgt | 720 |
| ccgtgggcct gaggtccccg gaggatgacc tagcactgaa aagcccccggc cggcctcccc | 780 |

```
agggtccccg aggacgaagt tgaccctgac cgggccgtct cccagttctg aggcccgggt    840
cccactggaa ctcgcgtctg agccgccgtc ccggaccccc ggtgcccgcc ggtccgcaga    900
ccctgcaccg ggcttggact cgcagccggg actgacgtgt agaacaatcg tttctgttgg    960
aagaagggtt tttcccttcc ttttgggggtt tttgttgcct ttttttttc ttttttcttt   1020
gtaaaatttt ggagaaggga agtcggaaca caaggaagga ccgctcaccc gcggactcag   1080
ggctggcggc gggactccag gaccctgggt ccagcatgga ggtggtggac ccgcagcagc   1140
tgggcatgtt cacggagggc gagctgatgt cggtgggtat ggacacgttc atccaccgca   1200
tcgactccac cgaggtcatc taccagccgc gccgcaagcg gccaagctc atcggcaagt    1260
acctgatggg ggacctgctg ggggaaggct cttacggcaa ggtgaaggag gtgctggact   1320
cggagacgct gtgcaggagg gccgtcaaga tcctcaagaa gaagaagttg cgaaggatcc   1380
ccaacgggga ggccaacgtg aagaaggaaa ttcaactact gaggaggtta cggcacaaaa   1440
atgtcatcca gctggtggat gtgttataca cgaagagaa gcagaaaatg tatatggtga   1500
tggagtactg cgtgtgtggc atgcaggaaa tgctggacag cgtgccggag aagcgtttcc   1560
cagtgtgcca ggcccacggg tacttctgtc agctgattga cggcctggag tacctgcata   1620
gccagggcat tgtgcacaag gacatcaagc cggggaacct gctgctcacc accggtggca   1680
ccctcaaaat ctccgacctg ggcgtggccg aggcactgca cccgttcgcg gcggacgaca   1740
cctgccggac cagccagggc tccccggctt ccagccgcc cgagattgcc aacggcctgg   1800
acaccttctc cggcttcaag gtggacatct ggtcggctgg ggtcacccc tacaacatca    1860
ccacgggtct gtaccccttc gaggggggaca acatctacaa gttgtttgag aacatcggga   1920
aggggagcta cgccatcccg ggcgactgtg gccccccgct ctctgacctg ctgaaaggga   1980
tgcttgagta cgaaccggcc aagaggttct ccatccggca gatccggcag cacagctggt   2040
tccggaagaa acatcctccg gctgaagcac cagtgcccat cccaccgagc ccagacacca   2100
aggaccggtg gcgcagcatg actgtggtgc cgtacttgga ggacctgcac ggcgcggacg   2160
aggacgagga cctcttcgac atcgaggatg acatcatcta cactcaggac ttcacggtgc   2220
ccggacaggt cccagaagag gaggccagtc acaatggaca cgccggggc ctccccaagg    2280
ccgtgtgtat gaacggcaca gaggcggcgc agctgagcac caaatccagg cggagggcc    2340
gggcccccaa ccctgcccgc aaggcctgct ccgccagcag caagatccgc cggctgtcgg   2400
cctgcaagca gcagtgaggc tggccgcctg cagcccgtgt ccaggagccc cgccaggtgc   2460
ccgcgccagg ccctcagtct tcctgccggt tcccgcccgc ctcccggaga ggtgccgcc    2520
atgcttctgt gccgaccacg ccccaggacc tccggagcgc cctgcagggc cgggcagggg   2580
gacagcaggg accgggcgca gccctccccc ctcggccgcc cggcagtgca cgcggcttgt   2640
tgacttcgca gccccggggcg gagccttccc gggcgggcgt gggaggaggg aggcggcctc   2700
catgcacttt atgtggagac tactggcccc gccgtggcc tcgtgctccg cagggcgccc    2760
agcgccgtcc ggcggccccg ccgcagacca gctggcgggt gtggagacca ggctcctgac   2820
cccgccatgc atgcagcgcc acctggaagc cgcgcggccg cttggttttt tgtttggtt    2880
ggttccattt tctttttttc tttttttttt taagaaaaaa taaaaggtgg atttgagctg   2940
tggctgtgag gggtgtttgg gagctgctgg gtggcagggg ggctgtgggg tcgggctcac   3000
gtcgcggccg cctttgcgct ctcgggtcac cctgctttgg cggcccgcc ggagggcagg    3060
accctcacct ctcccccaag gccactgcgc tcttgggacc ccagagaaaa cccggagcaa   3120
gcaggagtgt gcggtcaata tttatatcat ccagaaaaga aaaacacgag aaacgccatc   3180
```

```
gcgggatggt gcagacgcgg cggggactcg gagggtgccg tgcgggcgag gccgcccaaa    3240
tttggcaata aataaagctt gggaagcttg gacctgaaaa aaaaaa                   3286

<210> SEQ ID NO 9
<211> LENGTH: 6767
<212> TYPE: DNA
<213> ORGANISM: Homo sapiens

<400> SEQUENCE: 9
aagtttccaa gtggtcaact tgaccgatgc tttggcaatt gaaaagggc agaaaggcgc      60 gggctagtgg gtggatgggg acaaagatct aagtcacctt cttccagcgt gtgagcctgg    120
gaggagggtg ggggtcctga ggagcaagag gtacgaggaa ggaaaaggag agggcttctg    180
ggttagtttc cacctcctgc tttccaactc acggcgcttt ccttccggaa aggacgctgg    240
attcagggcg cgccagtacg cgcagtagcg gcccgcgagt cggcaggtgg gtagccccgg    300
cgcgggagga agggaagtt accttcccct cggaagaggg cgctggctcc cccatcctgc    360 cttttataata aggccaccgg aggagaggaa gcagccagct gccgtctgcg ctttgcaaag    420
catgcagtta ggggagcagc tcttggtgag ctcagtgaac ctgcctggcg cgcacttcta    480
cccgctggag agtgcgcgag gcggcagcgg cgggagcgct ggccacctcc ccagcgcggc    540
cccctctcct cagaagttgg acttagacaa agcgtccaag aagttttccg gcagtctctc    600
ctgcgaggcg gtgagcgggg agcccgcagc cgccagcgca ggggccccccg cggccatgct    660 tagtgacacc gacgccgggg acgcatttgc cagcgctgcg gcagtggcca agccggggcc    720
cccggacggc cgcaagggct cccctgcgg ggaggaggag ctgccctccg ccgctgcagc    780
cgccgccgcc gccgccgccg cggctgcggc cactgcgcgc tactccatgg acagcctgag    840
ctccgagcgg tactacctcc agtccccccgg tcctcagggg tcggagctgg ctgcgccctg    900
ctcactcttc ccgtaccagg cggcggctgg ggcgccccac ggacctgtgt acccggctcc    960 taacgggggcg cgctacccct acggctccat gctgccccccc ggcggcttcc ccgcggctgt   1020
gtgcccaccc gggagggcgc agttcggccc aggagccggt gcgggcagtg gcgcgggcgg   1080
tagcagcggc ggggggcggcg gcccgggcac ctatcagtac agccagggggg ctccgctcta   1140 cggggccgtac cctggagccg cagcggcggg atcttgcgga ggactggggg gcctgggggt   1200
tccaggttct ggcttccgtg cccacgtcta cctgtgcaac cggcctctgt ggctcaaatt   1260
ccaccgccac caaactgaga tgatcattac gaaacagggc aggtgagcgc agcgtggagg   1320
ggcccctggg ttcggggata aagggtgacg tgtggtcctg gggaaggtcc gggatgaggg   1380
agctgaaccc agttgttccg cgcggtgctt agagtgtttc accgcgcgca ataaatctcc   1440
gtagacaccg catctccaat gcggtgtccc tctgtgtcag tgccccggcg gctcttgcag   1500
ggtgccaatg ttacggctgt acaccgcttt tccctcccat catcctcacc tgaacagacc   1560
tggaggaggc ggaaatggaa attagggcat gtccacaagc tggattcgtt agatcctcct   1620
gctcggcggt atgcttgtgc atgcctgcat gccggcaagg agccacggat agggaaggct   1680
caagagctgg ccacctgagc gcagtagatg ggctcccgca gttttaggcg ccagggtctc   1740
cacggggcgt ctccgggagg tgggcatgaa ggctagagcc ccggcctcgg aagctcggtc   1800
ggagtaggtg gttagatctg ccctggagcc agacctggct cgggttcggt gcgcgagaaa   1860
gttctgatat acatccaact gctaacactg gctacttctg gggaaaggga ggggtgggtg   1920
ctgagagagg ggcactcaaa ggggactttt agcctaaagt tttaatatat attttaaca   1980
```

```
agaataacct aatattgttc tctggtactt ttcaaaatgg tgcatttaaa aattagtagt    2040
ttttaacatt ctaggagaaa aattttaaga gcgtctgaaa gggccgagaa tatgagcctt    2100
cggaagcacg cgcgaatttg aatataccg atgttggggc aagctttttt tttttttttt    2160
tttttttttt tttttttttt ttttgaaaag acggaaaggt tccaagagtt gccaactcaa    2220
aaatatttta catagtttca gaccacttga tctaccagca ttctgttcac tgcaaacttt    2280
taaatgtgtt ccgaccctat cccaggtgtc tggggaaccc gctggggcct gggcctgttc    2340
taggacatcc caattaaaat cgattttct gattctattc ccttgcacag gcgcatgttt    2400
cctttcttga gcttcaacat aaacggactc aatcccactg cccactacaa tgtgttcgta    2460
gaggtggtgc tggcggaccc caaccactgg cgcttccagg ggggcaaatg ggtgacctgt    2520
ggcaaagccg acaataacat gcagggtgag cagagaagag gctcgggccg gggaggaacg    2580
ggcgggaaga aatcgtaacc ctcgactcac acaactcaca tttaaatgta gcactttttt    2640 tttcccttc cattctgagg cctagaggtg ttagtatgag tgtctttgag ttgcttgttt     2700
gacggagagg agagtttgct aagtcagatt tcttgtctgc caatatgtag atatttagaa    2760
cctttaacta agacatcacc ccaccccccca atccctacgt ttaacaaatc agtagtcata   2820
agctctccag gtgggaaggg ctcctgggat tctaatgttc acttgagaaa gcccagccaa    2880
agtttagttc acccataaat atccaactgt cttccatcgg atgttgccct tacagcttta    2940
gaaggcccca aattgacctt caagagtcat ctcttgttag ctccgtttct aaattctgaa    3000
atgccattca ggggagtccc tagtgcaagg aaggttggaa gcacaggggc ctgggaggga    3060 tatgatgta gtcctgctgg tctccactgg cctctttaag caacttttac tgggagacca    3120
actgtaagtc tagctcttat atcttgctca tagctaagag acatccctcc gctttctcca    3180
tttgtaaaca gccctatatg cttgggtttt gtgttttgtt tcattttctc ttaggcaaca    3240
aaatgtatgt tcacccagag tctcctaata ctggttccca ctggatgaga caggagattt    3300
cattcgggaa attaaaactc accaataaca aaggcgcaaa taacaacaac acccaggtag    3360
agtgacagag caggagggga tatcttctgg ctttgactat aaggctttt tctaataaga    3420 gtccctactc ttttcactgt atttataata tttgcatttg tgacctgttt gctcgcctat    3480
ttctaaccat ttttgttctt ttgacctttc tcatcttcac tttcttattg gatttcgata    3540
acagtgagtt gactattaag aacagaaata gcgaagtatt tgggaatttt aggaaaccaa    3600
gaggaaagca tatctatcac aaccacatac ccagctatga tttaaatttc aaaaaaaaag    3660 tggggggca ataatgagac ctttaaactt gcaataaaca aagctgttag tgaggagcat     3720
ttagaagtcc aataccaaaa tacataattt gtcaaaatct aattttgttg aaccactaag    3780
aggcttttta gatttagcaa ttttttttctg tactctttcc agatgatagt cttacaatcc    3840
ttacacaaat accaaccccg actgcatatt gttgaagtta cagaggatgg cgtggaggac    3900
ttgaatgagc cctcaaagac ccagactttt accttctcag aaacgcaatt cattgcagtg    3960
actgcctacc aaaacaccga tgtgagtgtc ccagacatct caagaatctc taaagctaag    4020
gtccagcatg ataaatcact caatgactgt ttttctcccc tatctagatt actcaactaa    4080
agattgatca taaccccttt gcaaaaggct tcagagacaa ctatgattcg taagtgcagc    4140
ttttatccac acttgcctga tcatctctga gcaggacata catcaacagg cactttgctg    4200
ataatgtatt ttaggaagag cttttacctt tgggattttt acatattttt cttttttccaa   4260 aattttttcc tttactaatc ttgctttaga ttttttctcag aaaggttgtg ttaatttctg    4320
aagaaatgtt aaggacttaa aaatgaagag gttttttttag catttgagtg aagatttgaa   4380
```

```
attttaagaa tctgcattta tatataccgg tctttcatt tgatccattt tttatcctc    4440
ccaagagcag atattattac tctcccccac ccccactttt ttttttaaca taagaaaaaa    4500
ctgaaactaa gaggatgtaa tttcacaaca cgaaatagca aggccctgct cttttaaaa     4560
tctgagtttt ctaccgccac agccagtgtt ttttccatca cattgacaaa ggaggtttga    4620
tctgagtttt tcgtgttcta ggactagtaa aggtagattt tctatagttt aaatacttga    4680
tgcctaggag gaaacttttt cttgcatggt gggaaatttt tcccaataag ccaagagtcc    4740
agctaaaatg ggccagtgca tctcctgcct ctgttctttc agcccaacag accagcactt    4800
tcggtgtaga taaccaacac aagccttttt catttctggg aggtggtttg tttggggaca    4860
acattagggt tttttttttt ttttaagtgt ttctctttat attgtagcat gtacaccgct    4920
tcagaaaatg acaggttaac tccatctccc acgattctc ctagatccca tcagattgtc     4980
cctggaggtc ggtacggcgt tcaatccttc ttcccggagc cctttgtcaa cactttacct    5040
caagcccgct attataatgg cgagagaacc gtgccacaga ccaacggcct cctttcaccc    5100
caacagagcg aagaggtggc caaccctccc cagcggtggc ttgtcacgcc tgtccagcaa    5160
cctgggacca acaaactaga catcagttcc tatgaatctg aatatacttc tagcacattg    5220
ctcccatatg gcattaaatc cttgccccctt cagacatccc atgccctggg gtattaccca    5280
gacccaacct ttcctgcaat ggcagggtgg ggaggtcgag gttcttacca gaggaagatg    5340
gcagctggac taccatggac ctccagaaca agccccactg tgttctctga agatcagctc    5400
tccaaggaga aagtgaaaga ggaaattggc tcttcttgga tagagacacc cccttccatc    5460
aaatctctag attccaatga ttcaggagta tacaccagtg cttgtaagcg aaggcggctg    5520
tctcctagca actccagtaa tgaaaattca ccctccataa agtgtgagga cattaatgct    5580
gaagagtata gtaaagacac ctcaaaaggc atgggagggt attatgcttt ttacacaact    5640
ccctaaagag ttattttaac ctcaaaaatt agctaacttt tgcagatgg acttggtggt      5700
gttttttgtt gtcttctttg cctaggttgc caaaaagatg tttgccttcc accttgatgc    5760
atcctgtttt gtgcaattct ctaaaagaag gtgccaaagc ttttttgatg ctgcaggtaa     5820
ctgaaacaaa cctagcattt ttaaaaaata agattaatgg aagactttaa ggtattttaa    5880
aattcgaagg gtatccaagg ttctgtattt atttattggg gagacactaa cccttcaaag    5940
aagcaggctg tgaacattgg gtgcccagtg ctatcagatg agttaaaacc tttgattctc    6000
atttctattt gtaaattctt aagcaaatag aagccgagtg ttaaggtgtt ttgcttctga    6060
aagagggctg tgccttccgt ttcagaagga gacattttgc tgttacattc tgccaggggc    6120
aaaagatact aggcccagga gtcaagaaaa gcttttgtga agtgatagt ttcacctgac      6180
tttgattcct taaccccccgg cttttggaac aagccatgtt tgccctagtc caggattgcc    6240
tcacttgaga cttgctaggc ctctgctgtg tgctggggtg gccagtggga ctcaggagag    6300
agcaagctaa ggagtcacca aaaaaaaaaa aaaaaaaaag ggagaattta aaagtgtaca    6360
gttgtgtgtt tagatacact atagaataat gtggtatata ttgtacaaat agtctacata    6420
ggtgtctggg ataatgtaaa actggtgctt tggctttgta aagaatttgc aaatcactta    6480
acagctgcag gggcaagggg agagtttcat catccccatg atatttggga atattctgtt    6540
tacttcttag atagttaaga atgtattcag ctactatgta ctaacttgaa ccgtgtttaa    6600
ggaaaactcc tatttcatcc tcttcttgcg ccatcccctc tccctaactt ggtaatgtga    6660
agaaactaaa acctgatacc acagctccta taggcatttt agagatcttg gatttttatg    6720
```
tacagtctta gtcattttta ataaatgtgg ttcagtaagg aacgga        6767

<210> SEQ ID NO 10
<211> LENGTH: 2471
<212> TYPE: DNA
<213> ORGANISM: Homo sapiens

<400> SEQUENCE: 10

| | | | | | |
|---|---|---|---|---|---|
| ggggacgaag | ggaagctcca | gcgtgtggcc | ccggcgagtg | cggataaaag | ccgccccgcc | 60 |
| gggctcgggc | ttcattctga | gccgagcccg | gtgccaagcg | cagctagctc | agcaggcggc | 120 |
| agcggcggcc | tgagcttcag | ggcagccagc | tccctcccgg | tctcgccttc | cctcgcggtc | 180 |
| agcatgaaag | ccttcagtcc | cgtgaggtcc | gttaggaaaa | acagcctgtc | ggaccacagc | 240 |
| ctgggcatct | cccggagcaa | aaccctgtg | gacgacccga | tgagcctgct | atacaacatg | 300 |
| aacgactgct | actccaagct | caaggagctg | gtgcccagca | tcccccagaa | caagaaggtg | 360 |
| agcaagatgg | aaatcctgca | gcacgtcatc | gactacatct | tggacctgca | gatcgccctg | 420 |
| gactcgcatc | ccactattgt | cagcctgcat | caccagagac | ccgggcagaa | ccaggcgtcc | 480 |
| aggacgccgc | tgaccaccct | caacacggga | tcagcatcc | tgtccttgca | ggtaagacct | 540 |
| gctccggggt | ccccgcccg | ccgccgcaca | ctcccgcggt | cgtctgggct | gtcactagga | 600 |
| gatccgtagc | ccagacggtg | actttcgtat | gagctattta | actttatttt | cttcagaatc | 660 |
| tgctgtagat | tgagctgtgc | gtgaaattgc | tagtaagttc | tgacatgtta | atgcgtctgt | 720 |
| cttaaatct | gaattgttac | cataaacgtg | tttaatggaa | cttgctggtc | tgtggactac | 780 |
| aaaaaaaaa | aaaaaaaaa | aaaaccctt | tctacttaac | attgtcttaa | cctcgtactc | 840 |
| tttatcctct | ttcttccag | gcttctgaat | tccttctga | gttaatgtca | aatgacagca | 900 |
| aagcactgtg | tggctgaata | gcggtgagt | gtttgcttgt | gccacccgtg | ggtaaactgc | 960 |
| ccctcggtgt | gtgtgcgcgc | gcgcgcatgt | gttttgctt | gtgtatctat | aaaatgtctg | 1020 |
| atttggtaaa | tgcatgctta | cttcgcggtg | ttacccgtac | tacattgtct | cactagacat | 1080 |
| gaaggagctt | gtagctttgg | gtgctcgaga | tcacagaaca | ttttcctta | aaaggaaatg | 1140 |
| atgccaataa | cttactacga | aggcggccga | ggaacgtgtg | tattggcttt | gtagcaaatg | 1200 |
| taatgccctg | gatcttccta | cgagtcctct | ggtactatga | ggtactaacc | tccactgtaa | 1260 |
| ttaatcttac | cgccacaaat | tccatagtga | tcctccttcc | ctaaaactat | agtcctctgg | 1320 |
| gattctctgg | gctagttgag | gattgctacc | ctgtgccttc | aaccctgtga | tgtgggatcc | 1380 |
| cagacttccc | tatctgttaa | ctaaagggct | gtttcaatc | aaataattgt | tacgagaagc | 1440 |
| agactggcgc | ctgtagcact | gctgttggag | atccaaatag | gagattgggt | tgggaagttt | 1500 |
| ttcccttgag | tctctgctat | tttaatgttt | aatttgcgct | gtcgaggcga | gtgtgtgtgt | 1560 |
| tgcatctgga | cgccagggtt | tgcccaatct | ttgagtgttt | ggttaaatgt | tcaaactgtg | 1620 |
| gcttcctccc | ggcgccagtc | gcccgcctct | gcccttaggt | tacattctct | taaacatgcc | 1680 |
| tttctccccc | actctttcgc | aggtgttcat | gatttctttt | attctttgca | caacaacaac | 1740 |
| aacaacaaat | tcacggaatc | ttttaagtgc | tgaacttatt | tttcaaccat | ttcacaagga | 1800 |
| ggacaagttg | aatggacctt | tttaaaaaga | aaaaaaaat | ggaaggaaaa | ctaagaatga | 1860 |
| tcatcttccc | agggtgttct | cttacttgga | ctgtgatatt | cgttatttat | gaaaaagact | 1920 |
| tttaaatgcc | cttttctgcag | ttggaaggtt | ttctttatat | actattccca | ccatggggag | 1980 |
| cgaaaacgtt | aaaatcacaa | ggaattgccc | aatctaagca | gactttgcct | ttttcaaag | 2040 |
| gtggagcgtg | aataccagaa | ggatccagta | ttcagtcact | taaatgaagt | cttttggtca | 2100 |

| | |
|---|---|
| gaaattacct ttttgacaca agcctactga atgctgtgta tatatttata tataaatata | 2160 |
| tctatttgag tgaaaccttg tgaactcttt aattagagtt ttcttgtata gtggcagaga | 2220 |
| tgtctatttc tgcattcaaa agtgtaatga tgtacttatt catgctaaac tttttataaa | 2280 |
| agtttagttg taaacttaac ccttttatac aaaataaatc aagtgtgttt attgaatggt | 2340 |
| gattgcctgc tttatttcag aggaccagtg ctttgatttt tattatgcta tgttataact | 2400 |
| gaacccaaat aaatacaagt tcaaatttat gtagactgta taagattata ataaaacatg | 2460 |
| tctgaagtca a | 2471 |

<210> SEQ ID NO 11
<211> LENGTH: 4018
<212> TYPE: DNA
<213> ORGANISM: Homo sapiens

<400> SEQUENCE: 11

| | |
|---|---|
| caggcagcgc tgcgtcctgc tgcgcacgtg ggaagccctg ccccggcca ccccgcgat | 60 |
| gccgcgcgct ccccgctgcc gagccgtgcg ctccctgctg cgcagccact accgcgaggt | 120 |
| gctgccgctg ccacgttcg tcggcgcct ggggccccag ggctggcggc tggtgcagcg | 180 |
| cggggacccg gcggctttcc gcgcgctggt ggcccagtgc ctggtgtgcg tgccctggga | 240 |
| cgcacggccg ccccccgccg cccctcctt ccgccaggtg tcctgcctga aggagctggt | 300 |
| ggcccgagtg ctgcagaggc tgtgcgagcg cggcgcgaag aacgtgctgg ccttcggctt | 360 |
| cgcgctgctg acggggccc gcgggggccc cccgaggcc ttcaccacca gcgtgcgcag | 420 |
| ctacctgccc aacacggtga ccgacgcact gcggggagc gggcgtggg ggctgctgct | 480 |
| gcgccgcgtg ggcgacgacg tgctggttca cctgctggca cgctgcgcgc tctttgtgct | 540 |
| ggtggctccc agctgcgcct accaggtgtg cgggccgccg ctgtaccagc tcggcgctgc | 600 |
| cactcaggcc cggcccccgc cacacgctag tggaccccga aggcgtctgg gatgcgaacg | 660 |
| ggcctggaac catagcgtca gggaggccgg ggtccccctg ggcctgccag ccccgggtgc | 720 |
| gaggaggcgc gggggcagtg ccagccgaag tctgccgttg cccaagaggc ccaggcgtgg | 780 |
| cgctgcccct gagccggagc ggacgcccgt tgggcagggg tcctgggccc acccgggcag | 840 |
| gacgcgtgga ccgagtgacc gtggtttctg tgtggtgtca cctgccagac ccgccgaaga | 900 |
| agccacctct ttggagggtg cgctctctgg cacgcgccac tcccacccat ccgtgggccg | 960 |
| ccagcaccac gcgggccccc catccacatc gcggccacca cgtccctggg acacgccttg | 1020 |
| tcccccggtg tacgccgaga ccaagcactt cctctactcc tcaggcgaca aggagcagct | 1080 |
| gcggccctcc ttcctactca gctctctgag gcccagcctg actggcgctc ggaggctcgt | 1140 |
| ggagaccatc tttctggggtt ccaggccctg gatgccaggg actccccgca ggttgccccg | 1200 |
| cctgccccag cgctactggc aaatgcggcc cctgtttctg gagctgcttg ggaaccacgc | 1260 |
| gcagtgcccc tacggggtgc tcctcaagac gcactgcccg ctgcgagctg cggtcacccc | 1320 |
| agcagccggt gtctgtgccc gggagaagcc ccagggctct gtggcggccc ccgaggagga | 1380 |
| ggacacagac ccccgtcgcc tggtgcagct gctccgccag cacagcagcc cctggcaggt | 1440 |
| gtacggcttc gtgcgggcct gcctgcgccg gctggtgccc caggcctct ggggctccag | 1500 |
| gcacaacgaa cgccgcttcc tcaggaacac caagaagttc atctccctgg ggaagcatgc | 1560 |
| caagctctcg ctgcaggagc tgacgtggaa gatgagcgtg cgggactgcg cttggctgcg | 1620 |
| caggagccca gggggttggct gtgttccggc cgcagagcac cgtctgcgtg aggagatcct | 1680 |

-continued

```
ggccaagttc ctgcactggc tgatgagtgt gtacgtcgtc gagctgctca ggtcttcctt      1740
ttatgtcacg gagaccacgt ttcaaaagaa caggctcttt ttctaccgga agagtgtctg      1800
gagcaagttg caaagcattg gaatcagaca gcacttgaag agggtgcagc tgcgggagct      1860
gtcggaagca gaggtcaggc agcatcggga agccaggccc gccctgctga cgtccagact      1920
ccgcttcatc cccaagcctg acgggctgcg gccgattgtg aacatggact acgtcgtggg      1980
agccagaacg ttccgcagag aaaagagggc cgagcgtctc acctcgaggg tgaaggcact      2040
gttcagcgtg ctcaactacg agcgggcgcg gcgccccggc ctcctgggcg cctctgtgct      2100
gggcctggac gatatccaca gggcctggcg caccttcgtg ctgcgtgtgc gggcccagga      2160
cccgccgcct gagctgtact tgtcaaggt ggatgtgacg ggcgcgtacg acaccatccc       2220
ccaggacagg ctcacggagg tcatcgccag catcatcaaa ccccagaaca cgtactgcgt      2280
gcgtcggtat gccgtggtcc agaaggccgc ccatgggcac gtccgcaagg ccttcaagag      2340
ccacgtctct accttgacag acctccagcc gtacatgcga cagttcgtgg ctcacctgca      2400
ggagaccagc ccgctgaggg atgccgtcgt catcgagcag agctcctccc tgaatgaggc      2460
cagcagtggc ctcttcgacg tcttcctacg cttcatgtgc caccacgccg tgcgcatcag      2520
gggcaagtcc tacgtccagt gccagggat cccgcagggc tccatcctct ccacgctgct       2580
ctgcagcctg tgctacggcg acatggagaa caagctgttt gcggggattc ggcgggacgg      2640
gctgctcctg cgtttggtgg atgatttctt gttggtgaca cctcacctca cccacgcgaa      2700
aaccttcctc aggaccctgg tccgaggtgt ccctgagtat ggctgcgtgg tgaacttgcg      2760
gaagacagtg gtgaacttcc ctgtagaaga cgaggccctg ggtggcacgg cttttgttca      2820
gatgccggcc cacggcctat tcccctggtg cggcctgctg ctggatacc ggaccctgga       2880
ggtgcagagc gactactcca gctatgcccg gacctccatc agagccagtc tcaccttcaa      2940
ccgcggcttc aaggctggga ggaacatgcg tcgcaaactc tttggggtct gcggctgaa       3000
gtgtcacagc ctgtttctgg atttgcaggt gaacagcctc cagacggtgt gcaccaacat      3060
ctacaagatc ctcctgctgc aggcgtacag gtttcacgca tgtgtgctgc agctcccatt      3120
tcatcagcaa gtttggaaga accccacatt tttcctgcgc gtcatctctg acacggcctc      3180
cctctgctac tccatcctga agccaagaa cgcagggatg tcgctggggg ccaagggcgc       3240
cgccggccct ctgccctccg aggccgtgca gtggctgtgc caccaagcat tcctgctcaa      3300
gctgactcga caccgtgtca cctacgtgcc actcctgggg tcactcagga cagcccagac      3360
gcagctgagt cggaagctcc cggggacgac gctgactgcc ctggaggccg cagccaaccc      3420
ggcactgccc tcagacttca agaccatcct ggactgatgg ccacccgccc acagccaggc      3480
cgagagcaga caccagcagc cctgtcacgc cgggctctac gtcccaggga gggaggggcg      3540
gcccacaccc aggcccgcac cgctgggagt ctgaggcctg agtgagtgtt tggccgaggc      3600
ctgcatgtcc ggctgaaggc tgagtgtccg gctgaggcct gagcgagtgt ccagccaagg      3660
gctgagtgtc cagcacacct gccgtcttca cttccccaca ggctggcgct cggctccacc      3720
ccagggccag ctttcctca ccaggagccc ggcttccact ccccacatag aatagtcca       3780
tccccagatt cgccattgtt caccctcgc cctgccctcc tttgccttcc accccacca       3840
tccaggtgga gaccctgaga aggaccctgg gagctctggg aatttggagt gaccaaaggt      3900
gtgccctgta cacaggcgag gaccctgcac ctggatgggg gtccctgtgg gtcaaattgg      3960
ggggaggtgc tgtgggagta aaatactgaa tatatgagtt tttcagttt gaaaaaaa       4018
```

<210> SEQ ID NO 12
<211> LENGTH: 2335
<212> TYPE: DNA
<213> ORGANISM: Homo sapiens

<400> SEQUENCE: 12

```
gttattctct ggaacatgaa acattctgtt gtgctcatat catgcaaatt atcactagta      60
ggagagcaga gagtggaaat gttccaggta taaagaccca caagataaag aagctcagag     120
tcgttagaaa caggagcaga tgtacagggt ttgcctgact cacactcaag gttgcataag     180
caagatttca aaattaatcc tattctggag acctcaaccc aatgtacaat gttcctgact     240
ggaaaagaag aactatattt ttctgatttt tttttcaaa tctttaccat tagttgccct      300
gtatctccgc cttcactttc tgcaggaaac tttatttcct acttctgcat gccaagtttc     360
tacctctaga tctgtttggt tcagttgctg agaagcctga cataccagga ctgcctgaga     420
caagccacaa gctgaacaga gaaagtggat tgaacaagga cgcatttccc cagtacatcc     480
acaacatgct gtccacatct cgttctcggt ttatcagaaa taccaacgag agcggtgaag     540
aagtcaccac cttttttgat tatgattacg gtgctccctg tcataaattt gacgtgaagc     600
aaaattgggc ccaactcctg cctccgctct actcgctggt gttcatcttt ggttttgtgg     660
gcaacatgct ggtcgtcctc atcttaataa actgcaaaaa gctgaagtgc ttgactgaca     720
tttacctgct caacctggcc atctctgatc tgcttttct tattactctc ccattgtggg      780
ctcactctgc tgcaaatgag tgggtctttg gaatgcaat gtgcaaatta ttcacagggc      840
tgtatcacat cggttatttt ggcggaatct tcttcatcat cctcctgaca atcgatagat     900
acctggctat tgtccatgct gtgtttgctt taaaagccag gacggtcacc tttggggtgg     960
tgacaagtgt gatcacctgg ttggtggctg tgtttgcttc tgtcccagga atcatcttta    1020
ctaaatgcca gaaagaagat tctgtttatg tctgtggccc ttattttcca cgaggatgga    1080
ataatttcca cacaataatg aggaacattt tggggctggt cctgccgctg ctcatcatgg    1140
tcatctgcta ctcgggaatc ctgaaaaccc tgcttcggtg tcgaaacgag aagaagaggc    1200
ataggggcagt gagagtcatc ttcaccatca tgattgttta ctttctcttc tggactccct    1260
ataatattgt cattctcctg aacaccttcc aggaattctt cggcctgagt aactgtgaaa    1320
gcaccagtca actggaccaa gccacgcagg tgacagagac tcttgggatg actcactgct    1380
gcatcaatcc catcatctat gccttcgttg gggagaagtt cagaaggtat ctctcggtgt    1440
tcttccgaaa gcacatcacc aagcgcttct gcaaacaatg tccagttttc tacagggaga    1500
cagtggatgt agtgacttca acaaacacgc cttccactgg ggagcaggaa gtctcggctg    1560
gtttataaaa cgaggagcag tttgattgtt gtttataaag ggagataaca atctgtatat    1620
aacaacaaac ttcaagggtt tgttgaacaa tagaaacctg taaagcaggt gcccaggaac    1680
ctcagggctg tgtgtactaa tacagactat gtcacccaat gcatatccaa catgtgctca    1740
gggaataatc cagaaaaact gtgggtagag actttgactc tccagaaagc tcatctcagc    1800
tcctgaaaaa tgcctcatta ccttgtgcta atcctctttt tctagtcttc ataatttctt    1860
cactcaatct ctgattctgt caatgtcttg aaatcaaggg ccagctggag gtgaagaaga    1920
gaatgtgaca ggcacagatg aatggagtg agggatagtg gggtcagggc tgagaggaga     1980
aggagggaga catgagcatg gctgagcctg acaaagacaa aggtgagca aagggctcac     2040
gcattcagcc aggagatgat actggtcctt agccccatct gccacgtgta tttaaccttg    2100
aagggttcac caggtcaggg agagtttggg aactgcaata acctgggagt tttggtggag    2160
```

```
tccgatgatt ctcttttgca taagtgcatg acatattttt gctttattac agtttatcta    2220
tggcacccat gcaccttaca tttgaaatct atgaaatatc atgctccatt gttcagatgc    2280
ttcttaggcc acatccccct gtctaaaaat tcagaaaatt tttgtttata aaaga         2335

<210> SEQ ID NO 13
<211> LENGTH: 1657
<212> TYPE: DNA
<213> ORGANISM: Homo sapiens

<400> SEQUENCE: 13
tctcacagga agccacgcac ccttgaaagg caccgggtcc ttcttagcat cgtgcttcct      60
gagcaagcct ggcattgcct cacagacctt cctcagagcc gctttcagaa aagcaagctg     120
cttctggttg ggcccagacc tgccttgagg agcctgtaga gttaaaaaat gaaccccacg     180
gatatagcag acaccaccct cgatgaaagc atatacagca attactatct gtatgaaagt     240
atccccaagc cttgcaccaa agaaggcatc aaggcatttg gggagctctt cctgccccca     300
ctgtattcct tggttttgt atttggtctg cttggaaatt ctgtggtggt tctggtcctg     360
ttcaaataca agcggctcag gtccatgact gatgtgtacc tgctcaacct tgccatctcg     420
gatctgctct tcgtgttttc cctcccttt tggggctact atgcagcaga ccagtgggtt     480
tttgggctag gtctgtgcaa gatgatttcc tggatgtact tggtgggctt ttacagtggc     540
atattctttg tcatgctcat gagcattgat agatacctgg caattgtgca cgcggtgttt     600
tccttgaggg caaggacctt gacttatggg gtcatcacca gtttggctac atggtcagtg     660
gctgtgttcg cctcccttcc tggctttctg ttcagcactt gttatactga gcgcaaccat     720
acctactgca aaccaagta ctctctcaac tccacgacgt ggaaggttct cagctccctg     780
gaaatcaaca ttctcggatt ggtgatcccc ttagggatca tgctgttttg ctactccatg     840
atcatcagga ccttgcagca ttgtaaaaat gagaagaaga caaggcggt gaagatgatc     900 tttgccgtgg tggtcctctt ccttgggttc tggacacctt acaacatagt gctcttccta     960
gagaccctgg tggagctaga agtccttcag gactgcacct ttgaaagata cttggactat    1020
gccatccagg ccacagaaac tctggctttt gttcactgct gccttaatcc catcatctac    1080
ttttttctgg gggagaaatt tcgcaagtac atcctacagc tcttcaaaac ctgcaggggc    1140 cttttttgtgc tctgccaata ctgtgggctc ctccaaattt actctgctga cacccccagc    1200
tcatcttaca cgcagtccac catggatcat gatctccatg atgctctgta gaaaaatgaa    1260
atggtgaaat gcagagtcaa tgaacttttcc acattcagag cttacttaaa attgtatttt    1320
agtaagagat tcctgagcca gtgtcaggag gaaggcttac acccacagtg gaaagacagc    1380
ttctcatcct gcaggcagct tttctctcc cactagacaa gtccagcctg gcaagggttc    1440
acctgggctg aggcatcctt cctcacacca ggcttgcctg caggcatgag tcagtctgat    1500
gagaactctg agcagtgctt gaatgaagtt gtaggtaata ttgcaaggca aagactattc    1560
ccttctaacc tgaactgatg ggtttctcca gagggaattg cagagtactg gctgatggag    1620
taaatcgcta cctttttgctg tggcaaatgg gccctct                            1657

<210> SEQ ID NO 14
<211> LENGTH: 750
<212> TYPE: PRT
<213> ORGANISM: Homo sapiens

<400> SEQUENCE: 14

Met Trp Asn Leu Leu His Glu Thr Asp Ser Ala Val Ala Thr Ala Arg
```

```
1               5                   10                  15
Arg Pro Arg Trp Leu Cys Ala Gly Ala Leu Val Leu Ala Gly Gly Phe
                20                  25                  30

Phe Leu Leu Gly Phe Leu Phe Gly Trp Phe Ile Lys Ser Ser Asn Glu
                35                  40                  45

Ala Thr Asn Ile Thr Pro Lys His Asn Met Lys Ala Phe Leu Asp Glu
        50                  55                  60

Leu Lys Ala Glu Asn Ile Lys Lys Phe Leu Tyr Asn Phe Thr Gln Ile
65                  70                  75                  80

Pro His Leu Ala Gly Thr Glu Gln Asn Phe Gln Leu Ala Lys Gln Ile
                85                  90                  95

Gln Ser Gln Trp Lys Glu Phe Gly Leu Asp Ser Val Glu Leu Ala His
                100                 105                 110

Tyr Asp Val Leu Leu Ser Tyr Pro Asn Lys Thr His Pro Asn Tyr Ile
            115                 120                 125

Ser Ile Ile Asn Glu Asp Gly Asn Glu Ile Phe Asn Thr Ser Leu Phe
    130                 135                 140

Glu Pro Pro Pro Gly Tyr Glu Asn Val Ser Asp Ile Val Pro Pro
145                 150                 155                 160

Phe Ser Ala Phe Ser Pro Gln Gly Met Pro Glu Gly Asp Leu Val Tyr
                165                 170                 175

Val Asn Tyr Ala Arg Thr Glu Asp Phe Phe Lys Leu Glu Arg Asp Met
                180                 185                 190

Lys Ile Asn Cys Ser Gly Lys Ile Val Ile Ala Arg Tyr Gly Lys Val
                195                 200                 205

Phe Arg Gly Asn Lys Val Lys Asn Ala Gln Leu Ala Gly Ala Lys Gly
        210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Gly Val Gln Arg Gly
                245                 250                 255

Asn Ile Leu Asn Leu Asn Gly Ala Gly Asp Pro Leu Thr Pro Gly Tyr
                260                 265                 270

Pro Ala Asn Glu Tyr Ala Tyr Arg Arg Gly Ile Ala Glu Ala Val Gly
            275                 280                 285

Leu Pro Ser Ile Pro Val His Pro Ile Gly Tyr Tyr Asp Ala Gln Lys
    290                 295                 300

Leu Leu Glu Lys Met Gly Gly Ser Ala Pro Pro Asp Ser Ser Trp Arg
305                 310                 315                 320

Gly Ser Leu Lys Val Pro Tyr Asn Val Gly Pro Gly Phe Thr Gly Asn
                325                 330                 335

Phe Ser Thr Gln Lys Val Lys Met His Ile His Ser Thr Asn Glu Val
                340                 345                 350

Thr Arg Ile Tyr Asn Val Ile Gly Thr Leu Arg Gly Ala Val Glu Pro
                355                 360                 365

Asp Arg Tyr Val Ile Leu Gly Gly His Arg Asp Ser Trp Val Phe Gly
        370                 375                 380

Gly Ile Asp Pro Gln Ser Gly Ala Ala Val Val His Glu Ile Val Arg
385                 390                 395                 400

Ser Phe Gly Thr Leu Lys Lys Glu Gly Trp Arg Pro Arg Arg Thr Ile
                405                 410                 415

Leu Phe Ala Ser Trp Asp Ala Glu Glu Phe Gly Leu Leu Gly Ser Thr
                420                 425                 430
```

```
Glu Trp Ala Glu Glu Asn Ser Arg Leu Leu Gln Glu Arg Gly Val Ala
            435                 440                 445

Tyr Ile Asn Ala Asp Ser Ser Ile Glu Gly Asn Tyr Thr Leu Arg Val
        450                 455                 460

Asp Cys Thr Pro Leu Met Tyr Ser Leu Val His Asn Leu Thr Lys Glu
465                 470                 475                 480

Leu Lys Ser Pro Asp Glu Gly Phe Glu Gly Lys Ser Leu Tyr Glu Ser
                485                 490                 495

Trp Thr Lys Lys Ser Pro Ser Pro Glu Phe Ser Gly Met Pro Arg Ile
                500                 505                 510

Ser Lys Leu Gly Ser Gly Asn Asp Phe Glu Val Phe Phe Gln Arg Leu
            515                 520                 525

Gly Ile Ala Ser Gly Arg Ala Arg Tyr Thr Lys Asn Trp Glu Thr Asn
        530                 535                 540

Lys Phe Ser Gly Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
                565                 570                 575

Ala Gln Val Arg Gly Gly Met Val Phe Glu Leu Ala Asn Ser Ile Val
                580                 585                 590

Leu Pro Phe Asp Cys Arg Asp Tyr Ala Val Val Leu Arg Lys Tyr Ala
            595                 600                 605

Asp Lys Ile Tyr Ser Ile Ser Met Lys His Pro Gln Glu Met Lys Thr
        610                 615                 620

Tyr Ser Val Ser Phe Asp Ser Leu Phe Ser Ala Val Lys Asn Phe Thr
625                 630                 635                 640

Glu Ile Ala Ser Lys Phe Ser Glu Arg Leu Gln Asp Phe Asp Lys Ser
                645                 650                 655

Asn Pro Ile Val Leu Arg Met Met Asn Asp Gln Leu Met Phe Leu Glu
                660                 665                 670

Arg Ala Phe Ile Asp Pro Leu Gly Leu Pro Asp Arg Pro Phe Tyr Arg
            675                 680                 685

His Val Ile Tyr Ala Pro Ser Ser His Asn Lys Tyr Ala Gly Glu Ser
        690                 695                 700

Phe Pro Gly Ile Tyr Asp Ala Leu Phe Asp Ile Glu Ser Lys Val Asp
705                 710                 715                 720

Pro Ser Lys Ala Trp Gly Glu Val Lys Arg Gln Ile Tyr Val Ala Ala
                725                 730                 735

Phe Thr Val Gln Ala Ala Ala Glu Thr Leu Ser Glu Val Ala
            740                 745                 750

<210> SEQ ID NO 15
<211> LENGTH: 123
<212> TYPE: PRT
<213> ORGANISM: Homo sapiens

<400> SEQUENCE: 15

Met Lys Ala Val Leu Leu Ala Leu Leu Met Ala Gly Leu Ala Leu Gln
1               5                   10                  15

Pro Gly Thr Ala Leu Leu Cys Tyr Ser Cys Lys Ala Gln Val Ser Asn
                20                  25                  30

Glu Asp Cys Leu Gln Val Glu Asn Cys Thr Gln Leu Gly Glu Gln Cys
            35                  40                  45

Trp Thr Ala Arg Ile Arg Ala Val Gly Leu Leu Thr Val Ile Ser Lys
```

```
                50                  55                  60
Gly Cys Ser Leu Asn Cys Val Asp Asp Ser Gln Asp Tyr Tyr Val Gly
 65                  70                  75                  80

Lys Lys Asn Ile Thr Cys Cys Asp Thr Asp Leu Cys Asn Ala Ser Gly
                 85                  90                  95

Ala His Ala Leu Gln Pro Ala Ala Ile Leu Ala Leu Leu Pro Ala
                100                 105                 110

Leu Gly Leu Leu Leu Trp Gly Pro Gly Gln Leu
            115                 120

<210> SEQ ID NO 16
<211> LENGTH: 622
<212> TYPE: PRT
<213> ORGANISM: Homo sapiens

<400> SEQUENCE: 16

Met Ala Leu Pro Thr Ala Arg Pro Leu Leu Gly Ser Cys Gly Thr Pro
  1               5                  10                  15

Ala Leu Gly Ser Leu Leu Phe Leu Leu Phe Ser Leu Gly Trp Val Gln
                 20                  25                  30

Pro Ser Arg Thr Leu Ala Gly Glu Thr Gly Gln Glu Ala Ala Pro Leu
             35                  40                  45

Asp Gly Val Leu Ala Asn Pro Pro Asn Ile Ser Ser Leu Ser Pro Arg
 50                  55                  60

Gln Leu Leu Gly Phe Pro Cys Ala Glu Val Ser Gly Leu Ser Thr Glu
 65                  70                  75                  80

Arg Val Arg Glu Leu Ala Val Ala Leu Ala Gln Lys Asn Val Lys Leu
                 85                  90                  95

Ser Thr Glu Gln Leu Arg Cys Leu Ala His Arg Leu Ser Glu Pro Pro
                100                 105                 110

Glu Asp Leu Asp Ala Leu Pro Leu Asp Leu Leu Leu Phe Leu Asn Pro
            115                 120                 125

Asp Ala Phe Ser Gly Pro Gln Ala Cys Thr His Phe Phe Ser Arg Ile
130                 135                 140

Thr Lys Ala Asn Val Asp Leu Leu Pro Arg Gly Ala Pro Glu Arg Gln
145                 150                 155                 160

Arg Leu Leu Pro Ala Ala Leu Ala Cys Trp Gly Val Arg Gly Ser Leu
                165                 170                 175

Leu Ser Glu Ala Asp Val Arg Ala Leu Gly Gly Leu Ala Cys Asp Leu
            180                 185                 190

Pro Gly Arg Phe Val Ala Glu Ser Ala Glu Val Leu Leu Pro Arg Leu
            195                 200                 205

Val Ser Cys Pro Gly Pro Leu Asp Gln Asp Gln Glu Ala Ala Arg
210                 215                 220

Ala Ala Leu Gln Gly Gly Gly Pro Pro Tyr Gly Pro Pro Ser Thr Trp
225                 230                 235                 240

Ser Val Ser Thr Met Asp Ala Leu Arg Gly Leu Leu Pro Val Leu Gly
                245                 250                 255

Gln Pro Ile Ile Arg Ser Ile Pro Gln Gly Ile Val Ala Ala Trp Arg
            260                 265                 270

Gln Arg Ser Ser Arg Asp Pro Ser Trp Arg Gln Pro Glu Arg Thr Ile
        275                 280                 285

Leu Arg Pro Arg Phe Arg Arg Glu Val Glu Lys Thr Ala Cys Pro Ser
    290                 295                 300
```

-continued

```
Gly Lys Lys Ala Arg Glu Ile Asp Glu Ser Leu Ile Phe Tyr Lys Lys
305                 310                 315                 320

Trp Glu Leu Glu Ala Cys Val Asp Ala Ala Leu Leu Ala Thr Gln Met
            325                 330                 335

Asp Arg Val Asn Ala Ile Pro Phe Thr Tyr Glu Gln Leu Asp Val Leu
        340                 345                 350

Lys His Lys Leu Asp Glu Leu Tyr Pro Gln Gly Tyr Pro Glu Ser Val
    355                 360                 365

Ile Gln His Leu Gly Tyr Leu Phe Leu Lys Met Ser Pro Glu Asp Ile
370                 375                 380

Arg Lys Trp Asn Val Thr Ser Leu Glu Thr Leu Lys Ala Leu Leu Glu
385                 390                 395                 400

Val Asn Lys Gly His Glu Met Ser Pro Gln Val Ala Thr Leu Ile Asp
            405                 410                 415

Arg Phe Val Lys Gly Arg Gly Gln Leu Asp Lys Asp Thr Leu Asp Thr
        420                 425                 430

Leu Thr Ala Phe Tyr Pro Gly Tyr Leu Cys Ser Leu Ser Pro Glu Glu
    435                 440                 445

Leu Ser Ser Val Pro Pro Ser Ser Ile Trp Ala Val Arg Pro Gln Asp
450                 455                 460

Leu Asp Thr Cys Asp Pro Arg Gln Leu Asp Val Leu Tyr Pro Lys Ala
465                 470                 475                 480

Arg Leu Ala Phe Gln Asn Met Asn Gly Ser Glu Tyr Phe Val Lys Ile
            485                 490                 495

Gln Ser Phe Leu Gly Gly Ala Pro Thr Glu Asp Leu Lys Ala Leu Ser
        500                 505                 510

Gln Gln Asn Val Ser Met Asp Leu Ala Thr Phe Met Lys Leu Arg Thr
    515                 520                 525

Asp Ala Val Leu Pro Leu Thr Val Ala Glu Val Gln Lys Leu Leu Gly
530                 535                 540

Pro His Val Glu Gly Leu Lys Ala Glu Glu Arg His Arg Pro Val Arg
545                 550                 555                 560

Asp Trp Ile Leu Arg Gln Arg Gln Asp Asp Leu Asp Thr Leu Gly Leu
            565                 570                 575

Gly Leu Gln Gly Gly Ile Pro Asn Gly Tyr Leu Val Leu Asp Leu Ser
        580                 585                 590

Val Gln Glu Ala Leu Ser Gly Thr Pro Cys Leu Leu Gly Pro Gly Pro
    595                 600                 605

Val Leu Thr Val Leu Ala Leu Leu Ala Ser Thr Leu Ala
610                 615                 620

<210> SEQ ID NO 17
<211> LENGTH: 556
<212> TYPE: PRT
<213> ORGANISM: Homo sapiens

<400> SEQUENCE: 17

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60
```

```
Ser Leu Gly Leu Pro Gly Leu Gly Ile His Met Arg Pro Leu Ala Ser
 65                  70                  75                  80

Trp Leu Phe Ile Phe Asn Val Ser Gln Gln Met Gly Gly Phe Tyr Leu
             85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
        130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Val Pro Pro
                165                 170                 175

Arg Asp Ser Leu Asn Gln Ser Leu Ser Gln Asp Leu Thr Met Ala Pro
                180                 185                 190

Gly Ser Thr Leu Trp Leu Ser Cys Gly Val Pro Pro Asp Ser Val Ser
            195                 200                 205

Arg Gly Pro Leu Ser Trp Thr His Val His Pro Lys Gly Pro Lys Ser
210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
                260                 265                 270

Glu Ile Thr Ala Arg Pro Val Leu Trp His Trp Leu Leu Arg Thr Gly
            275                 280                 285

Gly Trp Lys Val Ser Ala Val Thr Leu Ala Tyr Leu Ile Phe Cys Leu
        290                 295                 300

Cys Ser Leu Val Gly Ile Leu His Leu Gln Arg Ala Leu Val Leu Arg
305                 310                 315                 320

Arg Lys Arg Lys Arg Met Thr Asp Pro Thr Arg Arg Phe Phe Lys Val
                325                 330                 335

Thr Pro Pro Pro Gly Ser Gly Pro Gln Asn Gln Tyr Gly Asn Val Leu
                340                 345                 350

Ser Leu Pro Thr Pro Thr Ser Gly Leu Gly Arg Ala Gln Arg Trp Ala
            355                 360                 365

Ala Gly Leu Gly Gly Thr Ala Pro Ser Tyr Gly Asn Pro Ser Ser Asp
        370                 375                 380

Val Gln Ala Asp Gly Ala Leu Gly Ser Arg Ser Pro Pro Gly Val Gly
385                 390                 395                 400

Pro Glu Glu Glu Glu Gly Glu Gly Tyr Glu Glu Pro Asp Ser Glu Glu
                405                 410                 415

Asp Ser Glu Phe Tyr Glu Asn Asp Ser Asn Leu Gly Gln Asp Gln Leu
                420                 425                 430

Ser Gln Asp Gly Ser Gly Tyr Glu Asn Pro Glu Asp Glu Pro Leu Gly
            435                 440                 445

Pro Glu Asp Glu Asp Ser Phe Ser Asn Ala Glu Ser Tyr Glu Asn Glu
        450                 455                 460

Asp Glu Glu Leu Thr Gln Pro Val Ala Arg Thr Met Asp Phe Leu Ser
465                 470                 475                 480
```

```
Pro His Gly Ser Ala Trp Asp Pro Ser Arg Glu Ala Thr Ser Leu Gly
                485                 490                 495

Ser Gln Ser Tyr Glu Asp Met Arg Gly Ile Leu Tyr Ala Ala Pro Gln
            500                 505                 510

Leu Arg Ser Ile Arg Gly Gln Pro Gly Pro Asn His Glu Glu Asp Ala
        515                 520                 525

Asp Ser Tyr Glu Asn Met Asp Asn Pro Asp Gly Pro Asp Pro Ala Trp
    530                 535                 540

Gly Gly Gly Gly Arg Met Gly Thr Trp Ser Thr Arg
545                 550                 555

<210> SEQ ID NO 18
<211> LENGTH: 297
<212> TYPE: PRT
<213> ORGANISM: Homo sapiens

<400> SEQUENCE: 18

Met Thr Thr Pro Arg Asn Ser Val Asn Gly Thr Phe Pro Ala Glu Pro
1               5                   10                  15

Met Lys Gly Pro Ile Ala Met Gln Ser Gly Pro Lys Pro Leu Phe Arg
            20                  25                  30

Arg Met Ser Ser Leu Val Gly Pro Thr Gln Ser Phe Phe Met Arg Glu
        35                  40                  45

Ser Lys Thr Leu Gly Ala Val Gln Ile Met Asn Gly Leu Phe His Ile
    50                  55                  60

Ala Leu Gly Gly Leu Leu Met Ile Pro Ala Gly Ile Tyr Ala Pro Ile
65                  70                  75                  80

Cys Val Thr Val Trp Tyr Pro Leu Trp Gly Gly Ile Met Tyr Ile Ile
                85                  90                  95

Ser Gly Ser Leu Leu Ala Ala Thr Glu Lys Asn Ser Arg Lys Cys Leu
            100                 105                 110

Val Lys Gly Lys Met Ile Met Asn Ser Leu Ser Leu Phe Ala Ala Ile
        115                 120                 125

Ser Gly Met Ile Leu Ser Ile Met Asp Ile Leu Asn Ile Lys Ile Ser
    130                 135                 140

His Phe Leu Lys Met Glu Ser Leu Asn Phe Ile Arg Ala His Thr Pro
145                 150                 155                 160

Tyr Ile Asn Ile Tyr Asn Cys Glu Pro Ala Asn Pro Ser Glu Lys Asn
                165                 170                 175

Ser Pro Ser Thr Gln Tyr Cys Tyr Ser Ile Gln Ser Leu Phe Leu Gly
            180                 185                 190

Ile Leu Ser Val Met Leu Ile Phe Ala Phe Phe Gln Glu Leu Val Ile
        195                 200                 205

Ala Gly Ile Val Glu Asn Glu Trp Lys Arg Thr Cys Ser Arg Pro Lys
    210                 215                 220

Ser Asn Ile Val Leu Leu Ser Ala Glu Glu Lys Lys Glu Gln Thr Ile
225                 230                 235                 240

Glu Ile Lys Glu Glu Val Val Gly Leu Thr Glu Thr Ser Ser Gln Pro
                245                 250                 255

Lys Asn Glu Glu Asp Ile Glu Ile Ile Pro Ile Gln Glu Glu Glu Glu
            260                 265                 270

Glu Glu Thr Glu Thr Asn Phe Pro Glu Pro Pro Gln Asp Gln Glu Ser
        275                 280                 285

Ser Pro Ile Glu Asn Asp Ser Ser Pro
    290                 295
```

<210> SEQ ID NO 19
<211> LENGTH: 937
<212> TYPE: PRT
<213> ORGANISM: Homo sapiens

<400> SEQUENCE: 19

Met His Arg Pro Arg Arg Arg Gly Thr Arg Pro Pro Leu Leu Ala Leu
1               5                   10                  15

Leu Ala Ala Leu Leu Ala Ala Arg Gly Ala Ala Ala Gln Glu Thr
            20                  25                  30

Glu Leu Ser Val Ser Ala Glu Leu Val Pro Thr Ser Ser Trp Asn Ile
        35                  40                  45

Ser Ser Glu Leu Asn Lys Asp Ser Tyr Leu Thr Leu Asp Glu Pro Met
    50                  55                  60

Asn Asn Ile Thr Thr Ser Leu Gly Gln Thr Ala Glu Leu His Cys Lys
65                  70                  75                  80

Val Ser Gly Asn Pro Pro Thr Ile Arg Trp Phe Lys Asn Asp Ala
                85                  90                  95

Pro Val Val Gln Glu Pro Arg Arg Leu Ser Phe Arg Ser Thr Ile Tyr
            100                 105                 110

Gly Ser Arg Leu Arg Ile Arg Asn Leu Asp Thr Thr Asp Thr Gly Tyr
        115                 120                 125

Phe Gln Cys Val Ala Thr Asn Gly Lys Glu Val Val Ser Ser Thr Gly
    130                 135                 140

Val Leu Phe Val Lys Phe Gly Pro Pro Thr Ala Ser Pro Gly Tyr
145                 150                 155                 160

Ser Asp Glu Tyr Glu Glu Asp Gly Phe Cys Gln Pro Tyr Arg Gly Ile
                165                 170                 175

Ala Cys Ala Arg Phe Ile Gly Asn Arg Thr Val Tyr Met Glu Ser Leu
            180                 185                 190

His Met Gln Gly Glu Ile Glu Asn Gln Ile Thr Ala Ala Phe Thr Met
        195                 200                 205

Ile Gly Thr Ser Ser His Leu Ser Asp Lys Cys Ser Gln Phe Ala Ile
    210                 215                 220

Pro Ser Leu Cys His Tyr Ala Phe Pro Tyr Cys Asp Glu Thr Ser Ser
225                 230                 235                 240

Val Pro Lys Pro Arg Asp Leu Cys Arg Asp Glu Cys Glu Ile Leu Glu
                245                 250                 255

Asn Val Leu Cys Gln Thr Glu Tyr Ile Phe Ala Arg Ser Asn Pro Met
            260                 265                 270

Ile Leu Met Arg Leu Lys Leu Pro Asn Cys Glu Asp Leu Pro Gln Pro
        275                 280                 285

Glu Ser Pro Glu Ala Ala Asn Cys Ile Arg Ile Gly Ile Pro Met Ala
    290                 295                 300

Asp Pro Ile Asn Lys Asn His Lys Cys Tyr Asn Ser Thr Gly Val Asp
305                 310                 315                 320

Tyr Arg Gly Thr Val Ser Val Thr Lys Ser Gly Arg Gln Cys Gln Pro
                325                 330                 335

Trp Asn Ser Gln Tyr Pro His Thr His Thr Phe Thr Ala Leu Arg Phe
            340                 345                 350

Pro Glu Leu Asn Gly Gly His Ser Tyr Cys Arg Asn Pro Gly Asn Gln
        355                 360                 365

Lys Glu Ala Pro Trp Cys Phe Thr Leu Asp Glu Asn Phe Lys Ser Asp

```
            370             375             380
Leu Cys Asp Ile Pro Ala Cys Asp Ser Lys Asp Ser Lys Glu Lys Asn
385                 390                 395                 400

Lys Met Glu Ile Leu Tyr Ile Leu Val Pro Ser Val Ala Ile Pro Leu
                405                 410                 415

Ala Ile Ala Leu Leu Phe Phe Phe Ile Cys Val Cys Arg Asn Asn Gln
                420                 425                 430

Lys Ser Ser Ser Ala Pro Val Gln Arg Gln Pro Lys His Val Arg Gly
                435                 440                 445

Gln Asn Val Glu Met Ser Met Leu Asn Ala Tyr Lys Pro Lys Ser Lys
                450                 455                 460

Ala Lys Glu Leu Pro Leu Ser Ala Val Arg Phe Met Glu Glu Leu Gly
465                 470                 475                 480

Glu Cys Ala Phe Gly Lys Ile Tyr Lys Gly His Leu Tyr Leu Pro Gly
                485                 490                 495

Met Asp His Ala Gln Leu Val Ala Ile Lys Thr Leu Lys Asp Tyr Asn
                500                 505                 510

Asn Pro Gln Gln Trp Thr Glu Phe Gln Gln Glu Ala Ser Leu Met Ala
                515                 520                 525

Glu Leu His His Pro Asn Ile Val Cys Leu Leu Gly Ala Val Thr Gln
                530                 535                 540

Glu Gln Pro Val Cys Met Leu Phe Glu Tyr Ile Asn Gln Gly Asp Leu
545                 550                 555                 560

His Glu Phe Leu Ile Met Arg Ser Pro His Ser Asp Val Gly Cys Ser
                565                 570                 575

Ser Asp Glu Asp Gly Thr Val Lys Ser Ser Leu Asp His Gly Asp Phe
                580                 585                 590

Leu His Ile Ala Ile Gln Ile Ala Ala Gly Met Glu Tyr Leu Ser Ser
                595                 600                 605

His Phe Phe Val His Lys Asp Leu Ala Ala Arg Asn Ile Leu Ile Gly
                610                 615                 620

Glu Gln Leu His Val Lys Ile Ser Asp Leu Gly Leu Ser Arg Glu Ile
625                 630                 635                 640

Tyr Ser Ala Asp Tyr Tyr Arg Val Gln Ser Lys Ser Leu Leu Pro Ile
                645                 650                 655

Arg Trp Met Pro Pro Glu Ala Ile Met Tyr Gly Lys Phe Ser Ser Asp
                660                 665                 670

Ser Asp Ile Trp Ser Phe Gly Val Val Leu Trp Glu Ile Phe Ser Phe
                675                 680                 685

Gly Leu Gln Pro Tyr Tyr Gly Phe Ser Asn Gln Glu Val Ile Glu Met
                690                 695                 700

Val Arg Lys Arg Gln Leu Leu Pro Cys Ser Glu Asp Cys Pro Pro Arg
705                 710                 715                 720

Met Tyr Ser Leu Met Thr Glu Cys Trp Asn Glu Ile Pro Ser Arg Arg
                725                 730                 735

Pro Arg Phe Lys Asp Ile His Val Arg Leu Arg Ser Trp Glu Gly Leu
                740                 745                 750

Ser Ser His Thr Ser Ser Thr Thr Pro Ser Gly Gly Asn Ala Thr Thr
                755                 760                 765

Gln Thr Thr Ser Leu Ser Ala Ser Pro Val Ser Asn Leu Ser Asn Pro
                770                 775                 780

Arg Tyr Pro Asn Tyr Met Phe Pro Ser Gln Gly Ile Thr Pro Gln Gly
785                 790                 795                 800
```

```
Gln Ile Ala Gly Phe Ile Gly Pro Ile Pro Gln Asn Gln Arg Phe
                805             810             815

Ile Pro Ile Asn Gly Tyr Pro Ile Pro Pro Gly Tyr Ala Ala Phe Pro
                820             825             830

Ala Ala His Tyr Gln Pro Thr Gly Pro Pro Arg Val Ile Gln His Cys
            835             840             845

Pro Pro Pro Lys Ser Arg Ser Pro Ser Ser Ala Ser Gly Ser Thr Ser
        850             855             860

Thr Gly His Val Thr Ser Leu Pro Ser Ser Gly Ser Asn Gln Glu Ala
865             870             875             880

Asn Ile Pro Leu Leu Pro His Met Ser Ile Pro Asn His Pro Gly Gly
                885             890             895

Met Gly Ile Thr Val Phe Gly Asn Lys Ser Gln Lys Pro Tyr Lys Ile
                900             905             910

Asp Ser Lys Gln Ala Ser Leu Leu Gly Asp Ala Asn Ile His Gly His
                915             920             925

Thr Glu Ser Met Ile Ser Ala Glu Leu
        930             935

<210> SEQ ID NO 20
<211> LENGTH: 168
<212> TYPE: PRT
<213> ORGANISM: Homo sapiens

<400> SEQUENCE: 20

Met Gly His His His His His His His His Ser Ser Gly His
1               5                   10                  15

Ile Glu Gly Arg His Met Arg Arg Val Pro Gly Val Ala Pro Thr Leu
                20                  25                  30

Val Arg Ser Ala Ser Glu Thr Ser Glu Lys Arg Pro Phe Met Cys Ala
            35                  40                  45

Tyr Pro Gly Cys Asn Lys Arg Tyr Phe Lys Leu Ser His Leu Gln Met
        50                  55                  60

His Ser Arg Lys His Thr Gly Glu Lys Pro Tyr Gln Cys Asp Phe Lys
65                  70                  75                  80

Asp Cys Glu Arg Arg Phe Phe Arg Ser Asp Gln Leu Lys Arg His Gln
                85                  90                  95

Arg Arg His Thr Gly Val Lys Pro Phe Gln Cys Lys Thr Cys Gln Arg
                100                 105                 110

Lys Phe Ser Arg Ser Asp His Leu Lys Thr His Thr Arg Thr His Thr
            115                 120                 125

Gly Glu Lys Pro Phe Ser Cys Arg Trp Pro Ser Cys Gln Lys Lys Phe
        130                 135                 140

Ala Arg Ser Asp Glu Leu Val Arg His His Asn Met His Gln Arg Asn
145                 150                 155                 160

Met Thr Lys Leu Gln Leu Ala Leu
                165

<210> SEQ ID NO 21
<211> LENGTH: 347
<212> TYPE: PRT
<213> ORGANISM: Homo sapiens

<400> SEQUENCE: 21

Asp Pro Asn Phe Trp Leu Gln Val Gln Glu Ser Val Thr Val Gln Glu
1               5                   10                  15
```

```
Gly Leu Cys Val Leu Val Pro Cys Thr Phe Phe His Pro Ile Pro Tyr
             20                  25                  30

Tyr Asp Lys Asn Ser Pro Val His Gly Tyr Trp Phe Arg Glu Gly Ala
             35                  40                  45

Ile Ile Ser Arg Asp Ser Pro Val Ala Thr Asn Lys Leu Asp Gln Glu
 50                  55                  60

Val Gln Glu Glu Thr Gln Gly Arg Phe Arg Leu Leu Gly Asp Pro Ser
 65                  70                  75                  80

Arg Asn Asn Cys Ser Leu Ser Ile Val Asp Ala Arg Arg Arg Asp Asn
                 85                  90                  95

Gly Ser Tyr Phe Phe Arg Met Glu Arg Gly Ser Thr Lys Tyr Ser Tyr
                100                 105                 110

Lys Ser Pro Gln Leu Ser Val His Val Thr Asp Leu Thr His Arg Pro
                115                 120                 125

Lys Ile Leu Ile Pro Gly Thr Leu Glu Pro Gly His Ser Lys Asn Leu
130                 135                 140

Thr Cys Ser Val Ser Trp Ala Cys Glu Gln Gly Thr Pro Pro Ile Phe
145                 150                 155                 160

Ser Trp Leu Ser Ala Ala Pro Thr Ser Leu Gly Pro Arg Thr Thr His
                165                 170                 175

Ser Ser Val Leu Ile Ile Thr Pro Arg Pro Gln Asp His Gly Thr Asn
                180                 185                 190

Leu Thr Cys Gln Val Lys Phe Ala Gly Ala Gly Val Thr Thr Glu Arg
                195                 200                 205

Thr Ile Gln Leu Asn Val Thr Tyr Val Pro Gln Asn Pro Thr Thr Gly
210                 215                 220

Ile Phe Pro Gly Asp Gly Ser Gly Lys Gln Glu Thr Arg Ala Gly Val
225                 230                 235                 240

Val His Gly Ala Ile Gly Gly Ala Gly Val Thr Ala Leu Leu Ala Leu
                245                 250                 255

Cys Leu Cys Leu Ile Phe Phe Ile Val Lys Thr His Arg Arg Lys Ala
                260                 265                 270

Ala Arg Thr Ala Val Gly Arg Asn Asp Thr His Pro Thr Thr Gly Ser
                275                 280                 285

Ala Ser Pro Lys His Gln Lys Lys Ser Lys Leu His Gly Pro Thr Glu
290                 295                 300

Thr Ser Ser Cys Ser Gly Ala Ala Pro Thr Val Glu Met Asp Glu Glu
305                 310                 315                 320

Leu His Tyr Ala Ser Leu Asn Phe His Gly Met Asn Pro Ser Lys Asp
                325                 330                 335

Thr Ser Thr Glu Tyr Ser Glu Val Arg Thr Gln
                340                 345

<210> SEQ ID NO 22
<211> LENGTH: 11
<212> TYPE: PRT
<213> ORGANISM: Artificial Sequence
<220> FEATURE:
<223> OTHER INFORMATION: anti-CD19 scFV CDRL1

<400> SEQUENCE: 22

Arg Ala Ser Gln Asp Ile Ser Lys Tyr Leu Asn
1               5                   10

<210> SEQ ID NO 23
```

```
<211> LENGTH: 7
<212> TYPE: PRT
<213> ORGANISM: Artificial Sequence
<220> FEATURE:
<223> OTHER INFORMATION: anti-CD19 scFV  CDRL2

<400> SEQUENCE: 23

Ser Arg Leu His Ser Gly Val
1               5

<210> SEQ ID NO 24
<211> LENGTH: 9
<212> TYPE: PRT
<213> ORGANISM: Artificial Sequence
<220> FEATURE:
<223> OTHER INFORMATION: anti-CD19 scFV  CDRL3

<400> SEQUENCE: 24

Gly Asn Thr Leu Pro Tyr Thr Phe Gly
1               5

<210> SEQ ID NO 25
<211> LENGTH: 5
<212> TYPE: PRT
<213> ORGANISM: Artificial Sequence
<220> FEATURE:
<223> OTHER INFORMATION: anti-CD19 scFV  CDRH1

<400> SEQUENCE: 25

Asp Tyr Gly Val Ser
1               5

<210> SEQ ID NO 26
<211> LENGTH: 16
<212> TYPE: PRT
<213> ORGANISM: Artificial Sequence
<220> FEATURE:
<223> OTHER INFORMATION: anti-CD19 scFV  CDRH2

<400> SEQUENCE: 26

Val Thr Trp Gly Ser Glu Thr Thr Tyr Tyr Asn Ser Ala Leu Lys Ser
1               5                   10                  15

<210> SEQ ID NO 27
<211> LENGTH: 7
<212> TYPE: PRT
<213> ORGANISM: Artificial Sequence
<220> FEATURE:
<223> OTHER INFORMATION: anti-CD19 scFV  CDRH3

<400> SEQUENCE: 27

Tyr Ala Met Asp Tyr Trp Gly
1               5

<210> SEQ ID NO 28
<211> LENGTH: 734
<212> TYPE: DNA
<213> ORGANISM: Artificial Sequence
<220> FEATURE:
<223> OTHER INFORMATION: anti-CD19 scFv (VH-VL) FMC63

<400> SEQUENCE: 28
cacatccaga tgacccagac cacctccagc ctgagcgcca gcctgggcga ccgggtgacc      60
atcagctgcc gggccagcca ggacatcagc aagtacctga actggtatca gcagaagccc     120
gacggcaccg tcaagctgct gatctaccac accagccggc tgcacagcgg cgtgcccagc     180
```

```
cggtttagcg gcagcggctc cggcaccgac tacagcctga ccatctccaa cctggaacag    240
gaagatatcg ccacctactt ttgccagcag ggcaacacac tgccctacac ctttggcggc    300
ggaacaaagc tggaaatcac cggcagcacc tccggcagcg gcaagcctgg cagcggcgag    360
ggcagcacca agggcgaggt gaagctgcag gaaagcggcc ctggcctggt ggcccccagc    420
cagagcctga gcgtgacctg caccgtgagc ggcgtgagcc tgcccgacta cggcgtgagc    480
tggatccggc agccccccag gaagggcctg aatggctggg gcgtgatctg gggcagcgag    540 accaccctact acaacagcgc cctgaagagc cggctgacca tcatcaagga caacagcaag    600
agccaggtgt tcctgaagat gaacagcctg cagaccgacg acaccgccat ctactactgc    660
gccaagcact actactacgg cggcagctac gccatggact actggggcca gggcaccagc    720
gtgaccgtga gcag                                                      734
```

<210> SEQ ID NO 29
<211> LENGTH: 245
<212> TYPE: PRT
<213> ORGANISM: Artificial Sequence
<220> FEATURE:
<223> OTHER INFORMATION: anti-CD19 scFv (VH-VL) FMC63

<400> SEQUENCE: 29

```
Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Ser Thr Ser Gly
            100                 105                 110

Ser Gly Lys Pro Gly Ser Gly Glu Gly Ser Thr Lys Gly Glu Val Lys
        115                 120                 125

Leu Gln Glu Ser Gly Pro Gly Leu Val Ala Pro Ser Gln Ser Leu Ser
    130                 135                 140

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
            180                 185                 190

Thr Ile Ile Lys Asp Asn Ser Lys Ser Gln Val Phe Leu Lys Met Asn
        195                 200                 205

Ser Leu Gln Thr Asp Asp Thr Ala Ile Tyr Tyr Cys Ala Lys His Tyr
    210                 215                 220

Tyr Tyr Gly Gly Ser Tyr Ala Met Asp Tyr Trp Gly Gln Gly Thr Ser
225                 230                 235                 240

Val Thr Val Ser Ser
            245
```

```
<210> SEQ ID NO 30
<211> LENGTH: 11
<212> TYPE: PRT
<213> ORGANISM: Artificial Sequence
<220> FEATURE:
<223> OTHER INFORMATION: anti-ROR1 scFV CDRL1

<400> SEQUENCE: 30

Ala Ser Gly Phe Asp Phe Ser Ala Tyr Tyr Met
1               5                   10

<210> SEQ ID NO 31
<211> LENGTH: 7
<212> TYPE: PRT
<213> ORGANISM: Artificial Sequence
<220> FEATURE:
<223> OTHER INFORMATION: anti-ROR1 scFV CDRL2

<400> SEQUENCE: 31

Thr Ile Tyr Pro Ser Ser Gly
1               5

<210> SEQ ID NO 32
<211> LENGTH: 9
<212> TYPE: PRT
<213> ORGANISM: Artificial Sequence
<220> FEATURE:
<223> OTHER INFORMATION: anti-ROR1 scFV CDRL3

<400> SEQUENCE: 32

Ala Asp Arg Ala Thr Tyr Phe Cys Ala
1               5

<210> SEQ ID NO 33
<211> LENGTH: 6
<212> TYPE: PRT
<213> ORGANISM: Artificial Sequence
<220> FEATURE:
<223> OTHER INFORMATION: anti-ROR1 scFV CDRH1

<400> SEQUENCE: 33

Asp Thr Ile Asp Trp Tyr
1               5

<210> SEQ ID NO 34
<211> LENGTH: 16
<212> TYPE: PRT
<213> ORGANISM: Artificial Sequence
<220> FEATURE:
<223> OTHER INFORMATION: anti-ROR1 scFV CDRH2

<400> SEQUENCE: 34

Val Gln Ser Asp Gly Ser Tyr Thr Lys Arg Pro Gly Val Pro Asp Arg
1               5                   10                  15

<210> SEQ ID NO 35
<211> LENGTH: 8
<212> TYPE: PRT
<213> ORGANISM: Artificial Sequence
<220> FEATURE:
<223> OTHER INFORMATION: anti-ROR1 scFV CDRH3

<400> SEQUENCE: 35

Tyr Ile Gly Gly Tyr Val Phe Gly
1               5

<210> SEQ ID NO 36
```

```
<211> LENGTH: 123
<212> TYPE: DNA
<213> ORGANISM: Homo sapiens

<400> SEQUENCE: 36
cggagcaagc ggagcagagg cggccacagc gactacatga acatgacccc cagacggcct    60
ggccccaccc ggaagcacta ccagccctac gccccaccca gggactttgc cgcctacaga   120
agc                                                                 123

<210> SEQ ID NO 37
<211> LENGTH: 1476
<212> TYPE: DNA
<213> ORGANISM: Artificial Sequence
<220> FEATURE:
<223> OTHER INFORMATION: P28z CAR

<400> SEQUENCE: 37
gtggcctcac cgttgacccg ctttctgtcg ctgaacctgc tgctgctggg tgagtcgatt    60
atcctgggga gtggagaagc tgaggtgcag ctgcagcagt caggacctga actggtgaag   120
cctgggactt cagtgaggat atcctgcaag acttctggat acacattcac tgaatatacc   180
atacactggg tgaagcagag ccatggaaag agccttgagt ggattggaaa catcaatcct   240
aacaatggtg gtaccaccta caatcagaag ttcgaggaca aggccacatt gactgtagac   300
aagtcctcca gtacagccta catggagctc gcagcctaa catctgagga ttctgcagtc   360
tattattgtg cagctggttg gaactttgac tactggggcc aagggaccac ggtcaccgtc   420
tcctcaggtg gaggtggatc aggtggaggt ggatctggtg gaggtggatc tgacattgtg   480
atgacccagt ctcacaaatt catgtccaca tcagtaggag acagggtcag catcatctgt   540
aaggccagtc aagatgtggg tactgctgta gactggtatc aacagaaacc aggacaatct   600
cctaaactac tgatttattg ggcatccact cggcacactg gagtccctga tcgcttcaca   660
ggcagtggat ctgggacaga cttcactctc accattacta tgttcagtc tgaagacttg    720 gcagattatt tctgtcagca atataacagc tatcccctca cgttcggtgc tgggaccatg   780
ctggacctga acgggcggc cgcatctact actaccaagc cagtgctgcg aactccctca    840
cctgtgcacc ctaccgggac atctcagccc cagagaccag aagattgtcg ccccgtggc    900 tcagtgaagg gaccggatt ggacttcgcc tgtgatattt catctgggc acccttggcc     960 ggaatctgcg tggcccttct gctgtccttg atcatcactc tcatctgcta caatagtaga  1020
aggaacagac tccttcaaag tgactacatg aacatgactc cccggaggcc tgggctcact  1080
cgaaagcctt accagcccta cgcccctgcc agagactttg cagcgtaccg ccccagagca  1140
aaattcagca ggagtgcaga gactgctgcc aacctgcagg accccaacca gctctacaat  1200
gagctcaatc tagggcgaag agaggaatat gacgtcttgg agaagaagcg ggctcgggat  1260
ccagagatgg gaggcaaaca gcagaggagg aggaaccccc aggaaggcgt atacaatgca  1320
ctgcagaaag acaagatggc agaagcctac agtgagatcg gcacaaaagg cgagaggcgg  1380
agaggcaagg ggcacgatgg cctttaccag ggtctcagca ctgccaccaa ggacacctat  1440
gatgccctgc atatgcagac cctggcccct cgctaa                            1476

<210> SEQ ID NO 38
<211> LENGTH: 15
<212> TYPE: PRT
<213> ORGANISM: Artificial Sequence
<220> FEATURE:
<223> OTHER INFORMATION: Linker
```

<400> SEQUENCE: 38

Gly Gly Gly Gly Ser Gly Gly Gly Ser Gly Gly Gly Gly Ser
1               5                   10                  15

<210> SEQ ID NO 39
<211> LENGTH: 327
<212> TYPE: PRT
<213> ORGANISM: Artificial Sequence
<220> FEATURE:
<223> OTHER INFORMATION: IgG4-Fc

<400> SEQUENCE: 39

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325

-continued

```
<210> SEQ ID NO 40
<211> LENGTH: 229
<212> TYPE: PRT
<213> ORGANISM: Artificial Sequence
<220> FEATURE:
<223> OTHER INFORMATION: Hinge-CH2-CH3

<400> SEQUENCE: 40

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 41
<211> LENGTH: 119
<212> TYPE: PRT
<213> ORGANISM: Artificial Sequence
<220> FEATURE:
<223> OTHER INFORMATION: Hinge-CH3

<400> SEQUENCE: 41

Glu Ser Lys Tyr Gly Pro Pro Cys Pro Pro Cys Pro Gly Gln Pro Arg
1               5                   10                  15

Glu Pro Gln Val Tyr Thr Leu Pro Pro Ser Gln Glu Glu Met Thr Lys
            20                  25                  30

Asn Gln Val Ser Leu Thr Cys Leu Val Lys Gly Phe Tyr Pro Ser Asp
        35                  40                  45

Ile Ala Val Glu Trp Glu Ser Asn Gly Gln Pro Glu Asn Asn Tyr Lys
    50                  55                  60

Thr Thr Pro Pro Val Leu Asp Ser Asp Gly Ser Phe Phe Leu Tyr Ser
65                  70                  75                  80
```

```
Arg Leu Thr Val Asp Lys Ser Arg Trp Gln Glu Gly Asn Val Phe Ser
                85                  90                  95

Cys Ser Val Met His Glu Ala Leu His Asn His Tyr Thr Gln Lys Ser
            100                 105                 110

Leu Ser Leu Ser Leu Gly Lys
        115

<210> SEQ ID NO 42
<211> LENGTH: 12
<212> TYPE: PRT
<213> ORGANISM: Artificial Sequence
<220> FEATURE:
<223> OTHER INFORMATION: Hinge only

<400> SEQUENCE: 42

Glu Ser Lys Tyr Gly Pro Pro Cys Pro Pro Cys Pro
1               5                   10

<210> SEQ ID NO 43
<211> LENGTH: 28
<212> TYPE: PRT
<213> ORGANISM: Homo sapiens

<400> SEQUENCE: 43

Met Phe Trp Val Leu Val Val Val Gly Gly Val Leu Ala Cys Tyr Ser
1               5                   10                  15

Leu Leu Val Thr Val Ala Phe Ile Ile Phe Trp Val
            20                  25

<210> SEQ ID NO 44
<211> LENGTH: 41
<212> TYPE: PRT
<213> ORGANISM: Artificial Sequence
<220> FEATURE:
<223> OTHER INFORMATION: cytoplasmic domain of CD28 with LL to GG
      substitution

<400> SEQUENCE: 44

Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
            35                  40

<210> SEQ ID NO 45
<211> LENGTH: 42
<212> TYPE: PRT
<213> ORGANISM: Homo sapiens

<400> SEQUENCE: 45

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
            35                  40

<210> SEQ ID NO 46
<211> LENGTH: 112
<212> TYPE: PRT
<213> ORGANISM: Homo sapiens
```

<400> SEQUENCE: 46

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65              70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 47
<211> LENGTH: 24
<212> TYPE: PRT
<213> ORGANISM: Artificial Sequence
<220> FEATURE:
<223> OTHER INFORMATION: T2A ribosomal skip element

<400> SEQUENCE: 47

Leu Glu Gly Gly Gly Glu Gly Arg Gly Ser Leu Leu Thr Cys Gly Asp
1               5                   10                  15

Val Glu Glu Asn Pro Gly Pro Arg
            20

<210> SEQ ID NO 48
<211> LENGTH: 356
<212> TYPE: PRT
<213> ORGANISM: Artificial Sequence
<220> FEATURE:
<223> OTHER INFORMATION: tEGFR

<400> SEQUENCE: 48

Met Leu Leu Leu Val Thr Ser Leu Leu Leu Cys Glu Leu Pro His Pro
1               5                   10                  15

Ala Phe Leu Leu Ile Pro Arg Lys Val Cys Asn Gly Ile Gly Ile Gly
            20                  25                  30

Glu Phe Lys Asp Ser Leu Ser Ile Asn Ala Thr Asn Ile Lys His Phe
        35                  40                  45

Lys Asn Cys Thr Ser Ile Ser Gly Asp Leu His Ile Leu Pro Val Ala
    50                  55                  60

Phe Arg Gly Asp Ser Phe Thr His Thr Pro Pro Leu Asp Pro Gln Glu
65              70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
            100                 105                 110

Glu Ile Ile Arg Gly Arg Thr Gln His Gly Gln Phe Ser Leu Ala Val
        115                 120                 125

Val Ser Leu Asn Ile Thr Ser Leu Gly Leu Arg Ser Leu Lys Glu Ile
    130                 135                 140

Ser Asp Gly Asp Val Ile Ile Ser Gly Asn Lys Asn Leu Cys Tyr Ala
145                 150                 155                 160

```
Asn Thr Ile Asn Trp Lys Lys Leu Phe Gly Thr Ser Gly Gln Lys Thr
                165                 170                 175

Lys Ile Ile Ser Asn Arg Gly Glu Asn Ser Cys Lys Ala Thr Gly Gln
            180                 185                 190

Val Cys His Ala Leu Cys Ser Pro Glu Gly Cys Trp Gly Pro Glu Pro
        195                 200                 205

Arg Asp Cys Val Ser Cys Arg Asn Val Ser Arg Gly Arg Glu Cys Val
    210                 215                 220

Asp Lys Cys Asn Leu Leu Glu Gly Glu Pro Arg Glu Phe Val Glu Asn
225                 230                 235                 240

Ser Glu Cys Ile Gln Cys His Pro Glu Cys Leu Pro Gln Ala Met Asn
                245                 250                 255

Ile Thr Cys Thr Gly Arg Gly Pro Asp Asn Cys Ile Gln Cys Ala His
            260                 265                 270

Tyr Ile Asp Gly Pro His Cys Val Lys Thr Cys Pro Ala Gly Val Met
        275                 280                 285

Gly Glu Asn Asn Thr Leu Val Trp Lys Tyr Ala Asp Ala Gly His Val
    290                 295                 300

Cys His Leu Cys His Pro Asn Cys Thr Tyr Gly Cys Thr Gly Pro Gly
305                 310                 315                 320

Leu Glu Gly Cys Pro Thr Asn Gly Pro Lys Ile Pro Ser Ile Ala Thr
                325                 330                 335

Gly Met Val Gly Ala Leu Leu Leu Leu Val Val Ala Leu Gly Ile
            340                 345                 350

Gly Leu Phe Met
        355

<210> SEQ ID NO 49
<211> LENGTH: 8
<212> TYPE: PRT
<213> ORGANISM: Artificial Sequence
<220> FEATURE:
<223> OTHER INFORMATION: STREP TAG II

<400> SEQUENCE: 49

Trp Ser His Pro Gln Phe Glu Lys
1               5

<210> SEQ ID NO 50
<211> LENGTH: 10
<212> TYPE: PRT
<213> ORGANISM: Artificial Sequence
<220> FEATURE:
<223> OTHER INFORMATION: Myc tag

<400> SEQUENCE: 50

Glu Gln Lys Leu Ile Ser Glu Glu Asp Leu
1               5                   10

<210> SEQ ID NO 51
<211> LENGTH: 14
<212> TYPE: PRT
<213> ORGANISM: Artificial Sequence
<220> FEATURE:
<223> OTHER INFORMATION: V5 tag

<400> SEQUENCE: 51

Gly Lys Pro Ile Pro Asn Pro Leu Leu Gly Leu Asp Ser Thr
1               5                   10
```

```
<210> SEQ ID NO 52
<211> LENGTH: 8
<212> TYPE: PRT
<213> ORGANISM: Artificial Sequence
<220> FEATURE:
<223> OTHER INFORMATION: FLAG tag

<400> SEQUENCE: 52

Asp Tyr Lys Asp Asp Asp Asp Lys
1               5

<210> SEQ ID NO 53
<211> LENGTH: 20
<212> TYPE: DNA
<213> ORGANISM: Artificial Sequence
<220> FEATURE:
<223> OTHER INFORMATION: TRAC-Forward

<400> SEQUENCE: 53
cccgtgtcat tctctggact                                              20

<210> SEQ ID NO 54
<211> LENGTH: 20
<212> TYPE: DNA
<213> ORGANISM: Artificial Sequence
<220> FEATURE:
<223> OTHER INFORMATION: TRAC-Reverse

<400> SEQUENCE: 54
atcacgagca gctggtttct                                              20

<210> SEQ ID NO 55
<211> LENGTH: 20
<212> TYPE: DNA
<213> ORGANISM: Artificial Sequence
<220> FEATURE:
<223> OTHER INFORMATION: Foxo13A Forward

<400> SEQUENCE: 55
ggacagccta gaaagagcag                                              20

<210> SEQ ID NO 56
<211> LENGTH: 22
<212> TYPE: DNA
<213> ORGANISM: Artificial Sequence
<220> FEATURE:
<223> OTHER INFORMATION: Foxo13A Probe

<400> SEQUENCE: 56
aggtcggcgt agctcagatt gc                                           22

<210> SEQ ID NO 57
<211> LENGTH: 21
<212> TYPE: DNA
<213> ORGANISM: Artificial Sequence
<220> FEATURE:
<223> OTHER INFORMATION: Foxo13A Reverse

<400> SEQUENCE: 57
ctcttgacca tccactcgta g                                            21
```